(12) United States Patent
Sirhan et al.

(10) Patent No.: US 11,191,656 B2
(45) Date of Patent: Dec. 7, 2021

(54) METHODS AND DEVICES FOR HEART VALVE REPAIR

(71) Applicant: Elixir Medical Corporation, Milpitas, CA (US)

(72) Inventors: Motasim Sirhan, Los Altos, CA (US); Vinayak Bhat, Cupertino, CA (US); Joseph Paraschac, Campbell, CA (US); Benjamyn Serna, Gilroy, CA (US); John Yan, Los Gatos, CA (US)

(73) Assignee: Elixir Medical Corporation, Milpitas, CA (US)

( * ) Notice: Subject to any disclaimer, the term of this patent is extended or adjusted under 35 U.S.C. 154(b) by 0 days.

(21) Appl. No.: 17/195,478

(22) Filed: Mar. 8, 2021

(65) Prior Publication Data

US 2021/0186722 A1 Jun. 24, 2021

Related U.S. Application Data

(63) Continuation of application No. 17/073,052, filed on Oct. 16, 2020, now Pat. No. 10,973,662, which is a
(Continued)

(51) Int. Cl.
*A61F 2/24* (2006.01)
*A61F 2/89* (2013.01)
(Continued)

(52) U.S. Cl.
CPC .............. *A61F 2/89* (2013.01); *A61F 2/2445* (2013.01); *A61F 2/90* (2013.01); *A61F 2/915* (2013.01);
(Continued)

(58) Field of Classification Search
CPC .... A61F 2/2445; A61F 2/2442; A61F 2/2451; A61F 2/2418; A61F 2/2409; A61F 2/2475
See application file for complete search history.

(56) References Cited

U.S. PATENT DOCUMENTS 5,810,882 A 9/1998 Bolduc et al.
6,527,800 B1 3/2003 McGuckin, Jr. et al.
(Continued)

FOREIGN PATENT DOCUMENTS

EP 2068770 B1 2/2011
EP 2895111 A2 7/2015
(Continued)

OTHER PUBLICATIONS

PC/TUS19/32976 International Search Report dated Sep. 17, 2019.
(Continued)

*Primary Examiner* — Alvin J Stewart
(74) *Attorney, Agent, or Firm* — Wilson Sonsini Goodrich & Rosati

(57) ABSTRACT

A system for reshaping a valve annulus includes an elongate template having a length along a longitudinal axis and at least one concavity in a generally lateral direction along said length. The pre-shaped template is positioned against at least a region of an inner peripheral wall of the valve annulus, and at least one anchor on the template is advanced into a lateral wall of the valve annulus to reposition at least one segment of the region of the inner peripheral wall of the valve annulus into said concavity. In this way, a peripheral length of the valve annulus can be foreshortened and/or reshaped to improve coaption of the valve leaflets and/or to eliminate or decrease regurgitation of a valve.

30 Claims, 91 Drawing Sheets

Related U.S. Application Data continuation of application No. 16/740,172, filed on Jan. 10, 2020, now abandoned, and a continuation-in-part of application No. PCT/US2019/032976, filed on May 17, 2019.

(60) Provisional application No. 62/767,958, filed on Nov. 15, 2018, provisional application No. 62/673,680, filed on May 18, 2018, provisional application No. 62/937,417, filed on Nov. 19, 2019.

(51) Int. Cl.
*A61F 2/915* (2013.01)
*A61F 2/90* (2013.01)
*A61F 2/07* (2013.01)
*A61F 2/82* (2013.01)

(52) U.S. Cl.
CPC ....... A61F 2/2442 (2013.01); A61F 2002/075 (2013.01); A61F 2002/825 (2013.01); A61F 2002/91558 (2013.01); A61F 2002/91566 (2013.01); A61F 2002/91575 (2013.01); A61F 2002/91591 (2013.01); A61F 2210/0004 (2013.01); A61F 2210/0014 (2013.01); A61F 2210/0076 (2013.01); A61F 2220/0033 (2013.01); A61F 2220/0091 (2013.01); A61F 2230/001 (2013.01); A61F 2230/0006 (2013.01); A61F 2230/0008 (2013.01); A61F 2230/0069 (2013.01); A61F 2250/0031 (2013.01); A61F 2250/0036 (2013.01); A61F 2250/0048 (2013.01); A61F 2250/0067 (2013.01); A61F 2250/0071 (2013.01)

(56) References Cited

U.S. PATENT DOCUMENTS

| | | |
|---|---|---|
| 6,626,899 B2 | 9/2003 | Houser et al. |
| 6,726,717 B2 | 4/2004 | Alfieri et al. |
| 6,805,710 B2 | 10/2004 | Bolling et al. |
| 6,997,951 B2 | 2/2006 | Solem et al. |
| 7,007,698 B2 | 3/2006 | Thornton |
| 7,160,312 B2 | 1/2007 | Saadat |
| 7,160,322 B2 | 1/2007 | Gabbay |
| 7,311,729 B2 | 12/2007 | Mathis et al. |
| 7,314,485 B2 | 1/2008 | Mathis |
| 7,329,280 B2 | 2/2008 | Bolling et al. |
| 7,588,582 B2 | 9/2009 | Starksen et al. |
| 7,655,040 B2 | 2/2010 | Douk et al. |
| 7,914,576 B2 | 3/2011 | Navia et al. |
| 7,935,145 B2 | 5/2011 | Alfieri et al. |
| 7,942,927 B2 | 5/2011 | Kaye et al. |
| 7,988,725 B2 | 8/2011 | Gross et al. |
| 8,133,272 B2 | 3/2012 | Hyde |
| 8,167,933 B2 | 5/2012 | Lee et al. |
| 8,236,050 B2 | 8/2012 | Bolling et al. |
| 8,241,351 B2 | 8/2012 | Cabiri |
| 8,277,502 B2 | 10/2012 | Miller et al. |
| 8,337,390 B2 | 12/2012 | Ferrazzi |
| 8,382,829 B1 | 2/2013 | Call et al. |
| 8,454,683 B2 | 6/2013 | Rafiee et al. |
| 8,475,525 B2 | 7/2013 | Maisano et al. |
| 8,529,620 B2 * | 9/2013 | Altieri .................. A61F 2/2445 623/2.36 |
| 8,551,161 B2 | 10/2013 | Dolan |
| 8,579,967 B2 | 11/2013 | Webler et al. |
| 8,632,585 B2 | 1/2014 | Seguin et al. |
| 8,747,462 B2 | 6/2014 | Hill et al. |
| 8,784,482 B2 | 7/2014 | Rahdert et al. |
| 8,795,352 B2 | 8/2014 | O'Beirne et al. |
| 8,940,002 B2 | 1/2015 | Goertzen |
| 8,961,594 B2 | 2/2015 | Maisano et al. |
| 8,961,596 B2 | 2/2015 | Maisano et al. |
| 9,011,530 B2 | 4/2015 | Reich et al. |
| 9,072,511 B2 | 7/2015 | Tegzes |
| 9,180,005 B1 * | 11/2015 | Lashinski ............ A61F 2/2409 |
| 9,192,472 B2 | 11/2015 | Gross et al. |
| 9,241,702 B2 | 1/2016 | Maisano et al. |
| 9,307,980 B2 | 4/2016 | Gilmore et al. |
| 9,345,470 B2 | 5/2016 | Tuval |
| RE46,127 E | 8/2016 | Kirson |
| 9,402,719 B2 | 8/2016 | Lane et al. |
| 9,427,316 B2 | 8/2016 | Schweich, Jr. et al. |
| 9,492,276 B2 | 11/2016 | Lee et al. |
| 9,504,563 B2 | 11/2016 | Pintor et al. |
| 9,504,570 B2 | 11/2016 | Hauser et al. |
| 9,517,130 B1 | 12/2016 | Alon et al. |
| 9,526,610 B2 | 12/2016 | Jelich et al. |
| 9,539,093 B2 | 1/2017 | Jonsson |
| 9,585,754 B2 | 3/2017 | Seguin et al. |
| 9,610,156 B2 | 4/2017 | Lashinski |
| 9,615,926 B2 | 4/2017 | Lashinski et al. |
| 9,622,862 B2 | 4/2017 | Lashinski et al. |
| 9,713,530 B2 | 7/2017 | Cabiri et al. |
| 9,744,038 B2 | 8/2017 | Dahlgren et al. |
| 9,795,480 B2 | 10/2017 | Bolling et al. |
| 9,801,720 B2 | 10/2017 | Gilmore et al. |
| 9,848,983 B2 * | 12/2017 | Lashinski ............ A61F 2/2409 |
| 9,861,475 B2 | 1/2018 | Machold et al. |
| 9,867,703 B2 | 1/2018 | Dahlgren et al. |
| 9,872,769 B2 | 1/2018 | Gross et al. |
| 9,883,943 B2 | 2/2018 | Gross et al. |
| 9,907,547 B2 | 3/2018 | Gilmore et al. |
| 9,907,681 B2 | 3/2018 | Tobis et al. |
| 9,918,840 B2 | 3/2018 | Reich et al. |
| 9,987,135 B2 | 6/2018 | Lederman et al. |
| 9,999,505 B2 | 6/2018 | Dolan |
| 10,022,114 B2 | 7/2018 | Gilmore et al. |
| 10,028,832 B2 | 7/2018 | Quill et al. |
| 10,039,643 B2 | 8/2018 | Gilmore et al. |
| 10,052,095 B2 | 8/2018 | Gilmore et al. |
| 10,111,750 B2 | 10/2018 | Madjarov et al. |
| 10,130,472 B2 | 11/2018 | O'Beirne et al. |
| 10,136,985 B2 | 11/2018 | Lashinski et al. |
| 10,143,553 B2 | 12/2018 | Alon et al. |
| 10,182,908 B2 | 1/2019 | Tubishevitz et al. |
| 10,195,030 B2 | 2/2019 | Gross et al. |
| 10,226,342 B2 | 3/2019 | Kutzik et al. |
| 10,251,635 B2 | 4/2019 | Khairkhahan et al. |
| 10,258,466 B2 | 4/2019 | Lashinski et al. |
| 10,265,170 B2 | 4/2019 | Zipory et al. |
| 10,278,818 B2 | 5/2019 | Machold et al. |
| 10,335,275 B2 | 7/2019 | Lashinski et al. |
| 10,350,068 B2 | 7/2019 | Miller et al. |
| 10,357,365 B2 | 7/2019 | Kuehn |
| 10,357,366 B2 | 7/2019 | Gross et al. |
| 10,363,137 B2 | 7/2019 | Gross et al. |
| 10,376,266 B2 | 8/2019 | Herman et al. |
| 10,470,882 B2 | 11/2019 | Gross et al. |
| 10,470,883 B2 | 11/2019 | Khairkhahan et al. |
| 10,478,302 B2 | 11/2019 | Seguin et al. |
| 10,512,460 B2 | 12/2019 | Azar et al. |
| 10,512,542 B2 | 12/2019 | Khairkhahan et al. |
| 10,517,727 B2 | 12/2019 | Rowe et al. |
| 10,543,088 B2 * | 1/2020 | Lashinski ............ A61F 2/2466 |
| 10,548,731 B2 | 2/2020 | Lashinski et al. |
| 10,555,813 B2 | 2/2020 | Lashinski et al. |
| 10,751,180 B2 | 8/2020 | Schewel |
| 10,973,662 B2 * | 4/2021 | Sirhan ................. A61F 2/90 |
| 11,000,372 B2 * | 5/2021 | Khairkhahan ..... A61B 17/0401 |
| 2002/0002401 A1 | 1/2002 | McGuckin, Jr. et al. |
| 2002/0087169 A1 | 7/2002 | Brock et al. |
| 2003/0018377 A1 | 1/2003 | Berg et al. |
| 2003/0078465 A1 | 4/2003 | Pai et al. |
| 2003/0093148 A1 | 5/2003 | Bolling et al. |
| 2003/0199987 A1 | 10/2003 | Berg et al. |
| 2004/0106989 A1 | 6/2004 | Wilson et al. |
| 2004/0127982 A1 | 7/2004 | Machold et al. |
| 2004/0133240 A1 | 7/2004 | Adams et al. |
| 2004/0220654 A1 | 11/2004 | Mathis et al. |
| 2004/0236419 A1 | 11/2004 | Milo |
| 2004/0260393 A1 | 12/2004 | Rahdert et al. |

(56) References Cited

U.S. PATENT DOCUMENTS

| | | |
|---|---|---|
| 2004/0260394 A1 | 12/2004 | Douk et al. |
| 2005/0010240 A1 | 1/2005 | Mathis et al. |
| 2005/0010287 A1 | 1/2005 | Macoviak et al. |
| 2005/0038508 A1 | 2/2005 | Gabbay |
| 2005/0119734 A1 | 6/2005 | Spence et al. |
| 2005/0137449 A1 | 6/2005 | Nieminen et al. |
| 2005/0137700 A1 | 6/2005 | Spence et al. |
| 2005/0143811 A1 | 6/2005 | Realyvasquez |
| 2005/0192629 A1 | 9/2005 | Saadat et al. |
| 2005/0234508 A1 | 10/2005 | Cummins et al. |
| 2005/0278022 A1 | 12/2005 | Lim |
| 2006/0030885 A1 | 2/2006 | Hyde |
| 2006/0069429 A1 | 3/2006 | Spence et al. |
| 2006/0106279 A1 | 5/2006 | Machold et al. |
| 2006/0106456 A9 | 5/2006 | Machold et al. |
| 2006/0206203 A1 | 9/2006 | Yang et al. |
| 2006/0229708 A1 | 10/2006 | Powell et al. |
| 2006/0241746 A1 | 10/2006 | Shaoulian et al. |
| 2006/0247763 A1 | 11/2006 | Slater |
| 2007/0049942 A1 | 3/2007 | Hindrichs et al. |
| 2007/0061010 A1 | 3/2007 | Hauser et al. |
| 2007/0244553 A1 | 10/2007 | Rafiee et al. |
| 2007/0250161 A1 | 10/2007 | Dolan |
| 2007/0276478 A1 | 11/2007 | Marmureanu et al. |
| 2007/0293942 A1 | 12/2007 | Mirzaee |
| 2008/0065204 A1 | 3/2008 | Macoviak et al. |
| 2008/0140188 A1 | 6/2008 | Rahdert et al. |
| 2008/0275551 A1 | 11/2008 | Alfieri |
| 2008/0288060 A1 | 11/2008 | Kaye et al. |
| 2009/0149872 A1 | 6/2009 | Gross et al. |
| 2009/0177277 A1 | 7/2009 | Milo |
| 2009/0182419 A1 | 7/2009 | Bolling |
| 2009/0259306 A1 | 10/2009 | Rowe |
| 2009/0287304 A1 | 11/2009 | Dahlgren et al. |
| 2010/0022821 A1 | 1/2010 | Dubi et al. |
| 2010/0030328 A1 | 2/2010 | Seguin et al. |
| 2010/0030330 A1 | 2/2010 | Bobo et al. |
| 2010/0049314 A1* | 2/2010 | Kim ................ A61F 2/2451 623/2.37 |
| 2010/0152838 A1 | 6/2010 | Kang et al. |
| 2010/0152845 A1 | 6/2010 | Bloom et al. |
| 2010/0161047 A1 | 6/2010 | Cabiri |
| 2010/0249920 A1 | 9/2010 | Bolling et al. |
| 2010/0298929 A1 | 11/2010 | Thornton et al. |
| 2011/0106247 A1 | 5/2011 | Miller et al. |
| 2011/0118832 A1 | 5/2011 | Punjabi |
| 2011/0166649 A1 | 7/2011 | Gross et al. |
| 2011/0202127 A1 | 8/2011 | Mauch et al. |
| 2011/0257728 A1 | 10/2011 | Kuehn |
| 2011/0276091 A1 | 11/2011 | Melanson et al. |
| 2012/0053680 A1 | 3/2012 | Bolling et al. |
| 2012/0053687 A1* | 3/2012 | Migliazza ............ A61F 2/2466 623/2.37 |
| 2012/0136436 A1 | 5/2012 | Cabiri et al. |
| 2012/0179086 A1 | 7/2012 | Shank et al. |
| 2012/0283757 A1 | 11/2012 | Miller et al. |
| 2012/0296349 A1 | 11/2012 | Smith et al. |
| 2013/0184814 A1 | 7/2013 | Huynh et al. |
| 2013/0226289 A1 | 8/2013 | Shaolian et al. |
| 2013/0289710 A1 | 10/2013 | Leedle |
| 2014/0309730 A1 | 10/2014 | Alon et al. |
| 2015/0018940 A1 | 1/2015 | Quill et al. |
| 2015/0080945 A1 | 3/2015 | Michalak |
| 2015/0119981 A1 | 4/2015 | Khairkhahan et al. |
| 2015/0173899 A1 | 6/2015 | Braido et al. |
| 2015/0250461 A1 | 9/2015 | Berreklouw |
| 2015/0272586 A1 | 10/2015 | Herman et al. |
| 2015/0342737 A1 | 12/2015 | Biancucci et al. |
| 2015/0366556 A1 | 12/2015 | Khairkhahan et al. |
| 2015/0366666 A1 | 12/2015 | Khairkhahan et al. |
| 2016/0008130 A1 | 1/2016 | Hasin |
| 2016/0038285 A1 | 2/2016 | Glenn et al. |
| 2016/0038287 A1 | 2/2016 | Lederman et al. |
| 2016/0089234 A1 | 3/2016 | Gifford, III |
| 2016/0095704 A1 | 4/2016 | Whitman |
| 2016/0120647 A1 | 5/2016 | Rogers et al. |
| 2016/0135953 A1 | 5/2016 | Alon et al. |
| 2016/0242908 A1* | 8/2016 | Kim .................... A61F 2/2451 |
| 2016/0278920 A1 | 9/2016 | Braido et al. |
| 2016/0317302 A1 | 11/2016 | Madjarov et al. |
| 2016/0324639 A1 | 11/2016 | Nguyen et al. |
| 2016/0346084 A1 | 12/2016 | Taylor et al. |
| 2016/0361168 A1 | 12/2016 | Gross et al. |
| 2017/0135816 A1* | 5/2017 | Lashinski ............ A61F 2/2436 |
| 2017/0156731 A1 | 6/2017 | Mark et al. |
| 2017/0156860 A1 | 6/2017 | Lashinski |
| 2017/0189186 A1 | 7/2017 | Mohl |
| 2017/0209253 A1 | 7/2017 | Lashinski et al. |
| 2017/0245993 A1* | 8/2017 | Gross .................... A61F 2/2451 |
| 2017/0258465 A1 | 9/2017 | Maisano |
| 2017/0258589 A1 | 9/2017 | Pham et al. |
| 2017/0354500 A1 | 12/2017 | Martinez et al. |
| 2018/0008409 A1* | 1/2018 | Kutzik ................ A61F 2/2445 |
| 2018/0008412 A1 | 1/2018 | Callas et al. |
| 2018/0036119 A1 | 2/2018 | Wei et al. |
| 2018/0064535 A1 | 3/2018 | Gilmore et al. |
| 2018/0125657 A1 | 5/2018 | Dahlgren et al. |
| 2018/0214270 A1 | 8/2018 | Subramanian et al. |
| 2018/0228610 A1* | 8/2018 | Lashinski ............ A61F 2/2418 |
| 2018/0235640 A1 | 8/2018 | Slaughter et al. |
| 2018/0256330 A1 | 9/2018 | Wypych |
| 2019/0008641 A1 | 1/2019 | Dahlgren et al. |
| 2019/0038410 A1 | 2/2019 | Machold et al. |
| 2019/0070004 A1 | 3/2019 | Iflah et al. |
| 2019/0091022 A1 | 3/2019 | Yellin et al. |
| 2019/0091024 A1 | 3/2019 | Weber et al. |
| 2019/0125325 A1 | 5/2019 | Sheps et al. |
| 2019/0133765 A1 | 5/2019 | Yellin et al. |
| 2019/0151090 A1 | 5/2019 | Gross et al. |
| 2019/0159898 A1 | 5/2019 | Kutzik et al. |
| 2019/0240012 A1 | 8/2019 | Rowe et al. |
| 2019/0240022 A1* | 8/2019 | Rafiee .................. A61F 2/2466 |
| 2019/0269512 A9* | 9/2019 | Lashinski ............ A61F 2/2442 |
| 2019/0282364 A1 | 9/2019 | Khairkhahan et al. |
| 2019/0321176 A1 | 10/2019 | Lashinski et al. |
| 2019/0336289 A1 | 11/2019 | Miller et al. |
| 2019/0343628 A1 | 11/2019 | Glenn et al. |
| 2019/0350705 A1 | 11/2019 | Schewel et al. |
| 2019/0350707 A1 | 11/2019 | Zerkowski et al. |
| 2019/0350710 A1 | 11/2019 | Ketai et al. |
| 2019/0374343 A1 | 12/2019 | Lashinski et al. |
| 2020/0015971 A1 | 1/2020 | Brauon et al. |
| 2020/0022811 A1 | 1/2020 | Griswold et al. |
| 2020/0030096 A1 | 1/2020 | Zeitani |
| 2020/0030097 A1 | 1/2020 | Khairkhahan |
| 2020/0146854 A1 | 5/2020 | Sirhan et al. |
| 2020/0253733 A1* | 8/2020 | Subramanian ........ A61F 2/2454 |

FOREIGN PATENT DOCUMENTS

| | | |
|---|---|---|
| EP | 1748745 B1 | 12/2015 |
| EP | 2558031 B1 | 6/2016 |
| EP | 2482749 B1 | 8/2017 |
| EP | 2849681 B1 | 8/2017 |
| EP | 2427145 B1 | 12/2017 |
| EP | 2994073 B1 | 4/2018 |
| EP | 3377000 A1 | 9/2018 |
| EP | 3410984 A1 | 12/2018 |
| EP | 3476366 A1 | 5/2019 |
| EP | 3481335 A1 | 5/2019 |
| EP | 3542758 A1 | 9/2019 |
| EP | 3552584 A1 | 10/2019 |
| EP | 2358308 B1 | 11/2019 |
| WO | WO-2018008027 A1 | 1/2018 |
| WO | WO-2018026445 A1 | 2/2018 |
| WO | WO-2018083493 A1 | 5/2018 |
| WO | WO 2018109329 A1 | 6/2018 |
| WO | WO-2018178208 A1 | 10/2018 |
| WO | WO-2019015747 A1 | 1/2019 |
| WO | WO-2019145947 A1 | 8/2019 |
| WO | WO-2019222694 A1 | 11/2019 |

(56) References Cited

FOREIGN PATENT DOCUMENTS

| | | |
|---|---|---|
| WO | WO-2019224814 A1 | 11/2019 |
| WO | WO-2020018630 A1 | 1/2020 |

OTHER PUBLICATIONS

U.S. Appl. No. 16/740,172 Notice of Allowance dated Jul. 20, 2020.
U.S. Appl. No. 17/073,052 Notice of Allowance dated Jan. 29, 2021.
U.S. Appl. No. 16/740,172 Office Action dated Apr. 20, 2020.

* cited by examiner

METHODS AND DEVICES FOR HEART VALVE REPAIR

CROSS-REFERENCE TO RELATED APPLICATIONS

This application is a continuation of U.S. patent application Ser. No. 17/073,052, filed Oct. 16, 2020, which is a continuation of U.S. patent application Ser. No. 16/740,172, filed Jan. 10, 2020, which is a continuation-in-part of PCT/US2019/032976, filed on May 17, 2019, claiming the benefit of U.S. Provisional Application No. 62/767,958, filed Nov. 15, 2018, and of U.S. Provisional Application No. 62/673,680, filed May 18, 2018. U.S. patent application Ser. No. 16/740,172, filed Jan. 10, 2020, also claims the benefit of U.S. Provisional Application No. 62/937,417, filed Nov. 19, 2019, the full disclosures of each application being incorporated herein by reference.

BACKGROUND OF THE INVENTION

1. Field of the Invention

The invention generally pertains to mammalian body, specifically pertains to body lumens, vessels, openings, annuli, cavities, or organs. In particular this invention relates to the field of cardiology. More particularly, the invention pertains to heart valves treatment, repair, or replacement. More particularly, the invention pertains to devices and methods for repair of heart valves.

2. Description of the Background Art

Heart valves have important biological function, with a wide range of anatomical configuration including shapes, designs, and dimensions, and are subject to an array of different conditions such as disease conditions that can cause impairment or malfunction. The mitral valve, for example, consists of an annulus containing anterior and posterior leaflets located at the junction between the left atrium and the left ventricle. The valve leaflets are attached to the left ventricle heart papillary muscles via chordae tendineae. Valvular impairment or dysfunction can be caused or exacerbated by changes to the valve configuration including shape, size, and dimension of the valve (or annulus), the length or functionality of the chordae, the leaflets function, causing impairment or dysfunction of the valve.

An array of open heart surgical procedures have been utilized, including for example, surgical annuloplasty, implantation of artificial chordae or repair of chordae, and resection leaflet surgical valve repair. These procedures are performed typically via open heart typically using bypass surgery, including opening the patient's chest and heart, a risky and invasive procedure with long recovery times and associated complications.

Current less invasive surgical devices and less invasive percutaneous devices are undergoing to replace or repair the mitral valve. Less invasive surgical and percutaneous options for valve repair typically attempt to replicate more invasive surgical techniques. These devices have the disadvantage of one or more of being large in size, complex to use, and have limited efficacy or applicability to the various anatomical configurations of valves. Results have been typically inferior to open surgical valve repair procedures. What is needed is a device that can be incorporated into less invasive surgical and percutaneous techniques, address valve regurgitation, minimize or eliminate device migration, device that is applicable to broader patient population having various valve configurations. The invention meets at least some of these needs.

SUMMARY OF THE INVENTION

The present invention comprises devices and methods for less invasive surgical and/or percutaneous treatment or repair of a body organ, lumen, cavity, or annulus. In a preferred example, the present invention comprises devices and methods for open surgical, less invasive surgical, and percutaneous treatment or repair of heart valves comprising valve annulus and valve leaflets. An example of heart valves comprises aortic, mitral, pulmonary, and tricuspid valves. Although certain examples show a specific valve, the inventions described and claimed herein are applicable to all valves in the body and additionally other body annulus, lumen, cavity, and organs.

In one example, the devices comprise a template having a first end, a second end, and a body extending between said first and second ends, wherein the device is configured to reshape a section of annulus from a substantially smooth shape to a convoluted shape which can foreshorten or otherwise tighten the valve or other annulus. Typically, the template is coupled to the annulus in one or more locations between said first and second ends. For example, the first and second ends of said template may be coupled to the annulus at two or more annulus points or regions, and/or said body may include one or more coupled locations which pull said annulus radially inwardly while said first and second ends exert a radially outward force on the annulus, substantially opposing the inward pull of said one or more coupled locations.

In a preferred example, the template is coupled to the annulus at two or more location, and such locations are separated by a segment of the template body that exerts a radially outward force on the annulus substantially opposing the inward pull of said two or more coupled regions. In a preferred example, the body is coupled in one or more location to the annulus between the proximal and distal ends by means comprising one or more of: screws, clips, sutures, barbs, or other means. In another preferred example, the body is coupled to the annulus while the device is in a deflected configuration. In yet another preferred example, the body is coupled to the annulus at or near a mid-point between first and second ends. In yet another example, the body is coupled to the annulus at two locations, said locations lie between first and second ends. In yet another example, the body is coupled to the annulus in three locations wherein the locations lie between first and second ends of the template. In a preferred example, the device is formed from a material wherein the material comprises one or more of: rigid, self-expanding, elastic, super-elastic, plastically deformable, and has a form comprising one or more of: coil, screw, spiral, spring, barb, suture, hook staple, etc. In a preferred example, the means coupling one or more locations means on the body to the annulus comprises one or more of the following actions: penetrating the annulus, and holding together said annulus and body at the coupling location; penetrating the annulus, holding together said annulus and body at the coupling location, and pulling in said annulus to desired shape (configuration) upon deployment of the device; penetrating the annulus, holding together said annulus and body at the coupling location, and pulling in said annulus to desired shape (configuration) upon deployment of the device and coupling said proximal and distal ends to one or more annulus points or regions conforming to said body coupled region to said annulus, reshaping coupled annulus, reshaping coupled annulus to shape of body in the coupled region.

In a preferred example, the template has an undulating shape.

In another example, the template has an undulating shape with an even number of undulations pressing into the annulus, and an odd number of undulations which are coupled to the annulus by coupling mechanism(s) in tension.

In another example, the template has an undulating shape with an odd number of undulations pressing into the annulus, and an even number of undulations which are coupled to the annulus by coupling mechanism(s) in tension.

In another example, the template has an undulating shape with an even number of undulations pressing into the annulus, and an even number of undulations which are coupled to the annulus by coupling mechanism(s) in tension.

In a preferred example, the template surface is compatible with tissue in contact with the template. This compatibility can be achieved through a number of methods known to the arts including template material choice, template surface finish, coatings, flocking. The compatibility can also be achieved through a variety of covering materials including ePTFE, Dacron knits, other knit fabrics, and the like.

In a preferred example, the valve annulus comprises annulus and tissue adjacent to annulus.

In another example, the device is an implant or a temporary implant.

In one example, the device is formed from one or more of the following material: strong, stiff, resilient, shape memory, elastic, plastically deformable, capable of withstanding cyclic load of at least 10 million cycles.

In another example, multiple devices are implanted along the annulus.

In another example, multiple devices are implanted along the annulus and connected with rigid or semi-rigid connectors.

In one example, the device is formed from a degradable or non-degradable material.

Device comprises a template wherein the device comprises an expandable body, a ring, a body with one end, a body with two ends, a body with three ends or more.

In certain further examples, the implant of the present invention may comprise a tissue coupling mechanism configured to anchor, secure, or stabilize the template and position the undulating body of the template adjacent to the inner surface of the heart valve annulus. The tissue coupling mechanism may comprise a tissue penetrating element. The tissue coupling mechanism may have a first tissue penetrating element at a first connected end of the inner and outer arcuate members and a second tissue penetrating element at second connected end of the inner and outer arcuate members, and the tissue penetrating element(s) may comprise of projection(s) such as barb(s).

In one example, the device comprising a body wherein the body comprises a proximal end, a distal end, and a shaft extending between said proximal and distal ends, wherein the device is configured to being expandable from crimped configuration to an expanded configuration, and wherein the shaft is coupled to the annulus in one or more locations between said proximal and distal ends, and wherein the proximal and distal ends of said body are coupled to two or more annulus points or regions, and wherein said shaft one or more coupled locations pull said inward while proximal and distal ends stretch annulus coupled to said proximal and distal ends. In a preferred example, the shaft is coupled in one or more location to the annulus between the proximal and distal ends by means comprising one or more of: screws, clips, sutures, barbs, or other means. In another preferred example, the shaft is couple to the annulus while the device is in a crimped configuration. In yet another preferred example, the shaft is coupled to the annulus at a mid-point between proximal and distal ends. In yet another example the shaft is coupled to the annulus at two locations, said locations lie between proximal and distal ends. In yet another example, the shaft is coupled to the annulus in three locations wherein the locations lie between proximal and distal ends of the body. In a preferred example, the device is formed from a material wherein the material comprises one or more of: self-expanding, elastic, plastically deformable, coil, spring, etc. In a preferred example, the means coupling one or more locations means on the shaft to the annulus comprises one or more of the following actions: penetrating the annulus, penetrating the annuls and holding together said annulus and shaft at the coupling location, penetrating the annulus, holding together said annulus and shaft at the coupling location, and pulling in said annulus to desired shape (configuration) upon deployment of the device, penetrating the annulus, holding together said annulus and shaft at the coupling location, and pulling in said annulus to desired shape (configuration) upon deployment of the device and coupling said proximal and distal ends each to one or more annulus points or regions, conforming to said shaft coupled region to said annulus, reshaping coupled annulus, reshaping coupled annulus to shape of shaft in the coupled region.

In a preferred example, the valve annulus comprises annulus and tissue adjacent to annulus.

In another example, the device is an implant or a temporary implant.

In another example the device comprises a body and two ends. In another example, the device comprising a body and two ends, wherein each end comprising at least one prong, wherein the two ends push two or more tissue points or regions outwardly. In one example, the two ends bifurcate into two or trifurcate into three prongs. In a preferred example, the two ends are connected by a shaft. In another example, the two ends are connected by one or more shafts. In yet another example the two ends are connected by two or more shafts. In yet another example, the two ends are connected by a shaft wherein the shaft branches into multiple shafts along the path of said shaft. In a preferred example the shaft comprises a solid body, yet it may also in other examples comprise hollow (tubular) body, or other. In a preferred example the shaft has a round shape. In other examples, the shaft shape comprises oblong, rectangle, semi-circle, triangle, elliptical, dog bone, square, or other shapes. The two ends may have the same shape and geometry or may have different shapes and geometries. In yet another example, the two ends have the same shape and geometry as the shaft. In yet another example, the device ends comprise one or more prongs wherein the prongs have a shape or geometry comprising one or more of spear, barb, pad, flat, disc, rough surface, round, square, rectangle, bulbous, arc, or other. In yet another example, the one or more prongs maybe coupled to adjacent tissue wherein the prong coupling to the tissue comprises one or more of suturing, screw, geometry of the prong such as a barb configuration penetrating the tissue, coupling, placating, pressing, surface adhesion, surface friction, or other. In yet another example, each of the two ends comprises one or more prongs, wherein each end prongs have the same or different shape or geometry. In yet another example, each of the two ends comprises two or more prongs, wherein each of the prongs have the same or different shape or geometry. In yet another example, the device comprises at least one end wherein said end comprises at least two or more prongs bifurcate about the same location on the shaft. In yet another example, the two or more prongs bifurcate at different locations along the shaft length. In yet another example, the device comprises at least one end and wherein said at least one end has two or more prongs wherein the function of the two or more prongs may be the same or different. In yet another example, the device comprises at least one end and wherein said at least one end has two or more prongs and wherein at least one prong pushes adjacent tissue outwardly. In yet another example, the device comprises at least one end and wherein said at least one end has two or more prongs and wherein at least one prong pushes adjacent tissue outwardly and at least one prong pulls in adjacent tissue inwardly. In yet another example, the device comprises at least one end and wherein said at least one end has two or more prongs and wherein at least one prong pushes adjacent tissue outwardly and at least one prong holds adjacent tissue in place. In yet another example, the device comprises at least one end and wherein said at least one end comprises at least one prong and wherein the function of said prong comprises one or more of securing an end of the device to adjacent tissue, pushing adjacent tissue outwardly, holding in place adjacent tissue, pulling inward adjacent tissue, aligning tissue regions, configuring tissue regions to be out of plane (misaligned), controlling or limiting penetration depth of the device into the tissue, or other. In yet another example, the device comprising a body and two ends wherein each end comprising at least one prong, wherein the two ends push two or more tissue points or regions outwardly, and wherein other two or more tissue points or regions are pulled inwardly (or pulled in together). In yet another example, the device comprising a body and two ends wherein at least one end comprises at least two prongs, wherein at least one prong pushes adjacent tissue outwardly, and wherein at least one prong is pulling adjacent tissue inwardly, and wherein two or more tissue points or regions between the two ends are pulled inwardly. In a preferred example, the two or more tissue points or regions are adjacent to said body ends. In one example, the device is coupled to one or more tissue points or regions to push said tissue points or regions outwardly, and wherein the device is configured to exert outward force to said one or more tissue points or regions, and wherein the location of device coupling comprises one or more locations comprises the body of the device, device one or more ends, device one or more prongs, to affect an annulus shape wherein two or more points regions on the annulus are pushed outwardly while two or more points or regions on the annulus are pulled inwardly.

In one example, the device comprising a body, wherein said body is connected to at least two ends wherein each end comprising at least one prong, wherein the at least two ends push two or more tissue points or regions outwardly. In yet another example, the device comprising a body and at least two ends, each end comprising at least one prong, wherein the at least two ends push two or more tissue points or regions outwardly, and wherein two or more other tissue points or regions are pulled inwardly. In a preferred example, the two or more tissue points or regions pushed outwardly are adjacent to said body ends and the other two or more tissue points or regions pulled inwardly are located between said body ends. In a preferred example, the device is positions in a valve annulus wherein two or more tissue points or regions pushed outwardly are adjacent to said body ends at the annulus and the other two or more tissue points or regions pulled inwardly are located between said body ends at said the annulus. In one example, the device is attached or affixed to adjacent tissue in one or more locations to affect outward and/or inward movement of tissue and/or annulus shape.

In another example, the device comprises a body having at least two ends, wherein each end comprises at least one prong and wherein at least one end or at least one prong is pushing an adjacent tissue outwardly. In another example, the device comprising a body, wherein said body has at least two ends wherein each end comprising at least one prong, and wherein the device is coupled, in one or more locations, to one or more tissue points or regions and configured to pushing said tissue points or regions outwardly and wherein other tissue points or regions between said coupled locations are pull inwardly and wherein the device ends affect the tissue (including annulus) wherein an effect may comprise one or more of two ends pushing two or more tissue (including annulus) points or regions comprising one or more of apart, outwardly, in opposite direction, in plane, out of plane. In another example, the device comprising a body, wherein said body is connected to three ends wherein each end comprising at least one prong.

The device may be a rod with two ends, a device having body like a disc or a stent, or other comparable structures.

In one example, the device is formed from a resilient material shaped into a rod having two ends and a shaft connecting said two ends.

In one example, the device is formed from one or more of the following material: strong, stiff, resilient, shape memory, elastic, plastically deformable, capable of withstanding cyclic load of at least 10 million cycles.

In one example, the device is formed from a degradable or non-degradable material.

Device comprises a body wherein the device comprises an expandable body, a ring, a shaft with one end, a shaft with two ends, a shaft with three ends or more.

In a further aspect of the present invention, an implant is configured to reshape a heart valve having a valve annulus and valve leaflets. The implant comprises an inner arcuate member configured to conform to an inner surface of a heart valve annulus and an outer arcuate member configured to conform to an inner surface of a heart wall adjacent to the heart valve annulus. The inner and outer arcuate members are coupled together and are further configured to be attached to tissue in, on, or near the heart valve so that the inner arcuate member applies an inwardly acting radial force on at least a portion of the inner surface of the valve annulus and the outer arcuate member applies an outwardly acting radial force on the inner surface on the heart wall. Such forces will stabilize the annulus to promote enhanced leaflet coaptation with minimum stretching of the valve leaflets.

In certain examples of the implant, the inner and outer arcuate members are connected at their ends and have an annular space between an outer edge of the inner arcuate member and an inner edge of the outer arcuate member. A mechanism may be disposed in the annular space and be configured to adjust the relative positions of the inner and outer arcuate members in order to, for example, allow adjustment of the reshaping and stabilization of the annulus. The mechanism may comprise a threaded member or other suitable linear translation element. Alternatively, the mechanism may comprise a spring or other self-adjusting coupling structure. In still further examples, the implant may comprise a plurality of mechanisms disposed in the annular space and configured to adjust the relative positions of the inner and outer arcuate members.

In certain further examples, the implant of the present invention may comprise a tissue coupling mechanism configured to anchor the implant and position the inner arcuate member adjacent to the inner surface of the heart valve annulus and position the outer arcuate members adjacent to the inner surface of the heart valve wall. The tissue coupling mechanism may comprise a tissue penetrating element. The tissue coupling mechanism may have a first tissue penetrating element at a first connected end of the inner and outer arcuate members and a second tissue penetrating element at second connected end of the inner and outer arcuate members, and in all cases, the tissue penetrating element(s) comprise barb(s).

In yet another aspect of the present invention, a method for treating a heart valve having a heart valve annulus, valve leaflets and a heart valve wall surface adjacent to the annulus comprises providing an implant comprising an inner arcuate member configured to conform to an inner surface of the heart valve annulus and an outer arcuate member configured to conform to an inner surface of the heart wall adjacent to the heart valve annulus. The implant is implanted above the heart valve so that the inner arcuate member applies an inwardly acting radial force on at least a portion of the inner surface of the valve annulus and the outer arcuate member applies an outwardly acting radial force on the inner surface on the heart wall.

These methods may further comprise adjusting a width or other dimension, angle, or shape of an annular space between an outer edge of the inner arcuate member and an inner edge of the outer arcuate member to vary at least one of the inwardly acting radial force on at least a portion of the inner surface of the valve annulus and the outwardly acting radial force on the inner surface on the heart wall. Implanting may comprise anchoring the implant into tissue around the heart valve, for example by anchoring at least a first end on the implant and a second end of the implant wherein the inner and outer arcuate members are connected. Anchoring the implant into tissue around the heart valve may comprise penetrating elements into tissue in or adjacent to the annulus. For example, anchoring the implant into tissue around the heart valve may comprise inserting fasteners, such as barbs, helical anchors, screws, and the like which are attached or otherwise coupled to the implant, into tissue where the fasteners may be located at a first end on the implant and a second end of the implant wherein the inner and outer arcuate members are connected. In a further example, anchoring the implant into tissue in or adjacent to the annulus may comprise one or more tissue penetrating anchors intermediate to the first and second ends of the implant. In a further example, the tissue being pulled inward by the template may comprise valve leaflet tissue, which is stretched toward the opposing valve leaflet.

Various control and delivery mechanisms are illustrated herein, including torsion tubes and delivery devices that interact with the body of the template. These control mechanisms may be actuated manually by the operator, or by a remotely powered actuator system.

In various of the above examples, the surface of the template may be partially or fully covered with ePTFE, velour, knitting, weaving, spray coating, electrospun coatings, combinations thereof, or the like.

In various of the above examples, the surface may be partially or fully coated with anticoagulants, anti-thrombotic agents, thrombolytic agents, anti-thrombin agents, anti-fibrin agents, anti-platelet agents, combination thereof, or the like.

In various of the above examples, the surface or a surface covering may have pores at least partially filled with anticoagulants, anti-thrombotic agents, thrombolytic agents, anti-thrombin agents, anti-fibrin agents, anti-platelet agents, combination thereof, or the like.

In various of the above examples, an anchor surface may be partially or fully coated with anticoagulants, anti-thrombotic agents, thrombolytic agents, anti-thrombin agents, anti-fibrin agents, anti-platelet agents, combination thereof, or the like.

In various of the above examples, a proximal end of one or more anchors may collapse into a minimal structure upon removal of the torque tubing.

In various of the above examples, the annulus may also include tissue adjacent to the annulus.

In one exemplary embodiment, an implant constructed in accordance with the principles of the present invention for reshaping a valve annulus comprises a pre-shaped template and at least one anchor. The pre-shaped template has a length in an axial direction and at least one concavity extending in a lateral direction along the length. The concavity defines a concave surface on one side of the template, which concave surface is typically configured to be positioned against and/or adjacent to a peripheral wall of valve annulus. The at least one anchor on the template is configured to draw at least one segment (region) of the peripheral wall of the valve annulus into the concavity so that the segment (region) is brought up against the concave surface to at least partially conform to the shape and contour of the concave surface.

The pre-shaped template may have a variety of geometries. It will typically be a non-linear elongated member having a surface with a shape or contour which will be imparted to the segment of peripheral wall of valve annulus after the template has been anchored to the annulus tissue. In many examples, the pre-shaped template will be curved along its length, typically having a serpentine, undulating, angulated (having one or more abrupt bends or angles along its length), or have another wave-like or zig-zag profile which will cause the periphery of the annulus to fold or plicate, thereby shortening and/or repositioning a peripheral length of the annulus, in a manner mimicking annuloplasty when the template is attached to the annulus.

Although in many examples, the pre-formed template will be free from angled bends along its length, in other examples the concavity may be formed with angled bends (angulated) along the length of the template, for example the concavity may have a rectilinear periphery (four sequential bends of approximately 90° each defining the concavity). In other examples, angulated bends may be combined with curved or arcuate segments to shape the template.

In many examples, the concavities of the pre-shaped template will be symmetric about a lateral axis, usually having opposed legs joined by a curved junction region forming the bottom of the concavity. In some examples, either or both opposed legs may have a convex surface (convexity) formed at an outer termination or transition region thereof. Usually, such convex surfaces will be axially and laterally spaced-apart from the curved junction region of the concavity, and the at least one anchor of the implant will be further configured to draw adjacent segments of the peripheral wall of the valve annulus against the convex surfaces as well as into the concavity.

In still other specific examples, the pre-shaped template may have at least two concavities separated by a convexity therebetween. In such examples, the concavities may be disposed symmetrically about a lateral axis passing through a mid-point or apex of the convexity therebetween. The convexity will typically comprise a curved junction region which joins a pair of oppose legs, with each leg joined its lower end to one of the concavities, with each concavity being laterally spaced-apart from the mid-point of the convexity. In such examples, the at least one anchor on the template is further configured to draw adjacent segments of the peripheral wall of the valve annulus against the concave surfaces as well as against the convex surfaces therebetween.

In all such examples, the implants of the present invention may be used individually or in groups of two, three, four, or more. When used in groups, the implants may be left unattached after they have been implanted, or alternatively may be further joined together in tandem, for example by bonding or attaching terminal regions of one implant to terminal regions of an adjacent implant.

Implants of the present invention may be implanted in any cardiac valve, venous valve, or other vascular valve of a human or other patient. For example, the implants may be implanted into all or a portion of a patient's posterior mitral valve annulus, posterior tricuspid annulus, anterior-posterior tricuspid annulus, aortic annulus, pulmonary valve annulus, or the like.

The templates of the present invention will generally comprise an elongate structure having at least two of terminal ends, a pair of side edges, a tissue-engaging surface, and an inwardly facing surface, but can have other structures with various number of edges, surfaces, and terminal ends. The length of template, when in its non-linear form, will typically be from 10 mm to 185 mm, often being in a range 10 mm to 75 mm, and sometimes being in the range 20 mm to 60 mm. The width of the template will typically be in a range from 1 mm to 15 mm, usually from 2 mm to 8 mm, and often from 2 mm to 6 mm. The thickness of the template will typically be from 0.1 mm to 2 mm, more usually from 0.2 mm to 1.5 mm. In specific examples, the elongate structures of the templates may comprise of a plate, a ribbon, a mesh, a lattice, a beam, a tube, a rod, a cylinder, a coil, a spiral, a spring, or a combination thereof. Exemplary templates will be elongated, shape-memory metal ribbons which have been heat-set or otherwise shape-set to a desired non-linear geometry with one or more concavities.

The elongate structures of the templates may be formed from any material having sufficient strength, resiliency, and biocompatibility to be implanted in a patient's heart and to conform to a region of the patient's peripheral annulus to effect shortening thereof, typically being a metal, such as a nickel-titanium alloy, a stainless steel, or the like.

Individual implants according to the present invention may have a single concavity, at least two concavities, at least three concavities, at least four concavities, typically having from one to twelve concavities.

While the pre-shaped of the present invention templates will usually be a curved, elongated structure having and having first and second discrete ends, in other examples, they may comprise or be joined together as a continuous ring intended to be implanted about a full periphery of the patient's valve annulus. In some examples, a plurality implants (typically from two to six) having discrete ends may be configured to be joined end-to-end either before implantation or after implantation (in situ). In both examples, the templates will form a continuous structure about the entire periphery of the valve annulus.

In many examples, the implant templates of the present invention will be pre-shaped, i.e. will have an undulating, serpentine, and/or angulated shape imparted during manufacturing. In other examples, it may be possible to provide templates which are configured to be shaped in situ.

In some examples, the templates of the implants of the present invention may be covered in a biocompatible material, such as ePTFE, polyethylene terephthalate (Dacron®), or other materials intended to encourage tissue in-growth. Such biocompatible materials may be formed into suitable structures including open-cell foam structures, closed-cell foam structures, woven fabrics, non-woven fabrics, texture or surface finishes, and the like.

The anchors of the implants of the present invention will typically be tension anchors configured to draw at least a portion of a segment of an inner surface of annulus into the concavity. For example, the anchors may comprise a helix, a ratcheting tether, a screw, a coil, a spiral, a hook, a barb, a clip, a lock, a staple, or any other type of fastener which can both engage the target tissue and draw the target tissue into the concavity. Suitable tissue anchors may have one or more ribs, wings, barbs, expansion elements, wedges, extensions, protrusions, and combinations thereof.

In a specific instance, at least one anchor may comprise a helical anchor having a distal end and proximal end. The distal end may have a sharpened tip, and the proximal end may be rotatably secured in the concavity of the template, typically at a mid-point of a curved junction region. Usually, the helical anchor will be configured to be engaged by a detachable driver to rotate the helical anchor to drive the sharpened tip into the annulus and draw at least a segment of an inner surface of the annulus into the concavity. Such anchors may comprise a helical coil, a screw, a spiral, or the like, typically being a helical coil.

In further specific examples, the concavity in the template will have a depth in the lateral direction. The helical anchor may have a length which is greater than depth of the concavity. In this way, the sharpened tip will be positioned beyond an outer tissue-engaging surface of the template so that the tip can engage tissue without the need to deform the pre-shaped template. In other examples, however, the helical anchor may have a length which is less than a depth of the concavity. In such examples, the sharpened tip can engage tissue by pressing the template against the target tissue and deforming the template to allow the sharpened tip of the helical anchor to engage the target tissue.

In other exemplary examples of the present invention, the anchor may comprise any one or more of a ratcheting tether, hook, a barb, a fastener, a clip, a loop, or a staple. Such anchors have a distal end and a proximal end, where the distal may comprise a sharpened tip and the proximal end may be secured in concavity of the template and be configured to push and pull with a detachable driver. In this way, the anchor can push and pierce into the annulus to draw at least a segment of the inner surface of the annulus into the concavity and to lock that segment into place.

In still further specific examples, the implants of the present invention may comprise elements or components for stabilizing tissue. For example, a tissue-coupling mechanism may be attached at either or both of the ends of a pre-shaped template to stabilize the template and hold it in place after implantation. Such tissue coupling mechanisms may comprise, for example, helical anchors or other fasteners configured to be rotatably advanced into tissue, where such anchors are similar to the primary anchor intended to draw tissue into the concavity. Other stabilizing tissue coupling mechanisms may include self-penetrating barbs, staples, clips, or the like that can be used to secure the free ends of the template against the valve annulus tissue.

In still further specific examples of the present invention, the stabilizing mechanism for the template may comprise a stabilizing arm which extends laterally from the pre-shaped template, where the stabilizing arm may engage tissue above the annulus after the template has been implanted. The stabilizing arm may have a pad at its distal end, or may alternatively comprise a stabilizing anchor or other fastener similar to those described above for the ends of the template.

In still further aspects, the present invention comprises systems for reshaping a valve annulus. Such systems may include any of the implants described above in combination with a delivery catheter. The delivery catheter typically has proximal end and a distal end, where the implant is removably carried on the distal end. In exemplary examples, the delivery catheters may comprise at least one flexible tension member secured to the at least one anchor on the template, typically comprising a plurality of flexible tension members when the template includes a plurality of anchors. The flexible tension members are removably secured to the anchors so that the catheter may be detached from the implant after implantation has been completed. The flexible tension members are typically further configured to rotate the at least one anchor to advance said anchor into tissue. For example, the flexible tension members may comprise a flexible coil or other rotatable drive shaft having a distal coupling member configured to removably engage a drive element on the proximal end of the at least one anchor.

For example, the coupling member may comprise a sleeve or bushing with a hole or passage or other aperture formed in a wall thereof, and the flexible tension member may comprise a separate wire or elongate element for passing through the aperture in the coupling member so that rotation and attachment of the flexible tension member to the coupling member can controlled by advancing and retracting the elongate element into and out of the aperture.

The systems of the present invention may further comprise elongated control elements detachably secured to the ends of the pre-shaped template. For example, the elongated control elements may be configured to collapse the pre-shaped template about the anchor, typically so that the implant may be collapsed during delivery and opened after advancement from the delivery catheter. Alternatively, the elongated control elements may be configured to pull back the pre-shaped template away from the anchor, again to reduce its profile for delivery while allowing release to its original configuration after advancement toward the valve annulus.

In still further examples, the systems of the present invention may comprise a pre-anchor guide slidably coupled to delivery catheter. The pre-anchor guide may comprise a guide wire-like shaft having a coil or other tissue anchor at its distal tip. In this way, the pre-anchor guide may be advanced into the valve annulus at particular target location prior to advancement of the implant. The delivery catheter can then be advanced over the pre-anchor guide to properly position the implant prior to implantation.

In still further exemplary examples, the present invention provides methods for reshaping a valve annulus. Typically the methods comprise engaging a template against a peripheral surface of the valve annulus, where the template has both a tissue-engaging surface and at least one concavity formed in the surface in a radially inward direction relative to the valve annulus. At least one segment of peripheral surface of the annulus is drawn into the concavity, resulting in a shortening and/or repositioning of a peripheral length of the valve annulus, which can mimic annuloplasty and reduce valve regurgitation, particularly mitral valve regurgitation in at least most patients.

In specific examples of the methods herein, the template may be configured to be engaged against a peripheral surface of at least a length a posterior segment of a tricuspid valve annulus, an aortic valve annulus or a pulmonary valve annulus. The lengths of engagement will range from 10 mm to 185 mm, with other specific ranges as set forth above with regard to the implant design of the present invention.

The implanted templates will typically comprise an undulating, serpentine or angulated structure having the at least one concavity. Such undulating, serpentine or angulated structures may have two concavities, three concavities, four concavities, five concavities or more as described previously. The templates will typically be pre-shaped but in other examples could be formed in situ. In still other examples, multiple templates may be implanted and joined together prior to implantation or in situ to provide for a longer engagement against the valve annulus, and in some examples engaging an entire periphery of a valve annulus.

In many examples, applying tension to a peripheral wall segment to draw the segment in the concavity typically comprises advancing the anchor into a target region on the peripheral annulus in a manner that draws that tissue into the concavity on the template. Usually, the anchor comprises a helical coil, screw, or spiral having a proximal portion which is rotatably attached to the template, typically at a bottom of the concavity, so that the anchor will remain laterally fixed relative to the template while the anchor acts as "cork screw" in drawing tissue into the concavity.

In other examples, drawing a segment of the annulus into the concavity may comprise applying compression to the segment to compress the segment into the concavity. For example, compression may be applied by looping, tying, suturing, clipping or the like. In other examples, compression may be effected by a compression anchor configured to secure and stabilize the template to the tissue. Such compression anchors include a helix, a ratcheting tether, a screw, a coil, a spiral, a hook, a barb, a fastener, a clip, a hook, a staple or the like.

The methods of the present invention may comprise advancing the template intravascularly, percutaneously (such as via a transapical approach), or via a minimally invasive approach, such as a throacoscopic approach.

In specific examples, the templates may be attached to the target tissue of the annulus by rotating a helical end anchor on the template, where the anchor has a proximal end and sharpened distal end. Typically, rotating such anchors comprises rotating a flexible tension member in the delivery catheter to drive the sharpened distal tip into tissue and draw the tissue segment of the annulus into the concavity.

In still further exemplary examples, the methods for reshaping a valve annulus may comprise placing a semi-rigid template adjacent to a portion of the peripheral wall of the heart valve annulus. The semi-rigid template is fastened to the portion of the peripheral wall in a manner such that the annulus is caused to approximate the shape of the template. For example, the template may exert opposing radial forces on the inner wall of annulus to cause the annulus to partially plicate and foreshorten. Usually, the semi-rigid template will not substantially increase a diametric dimension of the annulus. The template as with previous examples may comprise multiple segments having substantially the same shape. Alternatively, the template may comprise multiple segments having distinct shapes.

In one example, the invention is a system to reshape a valve annulus comprises a template having a preformed shape with at least one concavity and at least one anchor on the at least one concavity, wherein the template is delivered to appose an annulus region, wherein said anchor is configured to reposition said annulus region into said concavity. In a further example, said template has two additional anchors to hold said template in place and prevent flipping or twisting of the template about its axis. In a further example, the template is releasably coupled to a delivery device, and wherein the delivery device is removed after anchoring said template to said annulus region. In yet another example, the said template having a length along a longitudinal axis and at least one concavity in a lateral direction along said length, and said template has two apex segments each segment connected by a leg to one side of said concavity, wherein each of said apex segment has an anchor configured to affix at least one region of said apex segment to adjacent annulus. In another example, the apex segment comprises one or more of convex region, flat region, and concave region(s). In yet another example, the template comprises a plurality of concavities and a plurality of apex segments, wherein some or all of the concavities has an anchor configured to reposition at least one region of an annulus into said concavities, and some, all, or none of the apex segments may have anchors to attach the apex segments to adjacent annulus regions. In yet another example, the template comprises a plurality of concavities and a plurality of apex segments, wherein each concavity has an anchor configured to reposition at least one region of an annulus into said concavities, and wherein said template further comprises at least two apex segments wherein at least one of said apex segments has an anchor configured to attach at least one region of the apex segment to the adjacent annulus. In another example, the said template has the advantage of repositioning selective regions of valve annulus. In another example, the template is configured to reposition one region of a valve annulus, wherein the region comprises a posterior annulus region, an anterior annulus region, a septal annulus region, or an anterior posterior region. In one example, annulus regions outside said template remain substantially unchanged. In another example, said template is configured to perform one or more of the following: reposition at least one region of an annulus into said concavity of the template, reduction of the valve annulus circumference, reducing an annulus configuration, reducing the annular area, reducing one or more dimensions of the annulus, reduction of a said annulus region circumference, configuration, or one or more dimension's. In another example, the template comprises at least one concavity joined by legs, wherein the legs comprise an apex segment and wherein each apex segment contains an anchor configured to attach at least one region of said segment to the adjacent annulus region, and wherein said concavity containing at least one anchor configured to pull in at least one region of an annulus into said concavity. In a preferred example, the apex segments have a substantially equal but opposite force to said anchor pulling in said annulus into said concavity. In another or same example, the apex segments are configured to prevent flipping or rotation of said template about its axis. In one example, the template is pre-formed before delivery into a patient body, in another example, the template is formed in situ. In a preferred example, the template comprising at least one concavity containing at least one anchor configured to pull in said adjacent and apposing annulus region into said concavity, wherein said annulus region conforms and/or contours substantially to the shape of said concavity. In another example, the template comprising at least one concavity may have various shapes of concavity, partial concavity, or a lateral space for an anchor to pull into said lateral space adjacent annulus region.

In another example, a system to reshape a valve annulus comprises a template having a preformed shape, comprising at least one concavity and at least two apex segments wherein each apex segment has a leg connected to said concavity, and at least one anchor disposed in the at least one concavity, the template being constrained in a first crimped, smaller configuration for delivery to the annulus region, and being configured to appose an annulus region and pull in said annulus region into said concavity. In a variation of this example, the template is released from the first crimped configuration prior to apposing the said annulus, and constrained to a second crimped configuration wherein said second crimped configuration is larger or different than said first crimped configuration to reduce the force required to pull in said annulus region into said concavity. In this example, the second crimped configuration constraint means is different than the first crimped configuration constraint. In another example, the template is released from a first and/or second constraint after anchor pulls in annulus region into said concavity. In yet another example, the template is released from a first and/or second constraint prior to anchor pulling in said annulus region into said concavity. In a further example, the template comprises at least one opening in at least one apex segment connected to said concavity via a leg, wherein an anchor affixes at least one portion of said apex segment to an annulus region adjacent to the apex segment. In a preferred example, the template is held in the first crimped configuration inside a tubular body or at least partially inside a tubular body. In another example, the template is constrained in the second crimped configuration by at least one control wire configured to control at least one said apex segment rotation and/or affixing of said segment to adjacent annulus region, the template being releasably attached to said control wire, and said wire extending through a or the tubular body proximally outside the patient body to allow control of the template configurations at a distance from the template. In a further example, the template is releasably coupled to a delivery catheter and the delivery catheter is removed after anchoring the template to the annulus region. In a further example, the delivery catheter is inserted into the body or vasculature percutaneously, or surgically, or a hybrid procedure. In one example, the template is pre-formed prior to delivery into the annulus region. In another example, the template is formed in situ. In yet another example, the said template having a length along a longitudinal axis and at least one concavity in a lateral direction along said length, and said template has two apex segments each segment connected by a leg to one side of said concavity, wherein each of said apex segment has an anchor configured to affix at least one region of said apex segment to adjacent annulus. In another example, the apex segment comprises one or more of convex region, flat region, and concave region(s). In yet another example, the template comprises a plurality of concavities and a plurality of apex segments, wherein each concavity has an anchor configured to reposition at least one region of an annulus into said concavities, and wherein said template further comprises at least two apex segments wherein at least one of said apex segments has an anchor configured to attach at least one region of the apex segment to the adjacent annulus. In another example, the said template has the advantage of repositioning selective regions of valve annulus. In one example, the template is configured to reposition one region of a valve annulus, wherein the region comprises a posterior annulus region, an anterior annulus region, a septal annulus region, or an anterior posterior region. In one example, annulus regions outside said template remain substantially unchanged. In another example, said template is configured to perform one or more of the following: reposition at least one region of an annulus into said concavity of the template, reduction of the valve annulus circumference, reducing annulus configuration, reducing one or more dimensions of the annulus, reduction of a said annulus region circumference, configuration, area, or one or more dimensions. In another example, the template comprises at least one concavity joined by legs, wherein the legs comprise an apex segment and wherein each apex segment contains an anchor configured to attach at least one region of said segment to the adjacent annulus region, and wherein said concavity containing at least one anchor configured to pull in at least one region of an annulus into said concavity. In a preferred example, the apex segments have a substantially equal but opposite force to said anchor pulling in said annulus into said concavity. In another example, the apex segments are configured to prevent flipping or rotation of said template about its axis. In one example, the template is pre-formed before delivery into a patient body, in another example, the template is formed in situ. In a preferred example, the template comprising at least one concavity containing at least one anchor configured to pull in said adjacent and apposing annulus region into said concavity, wherein said annulus region conforms and/or contours substantially to the shape of said concavity. In another example, the template comprising at least one concavity may have various shapes of concavity, partial concavity, or a lateral space for an anchor to pull into said lateral space adjacent annulus region. In one example, the template is pre-formed into a substantially Omega shape comprising a concavity connected to two apex segments via legs connected to said concavity, and wherein said concavity having at least one anchor configured to pull in an annulus region into said concavity, and wherein the two apex segments each has an anchor configured to connect to adjacent annulus region to the said apex segment, and wherein the template is crimped into first crimped configuration having substantially U shape, wherein said U shaped template is constraint inside a first constraint comprising a tubular catheter and delivered in proximity to a valve annulus, and wherein the U shaped template is at least partially released from the tubular catheter, and wherein the concavity anchor apposes the desired annulus region and engages said annulus region pulling in said region into said concavity, and wherein the apex segments are positioned apposing to annulus regions and affixed to said annulus regions. The concavity anchor and apex segments anchors are controlled and/or constrained by (second constraint or second crimped configuration constraint) one or more wires, tubes, or the like that extend to outside the patient body and are configured to control anchoring of the template to the annulus, adjust the position of the template or template component, and/or to release the template. In one example, the template is pre-formed into a substantially Omega shape comprising a concavity connected to two apex segments via legs connected to said concavity, and wherein said concavity having at least one anchor configured to pull in an annulus region into said concavity, and wherein the two apex segments each has an anchor configured to connect to adjacent annulus region to the said apex segment, and wherein the template is crimped into first crimped configuration, wherein said template is constrained inside a first constraint comprising a tubular catheter and delivered in proximity to a valve annulus, and wherein the template is at least partially released from the tubular catheter, and wherein the concavity anchor apposes the desired annulus region and engages said annulus region pulling in said region into said concavity, and wherein the apex segments are positioned apposing to annulus regions and affixed to said annulus regions. The concavity anchor and apex segments anchors are controlled and/or constrained by (second constraint or second crimped configuration constraint) one or more wires, tubes, or the like that extend to outside the patient body and are configured to control anchoring of the template to the annulus, adjust the position of the template or template component, and/or to release the template. The template maybe crimped into various shapes inside a constraint comprising U shape, helical shape, preformed shape, or other shapes configured to be deliverable into a patient body to an annulus region. In a preferred example, the apex segments are pulled or held in a proximal direction relative to the anchor to facilitate an easier anchoring of the concave anchor to the annulus and then the apex segments are positioned, anchored and released. In this example, the apex anchors enhance or augment the amount (or mass or volume or area) annulus region pulled into said concavity. In another example, the template concavity anchor engages the annulus pulling said annulus region into said concavity, while the apex segments are apposing an annulus regions, and then said apex segments apposing said annulus regions are affixed to said annulus region.

In one example, a system to reshape a valve annulus comprising advancing an anchor which is releasably attached to an elongate control wire through a tubular body and attaching that anchor to an annulus region, placing a template having a preformed shape having a concavity (such as a template comprising a concavity and two apex segments connected to said concavity via legs forming a substantially Omega shape template) in a crimped (smaller) configuration into a constraint catheter, sliding the template concavity over the control wire and coupling the template concavity to the anchor. In a further example, said template further has at least one apex segment and has at least one additional anchor coupling the at least one apex segment to an adjacent annulus region. In a further example, the template is releasably coupled to a delivery catheter and the delivery catheter is removed after anchoring the template to the annulus. In another example, the delivery catheter is inserted into the body or vasculature percutaneously.

In another example, a one or more segments of the template is coupled to an anchor to prevent translation along the axis of the anchor. In a further example, the one or more segments of the template is coupled to an anchor allowing the anchor to rotate about its axis relative to the template. In a further example, the anchor is coupled to the template in the region of a concavity.

In one example, an implant having a preformed template wherein the template comprises at least one concavity and at least one connected apex segment wherein the at least one apex segment has at least one tissue anchor to affix the template to adjacent annulus, and at least one anchor is releasably attached to at least one elongate anchor control device extending from the implant to outside the delivery catheter of the implant. In a further example, the anchor control device is a tube with cut features to control flexibility. In a further example, the anchor control device is a tube with a key wire in the lumen configured to releasably engage the anchor. In a further example pulling the key wire releases the anchor from the anchor control device.

In a preferred example, the template has at least one concave base and at least two apexes. In a further example, the width of the concave base is equal to the depth of the concavity. In a further example, the width of the concave base is greater than the depth of the concavity. In a further example, the width of the concavity is at least 1.5 times the depth of the concavity. In a further example, the width of the concavity is at least 2.5 times the depth of the concavity. In a further example, the width of the concavity ranges from 1× to 5× the depth of the concavity. In another example, the apex of the template has a flat or convex portion to it. In a preferred example, the template has a concave segment and two apexes, where the apexes have flat and/or convex segments. In a further example, the flat and/or convex segments of the apexes range from 2-40 mm long. In a further example, the flat and/or convex segments remain apposed to and/or affixed to the tissue. In another example, the implant has an apex segment comprising a length sufficient to inhibit tilting of the implant relative to the target tissue.

In a preferred example, the template flexes in at least one direction during contraction of target tissue. In a further example, the template flexes to allow a change in distance between ends of the template as tissue flexes under one or more of the following physiologic conditions: heartbeat, annulus contraction, blood pressure changes, atrial expansion, ventricular expansion, blood flow, etc. In another example, the maximum dimension of the template in situ changes in response to tissue motion and physiologic forces.

In one example, the implant template has at least one concave base and at least one apex connected to the concave base, wherein the apex and concave base are configured to be deformable and formed from one or more of the following materials: elastic, superelastic, shape memory, hard tempered, heat treated. Examples of said materials include one or more of the following: Nitinol, stainless steel, maraging steel, cobalt chromium, or the like.

In another example, the implant template has at least one concave segment and at least one apex segment wherein the at least one apex segment is apposed and/or affixed to the annulus. In a further example, the implant has two or more concave segments separated by one or more apex segments, the concave segments being apposed and affixed to the annulus while one or more apex segments are apposed and/or affixed to the annulus. In another example, said implant has at least one apex on each end of the implant, wherein said apexes are apposed and/or affixed to the annulus. In a further example, the implant has at least one concave segment and at least one apex segment wherein the at least one apex segment is apposed and affixed to the tissue to inhibit tilting and/or rotation of the implant relative to the annulus or tissue.

In a preferred example, the implant template is deployable from a crimped smaller configuration, to a larger or deployed configuration. In a further example, the crimped smaller configuration is smaller in at least one dimension than the deployed configuration. In a preferred example, the crimped smaller configuration passes through a smaller diameter tube than the larger or deployed configuration. In one example, in the crimped configuration, the ends of the implant are folded distally from the middle of the implant. In another example, in the crimped configuration, the ends of the implant are folded proximally from the middle of the implant. In a further example, in the crimped configuration, the ends of the implant are compressed toward the middle of the implant. In a further example, in the crimped configuration, the ends of the implant are compressed toward the middle of the implant and folded out of plane to form a substantially tubular shape.

In a preferred example, the implant template having a preformed shape is deployable from a crimped smaller configuration, to a larger or deployed configuration. In another example, the deployed configuration is the unconstrained shape of the implant. In a further example, the crimped configuration is elastically deformed from the preformed shape. In another example, the implant is held in the crimped configuration until delivered adjacent to the annulus and/or tissue. In another configuration the implant is held in the crimped configuration by being at least partially inserted into a tubular body. In another example, the implant is deployed from the crimped shape to the deployed configuration by disengaging it from the tubular body, allowing it to return substantially to its preformed shape.

In one example, the implant template comprises a preformed template configuration wherein the template comprises at least one concavity and at least one apex connected to said concavity, and a tissue anchor from the concavity and extending beyond the apex of the template in the preformed template configuration. In another example, the length of the anchor extends at least half way from the base of the concavity to the apex. In a further embodiment, the length of the anchor is greater than the depth from the base of the concavity to the apex such that as implant is in proximity to the tissue the anchor contacts tissue in advance of the apex of the template.

In another example, an implant template has a crimped configuration and a deployed configuration, where the implant is delivered in the crimped configuration adjacent to the annulus and/or tissue, and then deployed by forming it in situ to the desired template shape. In another example, an implant having a delivery configuration and a deployed configuration, where the implant is in the delivery configuration is delivered adjacent to the annulus and/or tissue, and then deployed by forming it in situ to the desired template shape.

In one example, an implant having a preformed template wherein the template comprises at least one concavity and at least one apex segment, wherein the apex and concavity are connected, defining the implant depth, and wherein the at least one apex segment has tissue engaging element to affix the template to adjacent annulus, and wherein the concavity comprises an opening to slidably engage a tissue engaging anchor element and lock to the tissue engaging anchor element. In another example, the implant system comprises a template having at least one concavity and at least one apex, and having a passage through which a tissue engaging anchor is slidably coupled.

In one example, an implant having a preformed template wherein the template comprises at least one concavity and at least one apex segment, wherein the apex and concavity are connected, and the radius of curvature of the apex segment is greater than the radius of curvature of the concavity, wherein the apex segment in one example comprises a radius of curvature of at least 1.5 times the radius of curvature of the convex segment, wherein the apex segment in one example comprises a radius of curvature of at least 2.5 times the radius of curvature of the convex segment, wherein the apex segment in one example comprises a radius of curvature ranging from 1× to 5× the radius of curvature of the convex segment.

In one example, an implant having a preformed template wherein the template comprises at least one concavity and at least one apex segment, wherein the apex and concavity are connected by legs, and the shape of the concavity and apex segments are configured to contact the tissue along substantially the entire inner surface of the implant when said tissue is pulled into said template.

In one example, an implant having a preformed template wherein the template comprises at least one concavity and at least one apex segment, wherein the apex and concavity are connected, the concavity having a substantially rounded shape to receive and be coupled substantially along the length of the implant to the tissue and/or annulus when the implant is deployed in the tissue and/or annulus.

In another example, an implant having a preformed template wherein the template comprises at least one concavity and at least one apex segment, wherein the apex and concavity are connected, and wherein the apex and concavity having substantially rounded shapes to receive and be coupled substantially along the length of the implant to the tissue and/or annulus when the implant is deployed in the tissue and/or annulus.

In a preferred example, an implant having a template with one or more concavities connected to one or more apex regions by one or more legs, wherein the one or more concavities have annulus pulling anchors configured to pull inward said annulus region into said concavities, and wherein said one or more apex regions have one or more regions positioned against the annulus region to exert a radially outward force on the annulus, substantially opposing the inward pull force of the one or more concavities annulus pulling anchors. In a preferred example, the outward forces exerted by the apex segments do not reposition the annulus, or do not substantially reposition the annulus, outwardly. In another example, the template concavity repositions an annulus region into said concavity, wherein the circumference of the annulus remains substantially the same.

In another example, an implant having a preformed template wherein the template comprises at least one concavity and at least one apex segment, wherein the apex and concavity are connected, and a tissue engaging anchor configured to draw at least a portion of a peripheral wall of a valve annulus at least partially into the concavity so that a peripheral length of the valve annulus can be foreshortened and/or reshaped to improve coapting of the valve leaflets and/or to eliminate or decrease regurgitation of a valve.

In still another aspect of the present invention, a stent prosthesis for valve repair or replacement comprises a scaffold having patterned structural elements, said stent being expandable from a crimped configuration to an expanded configuration and having sufficient strength to support a body annulus in the expanded configurations, wherein the scaffold comprises at least one circumferential ring comprising struts and crowns, wherein at least one strut in said at least one ring comprises at least one separation region and wherein said at least one separation region comprises a male-female junction and a biodegradable polymer and/or adhesive, said separation region being held together in the crimped configuration and is configured to separate after expansion of the stent under physiologic environment, and at least one valve configured to be coupled to said at least one ring, said valve allowing blood to flow in one direction during the cardiac cycle.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative examples, in which the principles of the invention are utilized, and the accompanying drawings of which:

FIG. 111 shows an undulating template with tissue held in place by a tissue coupling mechanism, causing the template to exert forces in a tensile manner normal to the original position of the tissue (via the tissue coupling mechanism) and in a combined inward compressive manner, directed between normal and tangential directions to the original position of the tissue.

FIG. 112 shows an undulating template with tissue held in place by a tissue coupling mechanism, causing the template to exert forces in a tensile manner normal to the original position of the tissue (via the tissue coupling mechanism) and in a combined inward compressive manner, directed between normal and tangential directions to the original position of the tissue.

FIG. 113 shows an undulating template with stabilizing tissue coupling mechanisms at each end, in addition to the primary tissue coupling mechanism in the middle. Also shown are removable devices for placing and manipulating the tissue coupling mechanisms.

FIG. 114 shows and undulating template with an additional stabilizing arm extending from the body, as well as stabilizing penetrating points.

FIG. 115 shows an undulating template with the ends folded away from the attachment point of the tissue coupling mechanism to a delivery position, where the tissue coupling mechanism attachment allows the template to fold alongside the tissue coupling mechanism.

FIG. 116 shows an undulating template in position adjacent to a mitral annulus in the untreated state.

FIG. 117 shows an undulating template with a mitral annulus, where the tissue coupling mechanism has drawn the annulus tightly against the template. The original position of the annulus from FIG. 116 is also shown.

FIG. 118 illustrates a delivery device for placing an undulating template over a pre-anchor guide. The pre-anchor guide runs through a receiving slot in the delivery device.

FIG. 119 shows percent area change for various templates implanted in-vivo.

FIG. 120 shows percent circumference change for various templates implanted in-vivo.

FIG. 121 shows percent minor axis change for various templates implanted in-vivo.

FIG. 122 shows percent A-P (minor axis) reduction for various multi-wave templates implanted in excised porcine mitral annuli.

Figure 123:
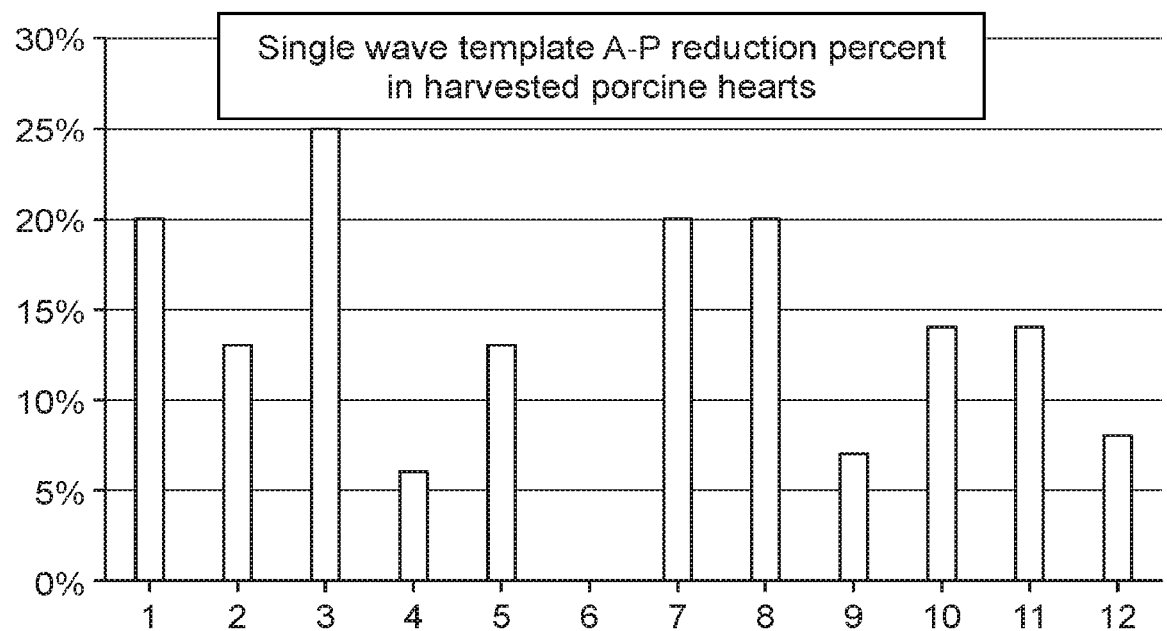

FIG. 123 shows percent A-P (minor axis) reduction for various single-wave templates implanted in excised porcine mitral annuli.

Figure 124:
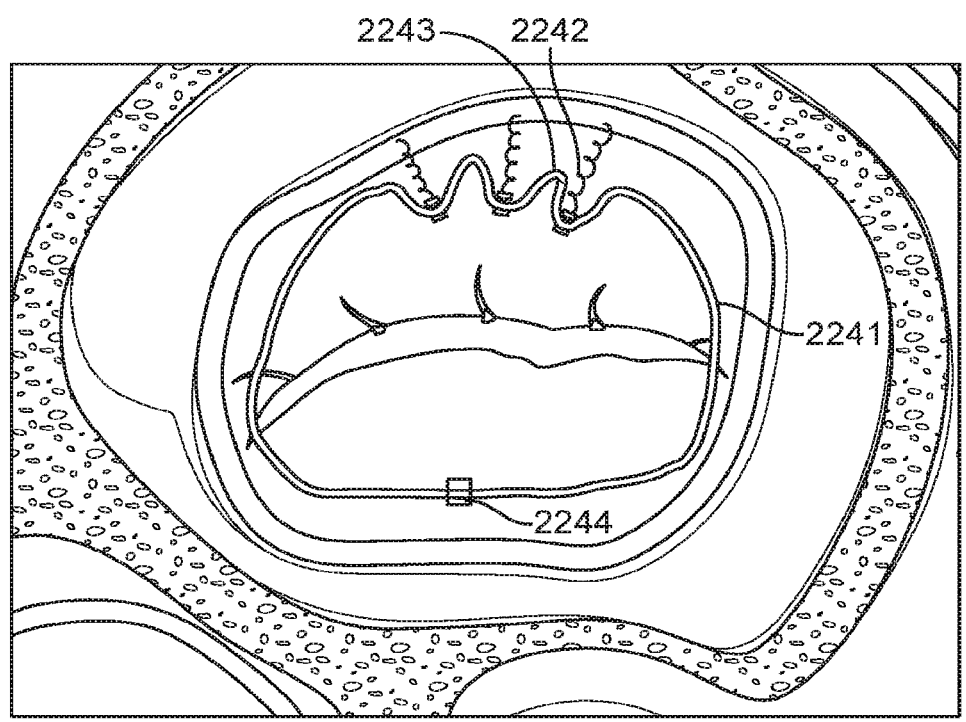

FIG. 124 shows a continuous template with one area of undulations.

Figure 125:
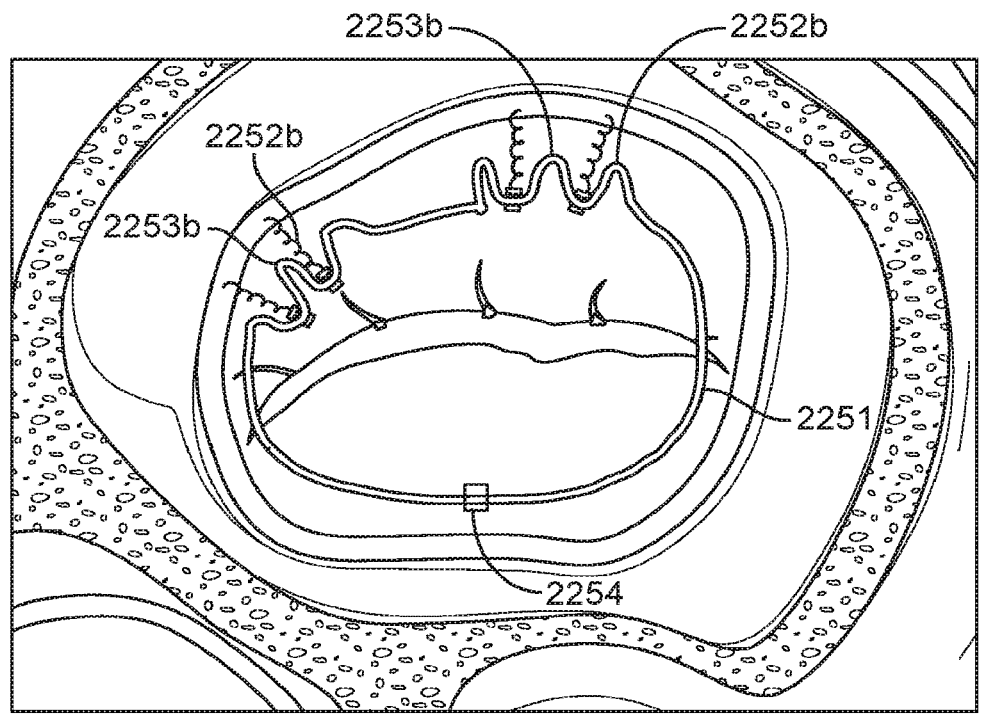

FIG. 125 shows a continuous template with two areas of undulations.

Figure 126:
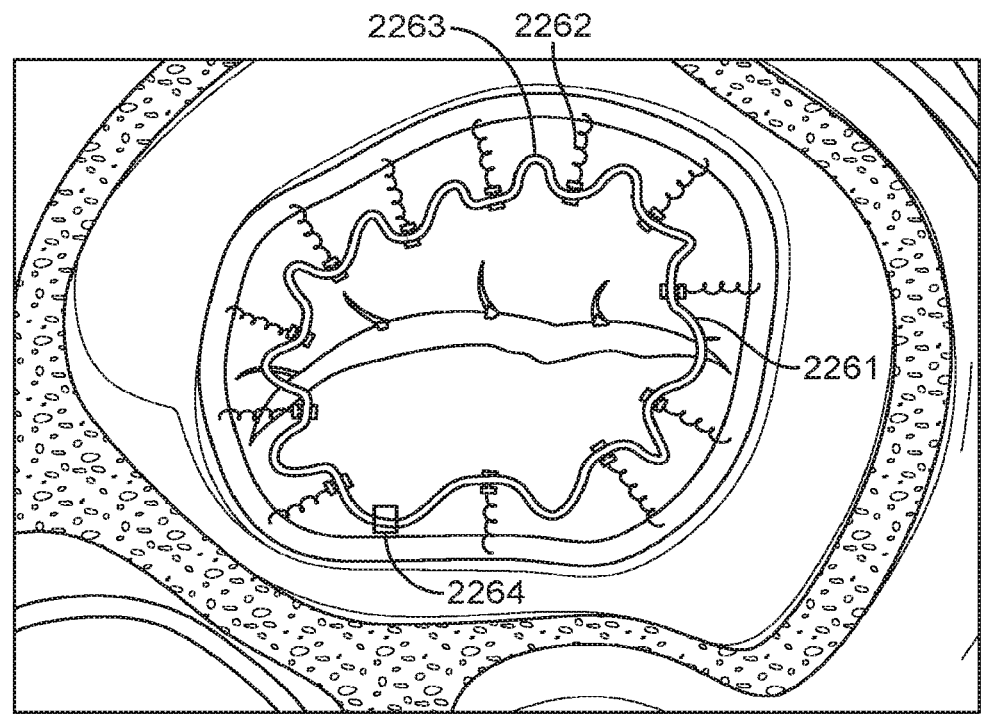

FIG. 126 shows a continuous template with undulations on the entire circumference.

Figure 127:
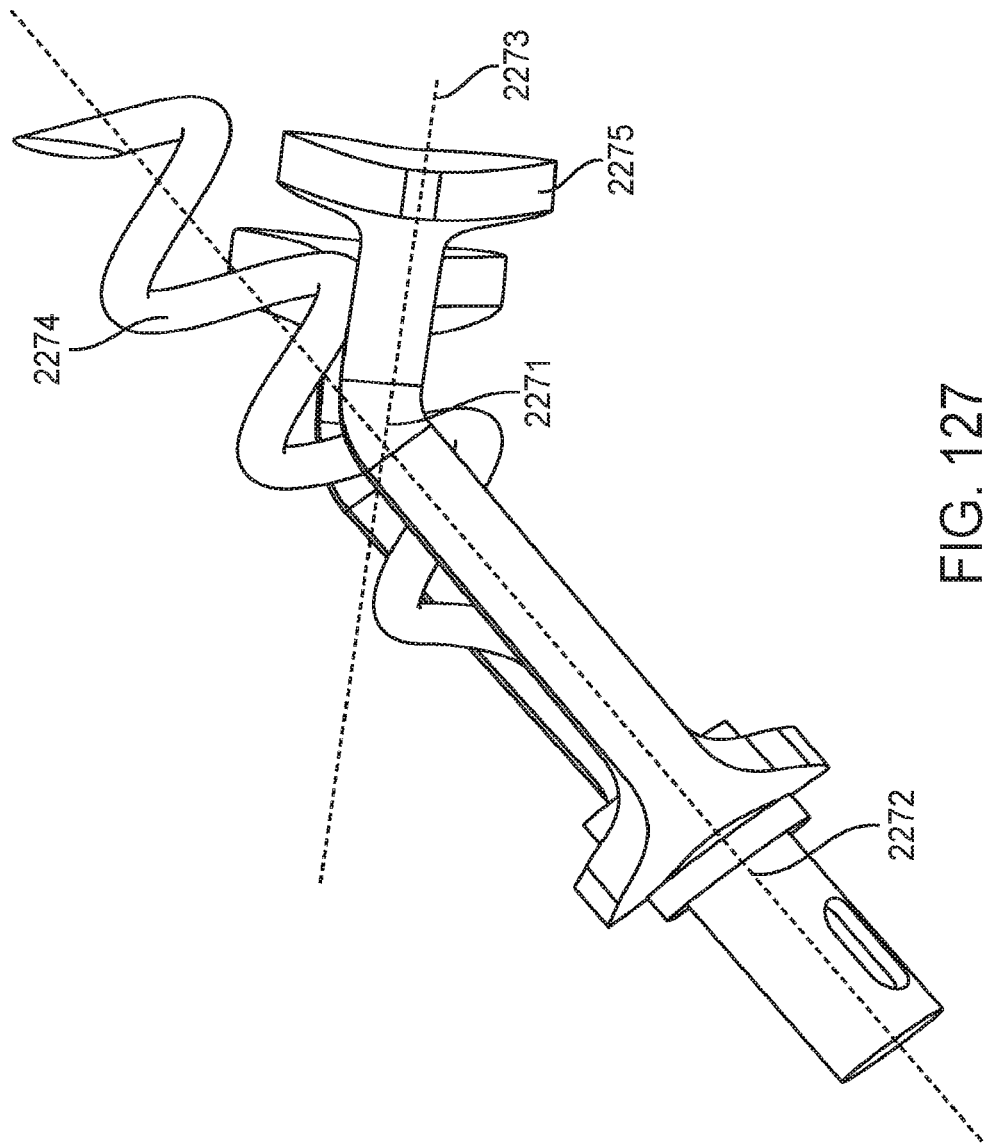

FIG. 127 shows a template where the compression points form an angle with an anchor point.

Figure 128:
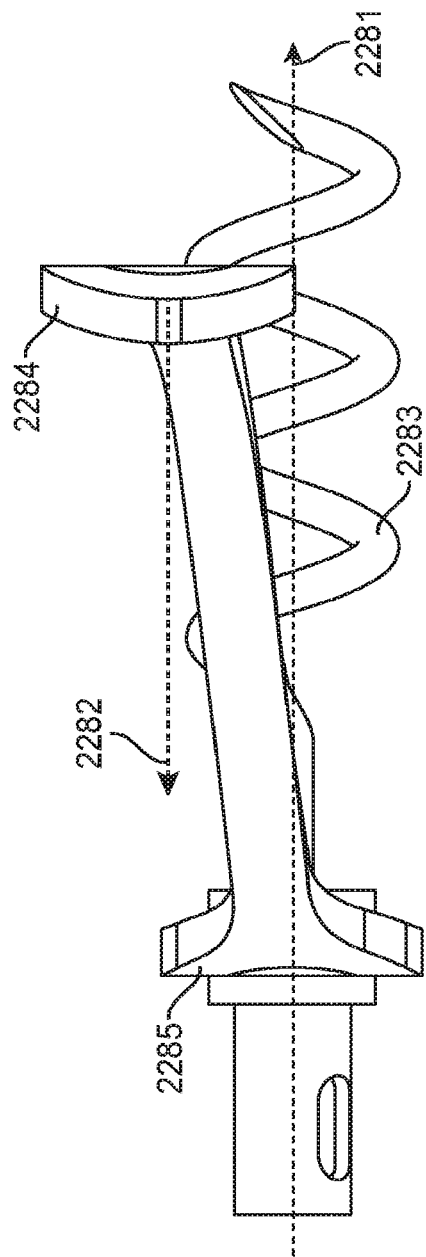
Figure 129:
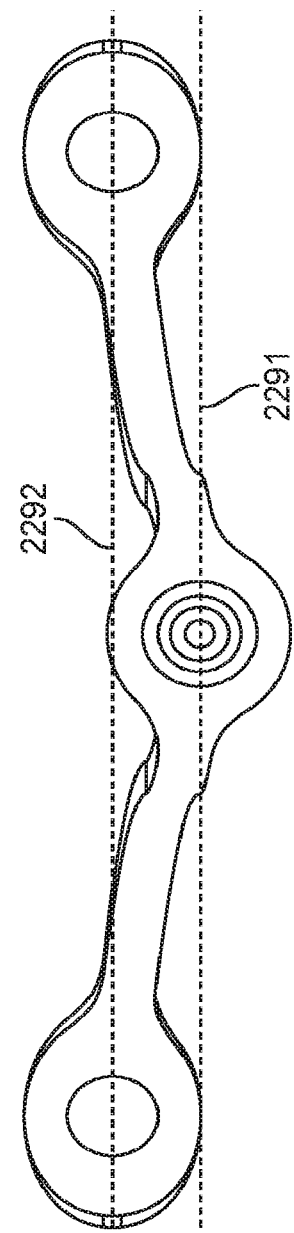
Figure 130A:
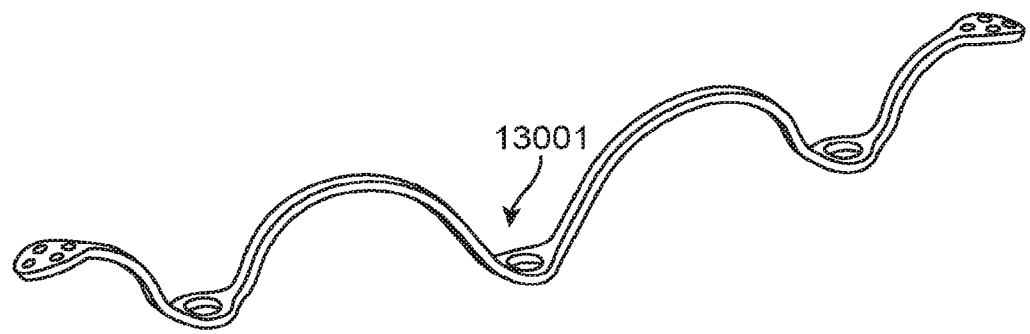

FIG. 128 shows a side view of a template where the compression points are offset to a different plane than the anchor point FIG. 129 shows a top view of a template where the compression points are offset to a different plane than the anchor point FIG. 130A shows a template in the preformed shape.

Figure 130B:
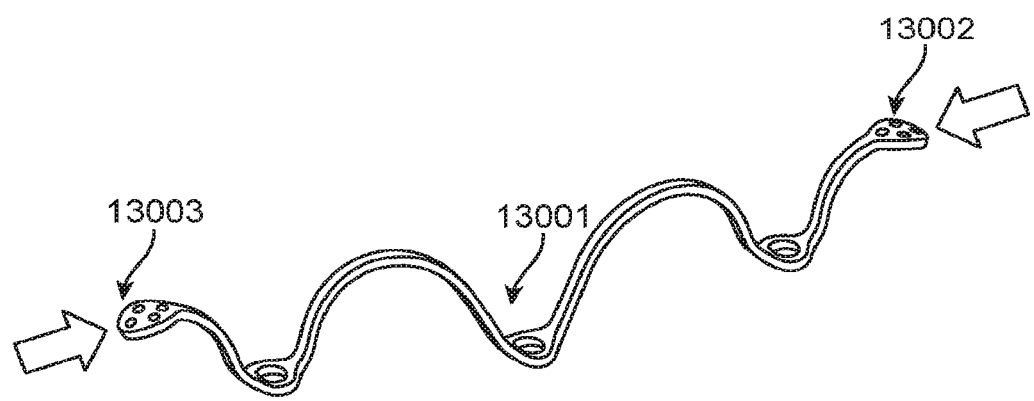

FIG. 130B shows a template in a crimped or partially crimped configuration with both ends pressed toward the center.

Figure 130C:
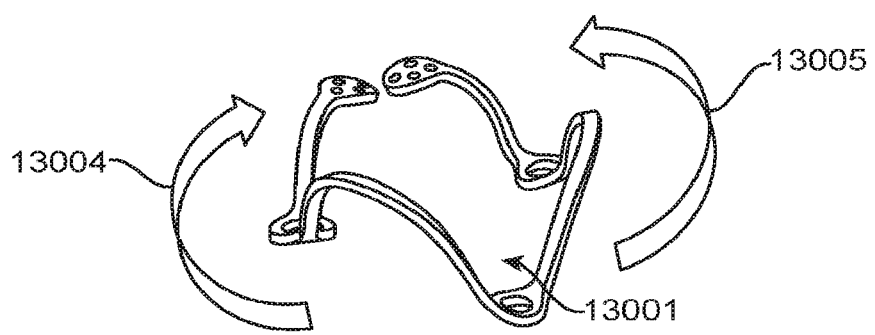

FIG. 130C shows a template in a crimped or partially crimped configuration with both ends rotated towards each other to a substantially circular shape.

Figure 131A:
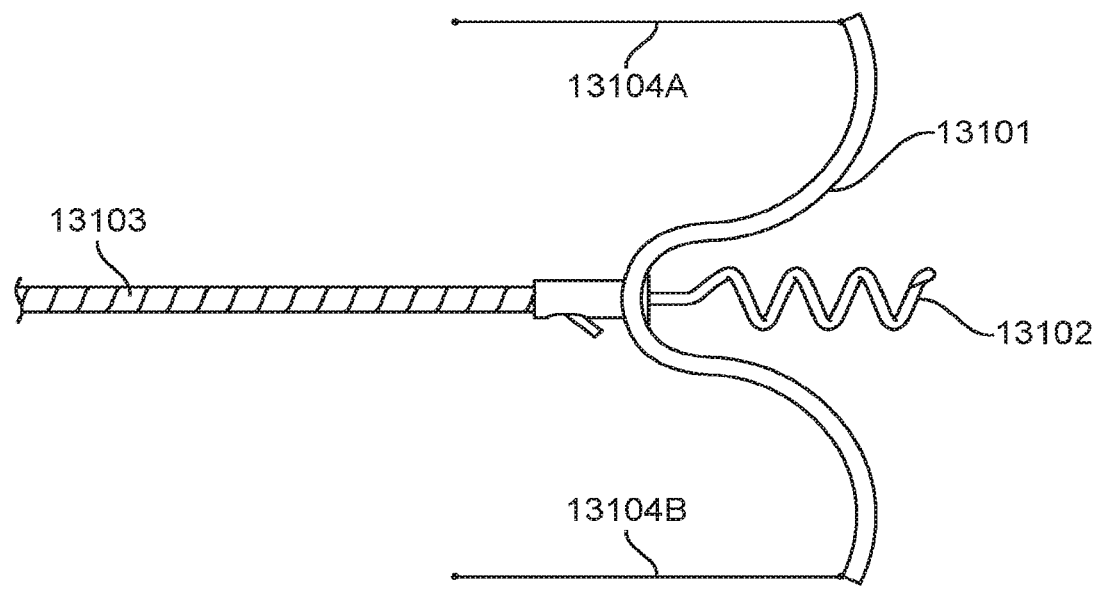
Figure 131B:
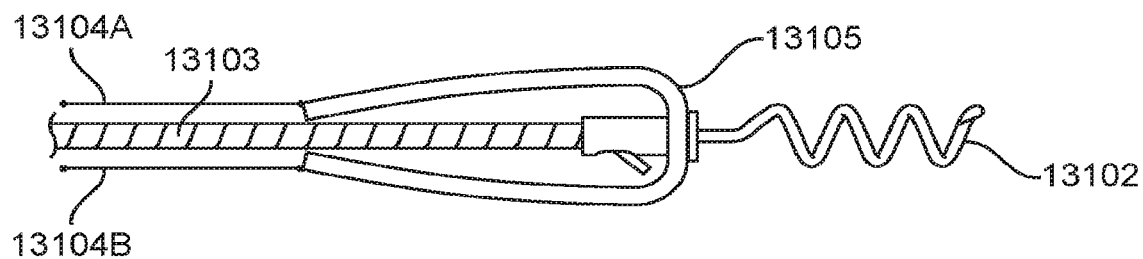

FIG. 131A shows a template with anchor, the template being in the preformed shape FIG. 131B shows a template with anchor, the template being constrained in a crimped state with the ends or wings of the template pulled proximally relative to the anchor.

Figure 132:
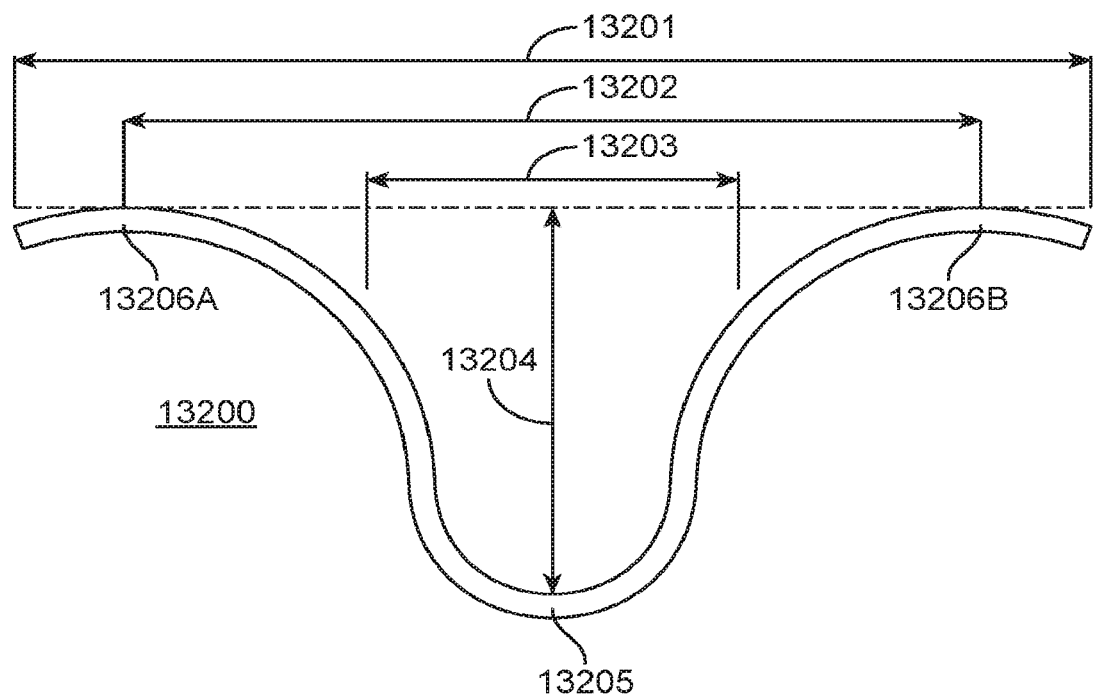

FIG. 132 shows a template, illustrating distance between ends, distance between apexes, width of concavity, and depth of concavity.

Figure 133A:
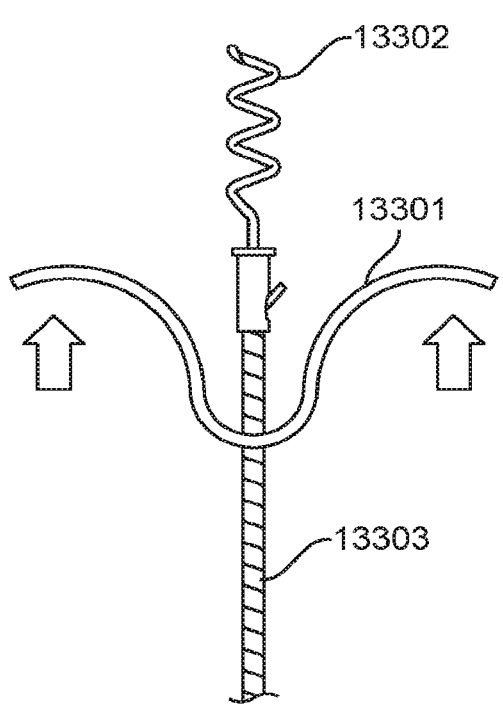
Figure 133B:
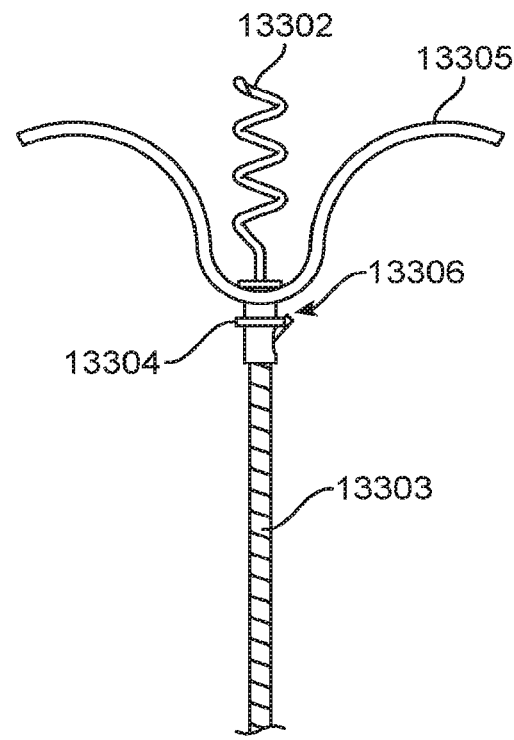

FIG. 133A shows a template slidably coupled to an anchor control device, in position to move toward the anchor FIG. 133B shows the template, anchor, and anchor control device of FIG. 133A, with the template coupled to the anchor by a template coupling mechanism.

DETAILED DESCRIPTION OF THE INVENTION

The phrase "valve annulus" as used herein and in the claims means a ring-like tissue structure surrounding the opening at base of a heart valve that supports the valve's leaflets. For example, the annulus of the mitral valve, the tricuspid valve, the aortic valve, the pulmonary valve, venous valves and other annuluses of valves in the body. In the mitral valve, the annulus typically is a saddle-shaped structure that supports the leaflets of the mitral valve.

The phrase "peripheral wall" as used herein and in the claims as applied to a valve annulus means a surface or portion of the tissue of the valve annulus, and/or a portion of the tissue adjacent to the valve annulus.

"Concavity" as used herein and in the claims means a depression or well formed in a surface of the template. The concavity may comprise flat regions joined at angles, e.g. being rectilinear, but will more typically have a curved bottom portion joining a pair of generally straight and/or curved walls or legs. The curved bottom portion will typically span an arc of at least 45°, often at least 60°, usually at least 90°, typically at least 135°, and sometimes spanning a full 180°, with exemplary ranges from 45° to 180°, from 60° to 180°, from 60° to 135°, and from 90° to 135°. The concavities of the present invention will typically be symmetric having opposed walls or legs on each side of a central axis. In other cases, however, a concavity may be asymmetric with walls or legs on each side having unequal lengths and, in some cases, having only a single wall. Examples of concavities include the inner surface of a circle or sphere or other.

"Convexity" as used herein and in the claims means a curved surface on the template like an exterior of a circle, parabola, ellipse, or the like. A convexity will typically be formed on a surface of the template on the side opposite to that of a concavity, and vice versa. Examples of convexities include the outer surface of a circle or sphere or other.

As used herein and in the claims, an "implant" means an article or device that is introduced into and left in place in a patient's body by surgical methods, including open surgery, intravascular surgical methods, percutaneous surgical methods, and least invasive or other methods. For example, aortic valve replacement implant, coronary stent implant, or other types of implants.

Figure 1:
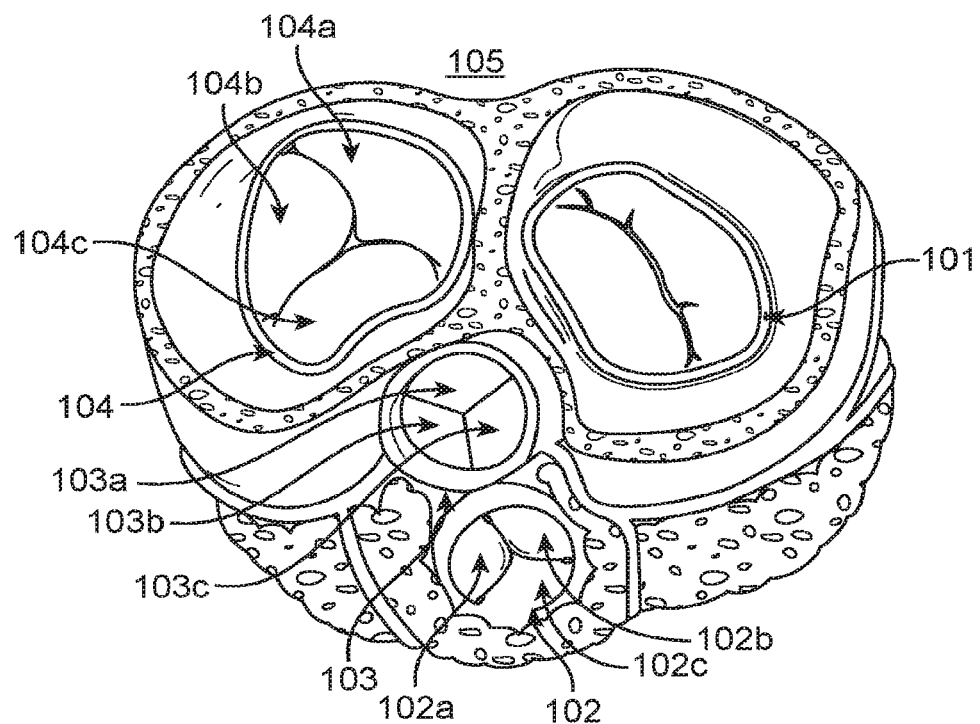
FIG. 1 shows a top down sectional view of the heart, illustrating the relative positions of the major valves of the heart.

As shown in FIG. 1, the heart 105, contains four major valves: the mitral or bicuspid valve 101, the pulmonary valve 102 with the Right Cusp 102a, Left Cusp 102b, and Anterior Cusp 102c, the aortic valve 103 with the Non-Coronary Cusp 103a, the Right Coronary Cusp 103b, and the Left Coronary Cusp 130c, and the tricuspid valve 104 with the Posterior leaflet 104a, the Anterior Leaflet 104b, and the Septal Leaflet 104c. Each valve has three leaflets, except for the mitral valve which has two.

Figure 2:
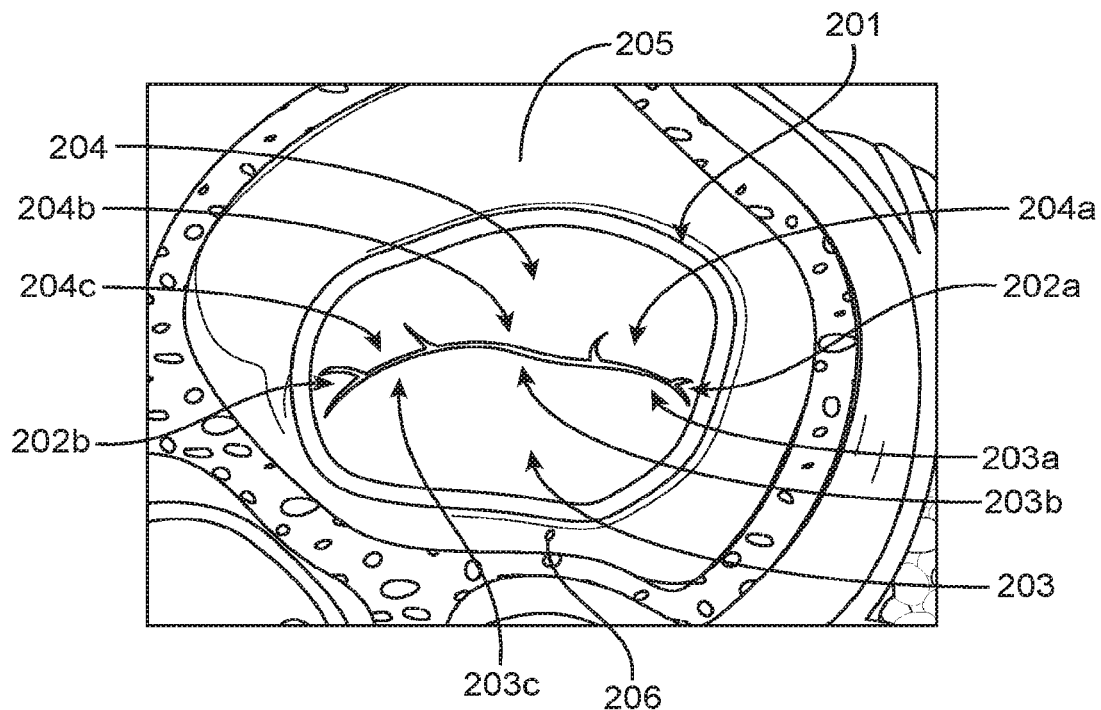
FIG. 2 shows a top view of the mitral valve in a closed configuration as visible from the left atrium.

As shown in FIG. 2, the mitral valve 101 comprises a mitral valve annulus 201, and has an anterior leaflet 203 with a first scallop (A1) 203a, a second scallop (A2) 203b, and a third scallop (A3) 203c, and a posterior leaflet 204 with a first scallop (P1) 204a, a second scallop (P2) 204b, and a third scallop (P3) 204c, which join at commissures 202a and 202b. Referring to FIG. 2, the septal aspect of the valve 206 is at the bottom of the figure, and the lateral aspect of the valve 205 is at the top.

Figure 3:
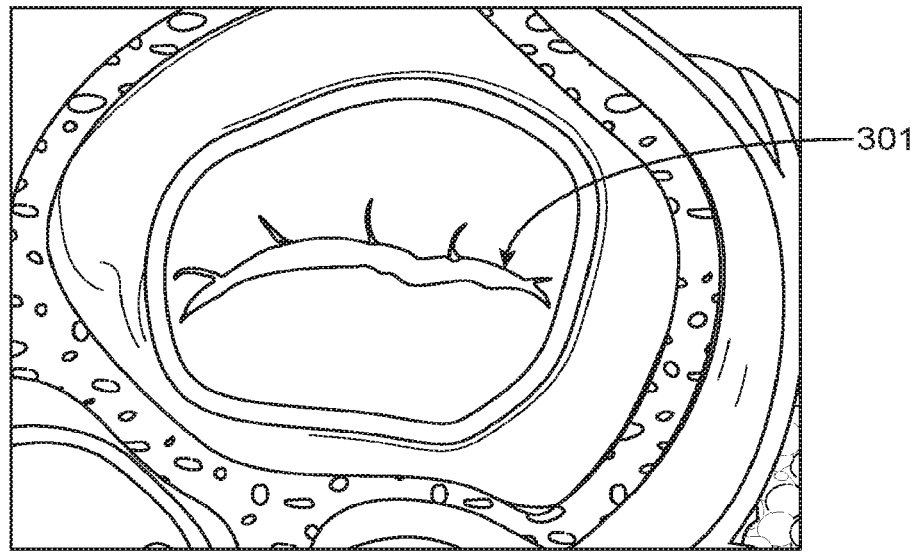
FIG. 3 shows a top view of the mitral valve having a gap between mitral valve leaflets preventing it from attaining a closed configuration thus causing Mitral Regurgitation (MR) or Functional Mitral Regurgitation (FMR). The valve typically has an enlarged annulus configuration.

As shown in FIG. 3, the mitral valve 101 can enlarge, leaving a gap between the anterior 203 and posterior 204 leaflets. This gap prevents the valve from closing, allowing blood to return from the left ventricle to the left atrium, a condition referred to as MR or Functional Mitral Regurgitation, or FMR.

Figure 4:
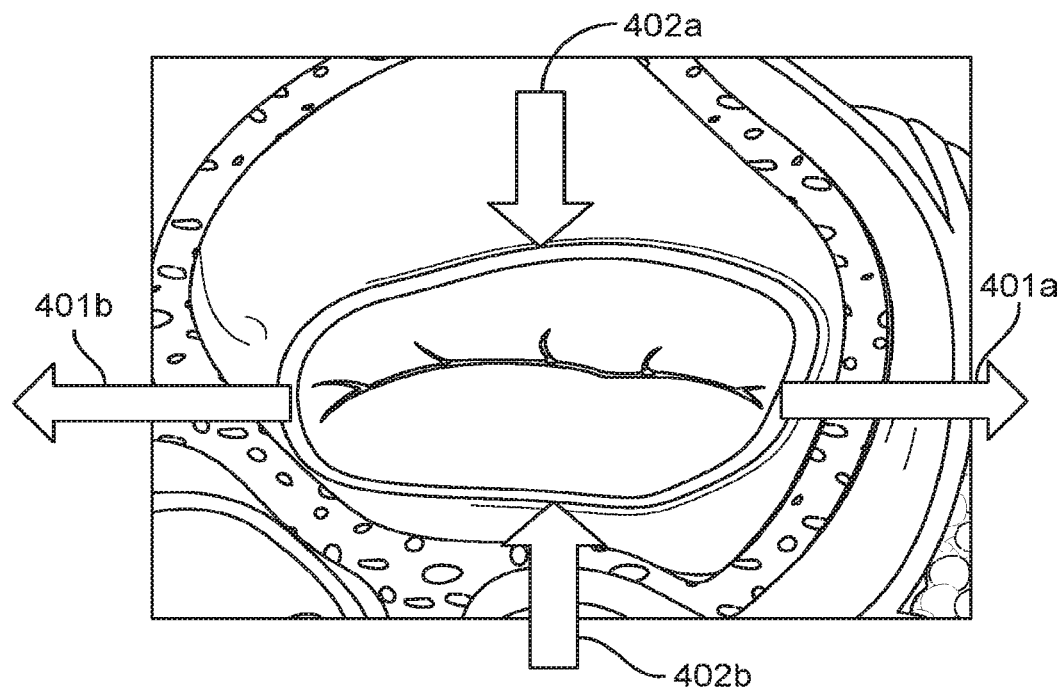
FIG. 4 shows the valve of FIG. 3 stretched (extended) in accordance with the present invention (device not shown), in this example stretched in the Commissure to Commissure (C-C) dimension as shown, causing the gap between the leaflets to close as shown, thus reducing or eliminating MR or FMR. In this example, the annulus configuration changes wherein the annulus dimension becomes larger across the stretched dimension and becomes smaller across a perpendicular or offset dimension to the stretched dimension.

As shown in FIG. 4, one object of this invention is to change the configuration of the valve to minimize or reduce MR. In this example, decreasing one dimension of a heart valve by increasing another using a stretching device (or implant). Referring to FIG. 4, the septal-lateral dimension of the mitral valve 402 a-b is decreased reducing the gap between the anterior and posterior valve leaflets by increasing the distance between the commissures, moving them in the approximate directions of arrows 401*a* and 401*b*. A decrease in the gap between the anterior and posterior leaflets may also be achieved by stretching locations adjacent to the annulus but not necessarily adjacent to the commissures, at an offset angle to the septal-lateral direction of the valve and stretching sufficiently to achieve the desired valve configuration and/or gap dimensions in the lateral septal-lateral direction.

Figure 5A:
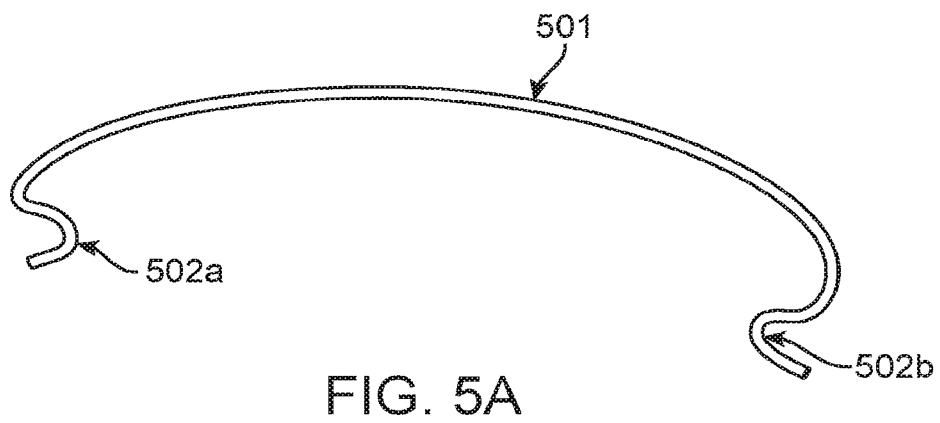
FIG. 5A shows an example of a device in accordance of the present invention, having an arch shaped device which interacts (engages) with the valve commissures to affect the stretching illustrated in FIG. 4.

As shown in FIG. 5A, one example of a device to accomplish the valve stretching (or reshaping) in accordance with this invention is an arch 501 of resilient material such as stainless steel, shape memory alloys such as nitinol, or spring material, with anchoring elements 502*a* and 502*b* to interact with or engage the commissures of the valve and stretch them. The material of the arch 501 may be super-elastic or shape memory material, in one example nitinol, hardened metal material, in one example hardened stainless steel, or a deformable metal which can be shaped and adjusted during deployment, in one example annealed cobalt chromium, or a composite material designed to achieve the required structural properties.

Figure 5B:
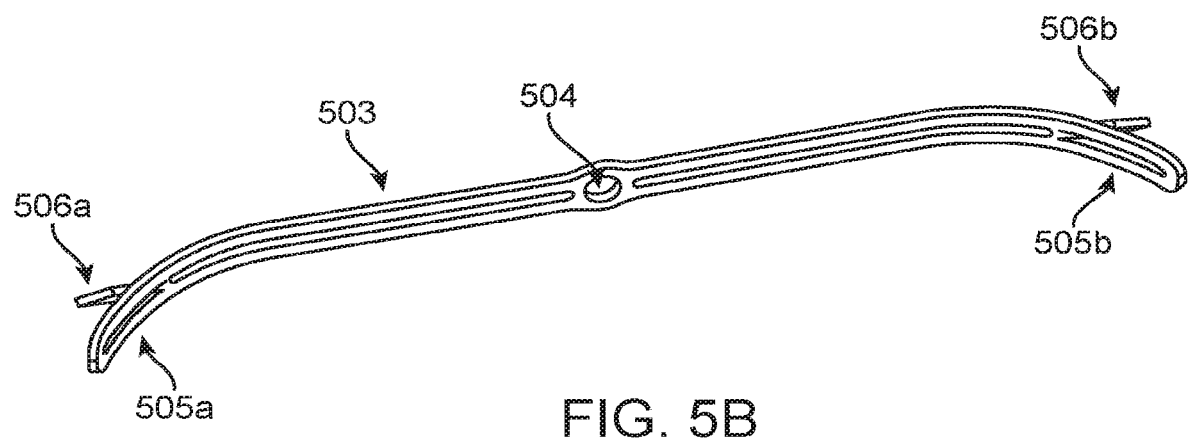
FIG. 5B shows an example of a device in accordance of the present invention, having a partial ring-shaped device which interacts (engages) with the valve annulus at multiple points to affect the stretching illustrated in FIG. 4.

As shown in FIG. 5B, a further example of a device to accomplish the valve stretching (or reshaping) in accordance with this invention is a partial ring 503 of resilient material such as stainless steel, shape memory alloys such as nitinol, or spring material, with an anchoring feature 504 and ends with barbs 505*a* and 505*b* to interact with or engage the valve annulus. The material of the partial ring 503 may be super-elastic or shape memory material, in one example nitinol, hardened metal material, in one example hardened stainless steel, or a deformable metal which can be shaped and adjusted during deployment, in one example annealed cobalt chromium, or a composite material designed to achieve the required structural properties. The anchoring feature 504 and ends with barbs 505*a* and 505*b* may apply opposing loads to the annulus, in one example pushing the ends with barbs 505*a* and 505*b* outward while pulling the anchoring feature 504 inward.

Figure 6:
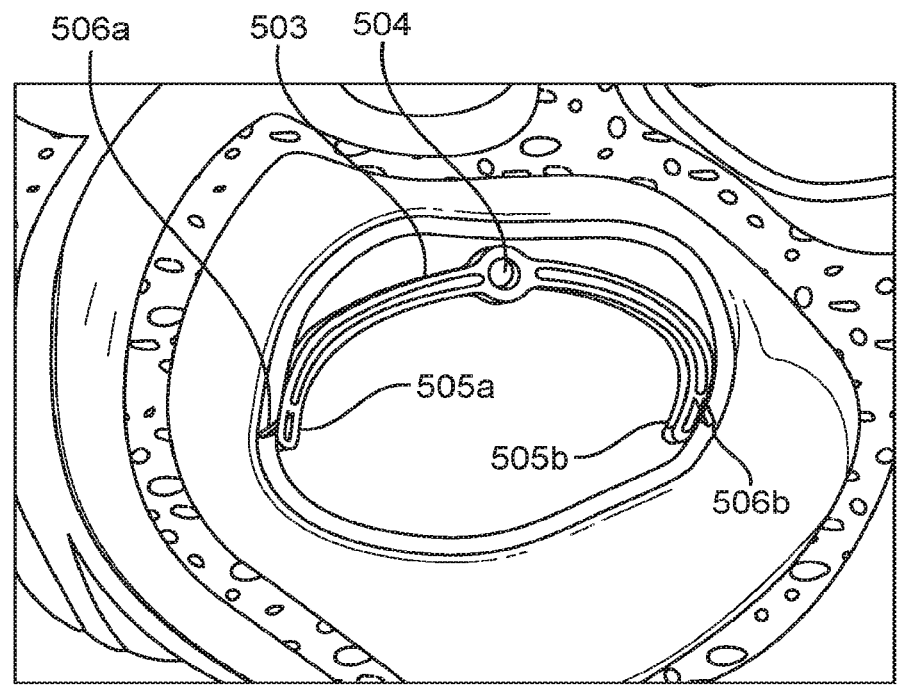
FIG. 6 shows an example of the arch shaped device of FIG. 5 in place in the mitral valve. In this example, the arch of the device contacts the valve posterior annulus and substantially contours to the posterior shape of the valve annulus.

FIG. 6 shows the partial ring 503 in place in the mitral valve 101. During delivery, a flexible tension member (not shown) may be employed to hold the anchor points at a separation distance that will allow easy placement relative to the valve annulus in its native state. Releasing the flexible tension member will allow the stretching member to move the anchor points farther apart, affecting the desired change in the valve annulus such as reducing a gap between the anterior and posterior leaflets of the valve. The device may be configured to have a partial ring 503 substantially contouring to annulus of the valve or have a different shape configuration (not shown). The device partial ring 503 may be in contact with annulus of the valve or other valve components, or maybe coupled to the annulus or other valve components through one or more fixing elements (not shown) along the length of the device in one or more locations. In one example, the fixing element (not shown) would couple to the partial ring 503 through the anchoring feature 504. Alternatively, the device partial ring 503 may be coupled to one or more locations in the atrium, above the valve, or coupled to locations in the ventricle, below the valve, along the length of the device partial ring 503 in one or more locations. The device may be a permanent implant, wherein the device is left in the body. The device maybe a removable device after stretching the valve in one or more dimensions and reduce the valve in other one or more dimensions, coupling (holding together) the stretched portion of the valve using clips, sutures or the like, and removing the stretching device after achieving minimal to no gap between the anterior and posterior leaflets. The implant may also be configured to stretch the valve in one or more directions for a period of time ranging from 1 month to 1 year, preferably ranging from 3 months to 6 months, and then is configured to have diminished or reduced stretching force. Typically, such implant is utilized when the annulus or heart remodels to the new valve configuration and continued stretching may not be needed. The material may be configured to fatigue over time, configured to have one or more separation regions forming one or more discontinuities in the implant along 503, 505*a*, or 505*b* path of the implant, or other means. The device may have a variety of shapes such as round, half circle, square, rectangle, elliptical, or other shapes. The cross-sectional area of the device ranges from 0.003 inches to 0.07 inches. The device may have constant or variable thickness, width, or dimensions along its length or at the anchoring elements 505*a* and 505*b*. The device may have a variety of shapes or geometries to stretch the valve (annulus) across a direction while reducing the valve (annulus) dimensions across a different direction, typically across a perpendicular direction to the stretching direction, but can also be at other offset angles to the stretching direction. The device maybe a single element having a straight, arched, zig-zag, serpentine, or other structure.

Figure 7:
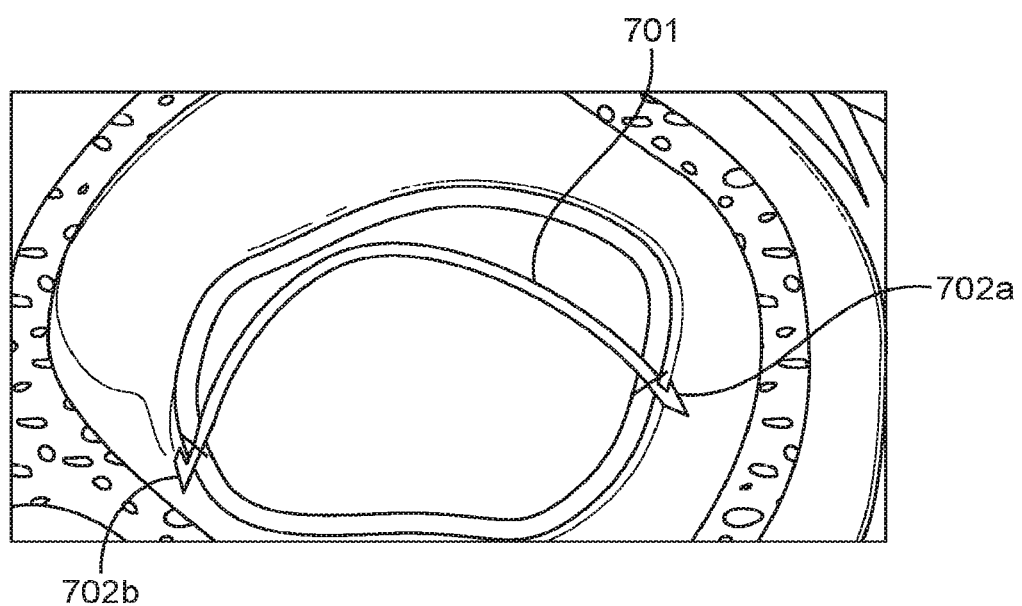
FIG. 7 shows an example of an arch shaped stretching device secured by barbed penetrating ends

FIG. 7 shows an alternative example of the present invention, where the arch 701 is attached to the mitral annulus 201 by penetrating barbed points 702*a* and 702*b*.

Figure 8:
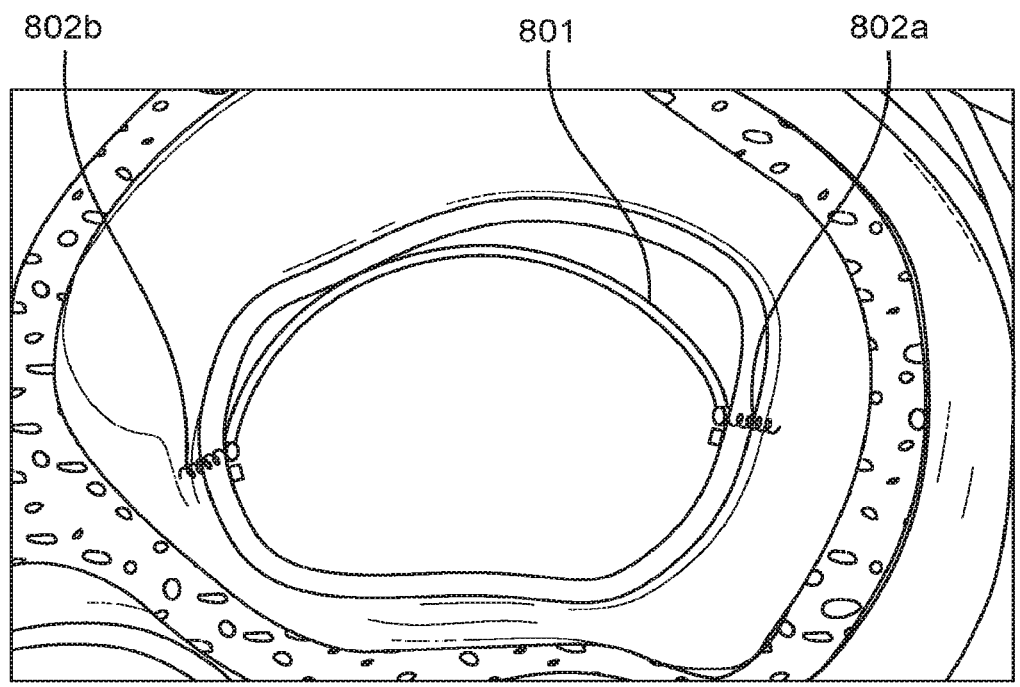
FIG. 8 shows and example of an arch shaped stretching device secured by helical fasteners at the ends.

FIG. 8 shows another alternative example of the present invention, where the arch 801 is attached to the mitral annulus 201 by spiral anchors 802*a* and 802*b*. The spiral anchors 802*a* and 802*b* may be constructed of the same material as arch 801, or a different material. In one example, it may be advantageous for the spiral anchors 802*a* and 802*b* to be constructed of hardened stainless steel, while the arch 801 is constructed of super-elastic nitinol.

Figure 9:
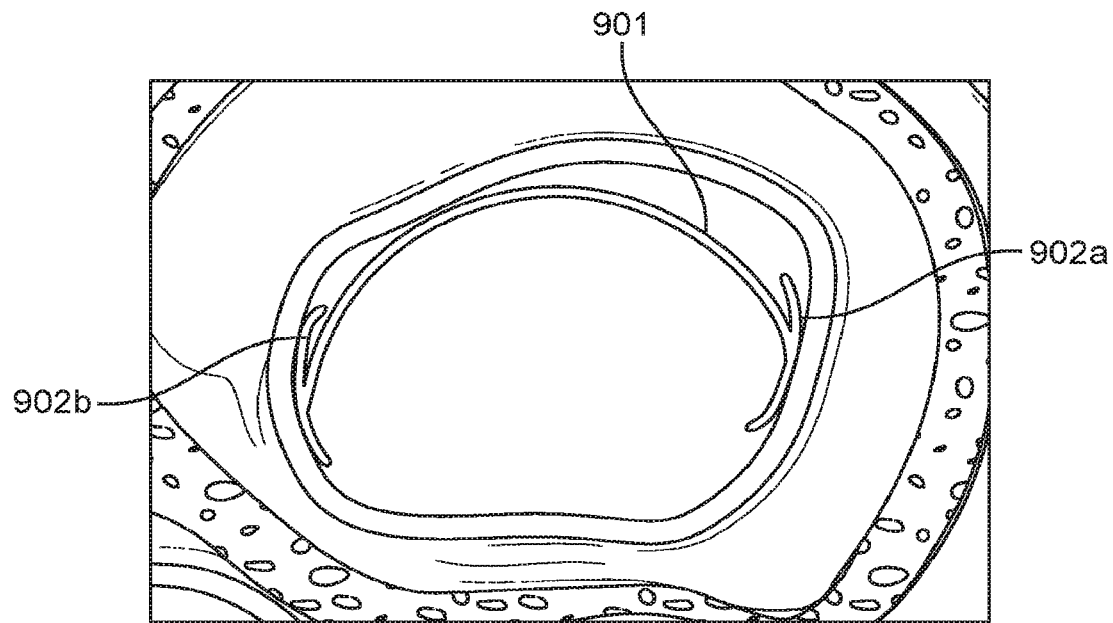
FIG. 9 shows an example of an arch shaped stretching device that stretches the annulus with shaped pads on each end.

FIG. 9 shows another alternative example of the present invention, where the arch 901 presses outward on the mitral annulus 201 acting through pads 902*a* and 902*b*. The pads 902*a* and 902*b* distribute the force the arc 901 exerts on the mitral valve annulus 201. The pads 902*a* and 902*b* may be anchored to the annulus using any of a number of anchoring techniques, or they may simply rest against the junction between the mitral valve annulus 201 and the wall of the left atrium (not shown). The pads 902*a* and 902*b* may be covered in a material that encourages tissue ingrowth. The pads 902*a* and 902*b* may be constructed of the same material as the arch, or of a different material to achieve the structural properties required. The pads 902*a* and 902*b* may be symmetric to each other to allow the device to be placed in two different orientations without loss of function, or they may be asymmetric to re-shape the valve annulus to different radii in the area of each pad.

Figure 10:
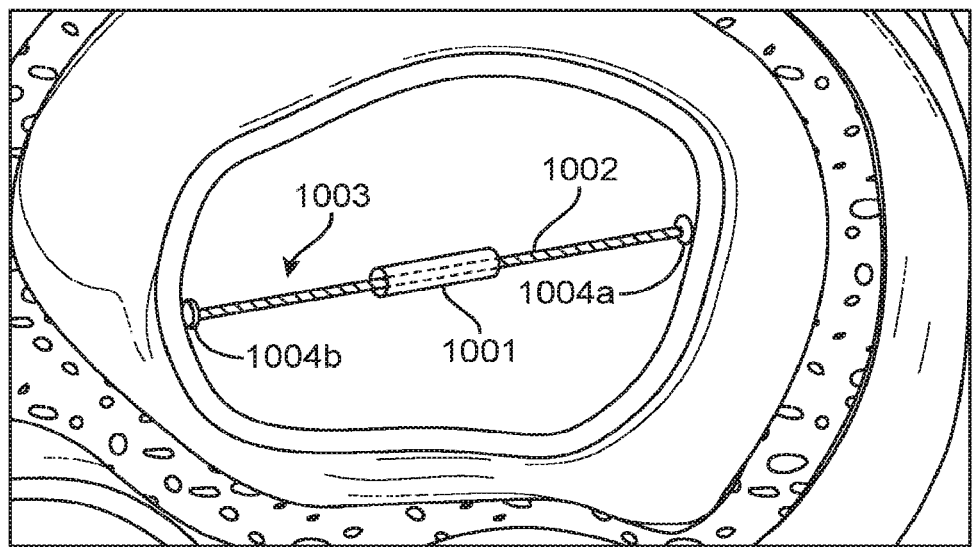
FIG. 10 shows a linear (straight) stretching device in a turnbuckle configuration.

An arch of resilient material is only one way to accomplish the valve re-shaping of the present invention. FIG. 10 shows an alternate, straight stretching member in a turnbuckle configuration which includes a rotating sleeve 1001 with two internal threads of opposite chirality (left and right handed), a first threaded rod 1002 with and anchor 1004*a* and with threads cut in a first chirality (in one example, right hand threads), and a second threaded rod 1003 with an anchor 1004*b* and with threads cut in a second chirality (in one example, left handed threads). Rotating the sleeve 1001 moves the threaded rods toward or away from each other, thus adjusting the length of the stretching member and effecting the desired change in valve shape.

Figure 11:
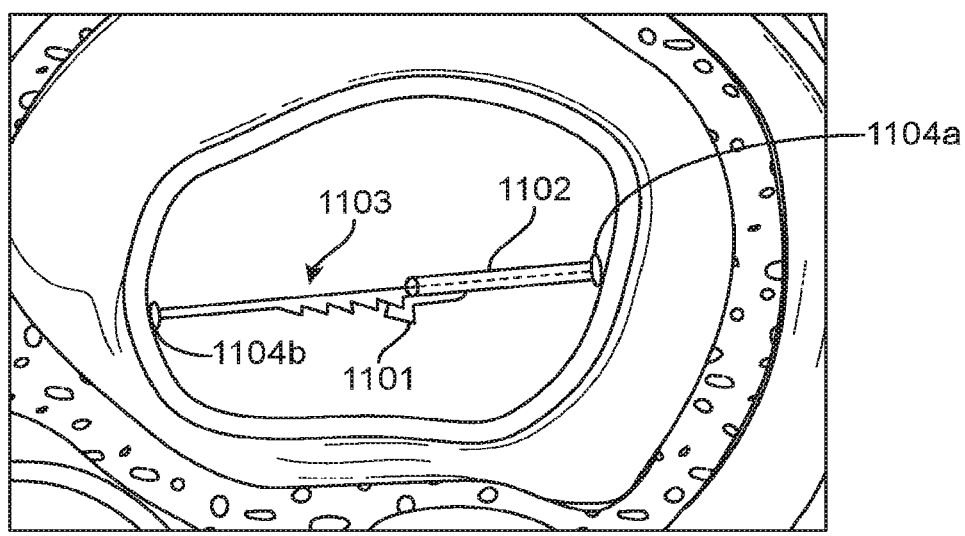
FIG. 11 shows a stretching device with a ratchet and pawl configuration.

FIG. 11 illustrates another example of a stretching member, this one based on a ratchet member 1103 containing a ratchet and anchored 1104b the valve annulus and pawl member 1102 containing a pawl 1101 and anchored to the valve annulus 1104a to hold the stretching member assembly in an extended length, affecting the desired change in valve shape.

Figure 12:
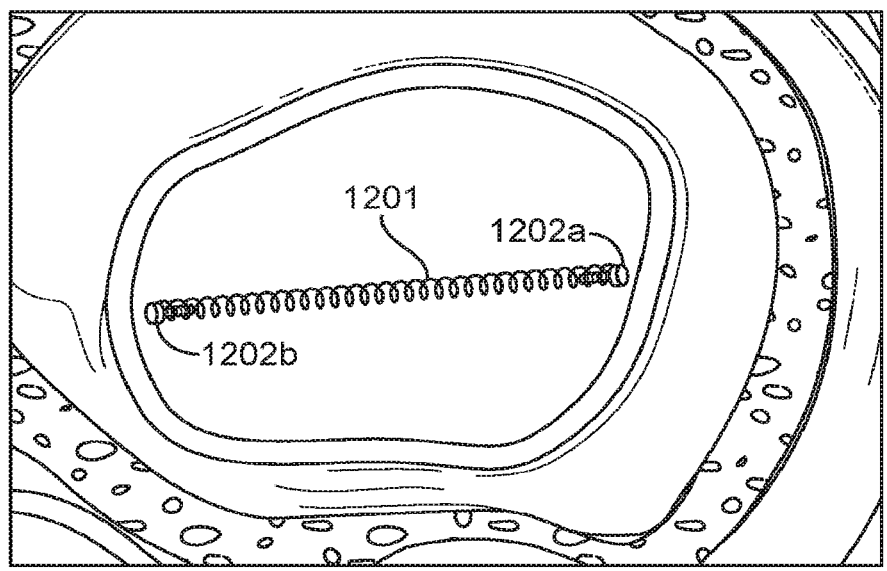
FIG. 12 shows a stretching device based on a compression spring.

FIG. 12 illustrates another example of a stretching member, based on a compression spring 1201 anchored at the ends 1202a and 1202b. The compression spring is biased to a free length longer than the distance between valve commissures, stretching the valve in the direction of application and affecting the desired change in valve shape. The compression spring as shown is a helical coil, but other compressible structures may be utilized. Examples of suitable structures include an expanding lattice or net formed of closed cells, a series of sinusoidal curves, a braid of resilient material, a stack of Bellville washers, or other compressible structures know to the art.

Figure 13:
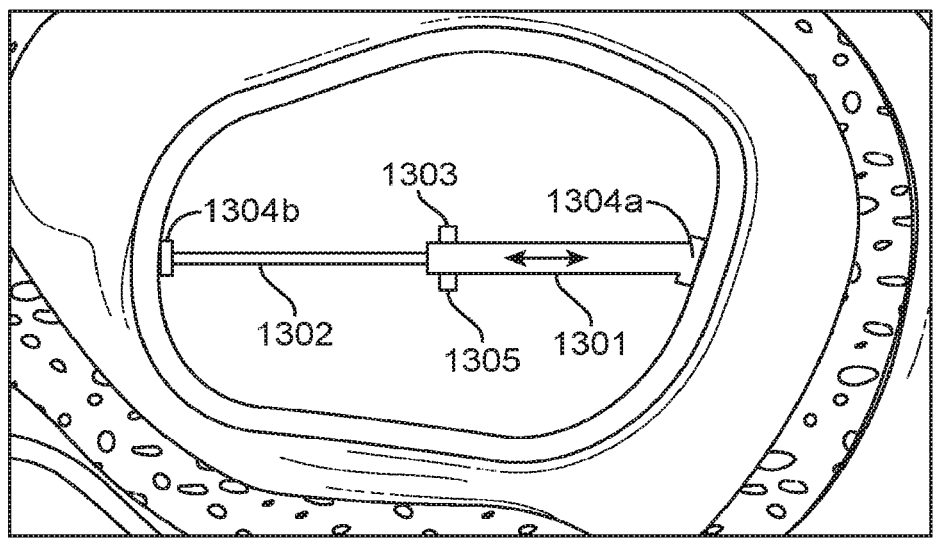
FIG. 13 shows a stretching device with an enclosed compression spring and a pin to hold it in a partially compressed state for delivery.

FIG. 13 illustrates another spring based stretching member, including a spring enclosure cylinder 1301 with anchor 1304a, a piston 1302 with anchor 1304b, and a pin 1305 that holds the assembly in a first length for placement. Removing the pin by pulling it out 1303 allows the spring to extend, affecting the desired change in valve shape.

Figure 14:
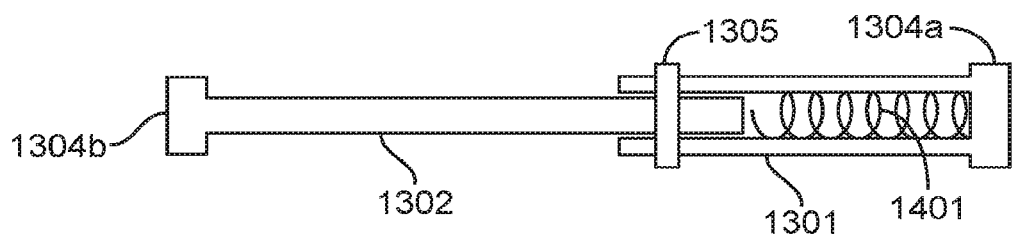
FIG. 14 shows a close-up of the stretching device from FIG. 13.

As shown in FIG. 14, the spring based stretching member of FIG. 13 contains a compression spring 1401 that is at least partially enclosed in cylinder 1301.

Figure 15:
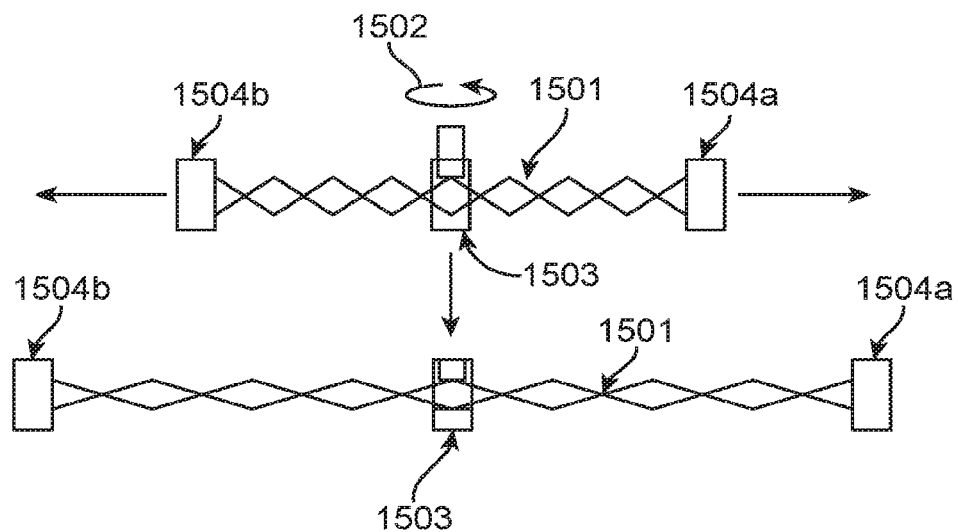
FIG. 15 shows an alternative example of a stretching device based on a linkage configuration.

FIG. 15 illustrates a stretching member based on a crossed linkage 1501 with anchors 1504a and 1504b. Turning 1502 the adjustment screw 1503 actuates the linkage to move the anchor points closer together or farther apart as required to affect the desired change in valve shape. While shown as a crossed linkage, other structures may be used. In one example, a closed cell structure, in a second example a repeating sinusoidal pattern structure, in a third example a spiral structure, or braid structure or other structures known to the art may be employed.

Figure 16:
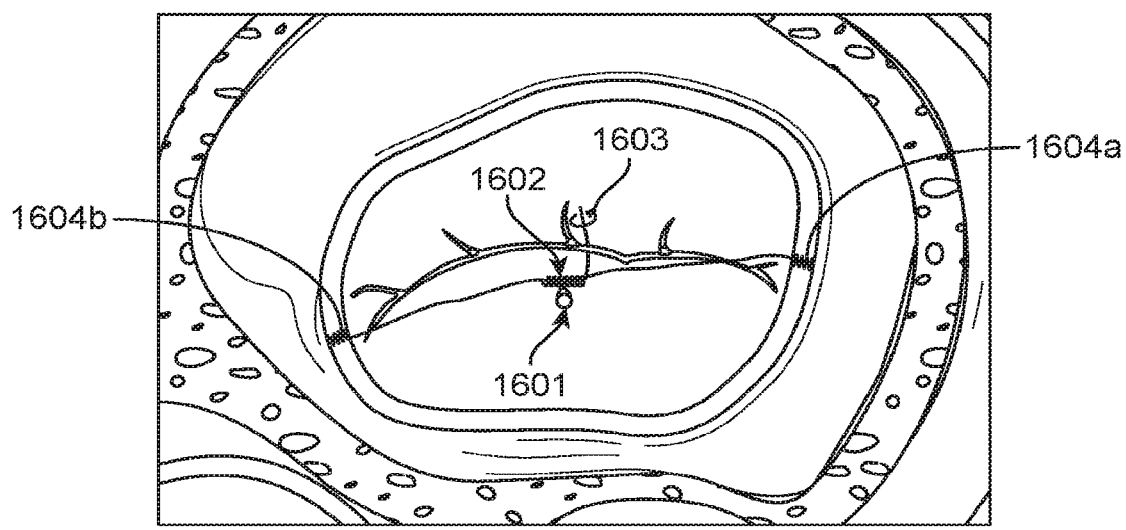
FIG. 16 shows an alternative example of a stretching device based on a torsion spring, which is held in position by a helical fastener during delivery and placement.

FIG. 16 illustrates a torsion spring 1601 based stretching member. The torsion spring 1601 is attached to anchors 1604a and 1604b and is held in a first position by a retention spring 1602. The retention spring 1602 can be removed by twisting 1603, allowing the torsion spring 1601 to move to a second position, affecting the desired change in valve shape.

Figure 17:
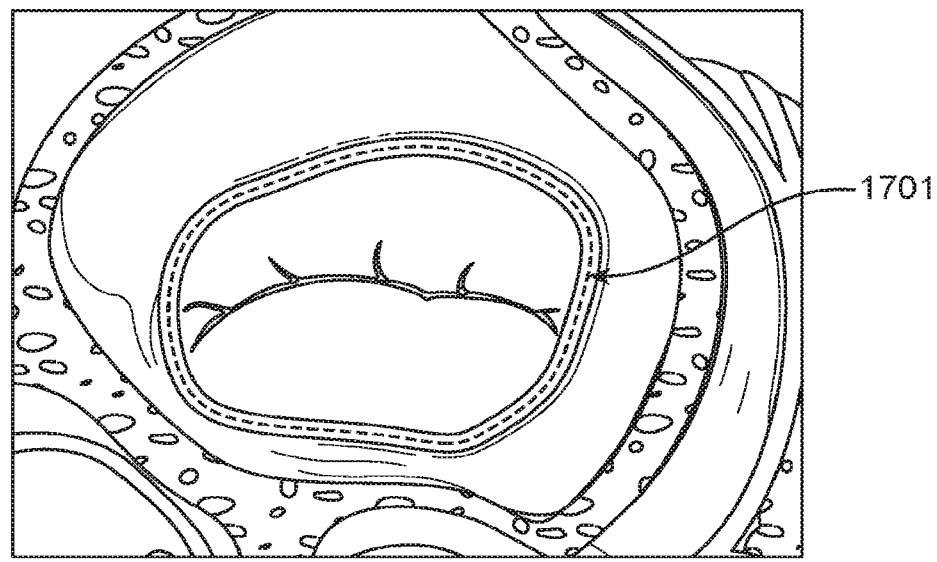
FIG. 17 shows an end view of one or more rings (or a stent-like structure) for stretching the mitral valve annulus across one or more dimensions.

As shown in FIG. 17, a valve shaping device 1701 (dashed line) can be placed along the annulus, conforming approximately to the shape of the annulus and/or the left atrial wall.

Figure 18A:
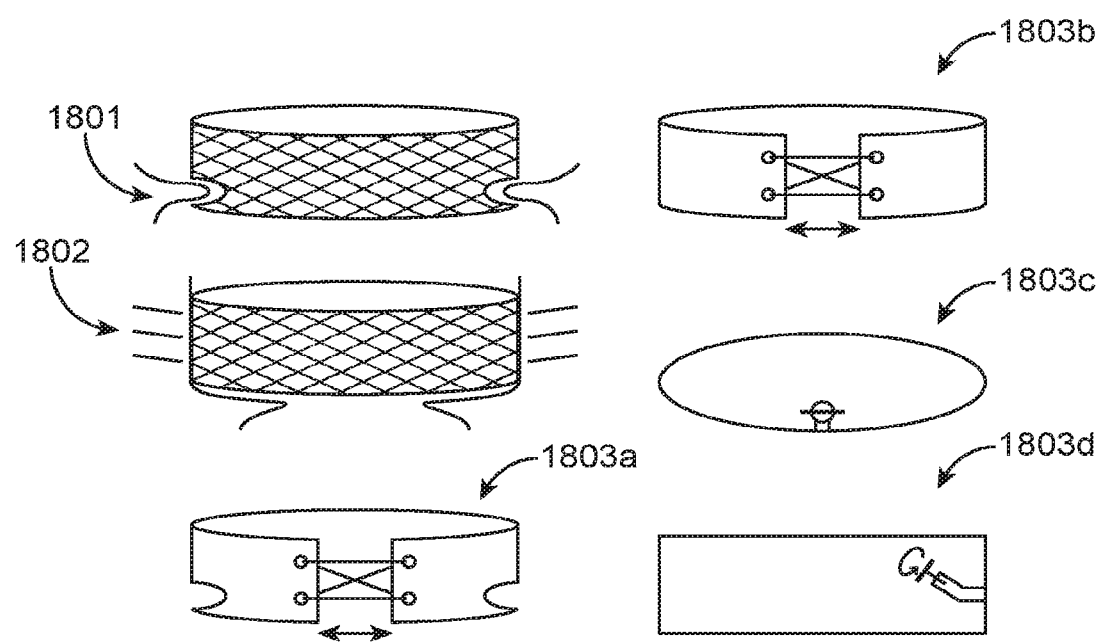
FIG. 18A and FIG. 18B show examples of placement of the stent-like structure.

FIG. 18A shows examples of valve shaping device 1701 which may be placed partially above and partially below the valve annulus (1801), or completely on one side of the annulus (1802). Such examples of valve shaping device 1701 may include an adjusting mechanism 1803, which employs any of a wide array of adjusting mechanisms including but not limited to linkages, screws, turnbuckles, or flexible tension members (sutures) with appropriate locking devices or knots. The adjustment device may be accessible from the inner aspect of the valve shaping device 1701 as shown in 1803c and may be angled relative to the body of the valve shaping device 1701 as shown in 1803d for ease of access to the adjustment mechanism. While the stent structure is not shown, a variety of stent structures may be used. In one example, a closed cell structure, in a second example a repeating sinusoidal pattern structure, in a third example a spiral structure, or braid structure or other structures known to the art may be employed. A variety of stent materials may be employed, including stainless steel, cobalt chromium, platinum, or super elastic Nitinol.

Figure 18B:
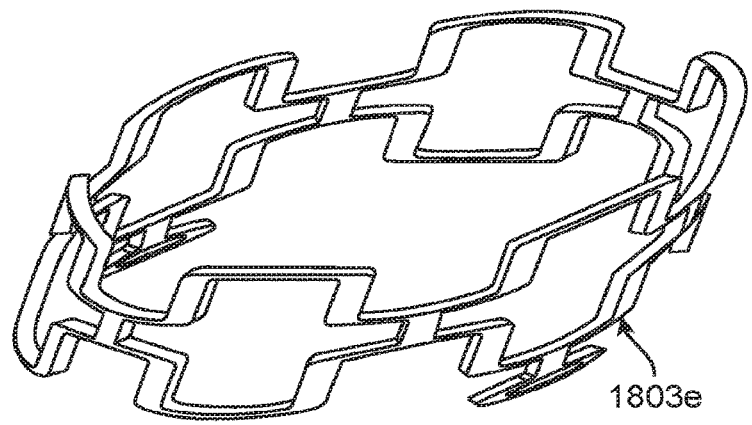

FIG. 18B shows an example of a valve shaping device 1803e with has two tissue engagement portions, and an elongated profile. This device configuration is a continuous loop without ends.

Figure 18C:
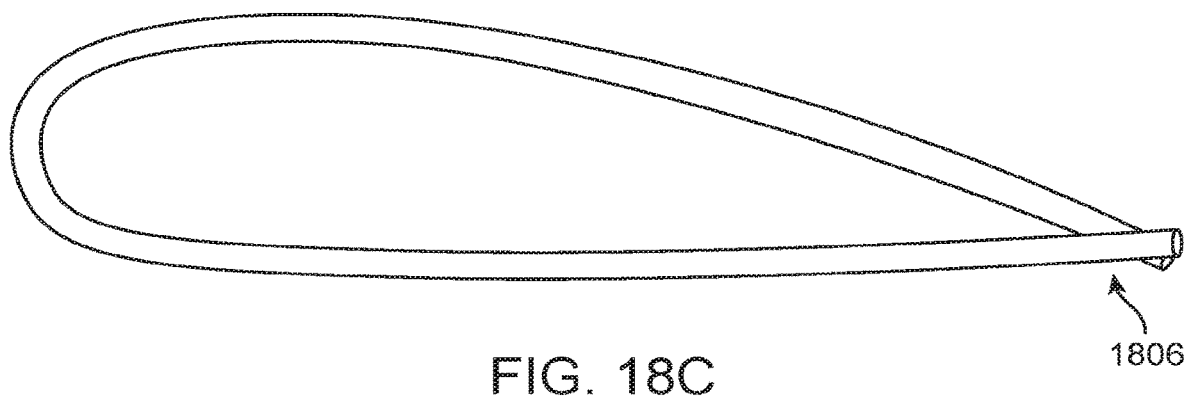
FIG. 18C shows an example of a structure with a single end.

FIG. 18C shows and example of a valve shaping device 1806 which is constructed of an elongate member whose ends are joined into a single end.

Figure 19:
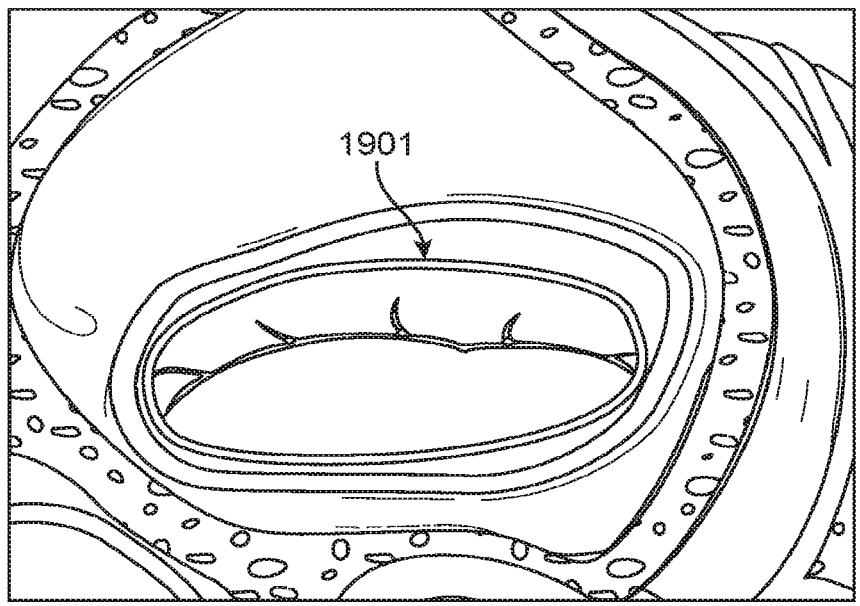
FIG. 19 shows an example of an elongated ring shape, applied to the annulus to stretch it in the C-C direction.

FIG. 19 shows a valve shaping ring 1901 of resilient material which alters the shape of the atrium and valve annulus 201. The valve shaping ring 1901 may include anchors in the area of the valve commissures or may act by pressing outward against the wall of the atrium in the area of the valve commissures. The valve shaping ring 1901 preferentially includes a coating or outer sleeve to encourage tissue ingrowth and/or encapsulation.

Figure 20:
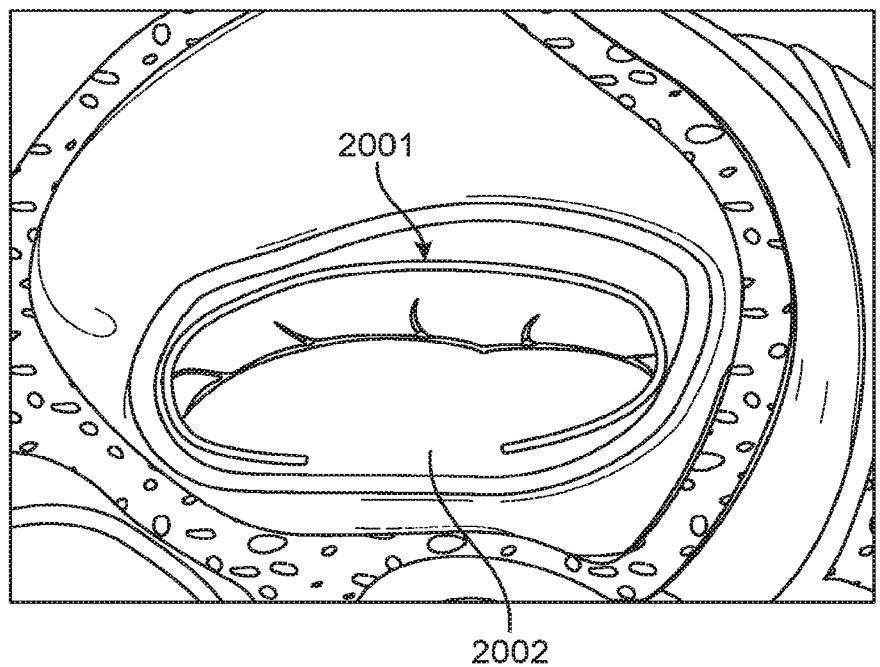
FIG. 20 shows an example of an elongated partial ring shape with a gap, applied to the annulus to stretch it in the C-C direction.

FIG. 20 shows a valve shaping c-ring 2001 of resilient material which alters the shape of the atrium and valve annulus 201, which includes a discontinuity 2002. The discontinuity allows for re-shaping the ring for easier delivery to the valve site. The discontinuity may also include an adjustment mechanism. In one example, a flexible tension member may connect the two ends of the c-ring, limiting outward pressure. By adjusting the length of this flexible tension member, the level of re-shaping effect on the valve can be adjusted. The valve shaping c-ring 2001 may include anchors in the area of the valve commissures or may act by pressing outward against the wall of the atrium in the area of the valve commissures. The valve shaping c-ring 2001 preferentially includes a coating or outer sleeve to encourage tissue ingrowth and/or encapsulation.

Figure 21:
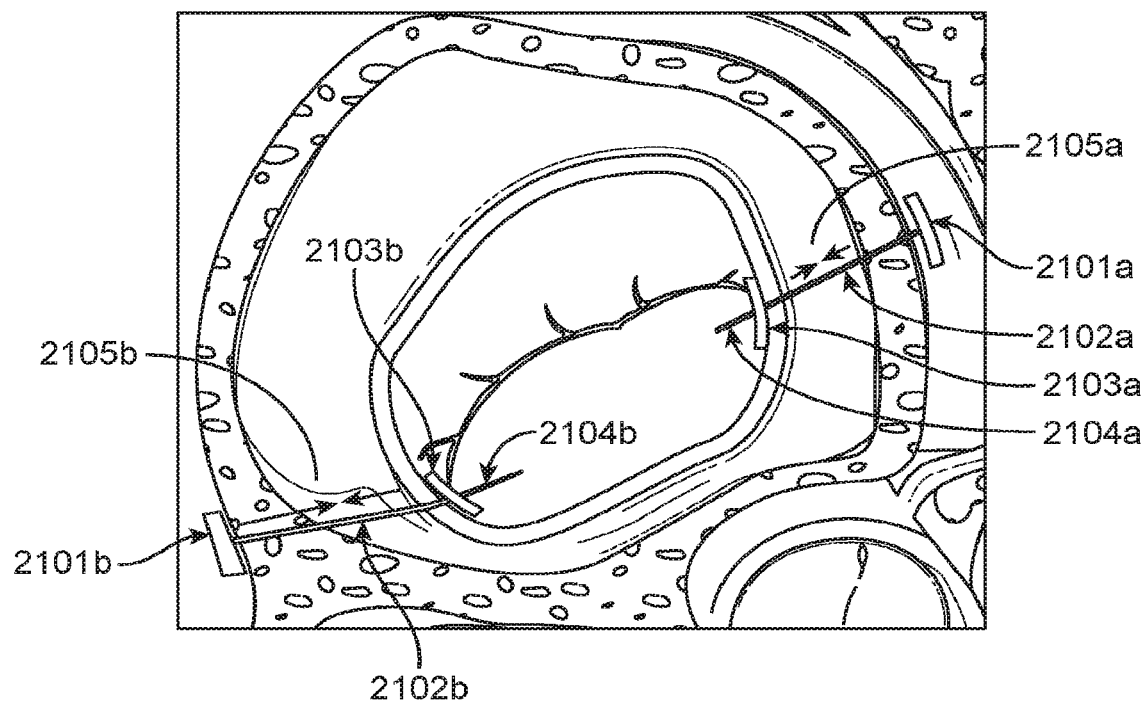
FIG. 21 shows an example of tightening pledgets applied to stretch the commissures of the valve.

The valve reshaping of the present invention can be accomplished by acting independently on different areas of the valve. As shown in FIG. 21, tensioning members 2501a and 2501b at locations around the valve annulus can create similar reshaping. Referring to FIG. 21, tensioning member 2105a includes an anchoring pledget 2101a, a flexible tension member 2102a, a sliding pledget 2103a, and an adjuster 2104a. The adjuster 2104a can be used to adjust the position of the sliding pledget along the flexible tension member 2102a, creating an area of compressed tissue between the pledget 2101a and the sliding pledget 2103a, and affecting the desired change to the valve shape. Examples of the mechanism used for the adjuster 2104a include screw threads, suture locking devices, knots, glue, heat stakes and/or crimp tubes. The adjuster 2104a may be built in to the sliding pledget 2103a, or a separate part. The adjuster may be partially or fully included in the removable deployment device. This example of the present invention may be advantageous in valves with three leaflets, such as the aortic valve 103, tricuspid valve 104, or pulmonary valve 102.

Figure 22:
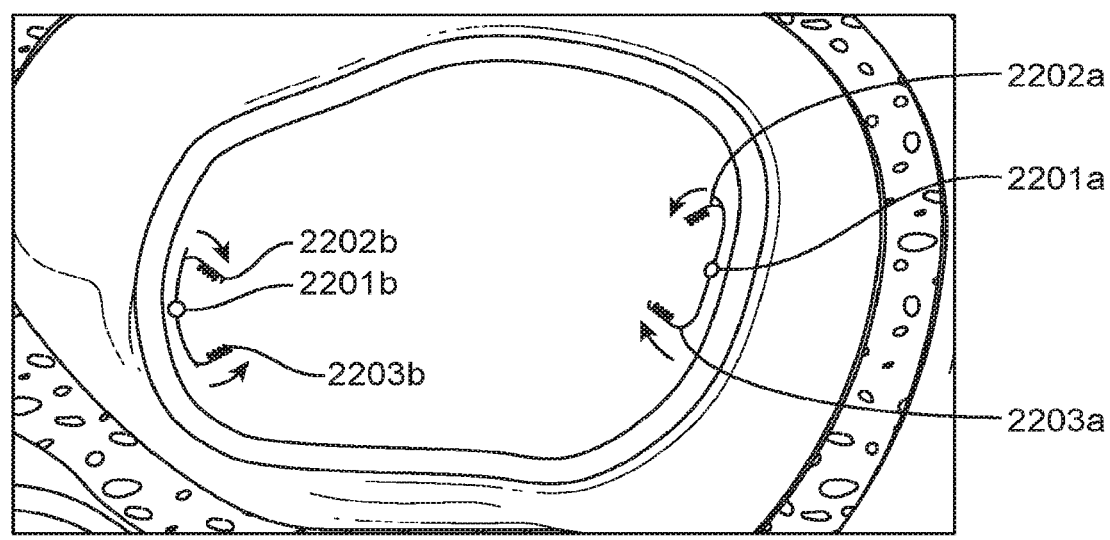
FIG. 22 shows an example of torsion springs attached at the commissures of the valve, configured to draw the leaflets together especially when the valve leaflets are out of plane while pushing the commissures apart.

FIG. 22 shows torsion spring 2201a and 2201b based reshaping devices which include anchors 2202a, 2202b, 2203a, and 2203b. The torsion spring acts to bring the anchors closer together to affect the desired change in valve shape. These torsion springs 2201a and 2201b may be held in a delivery position by a removable mechanism as shown in FIG. 16.

Figure 23:
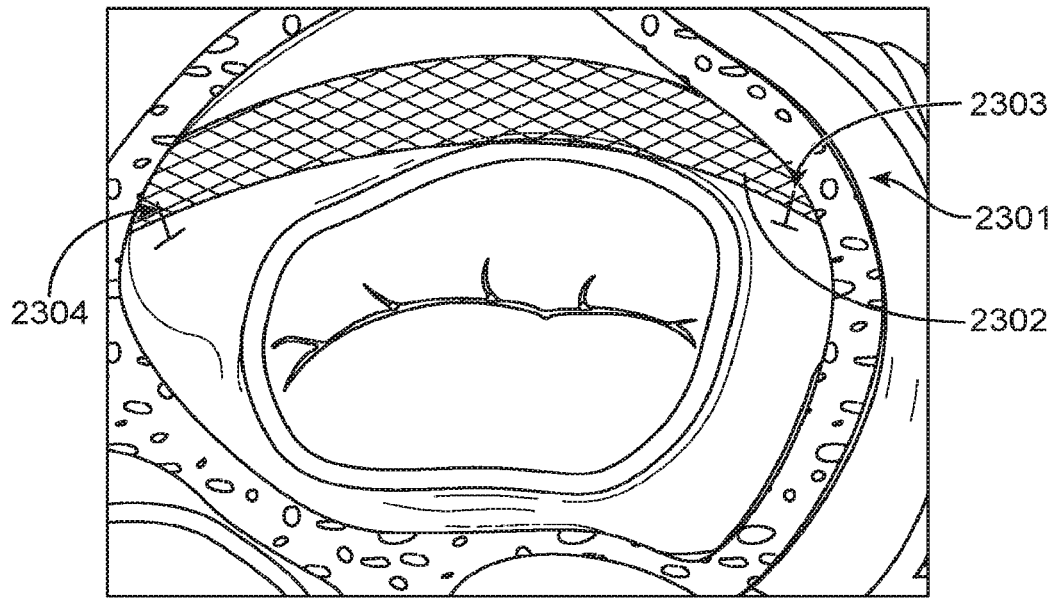
FIG. 23 shows an example of a semi-rigid, shape memory, or a spring like stent applied to the coronary sinus to straighten the sinus, creating a septal-lateral compression effect thus minimizing or eliminating MR or FMR.

The reshaping effect may also be achieved through application of devices external to the atrium. As shown in FIG. 23, a stent-like device 2302 can be placed in the coronary sinus 2301 and anchored to the wall of the heart adjacent to the mitral annulus by two anchors 2303 and 2304. The deployed shape of the stent is significantly straighter than the path of the coronary sinus, creating an inward pressure on the lateral aspect 205 of the valve annulus.

Figure 24:
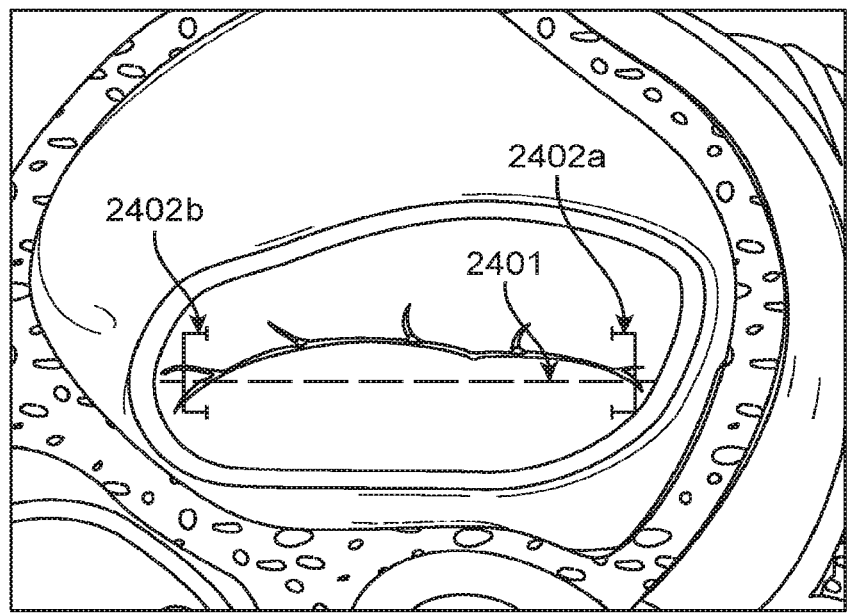
FIG. 24 shows an example of clips which attach to valve commissures or annulus in order to hold them in place, after using a stretching device to stretch the commissures or annulus thus allowing for removal of the stretching device while maintaining a smaller configuration (dimension) in the arterial-posterior direction of the valve or annulus.

The reshaping members as part of this present invention may be temporary, removable devices to aid in placement of permanent clip or anchoring members. As shown in FIG. 24, the stretching member 2401 represented by a dashed line, may be removed after placing permanent clips 2402a and 2402b. The permanent clips 2402a and 2402b maintain the desired change in valve shape after the stretching member 2401 has been removed.

Figure 25:
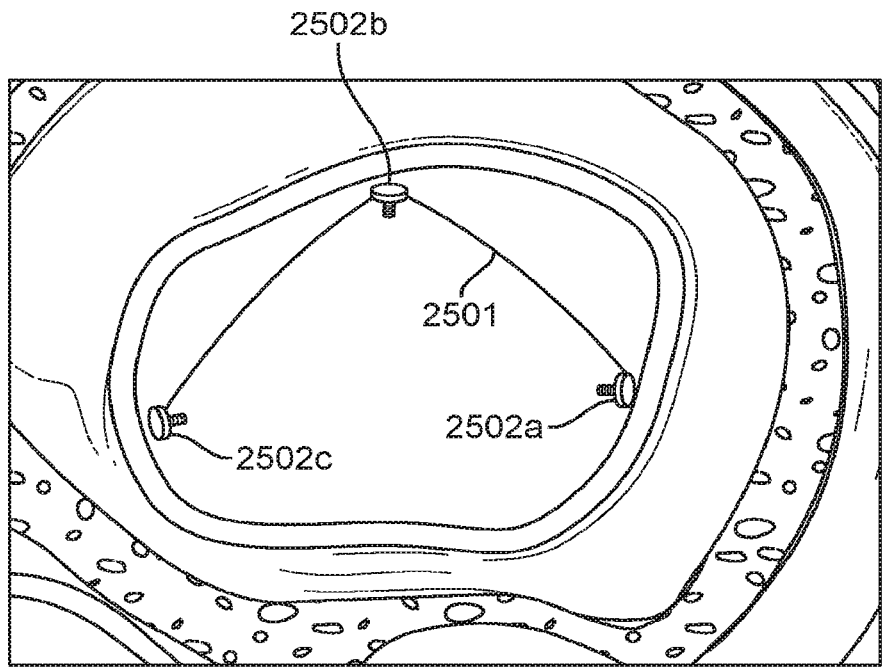
FIG. 25 shows a stretching device anchored at 3 points around the valve.

While much of the present invention has described stretching members targeted at affecting the position of two points around a valve annulus, it may be advantageous to combine two or more such members to affect three or more points along the valve annulus. As shown in FIG. 25, the three-point shaping member 2501 is anchored around the valve annulus with three anchors 2502a, 2502b, and 2502c. The combined directed motion can bring the anchor points 2502a-c towards a different triangular shape than their initial positions, or towards a straight line as required to affect the desired change in valve shape.

Figure 26:
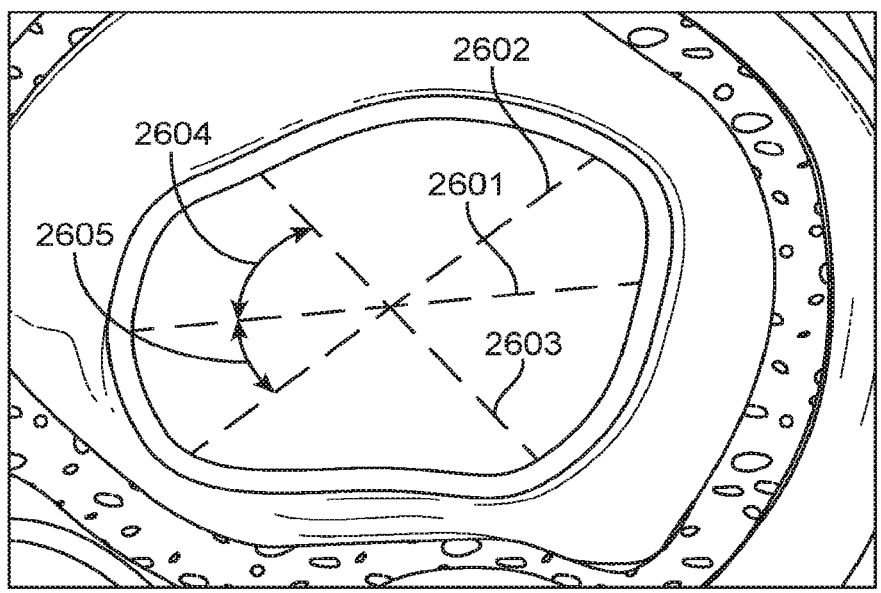
FIG. 26 shows a range of angles at which application of the stretching device may be advantageous to treat or repair a valve impairment.

While most figures in this disclosure indicate a stretching member situated approximately in line with the valve commissures, there are other stretching directions which may be advantageous in some situations. FIG. 26 shows the commissural line position 2601, a second position 2603 located at an angle 2604 clockwise from the commissural line position and a third position 2605 located at an angle 2605 counterclockwise from the commissural line position. It may be advantageous for the angles 2604 and 2605 to be within 45 degrees of the commissural line position 2601. In a further example, it may also be advantageous for the angles 2604 and 2605 to be within 60 degrees of the commissural line position 2601.

Figure 27:
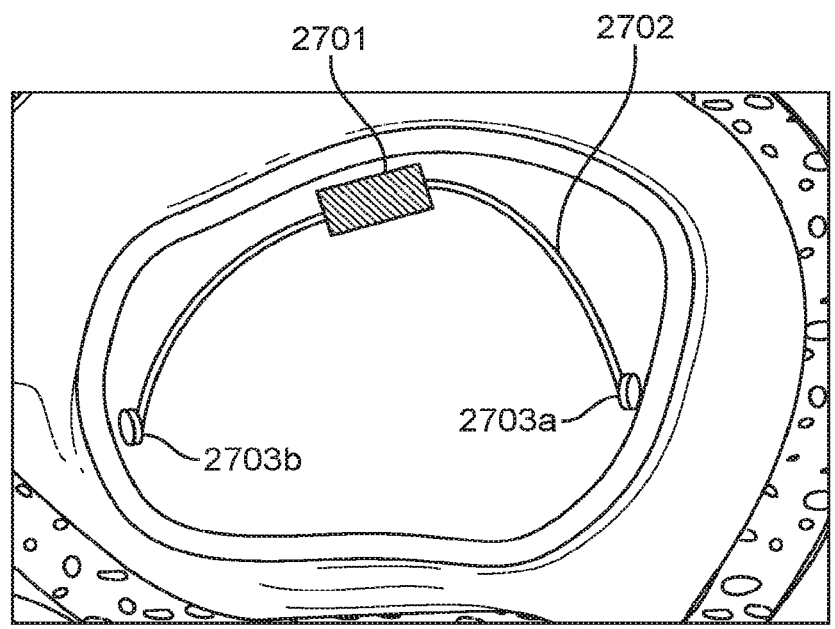
FIG. 27 shows a stretching device with a Force Changing Element that changes the stretching force over time, preferably to decrease the stretching force once healing and/or tissue remodeling have taken place.

The effect of the stretching member on the valve will be acute, reshaping the valve and restoring function during the implantation procedure. Configurations of the stretching member which apply a force that changes over time may be advantageous. The force may decrease, to prevent long term valve remodeling or increase, to accommodate for further expansion of the heart affecting valve function. FIG. 27 shows a stretching member 2702 with a time-alterable region 2701 and anchors 2703a and 2703b. The time alterable region may function via bioresorbable components that alter applied force by degrading, by fatigue elements which disconnect after exposure to a period of cyclic loading, or by other mechanisms known to the art.

Figure 28:
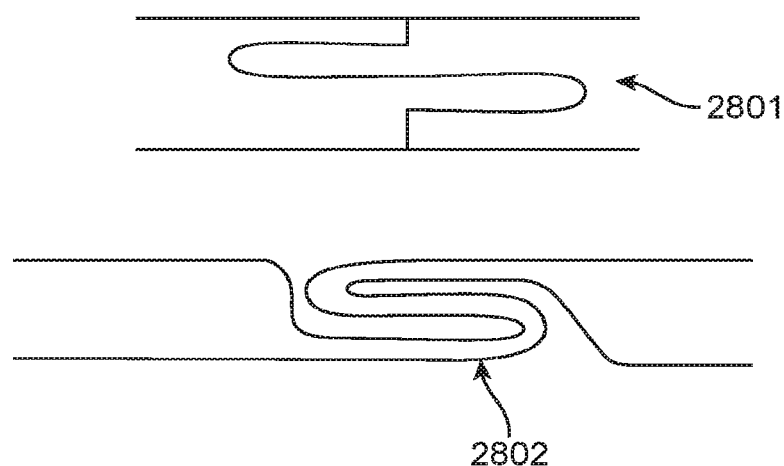
FIG. 28 shows two examples of the Force Changing Element, one of which is separable into multiple components, the second of which remains a continuous component.

As shown in FIG. 28, the discontinuity region 2701 may separate the stretching member 2702 into two or more detached components (2801), or may leave the stretching member as one continuous component with a more flexible structural shape (2802).

Figure 29A:
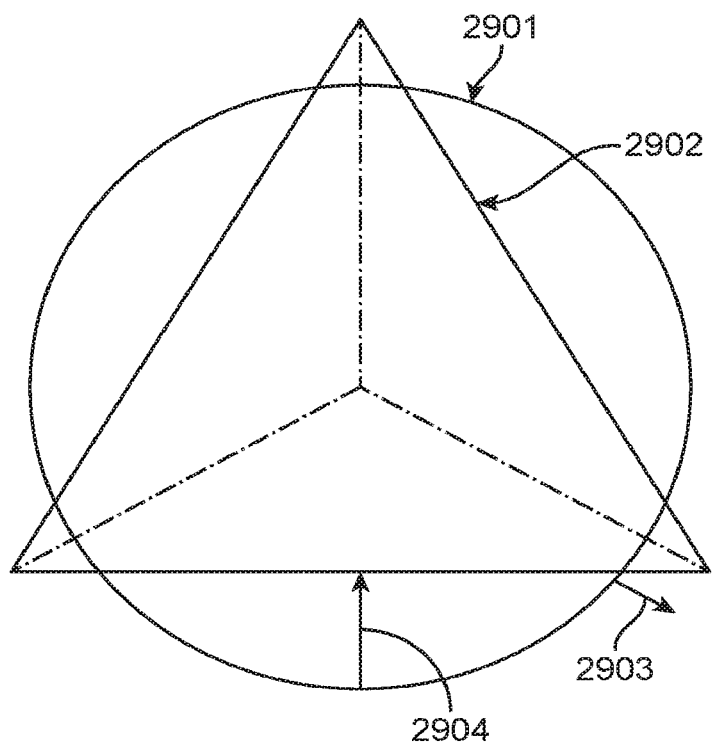
FIG. 29A shows an illustration of the application of stretching devices to re-shape a round annulus to more approximate a triangle. As shown, the circle and triangle have substantially the same perimeter but can also be configured to be different.

The present invention may also be applied advantageously to a substantially round valve with three leaflets, such as the pulmonary valve 102, the aortic valve 103, and/or the tricuspid valve 104. As shown in FIG. 29A, a round annulus 2901 can be shaped to a triangular annulus 2902 by moving three anchor points outward (2903). This results in substantial inward motion 2904 in segments of the valve annulus. These segments of the valve annulus which move inward may correspond to leaflets in an enlarged valve, or to commissures of a valve with stenosis.

Figure 29B:
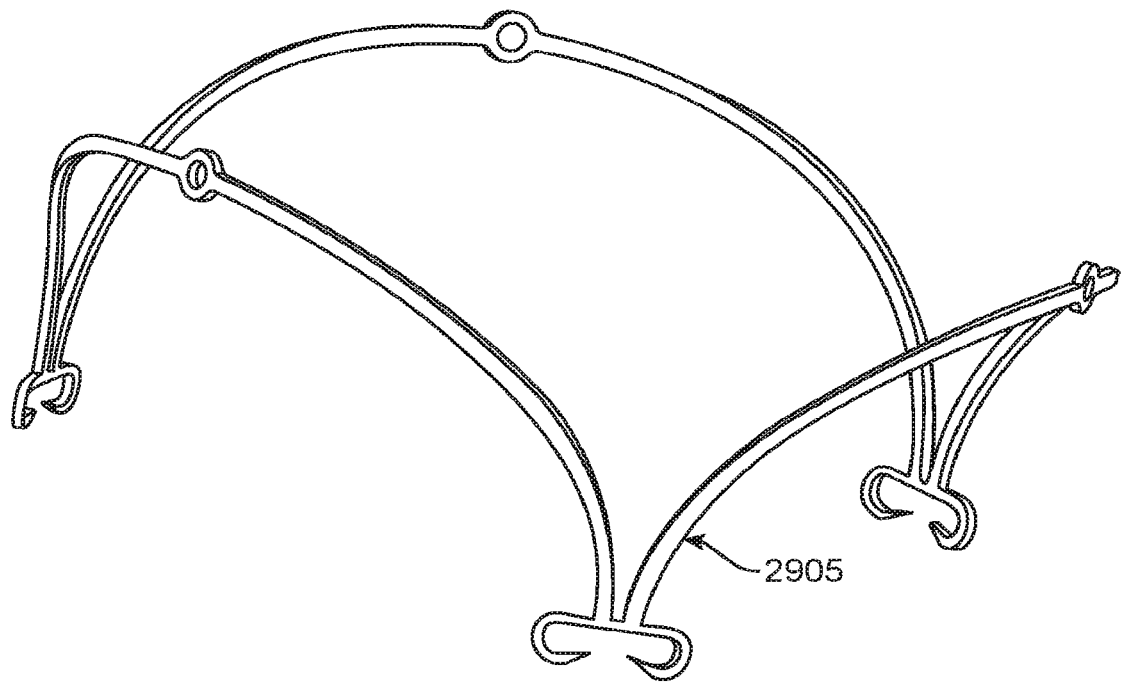
FIG. 29B shows an illustration of a stretching device configured to sit within a lumen and engage with three points around the circumference of the lumen, for example at a valve annulus, to re-shape it to more approximate a triangle.

FIG. 29B illustrates an example of a valve shaping device 2905 with a substantially circular shape, and three tissue engagement points arranged to shape a round annulus towards a more triangular shape.

Figure 30:
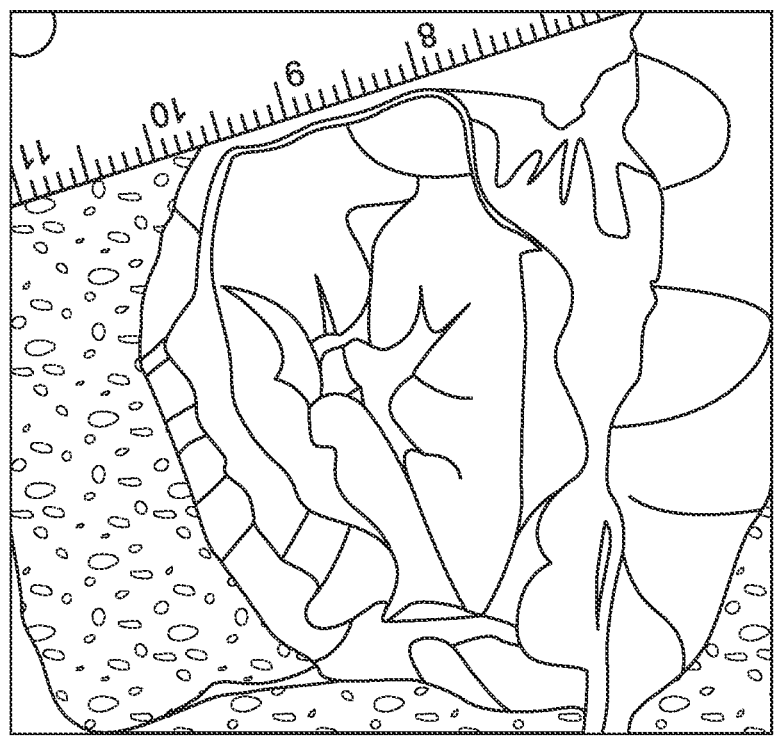
FIG. 30 shows the mitral valve of a pig in the at rest position.

FIG. 30 illustrates the mitral valve of a pig heart, with much of the left atrium removed for viewing.

Figure 31:
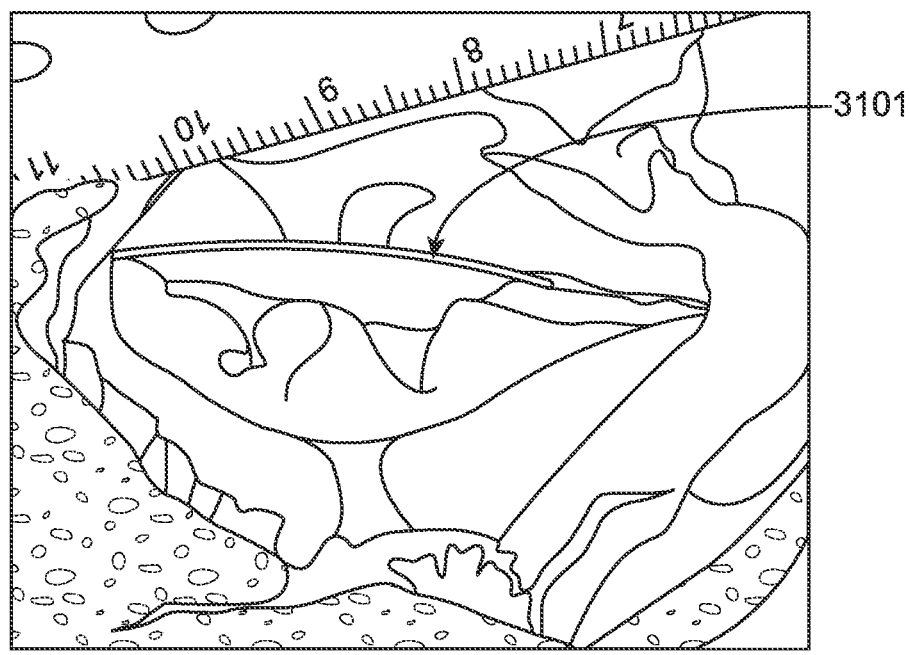
FIG. 31 shows the mitral valve of a pig with a stretching device in place. This stretching device arches above the plane of the mitral valve annulus. The stretching device increases the dimension of the annulus across the device path while decreasing the dimension of the annulus at an angle offset to the device path.

FIG. 31 illustrates the mitral valve of a pig heart with a stretching member 3101 in place, creating an elongation in the commissural linear direction and a reduction in size in the septal-lateral direction. In this configuration, the stretching member 3101 arches over the plane of the mitral valve, and may rest against the roof of the atrium, not shown.

Figure 32:
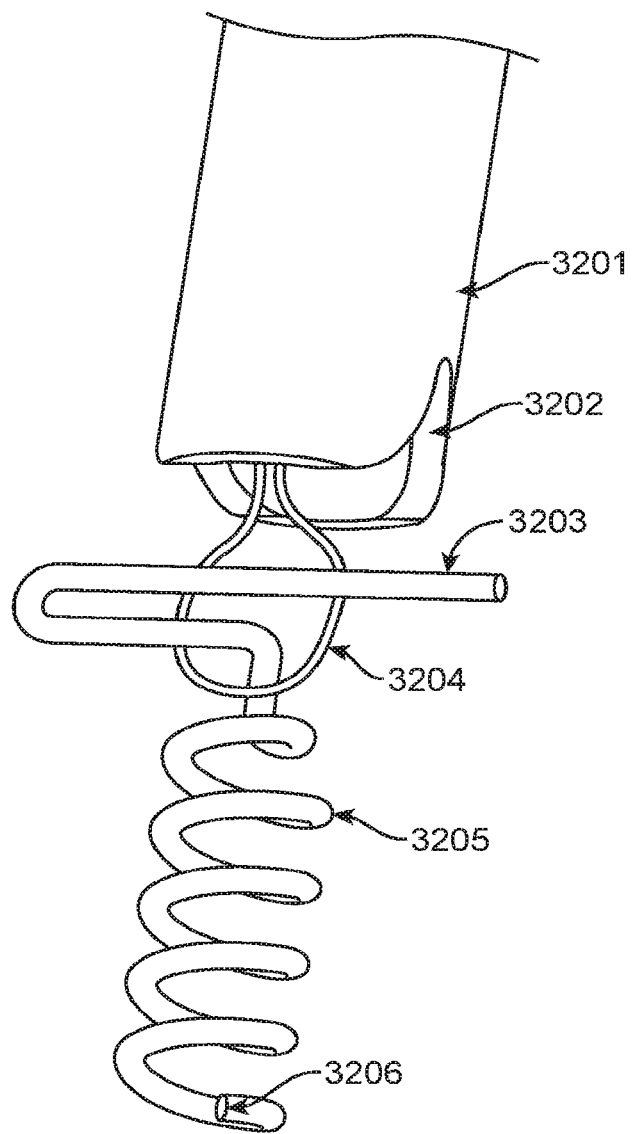
FIG. 32 shows a helical member with a T-handle for applying torque, along with a snare and torque tube.

FIG. 32 shows a helical member 3205 incorporating a T-handle 3203. The T-handle 3203 can be used to twist or untwist the helical member 3205 when it is held in the engagement slot 3202 of torsion tube 3201 through tension on the snare 3204. One example of the use of this device would be a helical member 3205 with a penetrating tip 3206 used to anchor a device (not shown) to tissue. The helical member 3205 may also take the form of a screw thread, and the torsion used to rotate it relative to an engaging thread (not shown), which could adjust the force or displacement provided by the stretching member. In addition, the T-handle 3203 may remain in place in the implant, to be accessed via snare to adjust or remove the implant peri-procedurally, or at a subsequent operative procedure. The torsion tube 3201 can interact remotely with a manual handle, or a powered remote actuator.

Accordingly, it is to be understood that the examples of the invention herein described are merely illustrative of the application of the principles of the invention. Reference herein to details of the illustrated examples is not intended to limit the scope of the claims, which themselves recite those features regarded as essential to the invention.

FIGS. 33 to 47 illustrate different adjustable elements, which may be used to adjust a stretching member such as that described in with a closed cell structure, repeating sinusoidal pattern structure, spiral structure, braid structure or other structures known to the art. Each adjustable element can draw the stretching member closer together and or farther apart as required to affect the desired change in valve shape.

Figure 33:
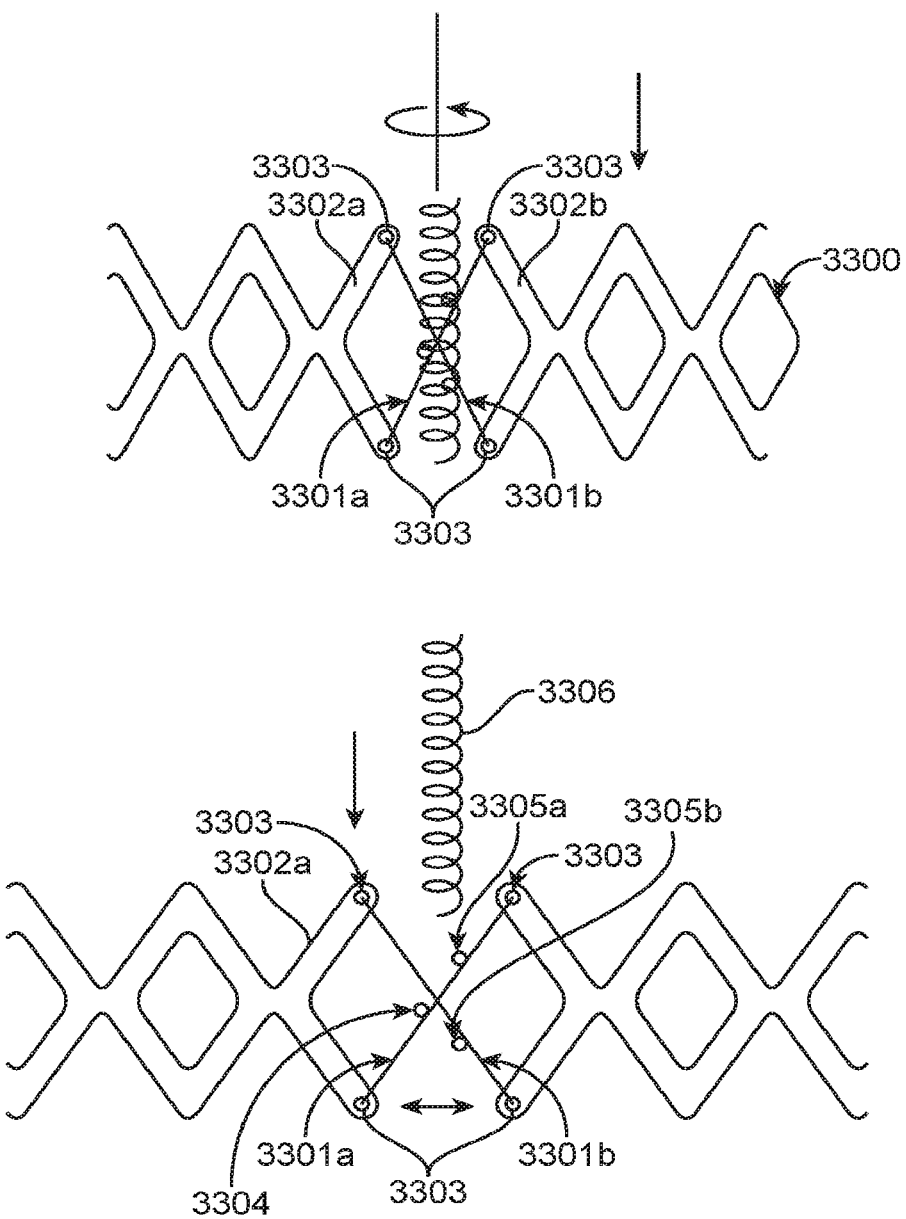
FIG. 33 shows a pair of adjustable arms that are connected to two adjacent cells of the stretchable member and can draw them farther apart after initial deployment with a spring.

FIG. 33 shows two straight arms 3301a and 3301b connected to adjacent cells 3302a and 3302b of the stretching member 3300. As shown, the ends of two arms 3301 enter holes 3303 located at the end of these cells 3302 such that it allows the arms to pivot at these points of connection. One arm 3301a is also inserted into a hole 3304 located on the other arm 3301b and is free to pivot. Both arms have additional holes 3305a and 3305b that allow a spring or spiral element 3306 to core through. The spring or spiral element 3306 prevents the arms from opening. After deployment of the stretching member 3300, the spring 3306 is turned such that it is released from the holes 3305a and 3305b of the two arms 3301a and 3301b. This allows the arms 3301a and 3301b to pivot and draws the stretchable member 3300 farther apart.

Figure 34:
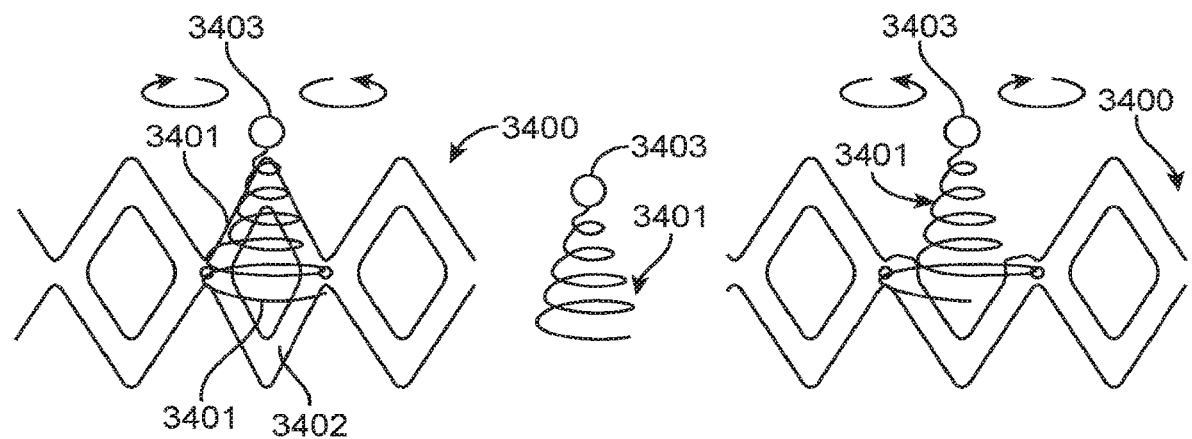
FIG. 34 shows a conical spring that fixes one or more cells of the stretchable member and can draw the stretching member closer together and or farther apart after initial deployment by rotating the spring.

FIG. 34 shows a conical or tapered spring 3401 cores around the arms of an unexpanded cell 3402 of the stretchable member 3400. The spring 3401 has a loop 3403 on top such that upon turning in clockwise or counterclockwise direction, it will narrow or widen the unexpanded cell 3402, and draw the stretching member 3400 closer together and or farther apart after initial deployment.

Figure 35A:
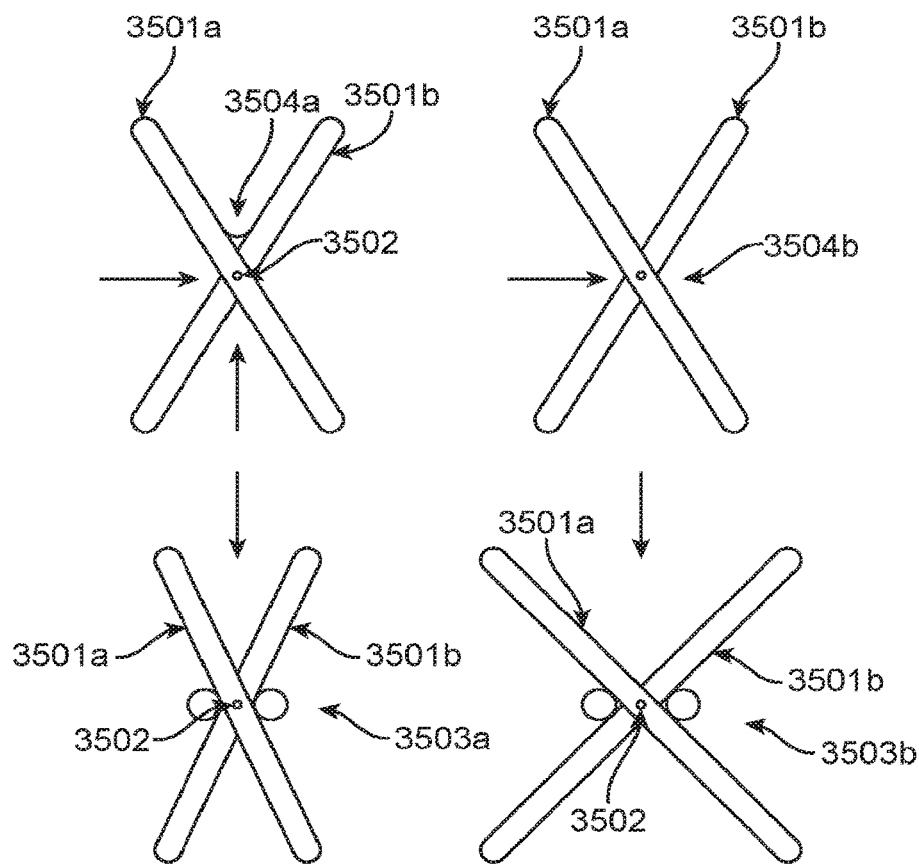
FIG. 35A shows an element consisting of two arms that pivots to open or close depending on where the force is applied or released at their point of intersection.
Figure 35B:
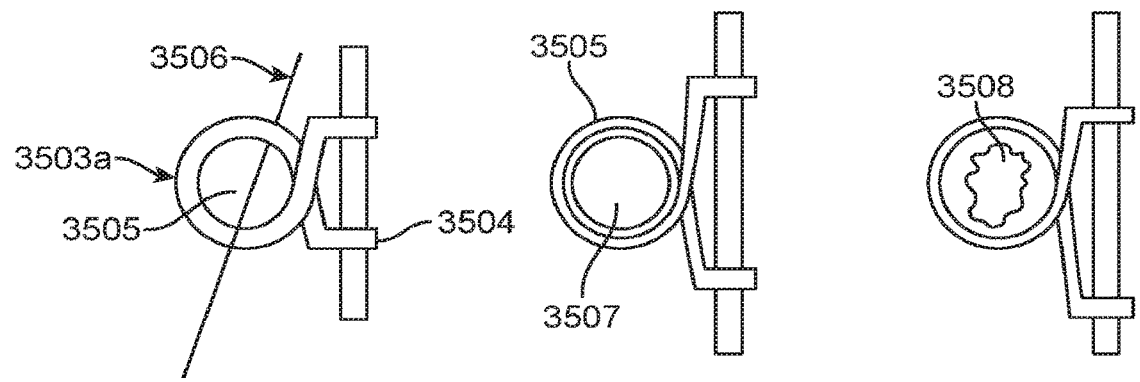
FIG. 35B illustrates the use of an expandable balloon to open or close the element in FIG. 35A.

FIG. 35A shows two straight arms 3501a and 3501b connected to adjacent cells (not shown) to the stretching member similar to FIG. 33 where the point of connections between the arms 3501a and 3501b and the holes on the cells allow pivoting of the arms 3501a and 3501b. The arms 3501a and 3501b can pivot at the point of their intersection 3502. One or more torsion springs 3503a made from ductile plastic, metal or alloy serve as a gripping mechanism to prevents the arms 3501*a* and 3501*b* from pivoting at the point of intersection 3502 by application of compressive forces 3504*a* and 3504*b*. FIG. 35B illustrates two extending arms 3504*a* and 3504*b* of FIG. 35A from the end of the torsion spring 3503*a* gripping the arms 3501*a* and 3501*b* together. After accessing the hole 3505 of the torsion spring 3503*a* with a guide wire 3506, a deflated balloon 3507 is inserted over the guide wire 3506 and into the hole 3505. This balloon is inflated and opens the torsion spring, thereby opening the grips 3504*a* and 3504*b* and releasing the arms 3501*a* and 3501*b* and allowing them to pivot at the point of intersection 3502. This allows the stretchable member 3500 to draw closer if the grips 3504*a* and 3504*b* applied a force from 3504*a*. It allows the stretchable member 3500 to become farther apart when the force is applied from 3504*b*.

Figure 36A:
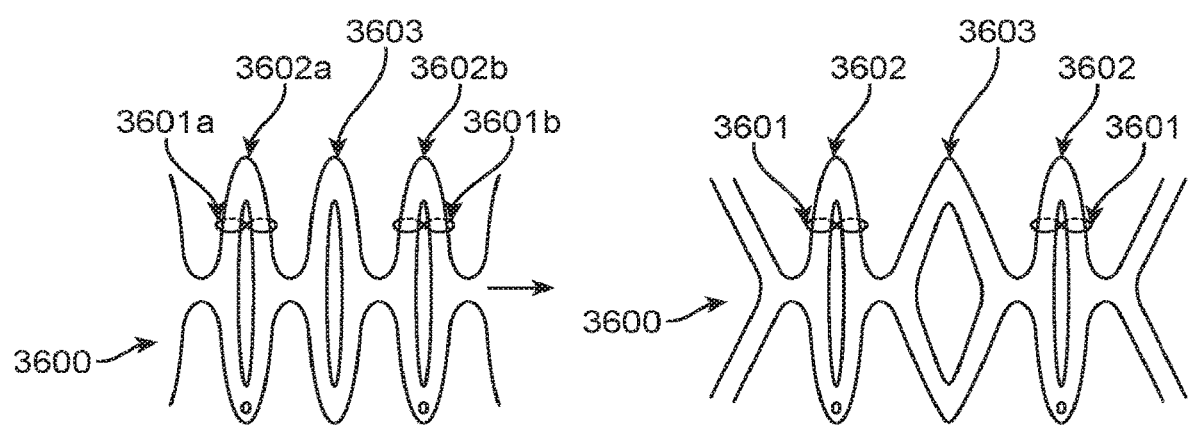
FIG. 36A shows a ring that fixed to the struts of one or more cells of the stretchable member.
Figure 36B:
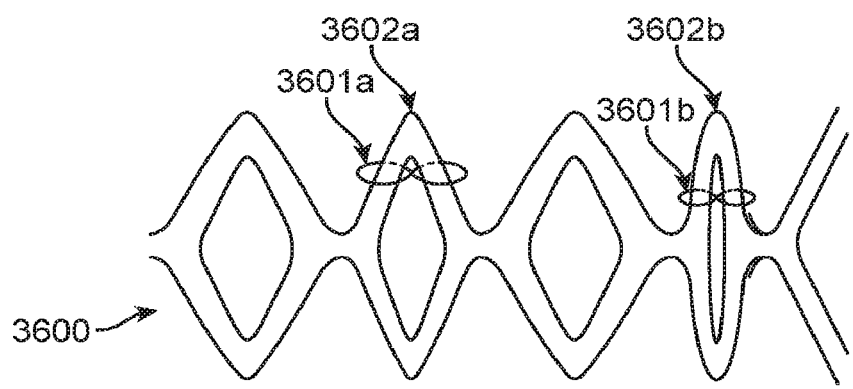
FIG. 36B illustrates the effect of the location of the ring with respect to the struts of a cell of stretchable member in causing the cell to open or close.

FIG. 36A shows two 'FIG. 8' ring element 3601*a* and 3601*b* around the fixed crowns 3602*a* and 3602*b* and a free crown 3603 before deployment. After deployment of the stretchable member 3600, the fixed crown 3602*a* and 3602*b* remain the same while the free crown 3603 opens. FIG. 36B illustrates that the left ring elements 3601*a* can be moved such that it becomes closer to the valley of the fixed crown 3602*a* after deployment, thereby, allowing the stretchable member 3600 to become farther apart.

Figure 37:
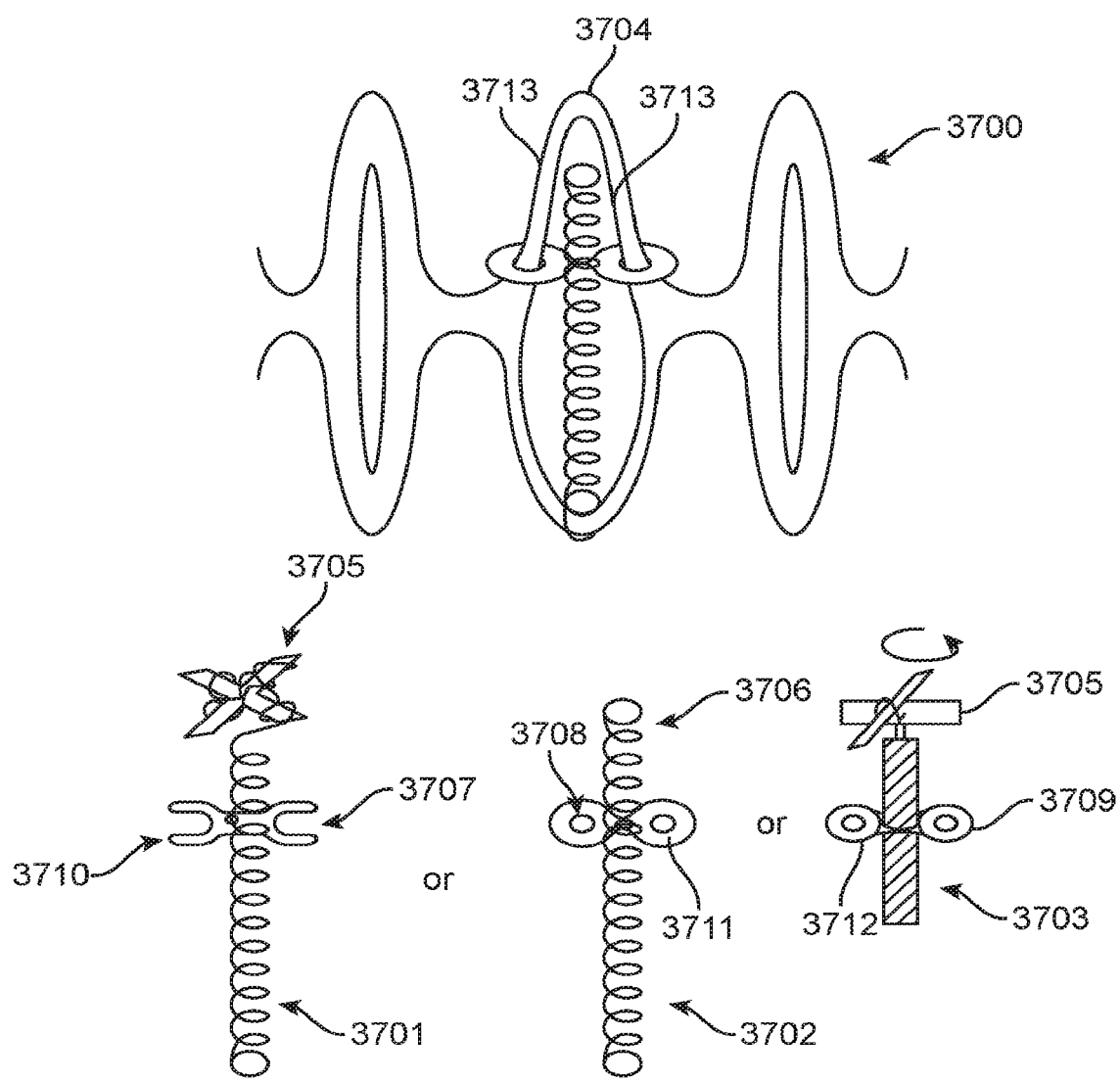
FIG. 37 shows different spring or screw with a ball nut fixed to one or more cells of the stretchable member and rotated to draw the stretching member closer together and or farther apart after initial deployment.

FIG. 37 shows different screw or spring driven adjustable elements 3701, 3702, and 3703 that fix to one or more cells 3704 of the stretchable member 3700. By rotating the screw or spring with a lever handle 3705, ring 3706, or other means, the nut block 3707, 3708, and 3709 with slots 3710 or holes 3711 and 3712, which encircles the two arms 3713 of the cell 3704 and matches the pitch of the screw or spring 3701, 3702, and 3703, moves along the length of the struts 3713 of the cell 3704. As the nut block 3707, 3708 and 3709 moves toward the middle of the cell 3704, it draws it together and spread the stretching member 3700 closer. As it moves towards the crown by rotating the screw or spring 3701, 3702, and 3703, it draws the cell 3704 apart, drawing the stretching member 3700 farther apart after initial deployment.

Figure 38:
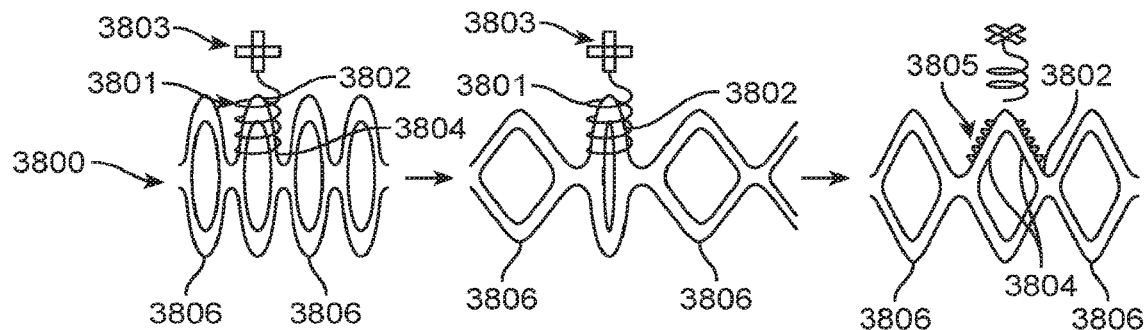
FIG. 38 shows a spring that fixes one or more cells of the stretchable member before and after the deployment of the stretchable member. Upon it removal, it allows the stretching member to go farther apart after initial deployment.

FIG. 38 shows a spring 3801 that surrounds a cell 3802 of the stretching member 3800. It has a lever handle 3803 that can be used to turn the spring 3801. The struts 3804 of the cell have linear teeth 3805 that match the pitch of the spring. During deployment, it fixes the cell 3802 while those adjacent freely openable cells 3806 that are not fixed with this spring open to their maximum predetermined size. As the spring 3801 is rotated with the lever handle 3803, it moves toward the middle of the cell 3802, it draws it together and spread the stretching member 3800 closer. As it moves towards the crown by rotating the spring 3801, it draws the cell 3802 apart, drawing the stretching member 3800 farther apart after initial deployment. When removed, it can let the cell 3802 open freely to the opening of the maximum predetermined size.

Figure 39:
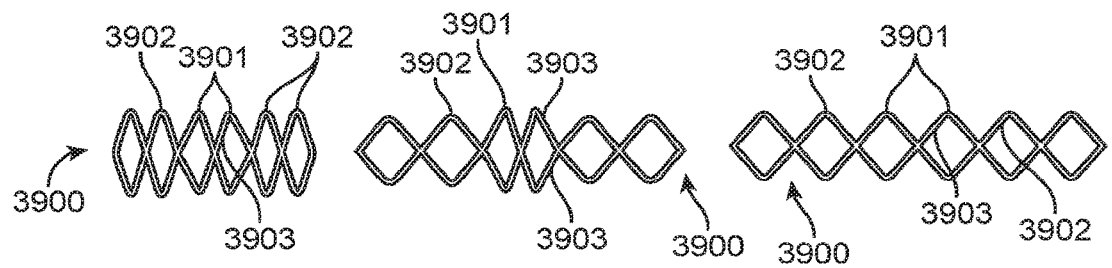
FIG. 39 illustrates the use of shape memory elements embedded between adjacent cells of the stretchable member. The element remains the same distance before and after deployment of the stretchable member. After heating to a temperature above the transition temperature, it widens and allows the stretching member to become father apart.

FIG. 39 illustrates the use of shape memory cells 3901 that are placed adjacent to superelastic cells 3902 of the stretchable member 3900. The shape memory cell 3901 remains closed before and after deployment of the stretchable member 3900. When heated to a temperature above the transformation temperature of the shape memory material 3903, the shape memory cell 3901 widens to its trained size and allows the stretching member 3900 to become father apart.

Figure 40:
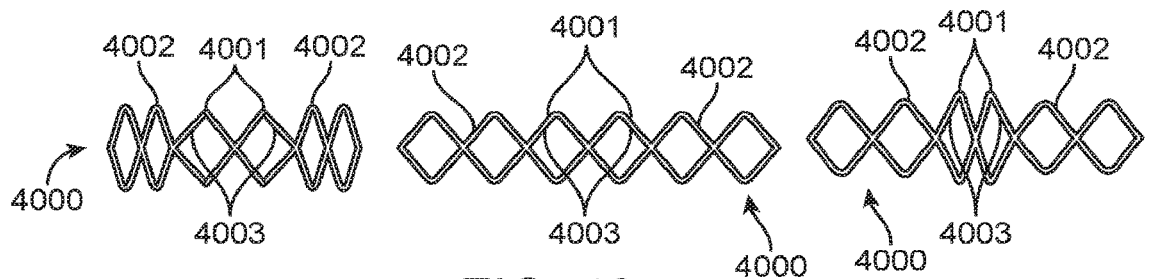
FIG. 40 illustrates the use of shape memory elements embedded between adjacent cells of the stretchable member. The element remains the same distance before and after deployment of the stretchable member. After heating to a temperature above the transition temperature, it narrows and draws the stretching member to closer together.

FIG. 40 illustrates the use of shape memory cells 4001 that are placed adjacent to superelastic cells 4002 of the stretchable member 4000. The shape memory cell 4001 remains open before and after deployment of the stretchable member 4000. When heated to a temperature above the transformation temperature of the shape memory material 4003, the shape memory cell 4001 narrows to its trained size and allows the stretching member 4000 to become closer.

Figure 41:
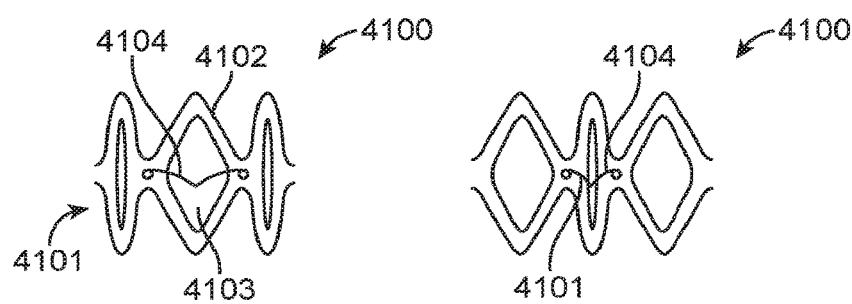
FIG. 41 illustrates the use of shape memory elements connecting to a cell of the stretchable member. The element remains the same distance before and after deployment of the stretchable member. After heating to a temperature above the transition temperature, it narrows or widens and draws the stretching member closer together or farther apart to optimally adjust the valve dimensions.

FIG. 41 illustrates the use of shape memory wire or arm 4101 that connects to the struts 4102 of a cell 4103 of the stretchable member 4100. This wire or arm 4101 remains the same distance before and after deployment of the stretchable member 4100. After heating to a temperature above the transformation temperature of the shape memory material 4104, it narrows or widens (not shown) and draws the stretching member 4100 to closer or farther apart.

Figure 42:
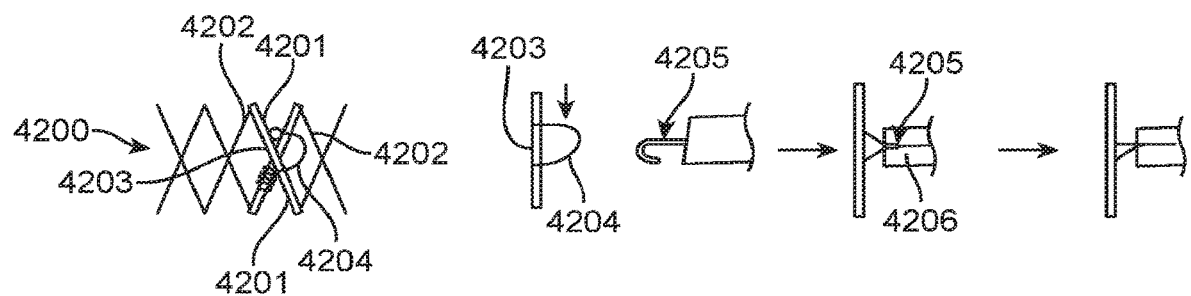
FIG. 42 shows an element consisting of two arms that pivots to open or close similar to FIG. 35A. It is fixed with a wire that can pivot the arms when it is twisted, causing the stretchable member to draw closer together or farther apart to optimally adjust the valve dimension.

FIG. 42 shows two arm pivoting element 4201 similar to FIG. 35A that are connected to adjacent cells 4202 of the stretchable member 4200. A wire 4204 is attached to the point of intersection 4203 between the arms 4201. After deployment of the stretchable member 4200, the wire 4204 can be latched with a hook 4205 and twisted 4206 to compress the point of intersection, which causes the arms to pivot and open. This results in drawing the stretchable member 4200 to farther apart. The wire can also be arranged to close the arms, which results in drawing the stretchable member 4200 closer.

Figure 43A:
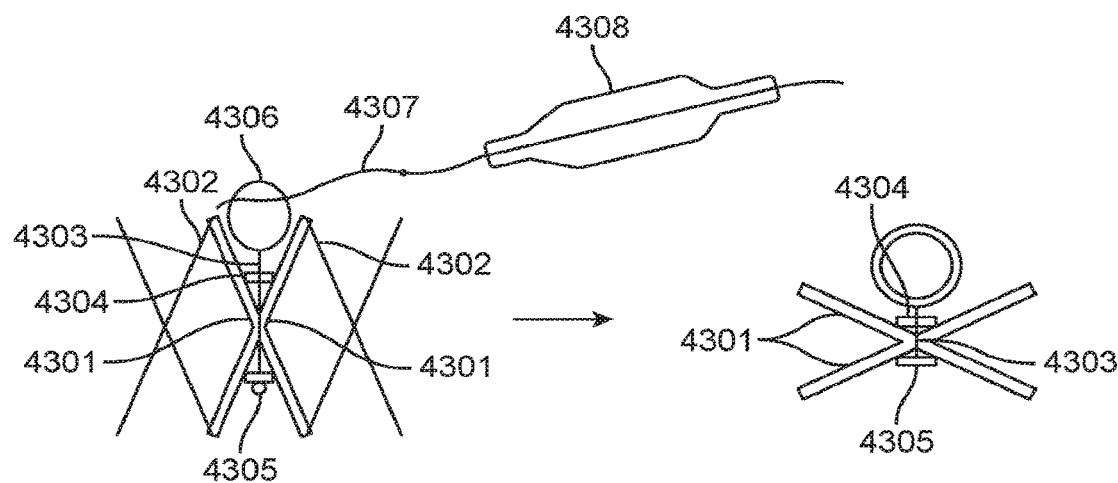
FIG. 43A shows an element consisting of two arms that pivots to open or close similar to FIG. 35A. It has a wire attached to two grippers that is secured to the arms at the point of their intersection. The wire is pulled by the use of an expandable balloon, causing the stretchable member to draw farther apart.
Figure 43B:
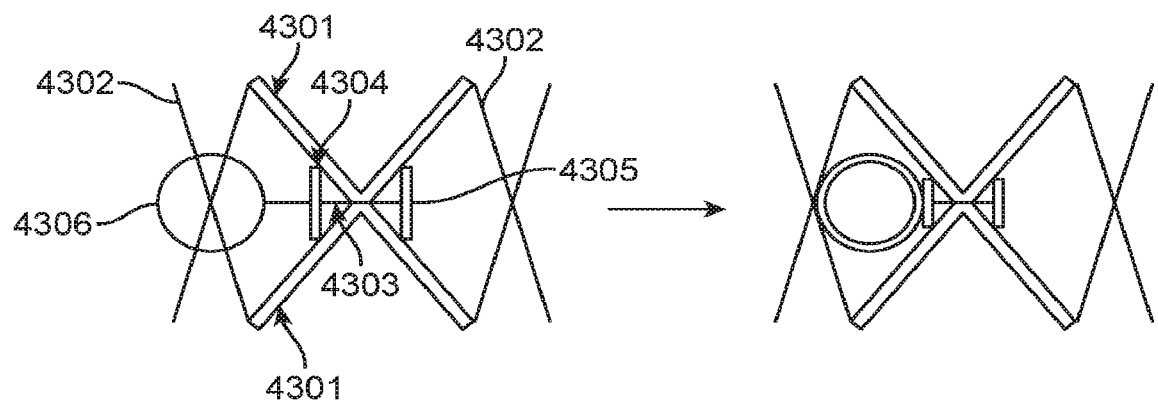
FIG. 43B shows an element consisting of two arms that pivots to open or close similar to FIG. 35A. It has a wire attached to two grippers that is secured to the arms at the point of their intersection. The wire is pulled by the use of an expandable balloon, causing the stretchable member to draw closer together.

FIG. 43A shows two arm pivoting element 4301 similar to FIG. 35A that is connected to adjacent cells 4302 of the stretchable member 4300. After deployment of the stretchable member 4200, a wire 4303 with two grips 4304 and 4305 are secured to the arms at the point of intersection 4306. The wire also has a loop 4306 at one end. A guidewire 4307 can be used to locate inside of the loop 4306. The balloon 4308 of a catheter can then be guided to the inside of the loop with this guidewire. Upon balloon expansion, the loop enlarges, and the arm at the point of intersection is compressed or released, causing the arms to pivot and open or closed. This results in drawing the stretchable member 4300 farther apart. FIG. 43B shows the wire 4303 at an alternate fixation point to close the arms 4301 when the balloon 4308 is expanded, which results in drawing the stretchable member 4300 closer.

Figure 44:
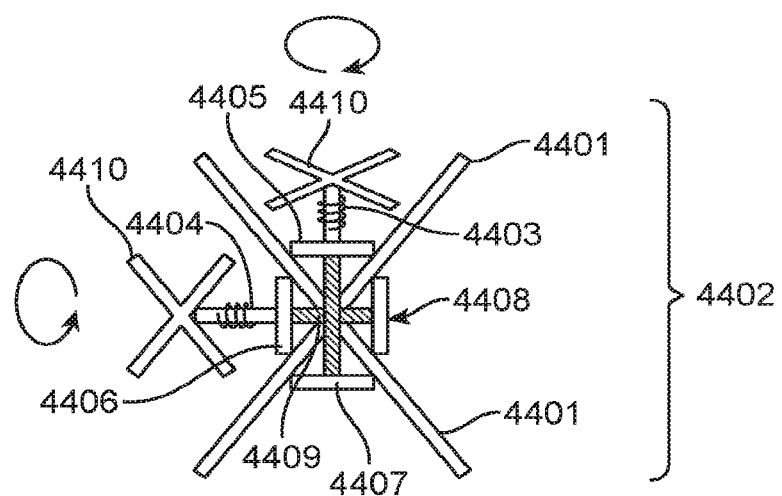
FIG. 44 shows an element consisting of two arms that pivots to open or close similar to FIG. 35A. A double lead screw or spring mechanism with ball nuts apply or release forces on the point of intersection of the arms, causing the stretchable member to draw closer together or farther apart.

FIG. 44 illustrates two arms 4401 forming a pivoting element 4402 similar to FIG. 35A that is connected to adjacent cells (not shown) of the stretchable member 4400. Two lead screws or springs 4403 and 4404, each with two ball nuts, 4405, 4406, 4407, and 4408, compress the arms 4401 together at the point of intersection 4409. Each lead screw or spring is attached to a lever handle 4410. When the lead screws or springs 4403 and 4404 are rotated with one or both handles 4410, the arms 4401 pivot to open or close the pivoting element 4402. This mechanism tightens or loosen the element 4402 such that it causes the stretchable member 4400 to draw closer together or farther apart.

Figure 45A:
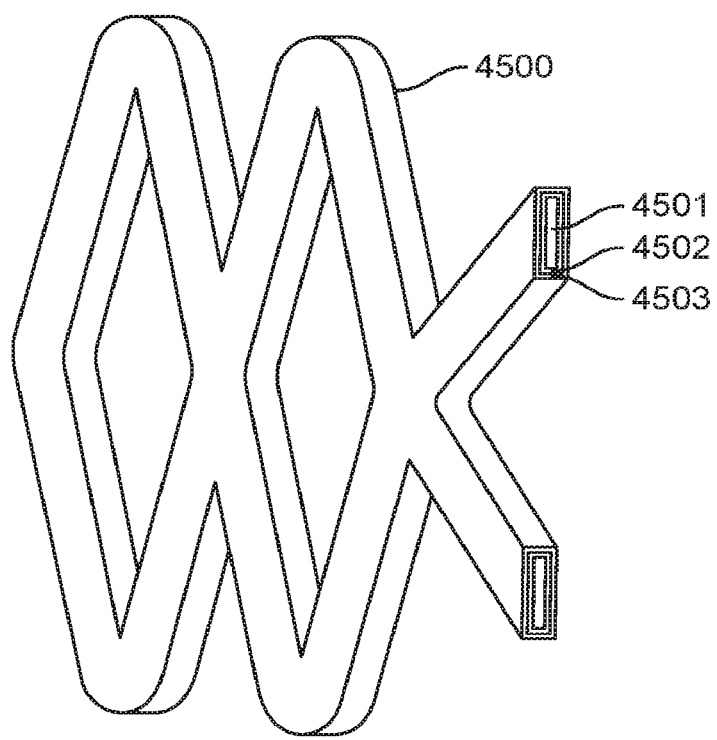
FIG. 45A shows a section view of one of the implants showing coating on the surface of the implant.

FIG. 45A illustrates a coated implant 4500 having a core 4501 and a first coating layer 4502 bonded to the core 4501. This coating can alter the surface properties of the implant, act as a drug delivery matrix, or provide a media for tissue ingrowth. It may also be advantageous to add a second coating 4503 on top of the first coating 4502 if one coating alone cannot provide all of the desired properties. In one example, the first layer of coating 4502 may bond well to the core 4501 and to the second coating layer 4503, and the second coating layer 4503 would alter the surface properties of the implant, act as a drug delivery matrix, or as a media for tissue ingrowth. Additional layers of coatings are conceivable. An example of a three-layer coating system would have a first layer (not shown) of corrosion protective material (metal plating, an oxide layer, etc.), and the two additional coating 4502 and 4503 as described above.

Figure 45B:
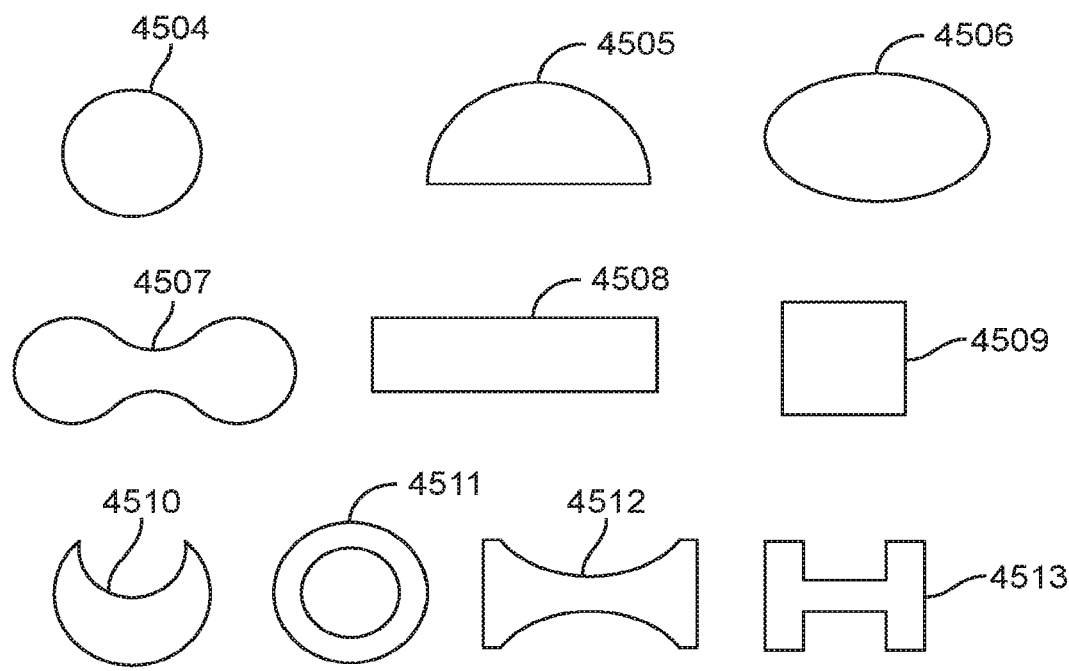
FIG. 45B shows a variety of cross sections that may be applicable to valve reshaping implants.

FIG. 45B illustrates a variety of alternate cross-sectional shapes, including circular 4504, semi-circular 4505, oval or elliptical 4506, pinched rounded 4507, rectangular 4508, square 4509, crescent shaped 4510, tubular 4511, hourglass 4512, or H-beam shaped 4513. Other cross-sectional shapes are also known to the art. Cross sectional shapes may be applied to any portion or portions of the stretching member to achieve desired structural properties, tissue interaction properties, shapes in bending, interaction with delivery and/or removal devices, interaction with tissue engagement mechanisms, interaction with additional valve shaping devices, interaction with coatings, drug release dynamics, or other properties of the valve shaping device.

Figure 46:
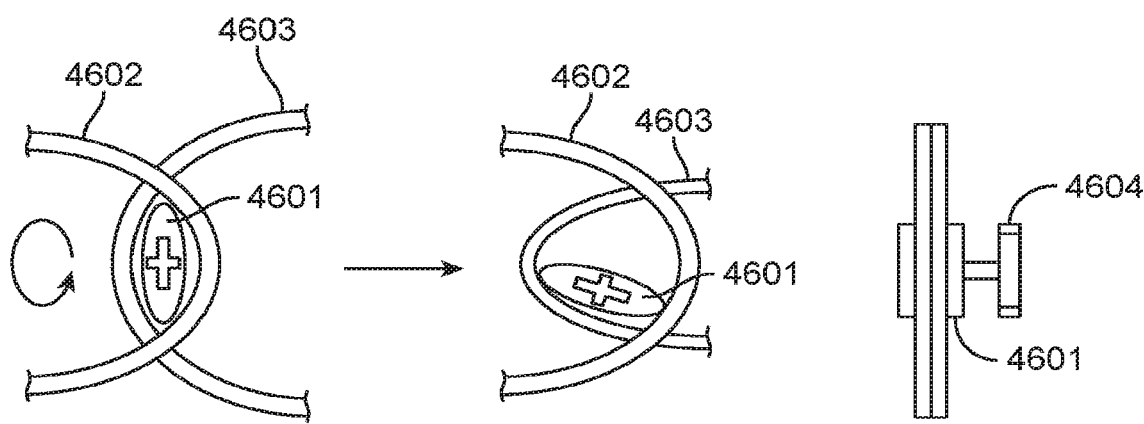
FIG. 46 shows a cam element attached to adjacent cells of the stretchable element. When the cam is rotated, it narrows or widens the distance between the cells, causing the stretchable member to draw closer together or farther apart.

FIG. 46 illustrates a cam drive element 4601 that is embedded between two overlapping adjacent cells 4602 and 4603 of the stretchable member 4600. It has a lever handle 4604 that rotates it. When the cam 4601 is rotated in clockwise or counter-clockwise direction, the distance between the adjacent cells 4602 and 4603 widens (not shown) or narrows (as shown) and results in drawing the stretchable member 4600 farther apart or closer.

Figure 47:
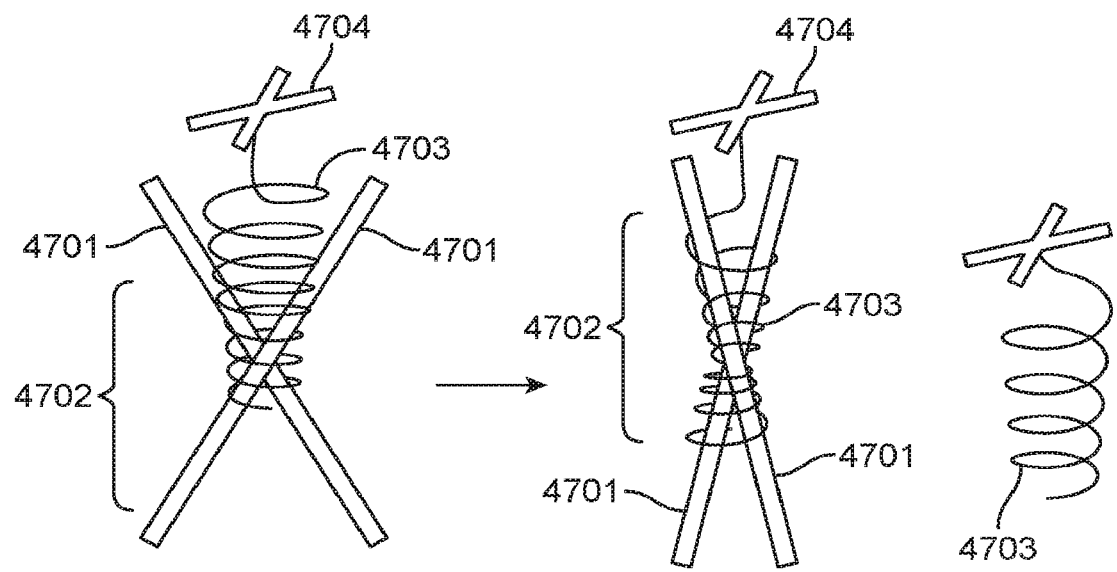
FIG. 47 shows an element consisting of two arms that pivots to open or close similar to FIG. 35A. A conical spring is wound over the arms. When rotated, it pivots the arms to open or close, causing the stretchable member to draw closer together or farther apart.

FIG. 47 illustrates two arms 4701 forming a pivoting element 4702 similar to FIG. 35A that is connected to adjacent cells (not shown) of the stretchable member 4700. A conical spring 4703 is wound over the arms 4701 and has a lever handle 4704. When the spring 4703 is rotated clockwise or counter-clockwise, the arms pivot to close or open, causing the stretchable member 4700 to draw closer together or farther apart.

Figure 48:
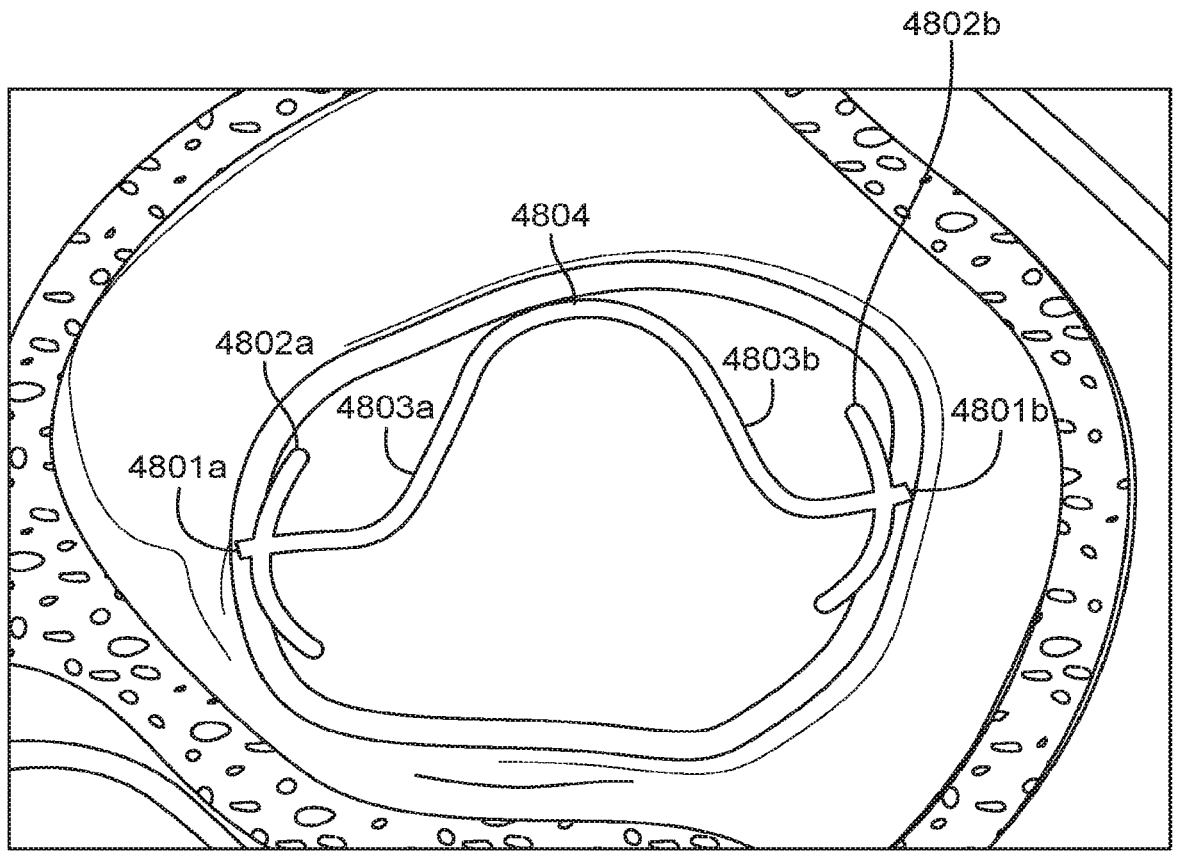
FIG. 48 shows an implant with a recurved spine which provides outward force to the anchor points.

FIG. 48 shows a stretching member with two anchor points 4801a and 4801b, tissue support members 4802a and 4802b, a primary curved section 4804 generally following the curvature of the annulus, and two reverse curve sections 4803a and 4803b curved in a different direction than the primary curved section 4804. The angular deflection of the primary curved section 4804 and the two secondary curved sections 4803a and 4803b partially offset, maintaining a more constant angle under flexure between the two anchor points 4801a and 4801b and tissue support members 4802a and 4802b than with a single curved section.

Figure 49:
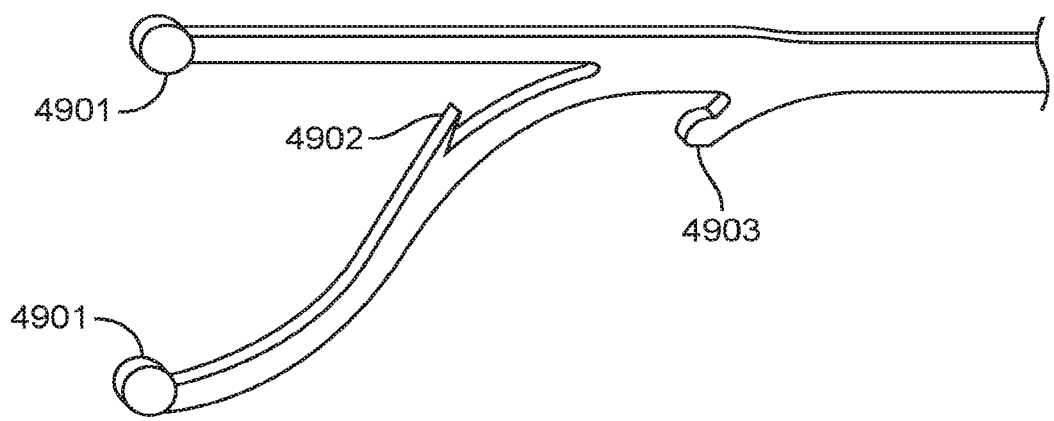
FIG. 49 shows a hook for capturing annular tissue with a barb to prevent inadvertent release of the device from the tissue.

FIG. 49 shows one end 4901 of a stretching member configured to interact with tissue featuring a barb 4902 to prevent inadvertent loss of tissue contact with the end 4901 of the stretching member during device placement. The barb 4902 may be present on one end only of the stretching member, or on two or more ends as needed. FIG. 49 additionally shows a placement hook 4903 which interacts with a placement device (not shown) by trapping a segment of the placement device between the placement hook 4903 and the main body of the stretching member to control position of the stretching member during placement.

Figure 50A:
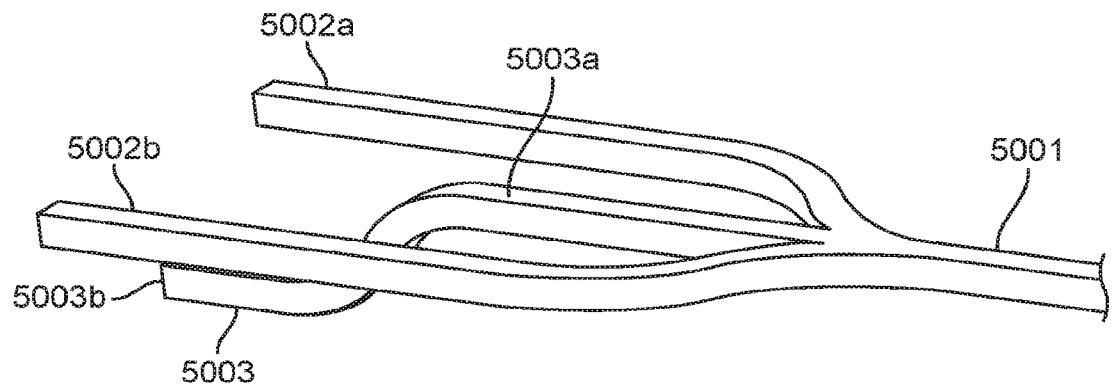
FIG. 50A shows a three-pronged end of an implant (device) arranged so that the two outer prongs are coplanar, and the middle prong is not coplanar.
Figure 50B:
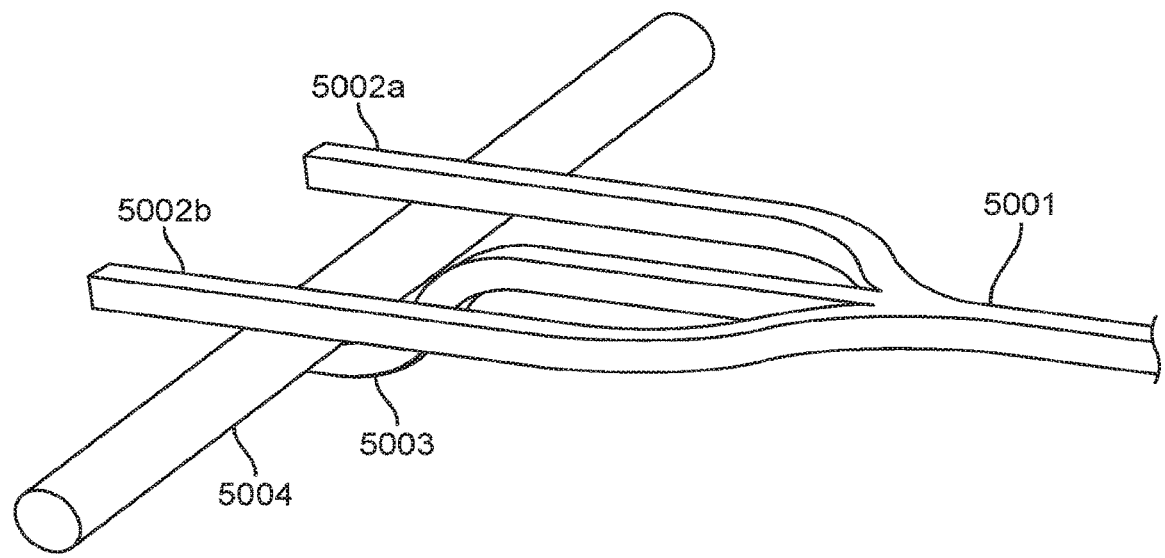
FIG. 50B shows the implant of FIG. 50A with an elastic tissue member in place in the distal portion of the prongs.
Figure 50C:
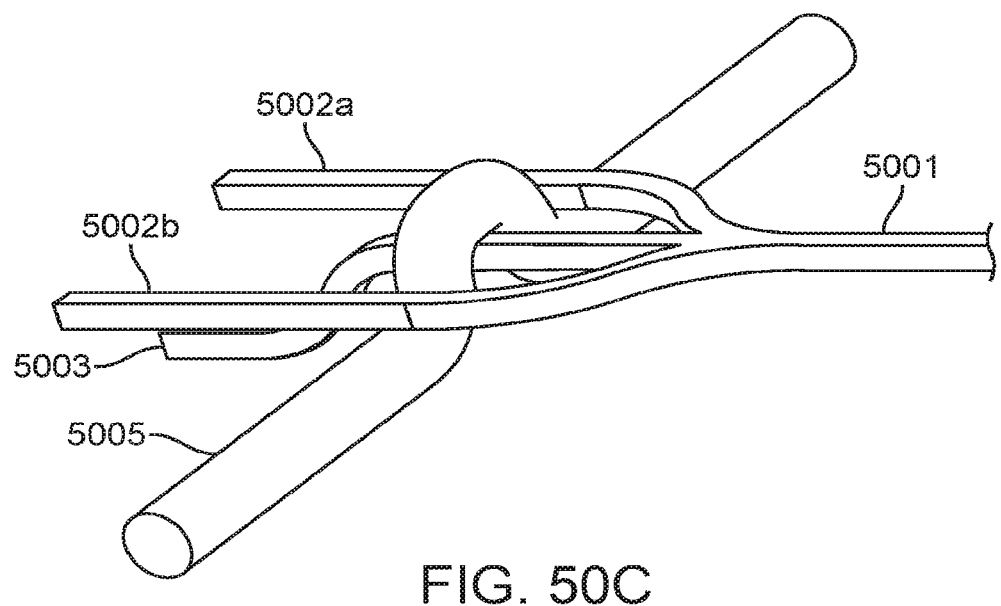
FIG. 50C shows the device (implant) of FIG. 50A with the elastic tissue member of FIG. 50B moved proximally in the prongs, resulting in a plication in the elastic tissue member.

FIG. 50 shows a tissue placating end of a stretching member 5001 consisting of three tines 5002a, 5002b, and 5003. As shown in FIG. 50A, tines 5002a and 5002b are approximately coplanar, while tine 5003 has a coplanar section 5003a and a non-coplanar section 5003b. FIG. 50B shows a tissue member 5004 in position adjacent to the non-coplanar section 5003b so that it is approximately un-deflected by the three tines 5002a, 5002b, and 5003. As the stretching member applies force to the surrounding tissue, the tissue member 5004 may be moved proximally along the tines to a plicated configuration 5005 as it approaches the coplanar section 5003 of the tines. This plication results in an overall shortening of the tissue member 5004 in addition to the stretching effect of the stretching member 5001. The tines 5002a, 5002b, and 5003 as shown have non-penetrating ends, but could be offered in an array of other ends common to the art, examples including sharp penetrating ends, barbed anchor ends, or helical anchor ends.

Figure 51A:
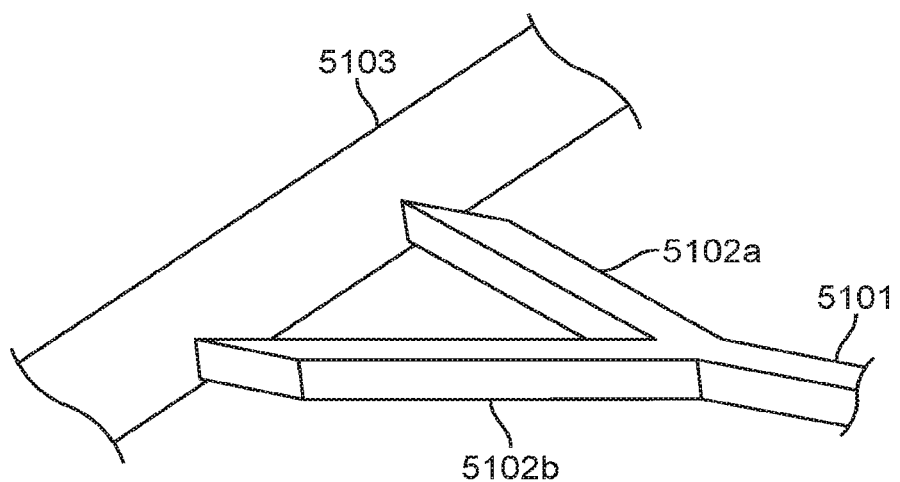
FIG. 51A shows a two-pronged implant with penetrating tips arranged at an angle to each other in proximity to an elastic tissue member.
Figure 51B:
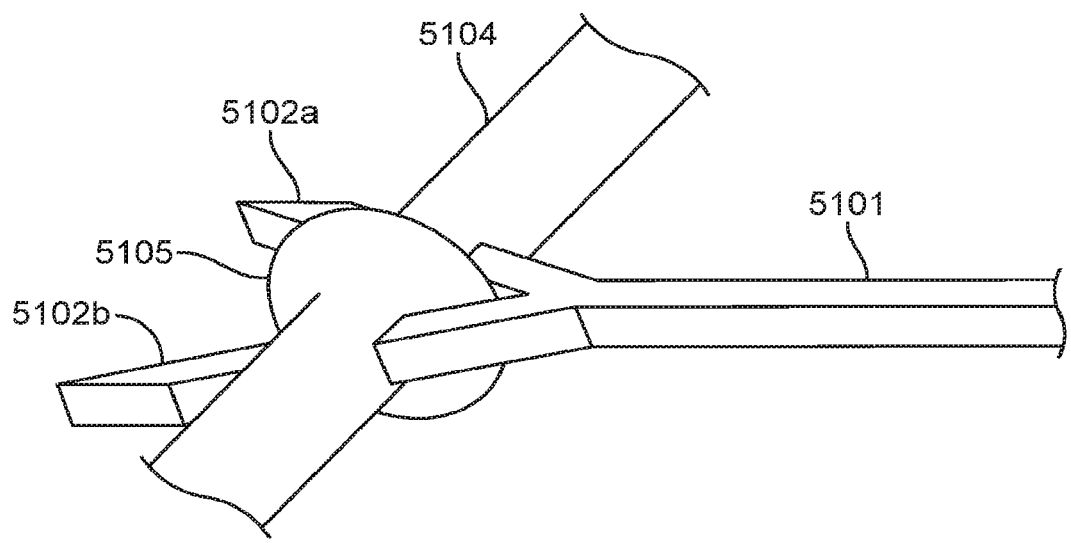
FIG. 51B shows the implant of FIG. 51A having penetrated the elastic tissue member, resulting in bunching the elastic tissue between the two angled prongs.

FIG. 51 illustrates one end of a stretching member 5101 with two diverging tines 5102a and 5102b. FIG. 51A shows the two diverging tines 5102a and 5102b with tissue penetrating ends in proximity to the free tissue member 5103. FIG. 51B shows the two diverging tines having entered penetrated tissue member 5104. As the penetrated tissue member moves proximally up the diverging tines 5102a and 5102b, the angle between the tines compresses the tissue member causing bunching 5105, resulting in an overall shortening of the penetrated tissue member 5104, in addition to the stretching effect of the stretching member 5101. The diverging tines 5102a and 5102b are shown with tissue penetrating ends, but could be offered in an array of other ends known to the art, examples including rounded ends, barbed anchor ends, or helical anchor ends.

Figure 52:
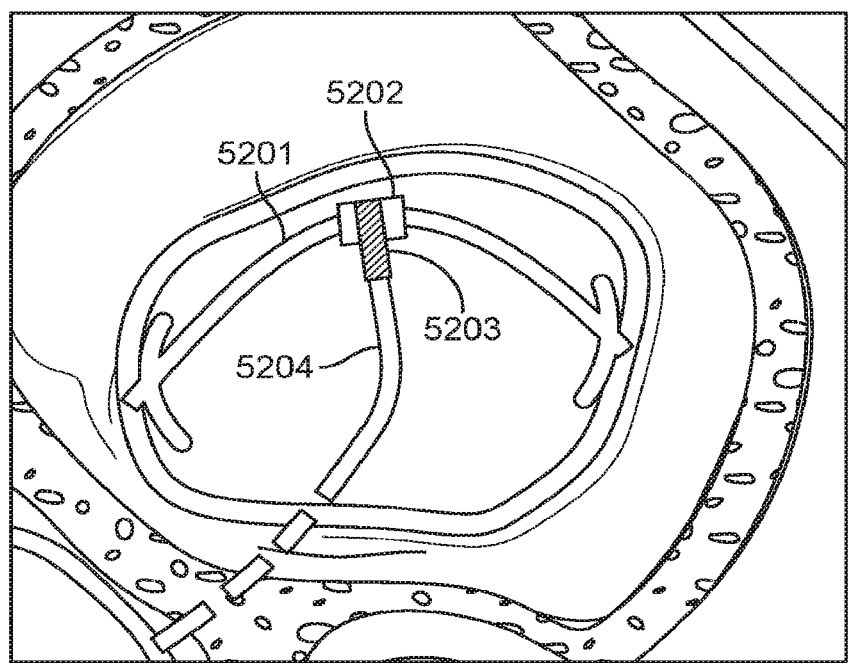
FIG. 52 shows a stretching device with a removable wire attached between the anchor points.

FIG. 52 illustrates a stretching member 5201 having a wire attachment point 5202 which releasably engages with a wire end 5203 which is attached to wire 5204. The wire 5204 would enhance control of the position of the stretching member 5201 during delivery and verification of position and appropriate function of the stretching member 5201. If the results of placement of the stretching member 5201 are acceptable, the wire 5204 and wire end 5203 can be disengaged from the wire attachment point 5202 and removed. If the results of placement are not acceptable, the wire can be used to retrieve the stretching member 5201. A number of suitable releasable attachment mechanisms exist in the art which would be applicable to this device configuration. Examples of releasable attachment mechanisms include screws, snap fits, and interference fits. The wire 5204 may also be anchored to the valve annulus prior to introduction of the stretching member 5201, and the stretching member 5201 advanced over the wire into position, where it attaches to the anchor.

Figure 53:
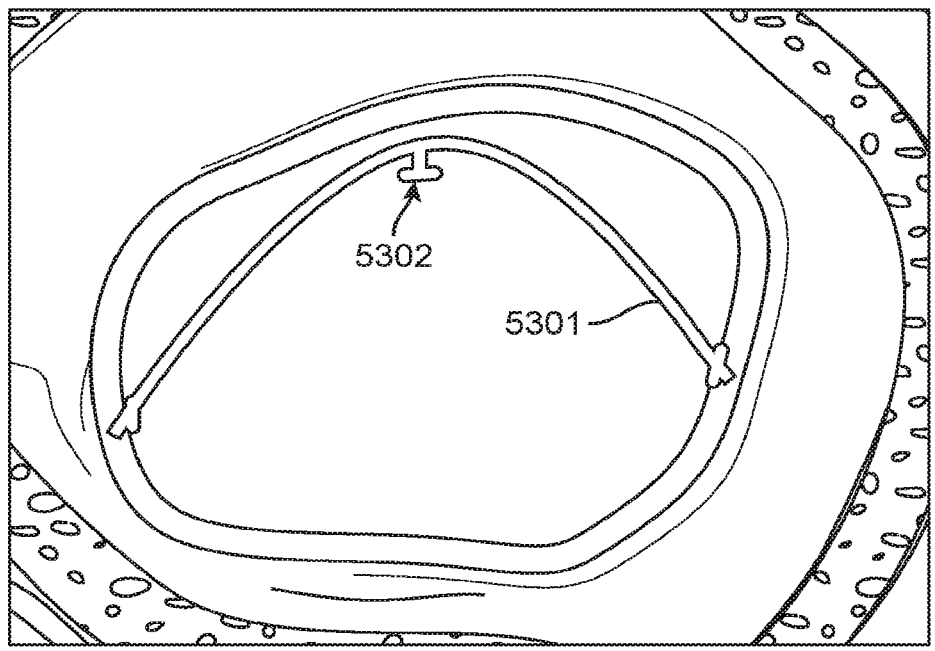
FIG. 53 shows a stretching device with a retrieval device interface feature between the anchor points that can be grasped and released.

FIG. 53 illustrates a stretching member 5301 with a retrieval device interface 5302 arranged between the ends of the stretching member 5301. A retrieval device (not shown) could attach to this retrieval device interface 5302 in order to retrieve a stretching member 5301. As shown, the retrieval device interface 5302 is a simple T-handle that could be accessed with a snare, but numerous appropriate mechanisms are documented in the art. Examples of such mechanisms include magnetic interfaces, threaded fasteners, ball and socket joints, wire snares, latches, or hooks and eyes.

Figure 54:
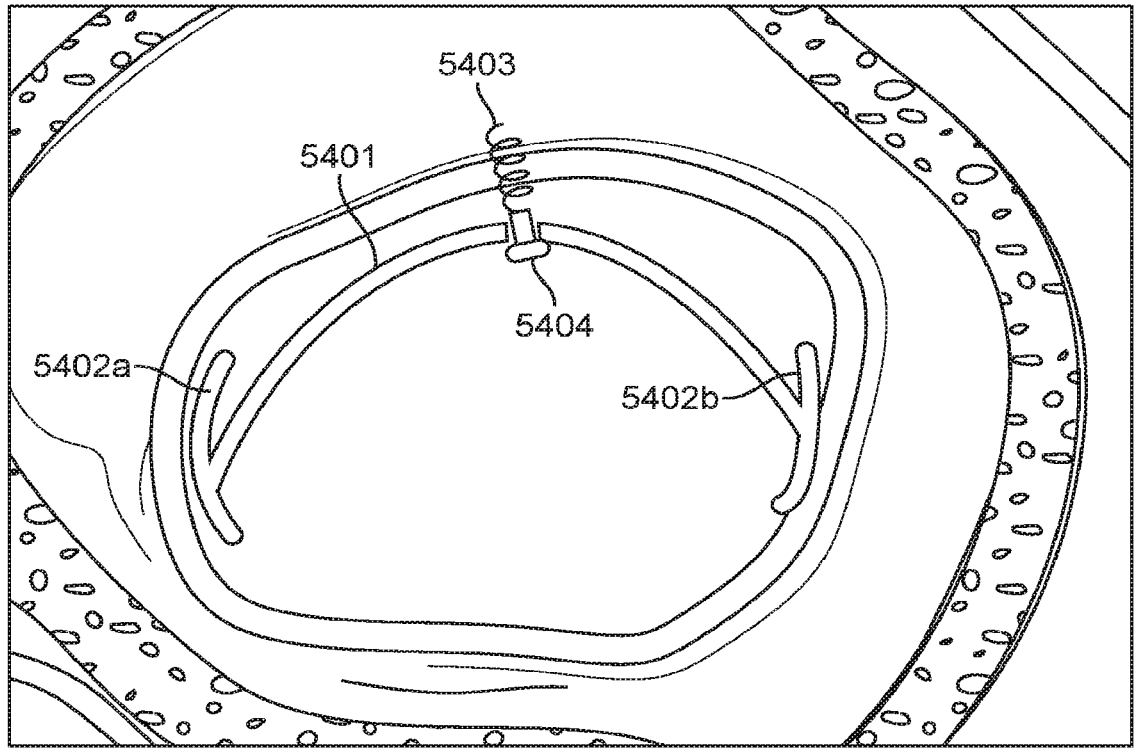
FIG. 54 shows a stretching device with a third anchor point between the primary anchor points near the ends of the stretching member.

FIG. 54 shows a stretching member 5401 with ends 5402a and 5402b, and an attachment point 5403 arranged between the two ends 5402a and 5402b. The attachment point 5403 includes a releasable placement feature 5404 which engages with an attachment device (not shown) to facilitate attachment of the attachment point 5403 to the target tissue. As shown, the attachment point 5403 consists of a helical anchor, and the releasable placement feature 5404 is a T-handle, but other configurations known to the art may be advantageous. Examples of alternate configurations for the attachment point 5403 include tissue penetrating points with or without barbs, tissue penetrating hooks with or without barbs, staples, or clips. Examples of alternate configurations for the releasable placement feature include magnetic interfaces, threaded fasteners, ball and socket joints, wire snares, or hooks and eyes.

Figure 55:
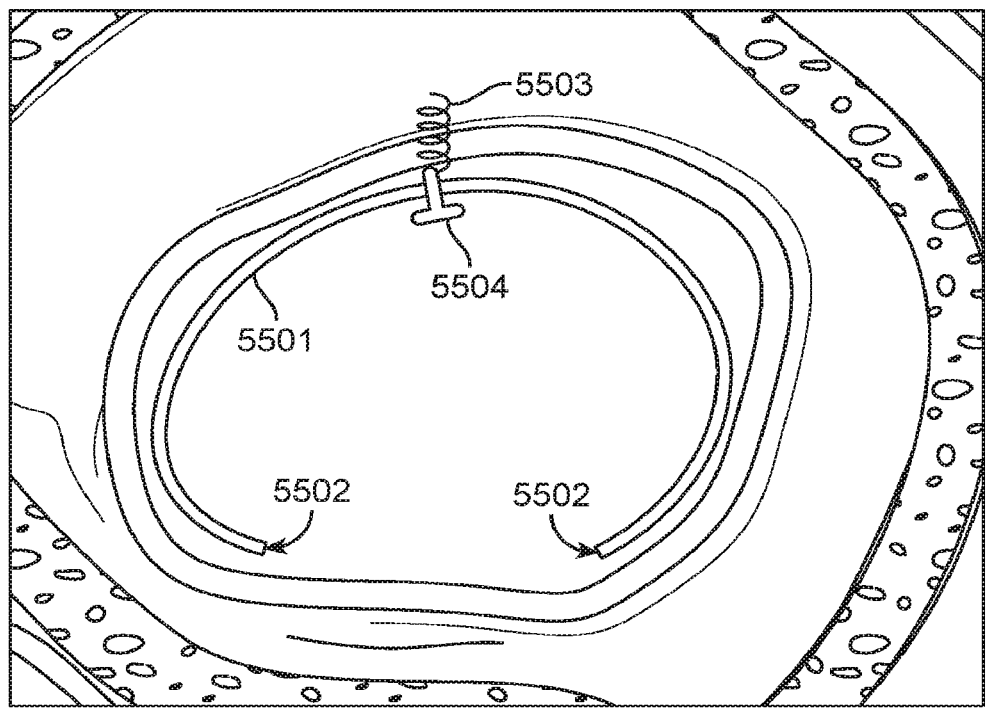
FIG. 55 shows a partial ring-shaped stretching device with an anchor point near mid-span.

FIG. 55 illustrates a valve shaping C-ring 5501 with two ends 5502 and an anchor point 5503 arranged in the span between the two ends of the valve shaping C-ring 5501. The anchor point 5503 has a releasable placement feature 5504 which engages with an attachment device (not shown) to facilitate attachment of the anchor point 5503 to the target tissue. As shown, the anchor point 5503 consists of a helical anchor, and the releasable placement feature 5504 is a T-handle, but other configurations known to the art may be advantageous. Examples of alternate configurations for the anchor point 5503 include tissue penetrating points with or without barbs, tissue penetrating hooks with or without barbs, staples, or clips. Examples of alternate configurations for the releasable placement feature include magnetic interfaces, threaded fasteners, ball and socket joints, wire snares, or hooks and eyes.

Figure 56:
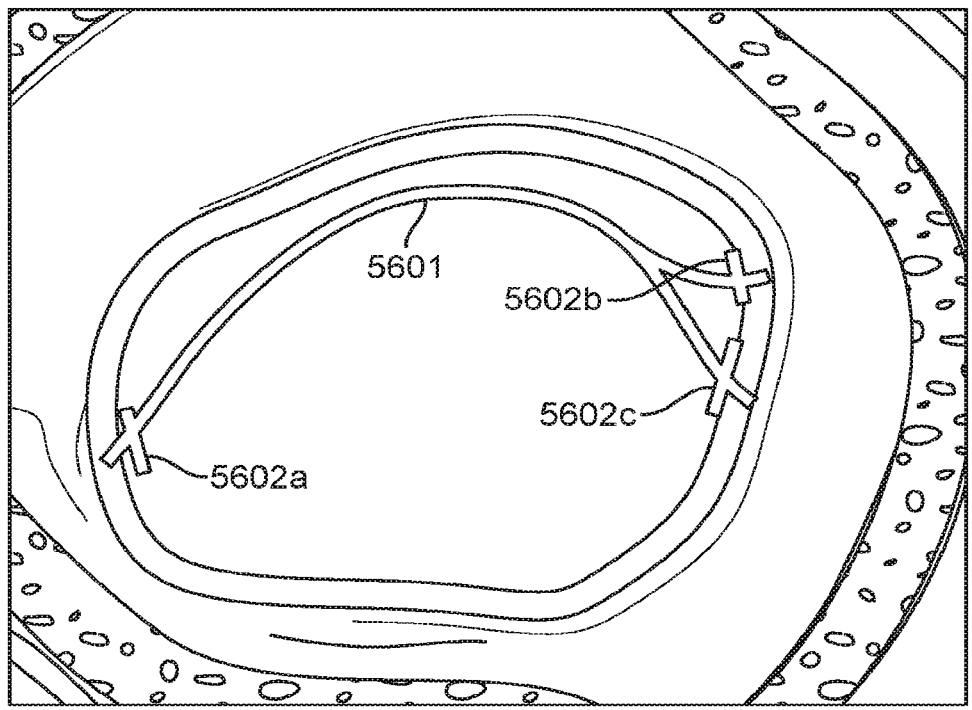
FIG. 56 shows a stretching device with a third anchor point branching from one of the primary anchor points near the ends of the stretching device.

FIG. 56 shows a stretching member 5601 with three branched attachment points 5602a, 5602b, and 5602c arranged to create a wider variety of forces among the attachment points than is possible with two attachment points. In principle, all forces created by two attachment points must be substantially along the line between those points and therefore aligned substantially with a diameter of the valve, while three attachment points allow applied forces to have a tangential component as well. In one example, the tangential component applied to attachment points 5602a and 5602c may have substantial component in the direction of the aortic valve (down the page as shown in FIG. 56), which is balanced by an opposed force applied at anchor point 5602b. Other combinations of force vectors may be advantageous. In one example, a substantial stretching force created between two attachment points and a tension at the third, the tension at the third point creating a local reduction of diameter in the valve annulus.

Figure 57:
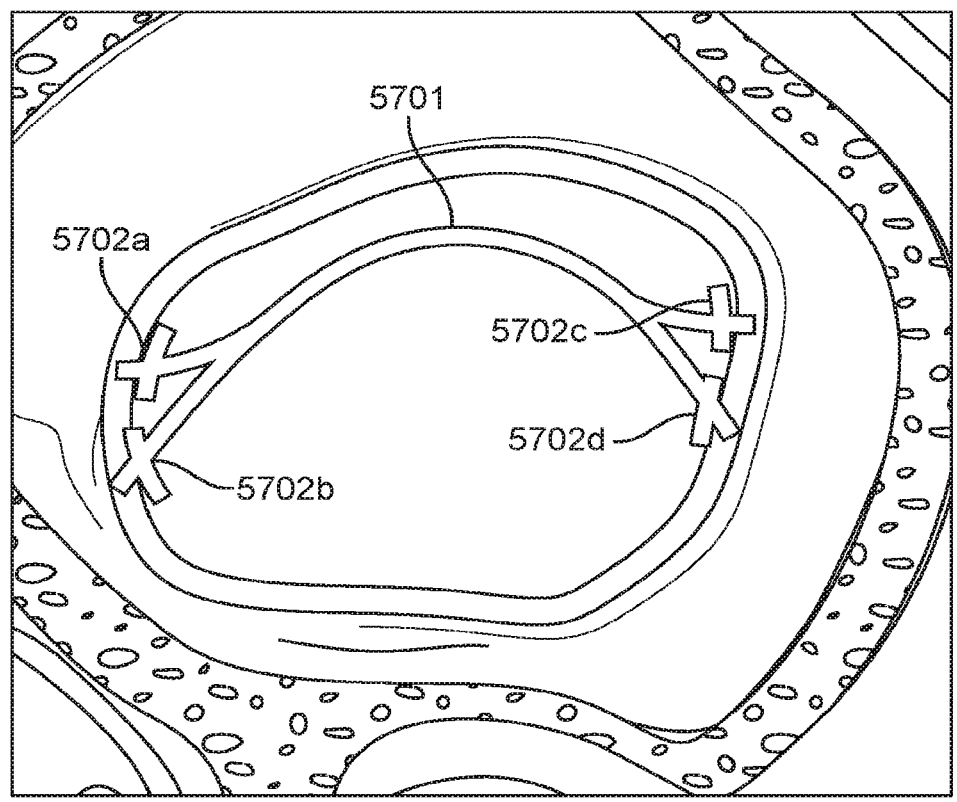
FIG. 57 shows a stretching device with third and fourth anchor points branching from each of the primary anchor points near the ends of the stretching member.

FIG. 57 shows a stretching member 5701 with four branched attachment points 5702a, 5702b, 5702c, and 5702d arranged to create a wider variety of forces among the attachment points than is possible with two or three attachment points. In one example, the attachment points may create an in-plane force couple, pushing attachment point 5702a away from the center of the valve while pulling attachment point 5702b toward the center of the valve, creating a twisting or torsional moment balanced by an opposed couple on the other end of the stretching member 5701, in particular pushing attachment point 5702c away from the center of the valve, while pulling attachment point 5702d toward the center of the valve. Other combinations of force vectors may be advantageous.

Figure 58A:
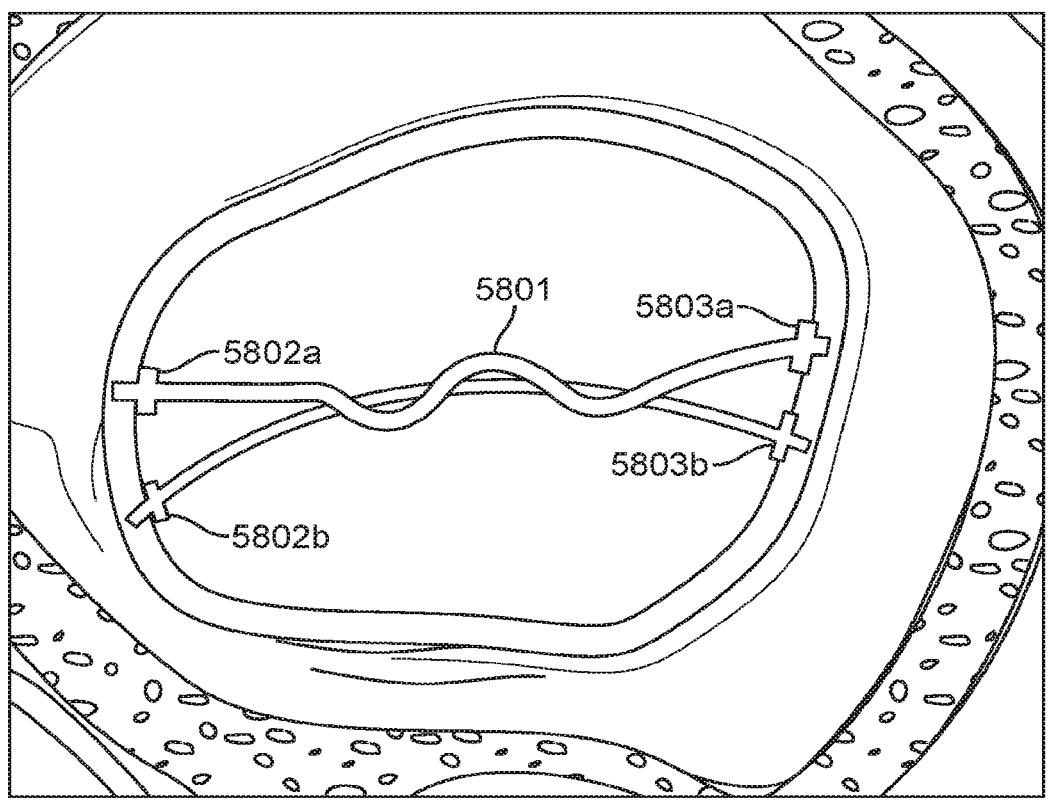
FIG. 58A shows a stretching device with four anchor points arranged to apply torsion between the pairs of anchors at each end point.

FIG. 58A shows a stretching member 5801 with four branched attachment points 5802a, 5802b, 5803a, and 5803b arranged to apply a torque between two pairs of attachment points. In one example, attachment point 5802a apply an upstream force on the valve annulus, while attachment point 5802b applies a downstream force on the valve annulus, creating a torque at one of the stretching member 5801 which is counterbalanced by a torque applied at the other end, with attachment point 5803a applying a downstream force on the valve annulus, and 5803b applying an upstream force on the valve annulus. In this example, upstream and downstream refer to the direction of flow through the valve. The net effect of these applied loads could deflect the valve annulus out of plane, in one example to restore or enhance a saddle shape present in healthy mitral valves.

Figure 58B:
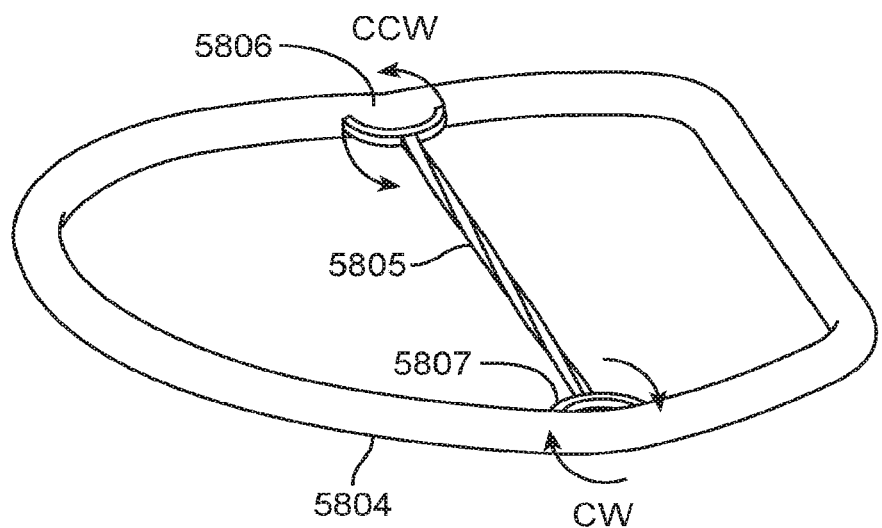
FIG. 58B shows an additional example of a valve shaping device with four anchor points arranged to apply torsion between the pairs of anchors at each end point.

FIG. 58B shows a further example of the device in FIG. 58A, in perspective view. In this example, torsion between the two ends is applied by a twisted torsion bar 5805, resulting in a counter-clockwise twist on the annulus 5804 at a first end 5806, and a clockwise twist on the annulus 5804 at a second end 5807. Each twist acts to shorten the annulus in the area of the applied twist. Further, each twist moves the annulus out of plane, potentially reducing flattening of the annulus and thereby improving valvular function.

Figure 59A:
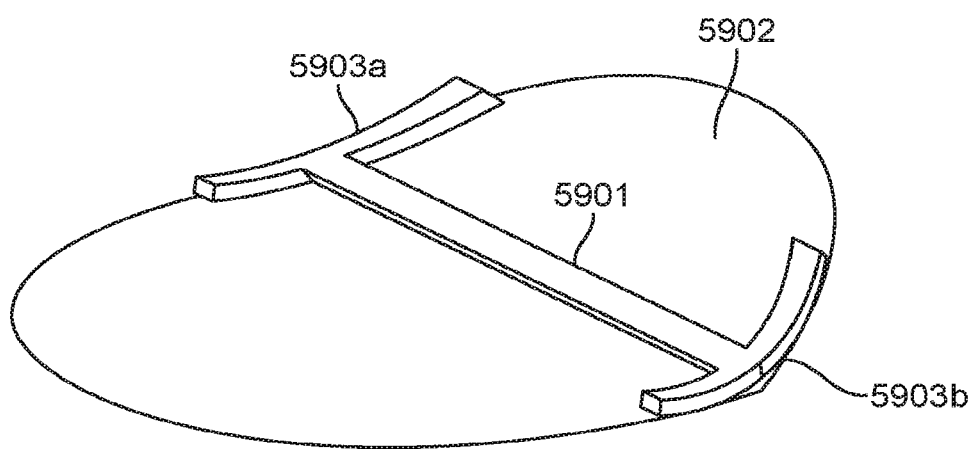
FIG. 59A shows a saddle shaped mitral annulus with a shaping device having ends that mate with the curvature of the saddle shape to substantially maintain the saddle shape after a stretching device is deployed to minimize or prevent MR or FMR.

FIG. 59A illustrates a mitral valve 5902 with a saddle shape and a stretching member 5901 applied at an out of plane bend in the valve annulus, the ends 5903a and 5903b of the stretching member 5901 having a corresponding out of plane curvature. In one example, the out of plane curvature of the ends of the stretching member enhances or maintains the saddle shape of the mitral valve 5902.

Figure 59B:
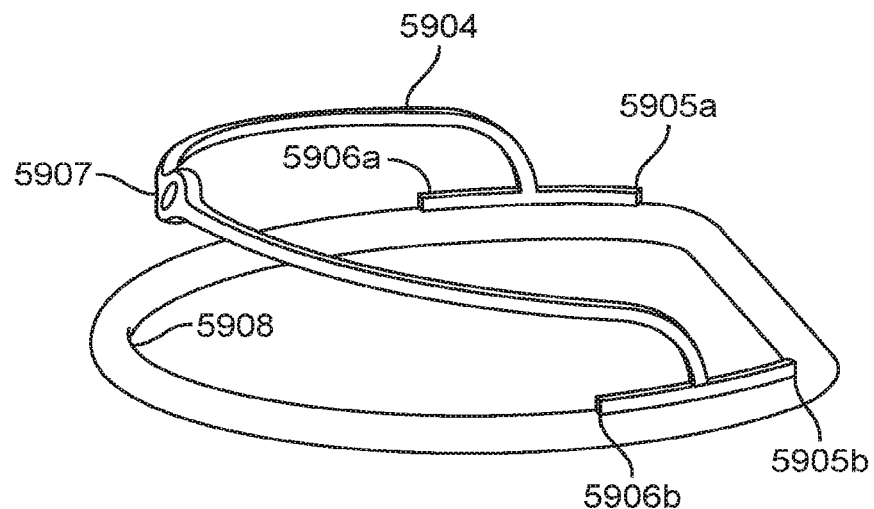
FIG. 59B shows a flattened mitral annulus with a shaping device having ends that mate with the annulus, and a third attachment point that is disposed at a distance from the annulus.
Figure 59C:
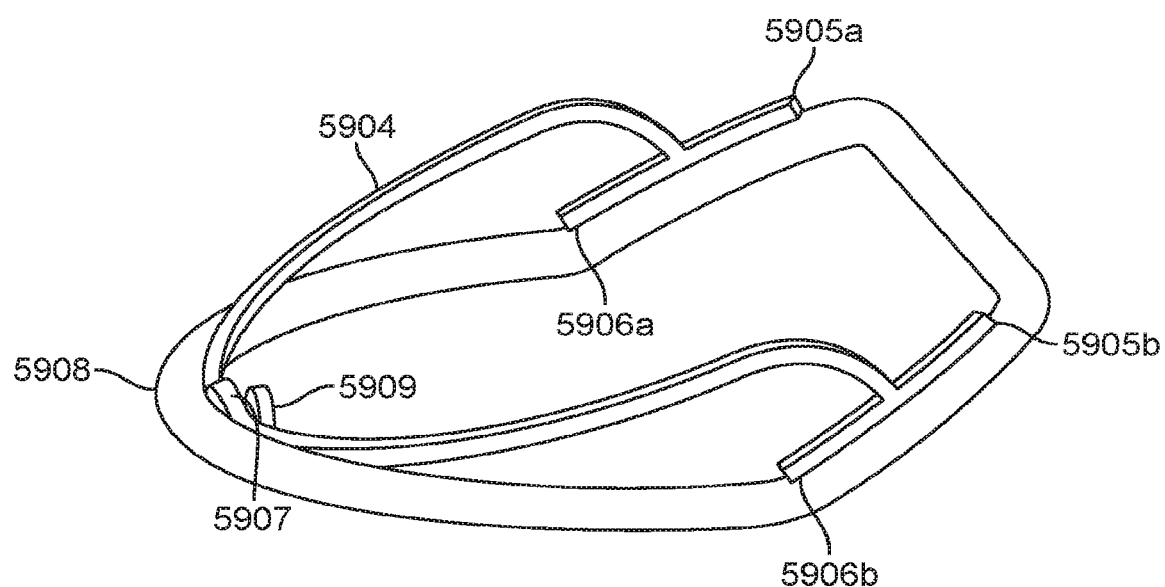
FIG. 59C shows the device of 59B with the third anchor point brought into opposition with the annulus, restoring a saddle shape.

FIG. 59B illustrates a flattened mitral valve with a posterior aspect 5908 and a shaping member 5904 applied to one area of the annulus. The shaping member 5904 has four attachment points, 5905a, 5905b. 5906a, and 5906b, and an attachment feature 5907 arranged to rest at a distance from the posterior aspect 5908 of the mitral valve annulus. The shaping member may additionally present an inward or outward force between the two ends, or match the native dimensions of the annulus and apply little or no inward or outward forces. Drawing the attachment feature 5907 toward the posterior aspect 5908 of the mitral annulus, as shown in FIG. 59C, causes upward force on the attachment points 5905a and 5905b, and downward force on the attachment points 5906a and 5906b, restoring, partially restoring, or enhancing a saddle shaped geometry to the mitral annulus. Drawing the attachment feature 5907 is only one example of the present invention. Attaching the attachment feature 5907 to other points within the atrium and ventricle may have advantageous effects. Examples of other attachment points include the atrial septum and the wall of the atrium adjacent to the coronary sinus.

FIGS. 60A-I illustrate a variety of valve shaping devices shown in place above the mitral valve.

Figure 60A:
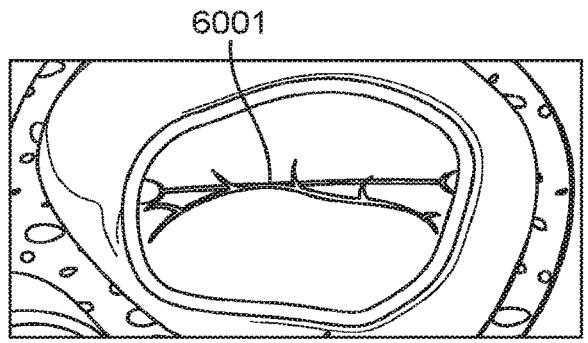
FIGS. 60A-60I show a variety of stretching device configurations illustrated in position on the mitral valve.

FIG. 60A shows a valve shaping device 6001 with a single stretching member in a substantially straight position.

Figure 60B:
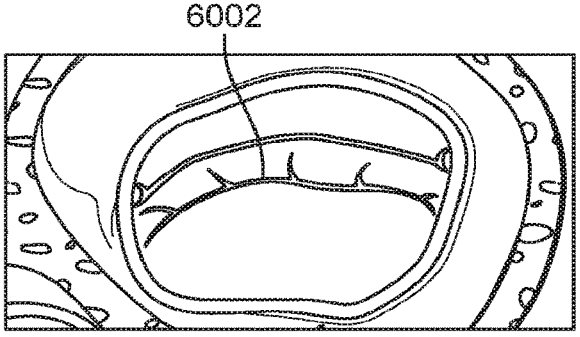

FIG. 60B shows a valve shaping device 6002 with a single stretching member in a curved position.

Figure 60C:
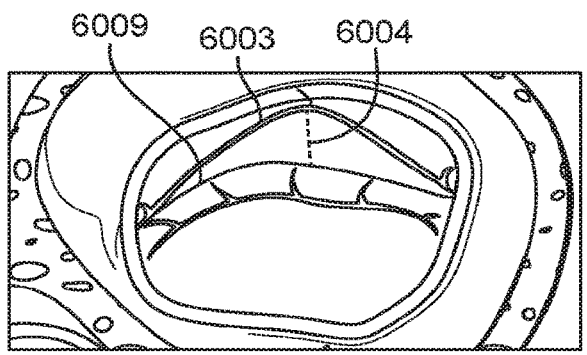

FIG. 60C shows a valve shaping device with dual stretching members 6003 and 6005, separated by a distance 6004, curved in substantially the same direction.

Figure 60D:
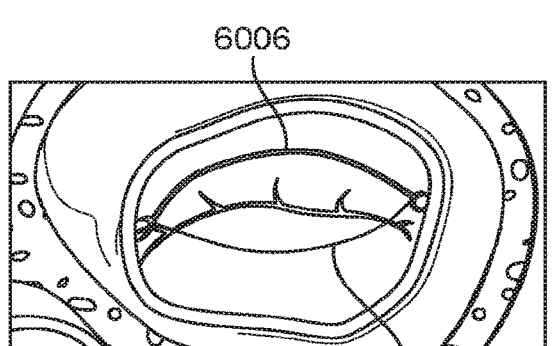

FIG. 60D shows a valve shaping device with dual stretching members 6006 and 6007, curved in substantially opposite directions.

Figure 60E:
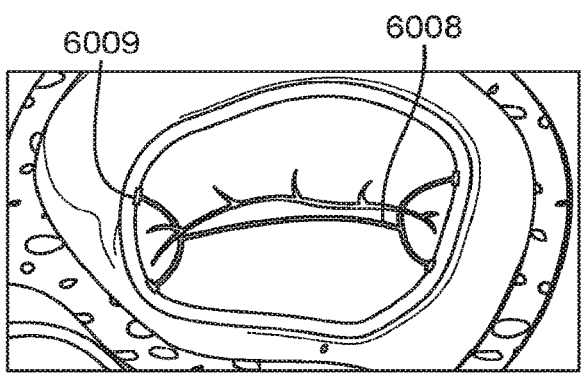

FIG. 60E shows a valve shaping device 6008 with a single stretching member in a substantially straight position, having at least one split end feature 6009, the split end feature having two distinct tissue engagement points. These distinct tissue engagement points can apply loads in different directions to the tissue, resulting in an applied moment, and/or an applied force with components that act out of the plane of the mitral valve.

Figure 60F:
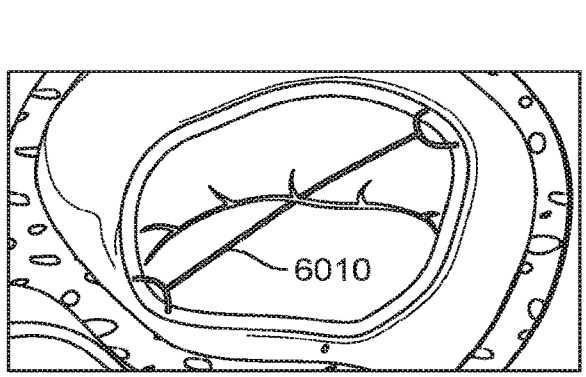

FIG. 60F shows a valve shaping device 6010 with a single stretching member in a substantially straight position, arranged at an angle to the valve commissures, the angle being counterclockwise as viewed from the atrium.

Figure 60G:
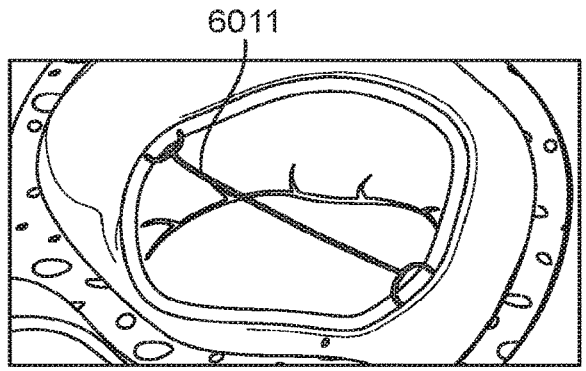

FIG. 60G shows a valve shaping device 6011 with a single stretching member in a substantially straight position, arranged at an angle to the valve commissures, the angle being clockwise as viewed from the atrium.

Figure 60H:
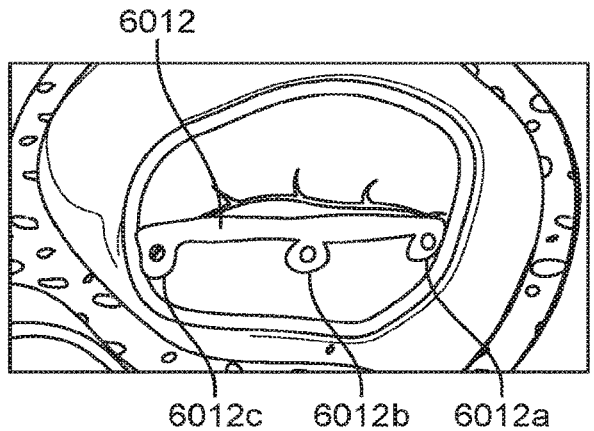

FIG. 60H shows a valve shaping device 6012 with a single stretching member in a substantially straight position, having three tissue engagement features 6012a, 6012b, and 6012c arranged on the same side of the body of the valve shaping device.

Figure 60I:
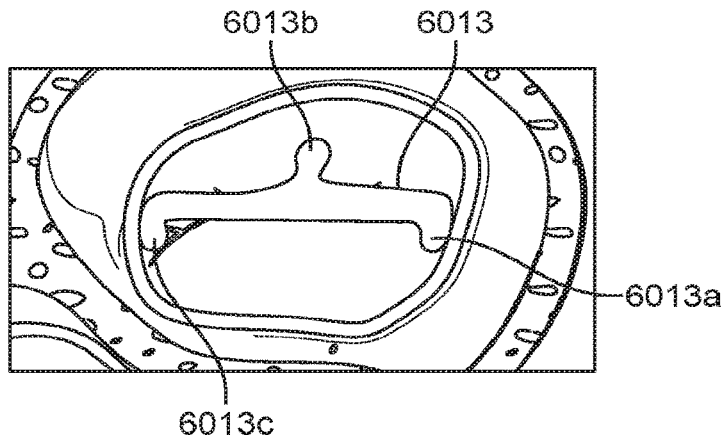

FIG. 60I shows a valve shaping device 6013 with a single stretching member in a substantially straight position, having three tissue engagement features 6013a, 6013b, and 6013c arranged on different sides of the body of the valve shaping device.

Figure 61A:
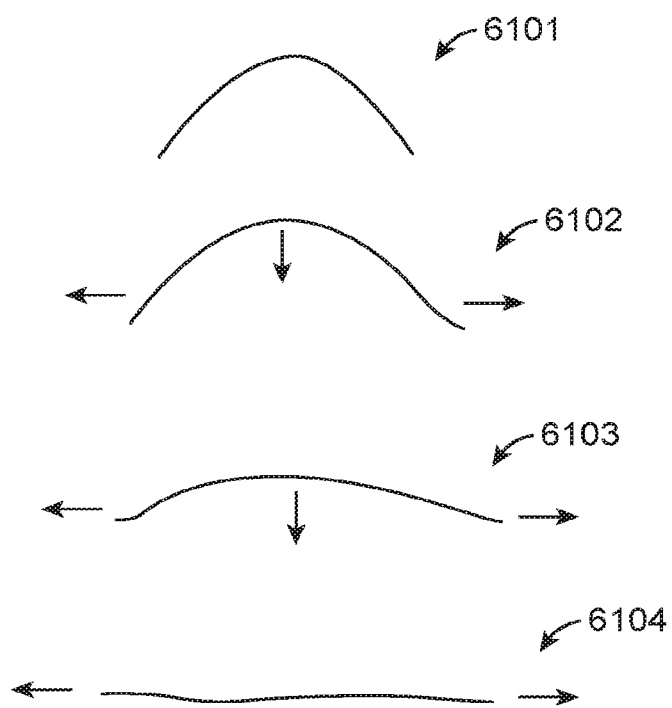
FIG. 61A shows a stretching device that starts in an arcuate configuration and moves to a substantially straight configuration.
Figure 61B:
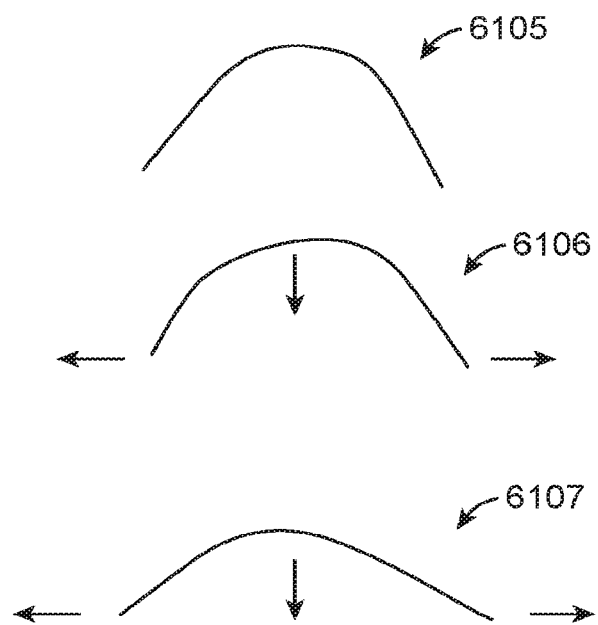
FIG. 61B shows a stretching device that starts in an initial arcuate configuration and moves to a configuration with an arcuate shape having a larger radius than the initial arcuate configuration, causing the angle of the ends to change as the distance between the ends increases.
Figure 61C:
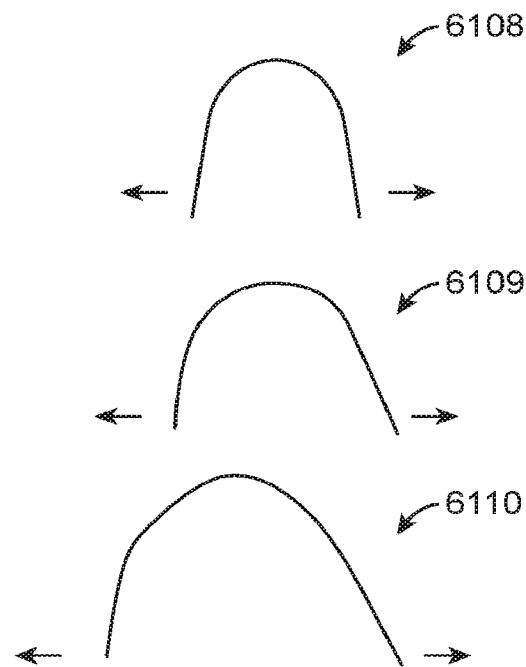
FIG. 61C shows a stretchable device that starts in an initial arcuate configuration and flattens in one portion while bending further in another, causing the angle of the ends to remain substantially constant as the distance between the ends increases.

FIGS. 61A through 61C illustrate a variety of functional diagrams of valve shaping devices of the present invention.

FIG. 61A shows a device placed in a curved configuration 6101, which straightens 6102 as it engages with tissue, stretching tissue further 6103 until the shaping device is essentially straight 6104. Throughout the motion, the ends of the shaping device move farther apart, and the crown of the bend moves closer to a line drawn between the two ends, until it substantially reaches that line. In one example, the ends of the tissue shaping device are engaged with the target tissue. In a further example, both the ends of the tissue shaping device, and one or more points along the span of the tissue shaping device engage with the target tissue.

FIG. 61B shows a device placed in a curved configuration 6105, which straightens 6106 as it engages with tissue, stretching 6107 until the tissue forces prevent further straightening, and the shaping device retains a substantially curved shape. Throughout the motion, the ends of the shaping device move farther apart, and the crown of the bend moves closer to a line drawn between the two ends, until it substantially reaches that line. In one example, the ends of the tissue shaping device are engaged with the target tissue. In a further example, both the ends of the tissue shaping device, and one or more points along the span of the tissue shaping device engage with the target tissue.

FIG. 61C shows a device placed in a curved configuration 6108, which flattens 6109 on the top of the arch as it engages with tissue, providing outward force on the tissue while the ends of the tissue shaping device exhibit a reduced degree of rotation relative to their initial angles relative to the tissue. Throughout the motion, the ends of the shaping device move farther apart, and the crown of the bend flattens. In one example, the ends of the tissue shaping device are engaged with the target tissue. In a further example, both the ends of the tissue shaping device, and one or more points along the span of the tissue shaping device engage with the target tissue.

Figure 62:
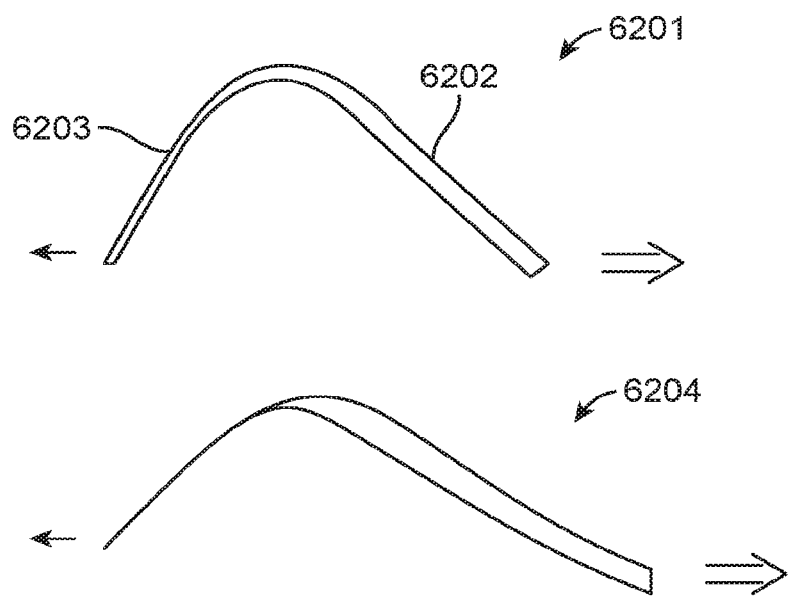
FIG. 62 shows a stretching device with a variable stiffness along the span between the ends, resulting in a stiffer end and a more flexible end.

FIG. 62 shows an asymmetrical tissue shaping device, with a more flexible side 6203 and a stiffer side 6202. The tissue shaping device expands in an asymmetrical manner from a first position 6201 to a second position 6204 where the ends have moved relative to one another. In one example, the ends of the tissue shaping device are engaged with the target tissue. In a further example, both the ends of the tissue shaping device, and one or more points along the span of the tissue shaping device engage with the target tissue, which results in a larger outward force at the end of the tissue shaping device on its stiffer side 6206 when compared to the outward force applied at the end of the tissue shaping device on the more flexible side 6203.

Figure 63A:
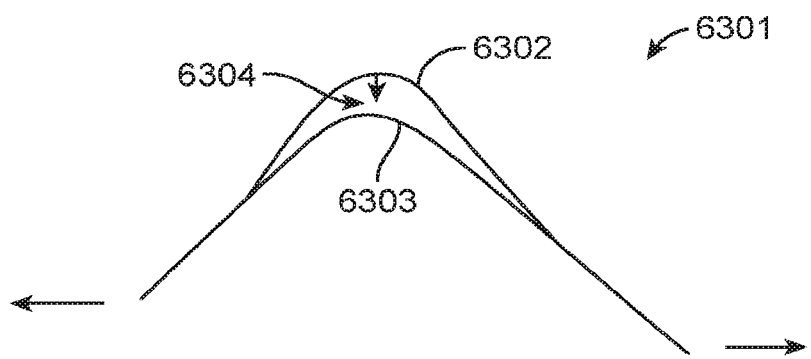
FIGS. 63A and 63B show a stretching device with two arches which move relative to each other as the length between the ends changes.
Figure 63B:
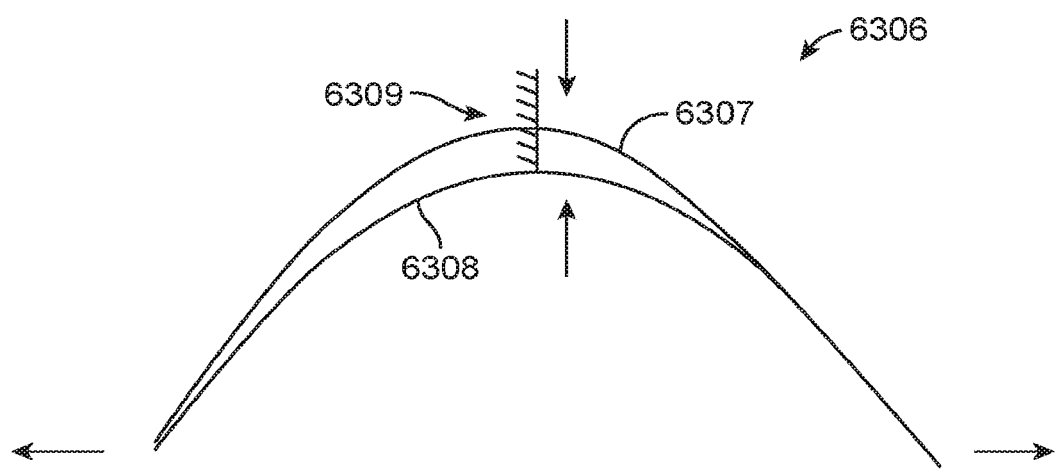

FIGS. 63A and 63B shows a tissue shaping device of the present invention 6301, having a first arch 6302 and a second arch 6303 separated by an initial distance 6304, where the position of and forces applied by the device ends vary in conjunction with the variation of the separation distance between the first arch 6302 and a second arch 6303. In one example, the arches are configured to increase the force at the device ends as the separation distance between the first arch 6302 and the second arch 6303 increases. In a further example, the arches are configured to increase the force at the device ends as the separation distance between the first arch 6302 and the second arch 6303 decreases. In a further example, the first arch 6302 and a second arch 6303 include a contact point that limits decreases in separation distance so that the force at the device ends decreases once contact between the first arch 6302 and the second arch 6303 is established.

FIG. 63B shows a tissue shaping device of the present invention 6306, having a first arch 6307 and a second arch 6308 separated by a variable distance 6309, where the position of and forces applied by the device ends vary in conjunction with the variation of the separation distance between the first arch 6307 and a second arch 6308. In one example, the variable distance 6309 can be adjusted by twisting a member with a helical adjustment feature, controlling the arch distance and thereby controlling the force at the ends of the tissue shaping device.

Figure 64A:
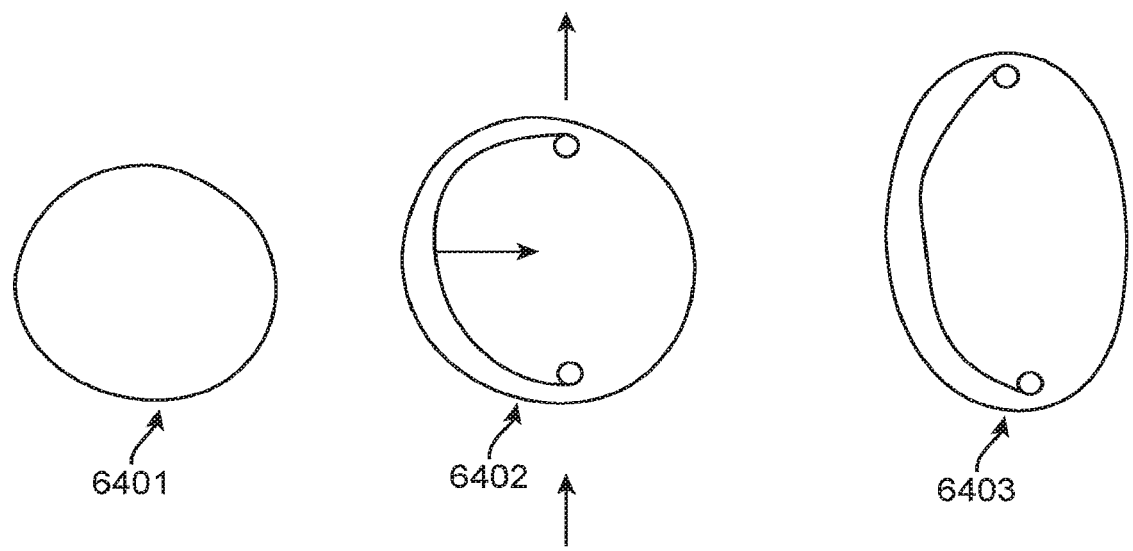
FIGS. 64A to 64C show various configurations of stretching devices.
Figure 64B:
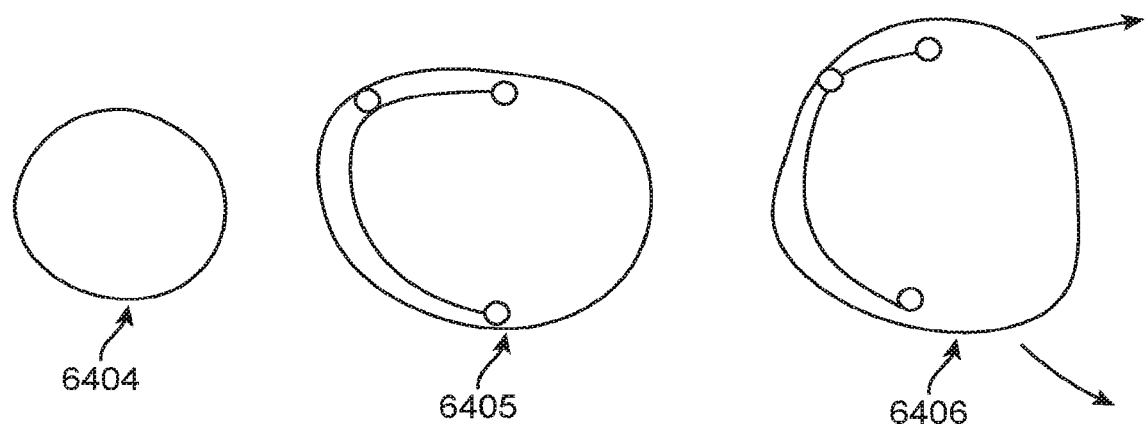
Figure 64C:
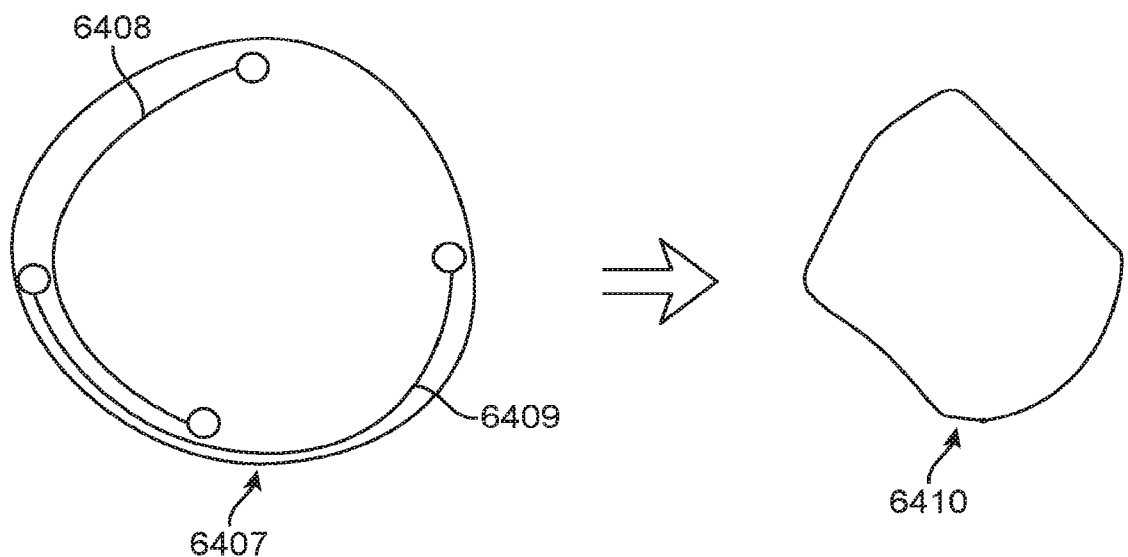

FIGS. 64A through 64C show arrangements of tissue shaping devices within a target tissue.

FIG. 64A shows a substantially circular target tissue 6401 and a tissue shaping device that engages 6402 with two points on the target tissue and moves it to an elongate configuration 6403. In one example, the forces on ends of the tissue shaping device act substantially along a line drawn between the two ends.

FIG. 64B shows a substantially circular target tissue 6404 and a tissue shaping device that engages 6405 with three points on the target tissue and moves it to an elongate configuration 6406. In one example the forces on the ends of the tissue shaping device have a component that is perpendicular to a line drawn between the two ends.

FIG. 64C shows a substantially circular target tissue 6407, a first tissue shaping device 6408 and a second tissue shaping device 6409 that each engage with two or more points on the target tissue and moves it to a non-circular configuration 6410.

Figure 65A:
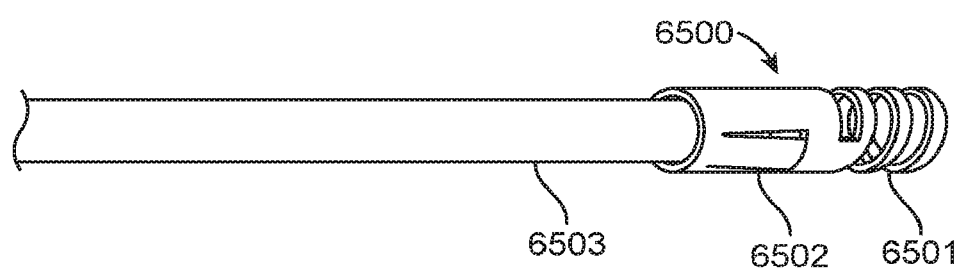
FIG. 65A shows a docking anchor with removable wire.

FIG. 65A shows a docking anchor 6500 with a removable wire 6503. The docking anchor 6500 has, in one example, a helical coil anchor 6501 that can engage with tissue by applying twist to the docking anchor 6500 via the removable wire 6503. The removable wire 6503 may also be used to guide the docking anchor 6500 into position against the target tissue. The docking tab 6502 of the docking anchor 6500 in this example is a tab that extends outside of the normal outer diameter of the docking anchor 6500.

Figure 65B:
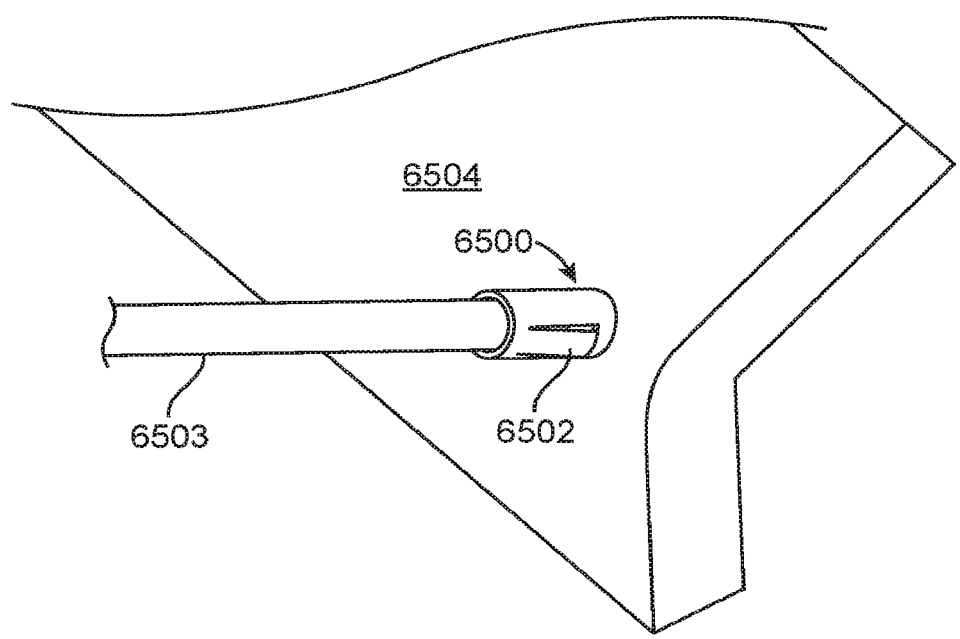
FIG. 65B shows a docking anchor with removable wire having been anchored to tissue.
Figure 65C:
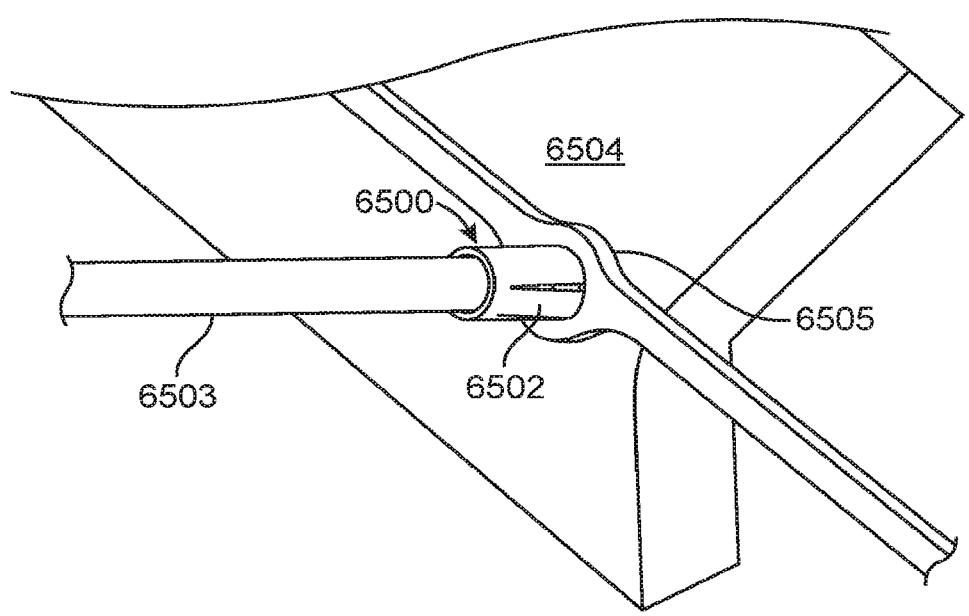
FIG. 65C shows a docking anchor with removable wire having been anchored to tissue, with a valve shaping device docked to the anchor.
Figure 65D:
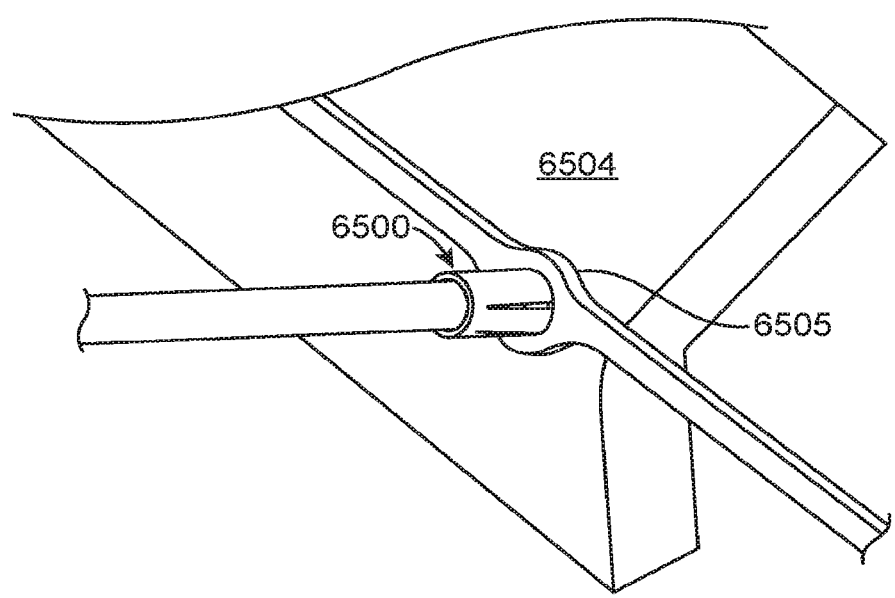
FIG. 65D shows the system of FIG. 65C, the removable wire having been removed.

FIG. 65B shows the docking anchor 6500 fully engaged with the tissue 6504. The shaping device 6505 is inserted over the proximal end of the removable wire 6503 (not shown in this figure.) FIG. 65C shows the shaping device 6505 in place and fully engaged with the docking anchor 6500. In this example, the docking feature in the shaping device 6505 slides over the outer diameter of the docking anchor 6500, compressing the docking tab 6502 until it has been inserted past the end of the docking tab 6502, allowing the docking tab 6502 to return to a position extending outside the normal diameter of the docking anchor 6500, and preventing motion of the shaping device 6505 in at least one direction relative to the docking anchor 6500. As shown in FIG. 65D, the removable wire is detached from the docking anchor 6500, leaving the shaping device 6505 attached to the target tissue 6504.

Figure 66A:
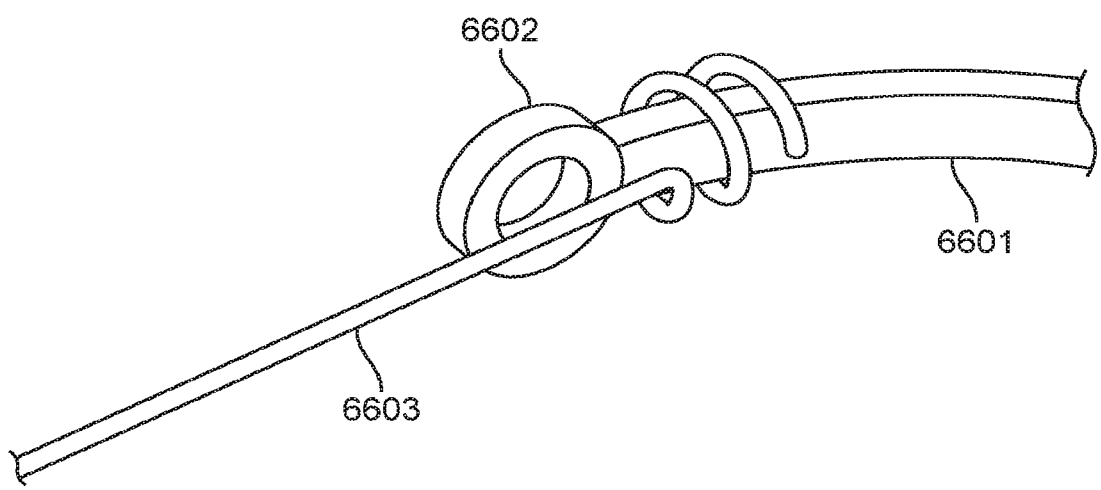
FIG. 66A shows one end of a tissue shaping device engaged with a removable control wire based on a helical coil.
Figure 66B:
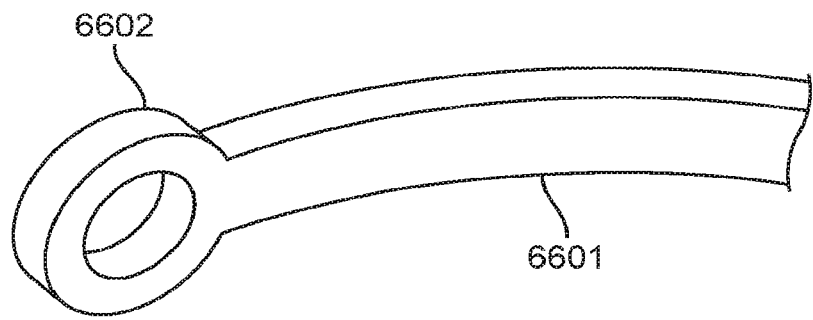
FIG. 66B shows the device of FIG. 66A with the control wire removed.

FIG. 66A shows one end of a shaping device 6601 with removable control wire 6603. In this example, the shaping device 6601 has an end feature 6602 having a diameter substantially larger than the inner diameter of a helical coil formed at or near the end of the control wire 6603. Twisting the control wire 6603 causes it to release from the end of the shaping device 6601, as shown in FIG. 66B.

Figure 67A:
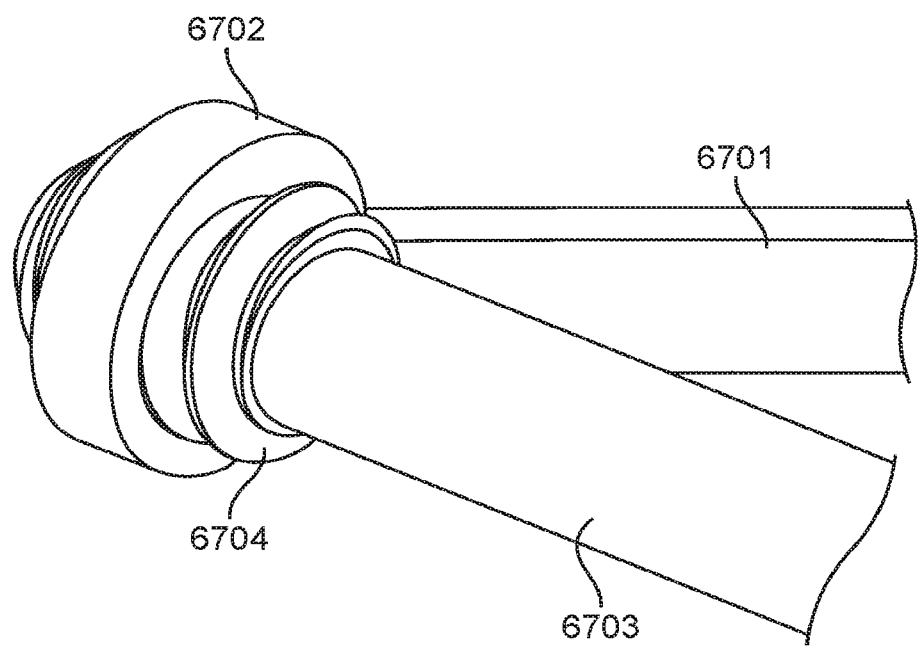
FIG. 67A shows one end of a tissue shaping device engaged with a removable control wire based on screw threads.
Figure 67B:
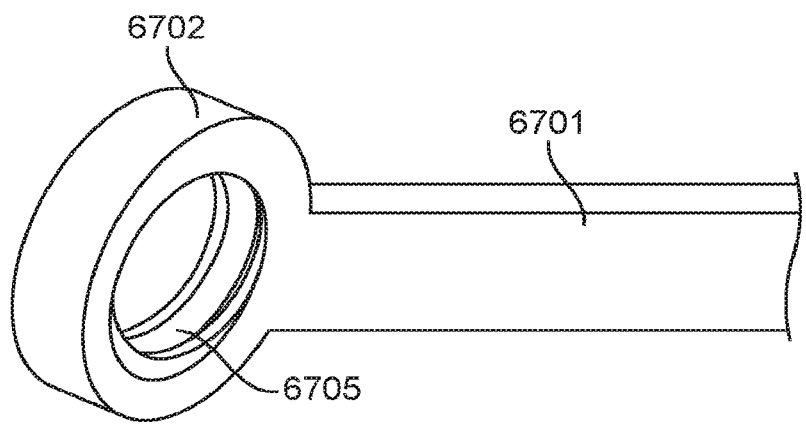
FIG. 67B shows the device of FIG. 67A with the removable control wire removed.

FIG. 67A shows a further example of a shaping device 6701 and removable control wire 6703. In this example, the control wire 6703 has a threaded section 6704 that mates with a threaded end feature 6702 of the shaping device 6701. Twisting the control wire 6704 causes it to unscrew from the end feature 6702 of the shaping device 6701, exposing the internal threads 6705 of the end feature 6702 as shown in FIG. 67B.

Figure 68A:
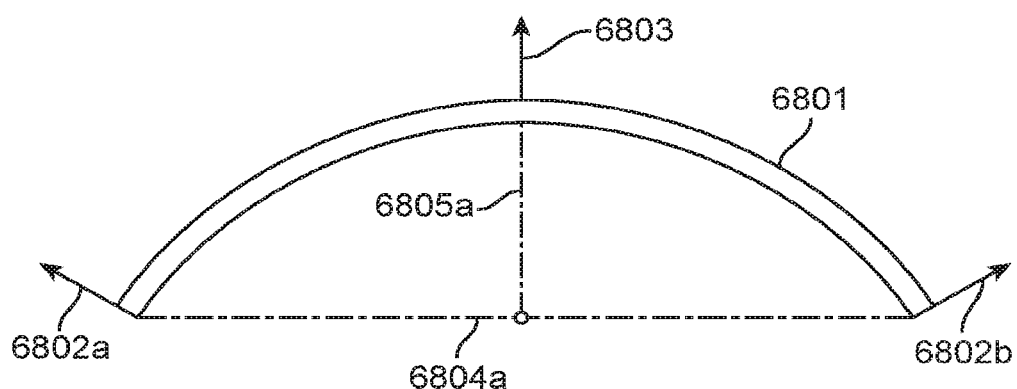
FIGS. 68A-68D show devices having multiple attachment points for flattening a segment of an annulus.
Figure 68B:
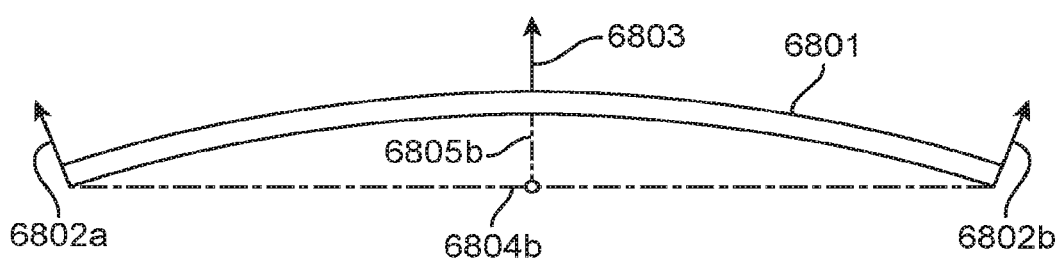

FIGS. 68A-68D illustrate the interaction of a flattening device with a segment of an annulus. In FIG. 68A, a flattening device 6801 with three tissue coupling points shown as arrows 6802a, 6802b, and 6803 is in a curved configuration as attached to an annulus. In this initial configuration, the lateral attachment points 6802a and 6802b define a first line 6804a, and the medial attachment point 6803 resides at a first distance 6805a from line 6804a. The flattening device 6801 acts to straighten the annulus to the configuration shown in FIG. 68B, where the lateral attachment points 6802a and 6802b define a second line 6804b, and the medial attachment point 6803 resides at a second distance 6805b from line 6804b. In one example, the second distance 6805b is shorter than the first distance 6805a, while the second line 6804b is longer than the first line 6804a.

Figure 68C:
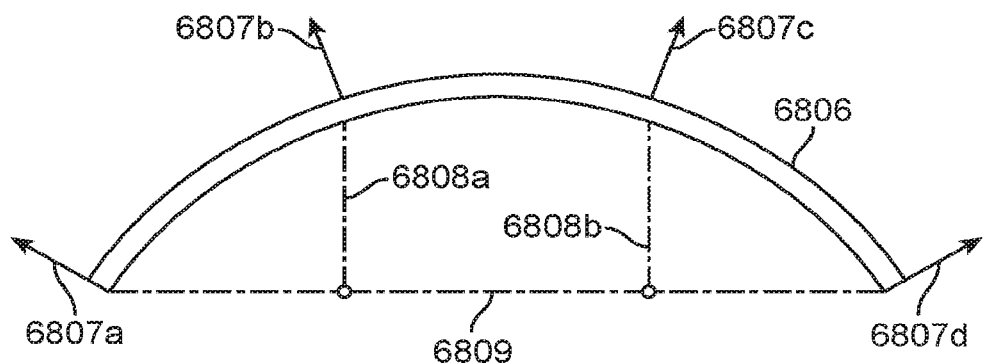
Figure 68D:
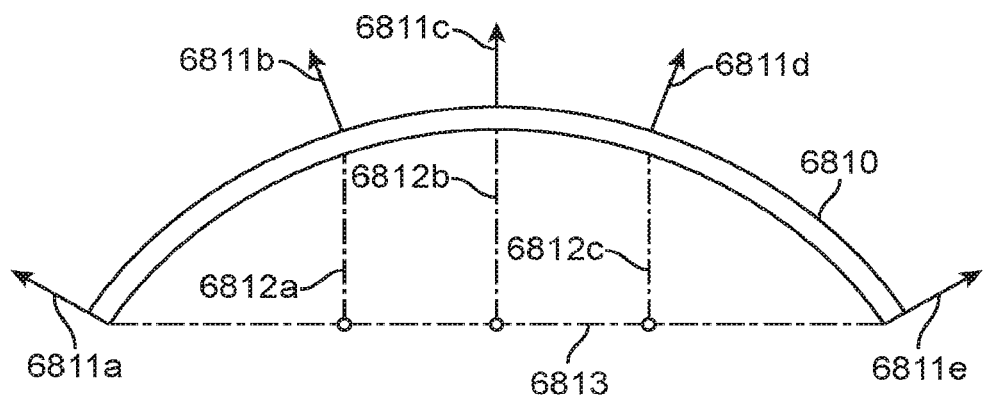

FIG. 68C shows a flattening device 6806 with four tissue coupling points 6807a-d. The most lateral coupling points 6807a and 6807d define a line 6809, and the intermediate coupling points 6807b and 6807c reside at distances 6808a and 6808b respectively from line 6809. In one example, the effect of the flattening device 6806 acts to reduce distances 6808a and 6808b, while increasing the length of line 6809. FIG. 68D shows a flattening device 6810 with five tissue coupling points 6811a-e. The most lateral coupling points 6811a and 6811e define a line 6813, and the intermediate coupling points 6811b, 6811c, and 6811d reside at distances 6812a, 6812b, and 6812c respectively from line 6813. In one example, the effect of the flattening device 6810 acts to reduce distances 6812a-c, while increasing the length of line 6813.

Figure 69A:
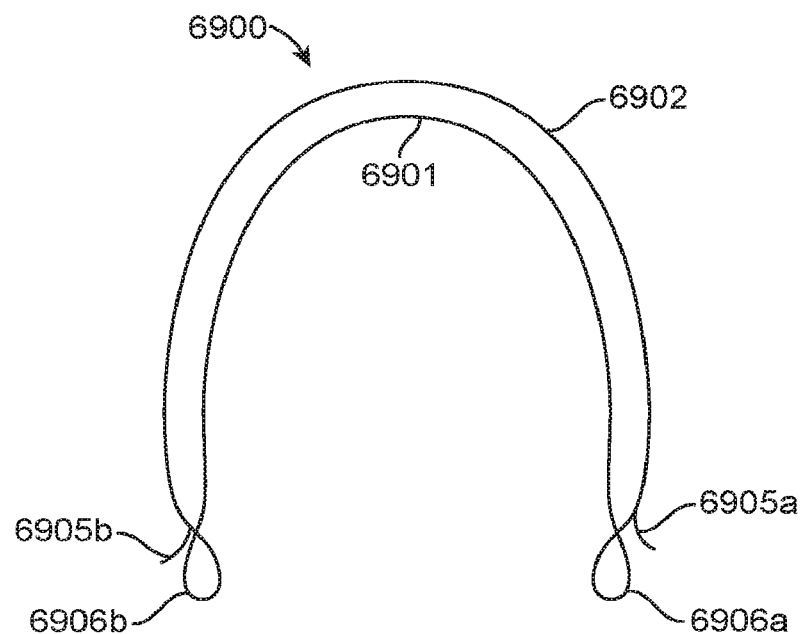
FIGS. 69A and 69B show a device with two partial rings configured to apply an inward force on an area of the valve annulus and an outward force on the adjacent muscular wall of the heart.
Figure 69B:
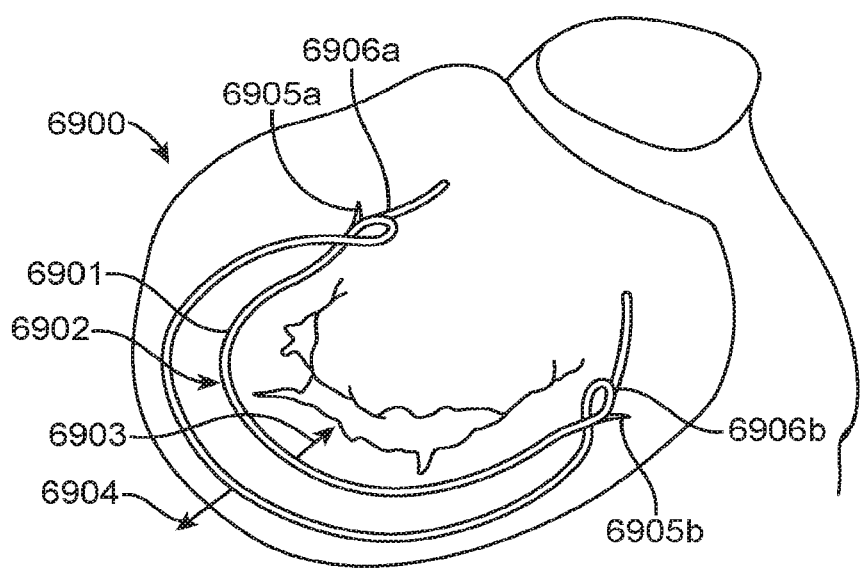

FIG. 69A shows an annuloplasty device 6900 comprising or consisting of an inner partial ring 6901 and an outer partial ring 6902, connected at connection points 6906a and 6906b. It includes tissue coupling mechanisms 6905a and 6905b, such as tissue penetrating barbs, near the connection points 6906a and 6906b respectively. As illustrated in FIG. 69B, the inner partial ring 6901 lies adjacent to or otherwise follows the contour of the valve annulus, and the outer partial ring 6902 engages and presses outwardly on the an adjacent muscular wall region of the heart. The outer partial ring 6902 may be in the same plane as the inner partial ring 6901, or on a plane at an angle to and/or offset from the valve annulus as desired, for example to enhance the ability of the inner and outer partial rings to separately engage the annulus and heart valve wall. In one example, the inner partial ring 6901 creates an inner acting force 6903 on the valve annulus, in response to an outer acting force 6904 applied by the outer partial ring 6902 on the muscular wall of the heart. In a further example, the inner partial ring 6901 is attached to the annulus at one or more points intermediate to the tissue coupling mechanisms 6905a and 6905b shown, as may be advantageous to create the desired shape in the valve annulus.

Figure 70A:
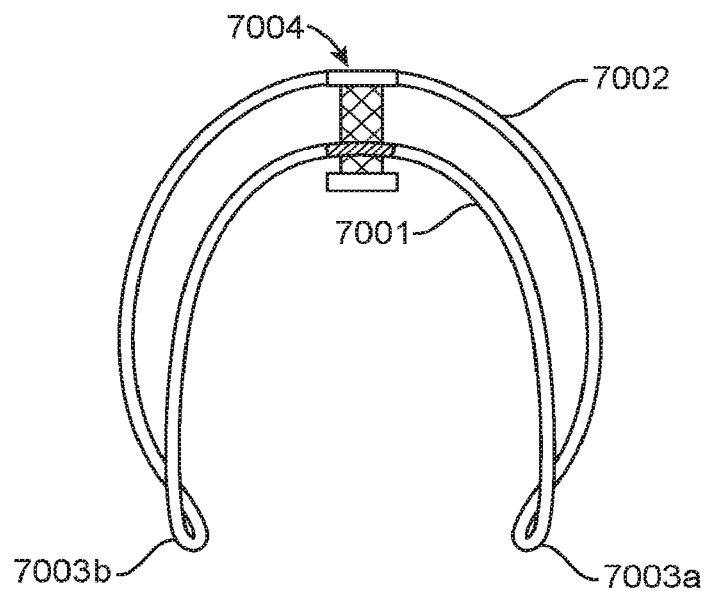
FIGS. 70A and 70B show adjacent partial rings configured to pull an annulus inwardly while pushing an adjacent muscular wall outwardly.

FIG. 70A shows an annuloplasty device comprising or consisting of an inner partial ring 7001 and an outer partial ring 7002 connected at connection points 7003a and 7003b and having a mechanism 7004 to adjust a relative position of a crown of the inner partial ring 7001 and a crown of the outer partial ring 7002. By adjusting the relative positions, the resulting force and/or displacement created on the valve annulus can be varied.

Figure 70B:
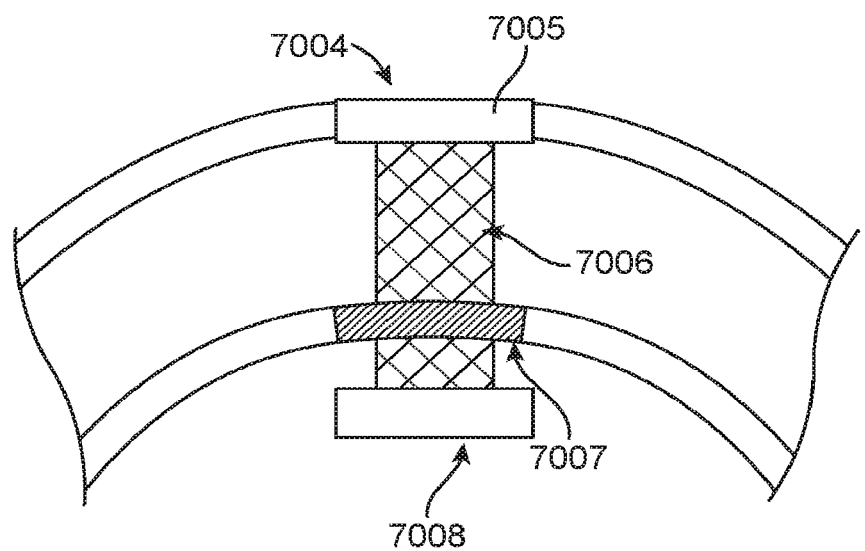

FIG. 70B shows a close-up of an exemplary adjustment mechanism 7004 having a helical screw 7006 having a distal tip that engages and presses against an inner surface of the outer partial ring 7002 at a contact point 7005. The helical screw 7006 passes through a threaded coupler 7007 formed in or attached to the inner partial ring 7001. A torque feature 7008, such as a screw head, on the helical screw 7006 allows it to engage with an adjustment device (not shown) to adjust the relative positions of the inner partial ring 7001 and an outer partial ring 7002 as needed to achieve the desired force and/or displacement in the valve annulus, typically by rotating the screw in the threaded coupler 7007. While this adjustment mechanism is illustrated as a helical screw, other adjustment devices are known to the art and would serve the appropriate function in this application.

Figure 71A:
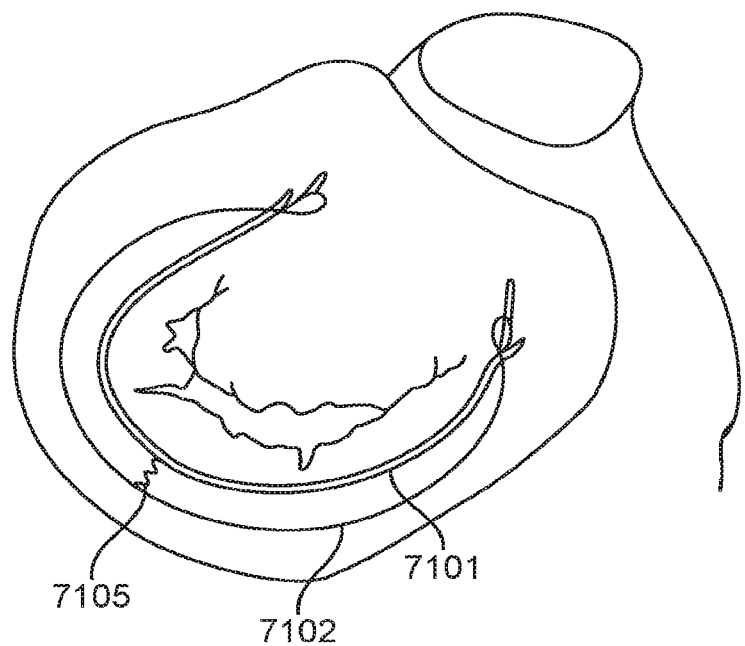
FIGS. 71A and 71B show adjustable device with two partial rings having a single adjustment point to pull in an annulus point or region while stretching out an adjacent partial ring at the adjustment point.
Figure 71B:
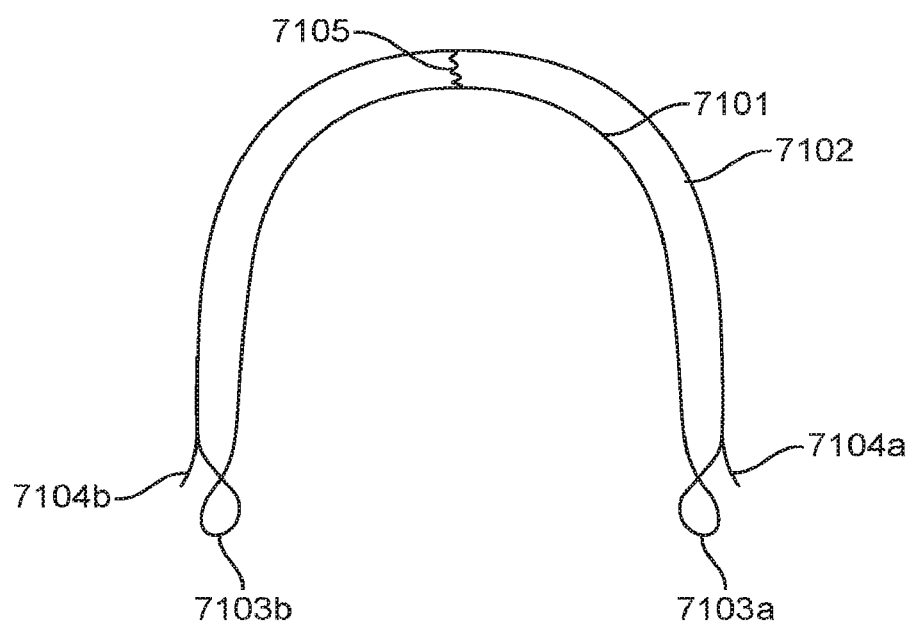

FIG. 71A shows an annuloplasty device consisting of an inner partial ring 7101 and an outer partial ring 7102 in place in a mitral heart valve. This example has a single adjustment mechanism 7105 disposed near the middle of the partial rings, in one example a spring adjusted by rotating relative to the rings. FIG. 71B shows a schematic representation of the device of FIG. 71A, showing inner partial ring 7101 and an outer partial ring 7102 connected at connection points 7103a and 7103b. It includes tissue coupling mechanisms 7104a and 7104b near the connection points 7103a and 7103b respectively. In one example, the single adjustment mechanism 7105 is disposed near the middle of the partial rings. In a further example, the single adjustment mechanism 7105 is disposed closer to one end than to the other end to bias the effect of the adjustment.

Figure 72A:
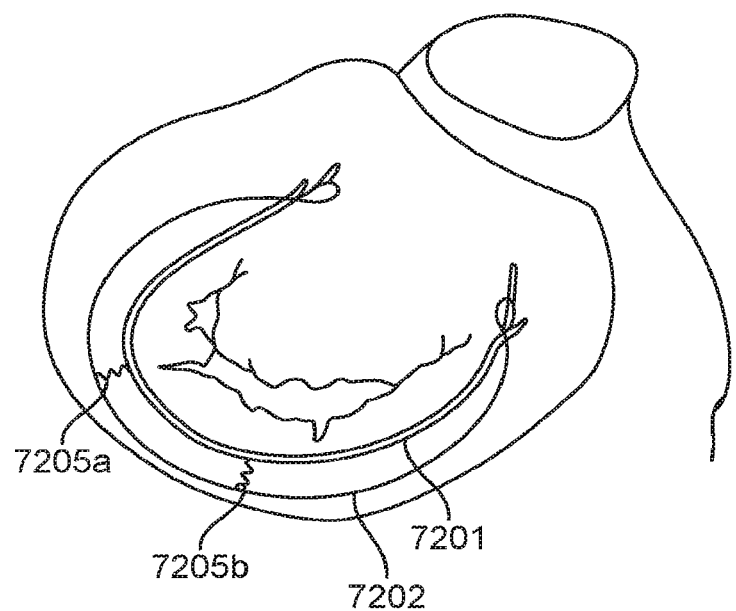
FIGS. 72A and 72B show an adjustable device with two partial rings having multiple adjustment points to pull in an annulus point or region and stretch out connected partial ring about the adjustment points.
Figure 72B:
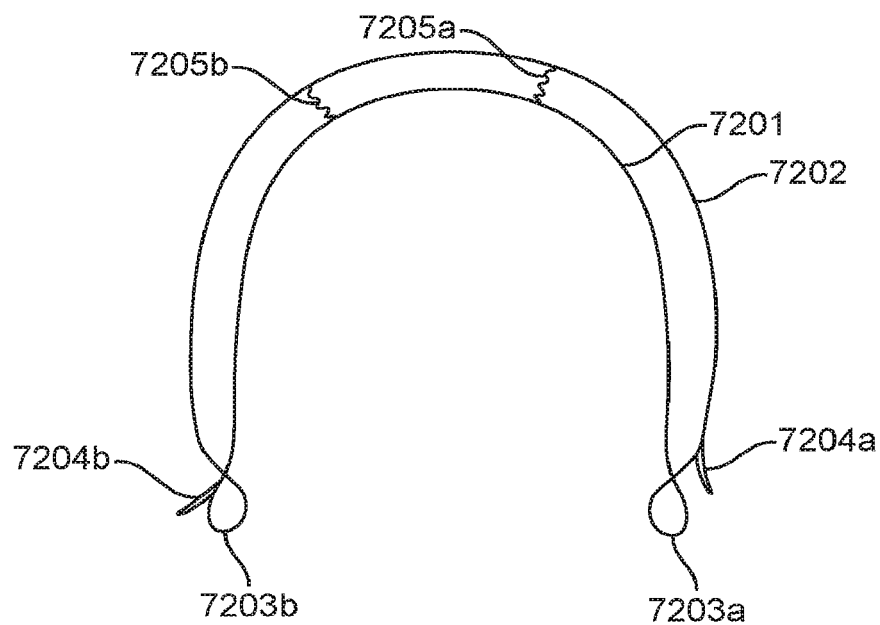

FIG. 72A shows an annuloplasty device 7200 comprising or consisting of an inner partial ring 7201 and an outer partial ring 7202 in place in a mitral heart valve. The annuloplasty device 7200 has two adjustment mechanisms 7205a and 7205b disposed along the partial ring, for example being disposed between an outer surface or edge of the inner ring and an inner surface or edge of the outer ring. FIG. 72B shows a schematic representation of the device of FIG. 72A, showing inner partial ring 7201 and an outer partial ring 7202 connected at connection points 7203a and 7203b. The annuloplasty device 7200 further includes tissue coupling mechanisms 7204a and 7204b, such as barbs, located near the connection points 7203a and 7203b respectively. In one example, the two adjustment mechanisms 7205a and 7205b are spaced symmetrically or near spaced from a midpoint of the span or "arc" of the partial rings. In a further example, the two adjustment mechanisms 7205a and 7205b may be spaced non-symmetrically relative to the midpoint of the span of the partial rings to bias the effect of the adjustment.

Although certain embodiments or examples of the disclosure have been described in detail, variations and modifications will be apparent to those skilled in the art, including embodiments or examples that may not provide all the features and benefits described herein. It will be understood by those skilled in the art that the present disclosure extends beyond the specifically disclosed embodiments or examples to other alternative or additional examples or embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments and examples may be made and still fall within the scope of the present disclosure. Accordingly, it should be understood that various features and aspects of the disclosed embodiments or examples can be combined with or substituted for one another in order to form varying modes or examples of the present disclosure. Thus, it is intended that the scope of the present disclosure herein disclosed should not be limited by the particular disclosed embodiments or examples described above. For all of the embodiments and examples described above, the steps of any methods for example need not be performed sequentially.

Figure 73A:
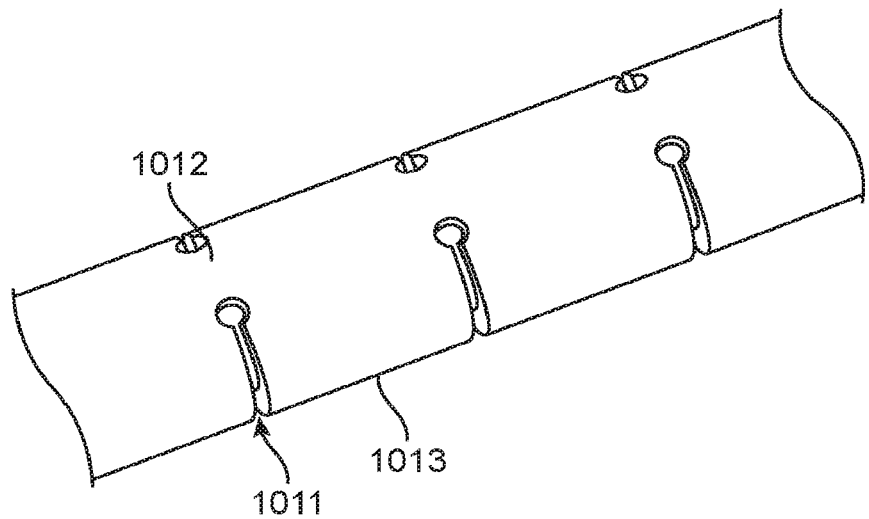
FIG. 73A shows a segment of a tube with controlled cuts, spaced relatively far apart to create a large bend radius.

FIG. 73A shows a tube with cuts 1011 to allow controlled flexibility. The cuts 1011 leave an attached spine 1012 that flexes to achieve a controlled bend radius. The controlled bend radius is determined by a first space 1013 between the cuts 1011. As shown in FIG. 73A, the cuts are at a spacing that creates a relatively large controlled bend radius.

Figure 73B:
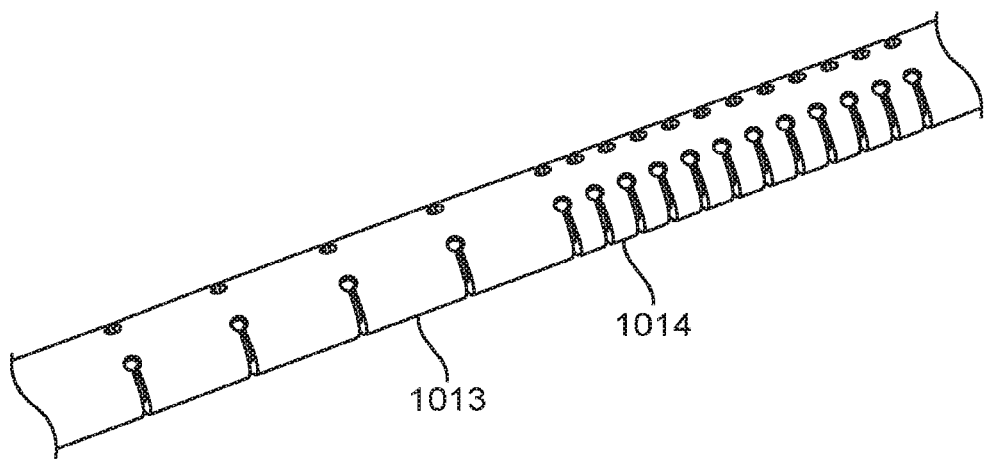
FIG. 73B shows a segment of a tube with widely spaced cuts and narrowly spaced cuts, to create bends with large and small radii, respectively.

FIG. 73B shows a tube with two groups of cuts 1011 having different spacings. In the first group, the first space 1013 between the cuts 1011 results in a relatively large controlled bend radius, and the second spacing 1014 results in a relatively smaller controlled bend radius.

Figure 74:
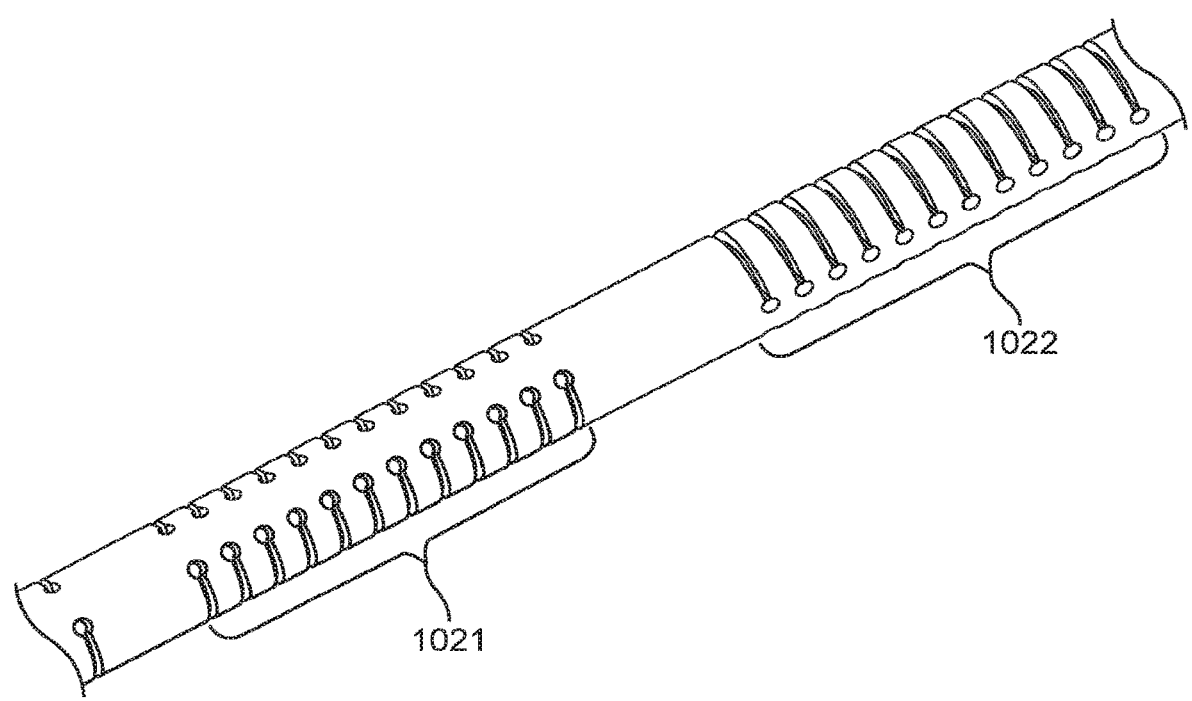
FIG. 74 shows a segment of a tube having cuts with different orientations, to create out of plane bends, or three-dimensional bend shapes.

FIG. 74 shows two groups of cuts, a first group 1021 arranged so that the spine is up as shown, and a second group 1022 arranged so the spine is at a different angle. The different orientation of the second group of cuts 1022 will result in a flexed shape outside of the plane defined by the curve created by the first group of cuts 1021. More complex combinations of changes in spacing and orientation can combine to cause the tube to deform into complex three-dimensional shapes.

Figure 75:
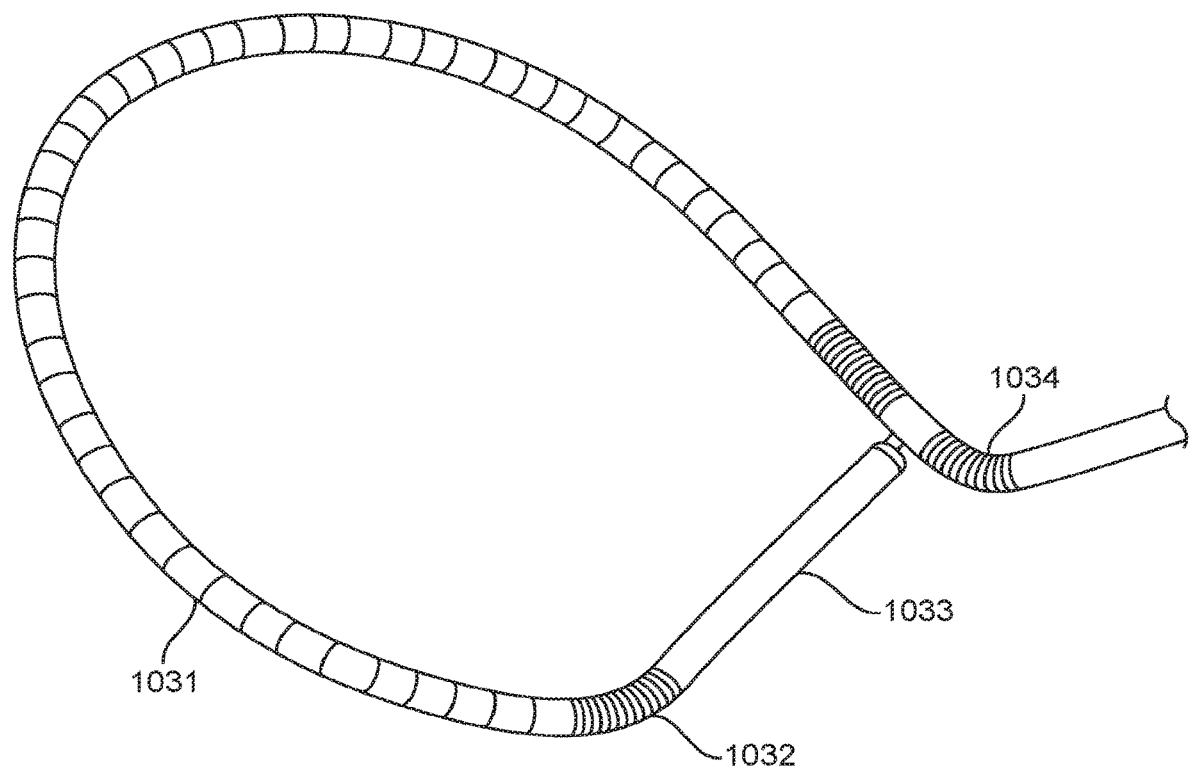
FIG. 75 shows a device with different bend radii and orientations which forms a "D" shape with an upright handle when subject to bending force, longitudinal compressive or tensile force, or a combination thereof.

FIG. 75 shows a tube of the present invention flexed into a controlled 3-dimensional shape, including a section of relatively large radius bend 1031, relatively small radius bends in plane 1032, a straight segment 1033, and an out of plane bend 1034. As shown, the in-plane bent shape approximates the letter "D", a shape relevant to target anatomies. Other combinations of bends of various radii allow other in-plane or out of plane shapes that may match, approximate, or re-shape anatomy in a desired manner. The out of plane bend 1034 allows the tube itself to act as a single locating handle, controlling both the rotation and axial position of the in-plane bent shape.

Figure 76:
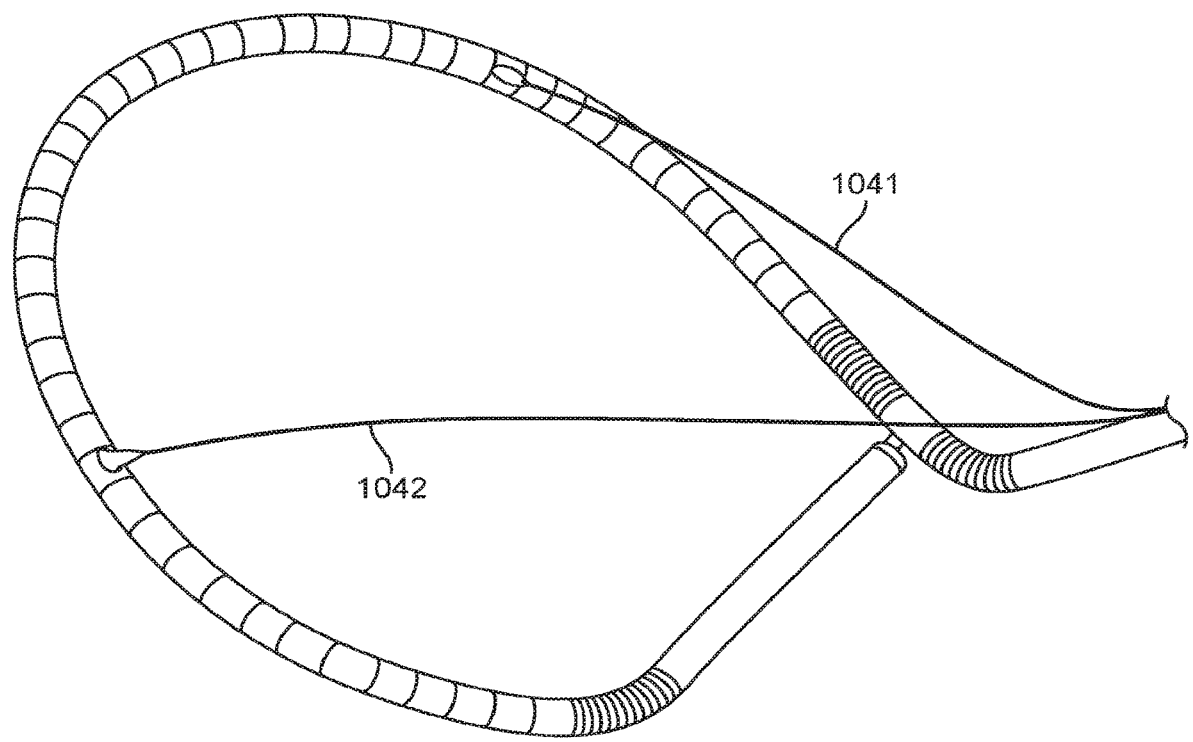
FIG. 76 shows the device of FIG. 4 with the addition of control arms that can help to adjust the planar orientation of a substantially hoop shaped portion of the device.

FIG. 76 shows the tube of FIG. 75 with the addition of two control arms 1041 and 1042 to allow control of the angle of the plane of the planar segment of the bend tube. Specifically, the rigid or semi rigid tube itself can control the planar segment's position in four degrees of freedom, including translation up-down, side-to-side, and forwards-backwards, as well as rotation about the tube axis, while two additional control wires control rotation of the planar segment about the remaining axes orthogonal to the tube axis, allowing fine control of the position of the flexed section of tube in a total of 6 degrees of freedom. This control arm approach also applies to non-planar complex 3d flexed shapes of tubes.

Figure 77:
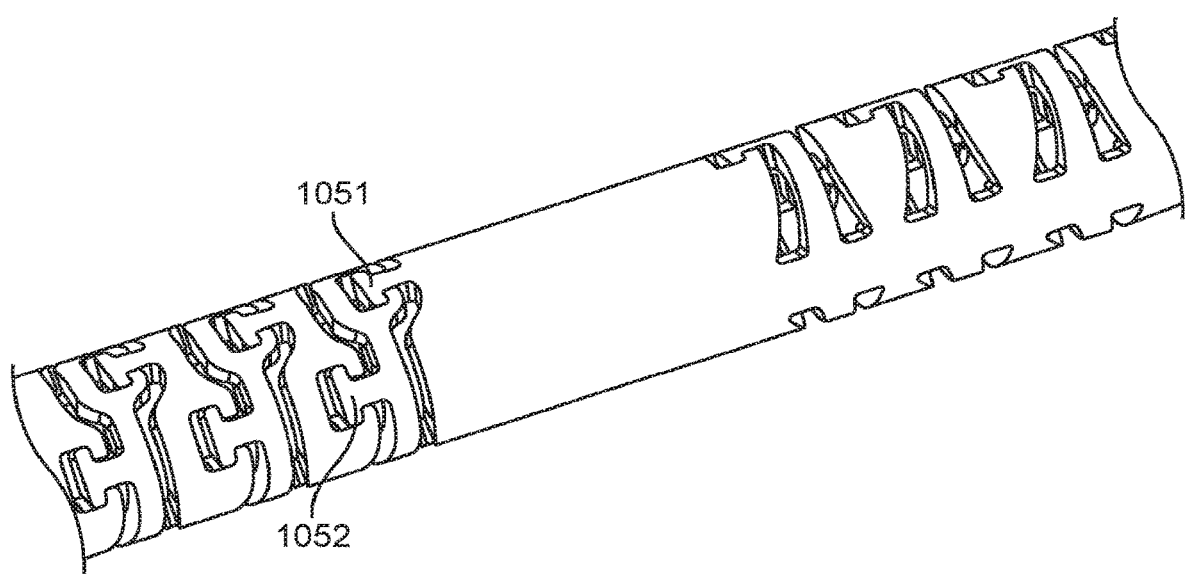
FIG. 77 shows alternative controlled cuts which include an interlocking feature of various designs.

FIG. 77 shows the tube of the present invention with cuts that have a locking feature 1051 to strengthen the tube against flexure in the opposite of the intended direction, as well as against torsion along the axis of the tube. To minimize distance between cuts, thereby minimizing the bend radius, cuts with the locking feature 1051 can be alternated with cuts having one or more offset locking features 1052, allowing combination of small space between cuts (and therefore small bend radius) with cuts having an interlocking feature.

Figure 78:
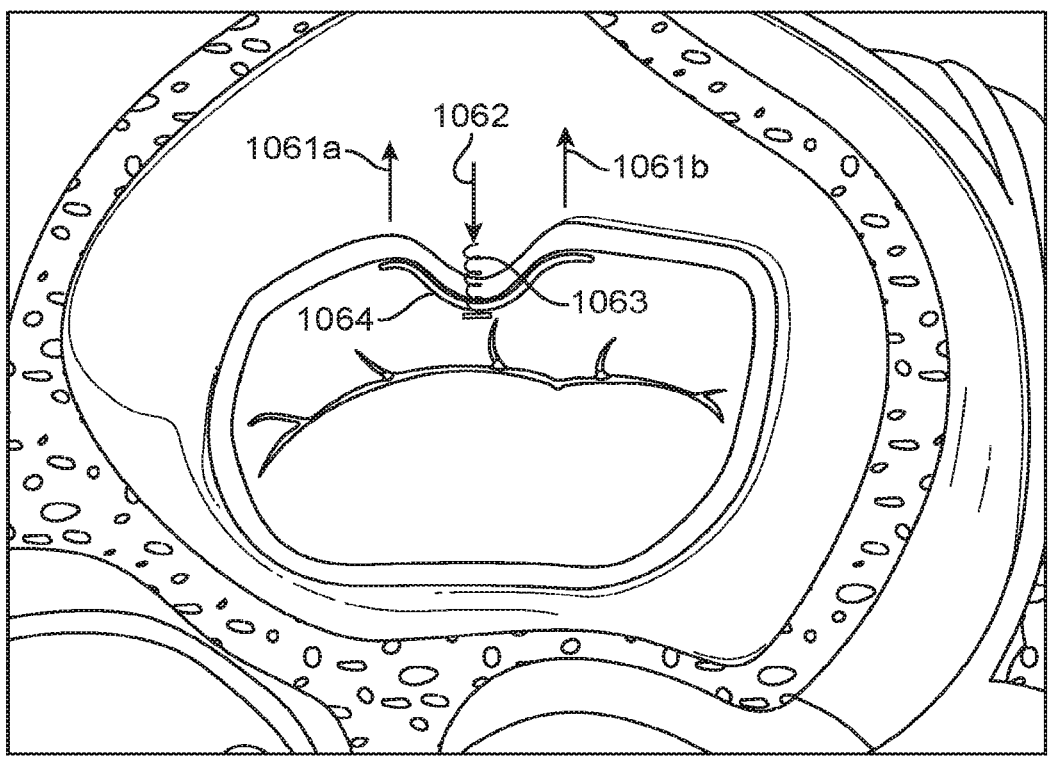
FIG. 78 shows an implant applied to a segment of the valve annulus having a curved shape

FIG. 78 shows a main implant template 1064 designed to create two areas of outward force 1061A and 1061B counterbalanced by an inward force 1062. These forces are applied by an anchor 1063, applying the inward force 1062, and a main implant template 1064, applying the outward forces 1061A-B. The curvature shape of the main implant template 1064 approximates a desired shape for the target segment of the annulus. An array of these implants could be applied to different annular segments to vary the total level of effect.

Figure 79:
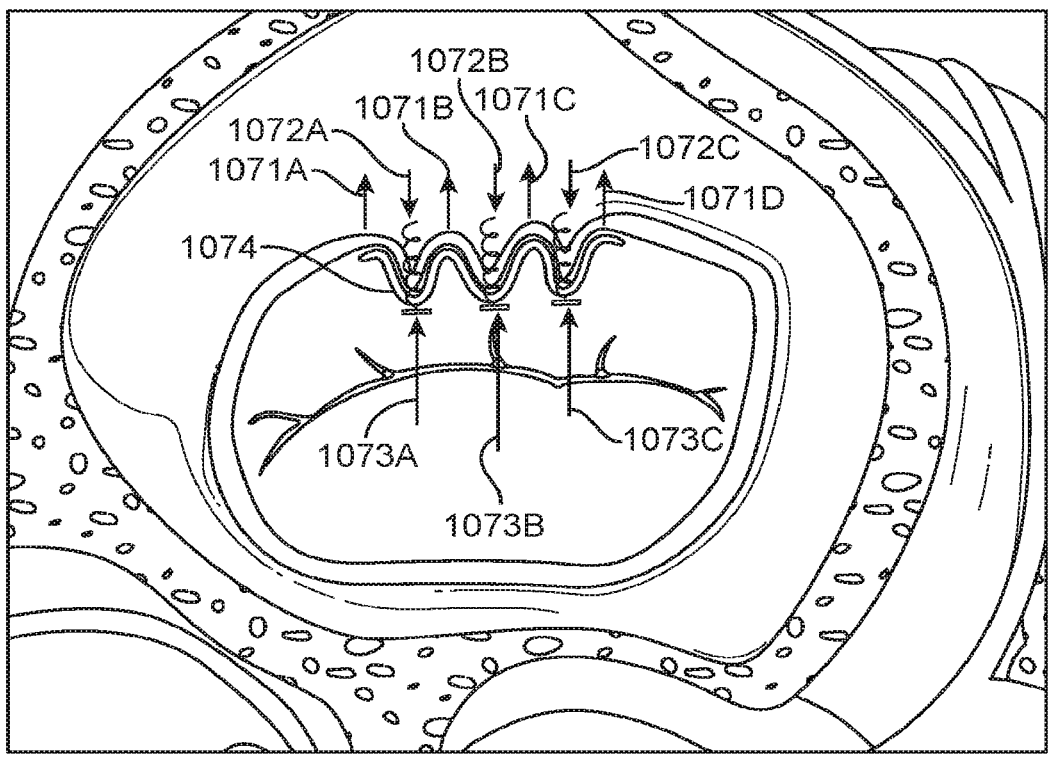
FIG. 79 shows an implant applied to a segment of the valve annulus having a shape with multiple curves

FIG. 79 shows a wavy implant 1074 having a repeating pattern of areas creating outward forces 1071A-D counterbalanced by inward forces 1072A-C. Each area of inward force is attached to the wavy implant 1074 by anchors 1073A-C. As shown, three inward force areas and 4 outward force areas are shown, but these numbers can be varied as needed to offer differing levels of effect.

Figure 80:
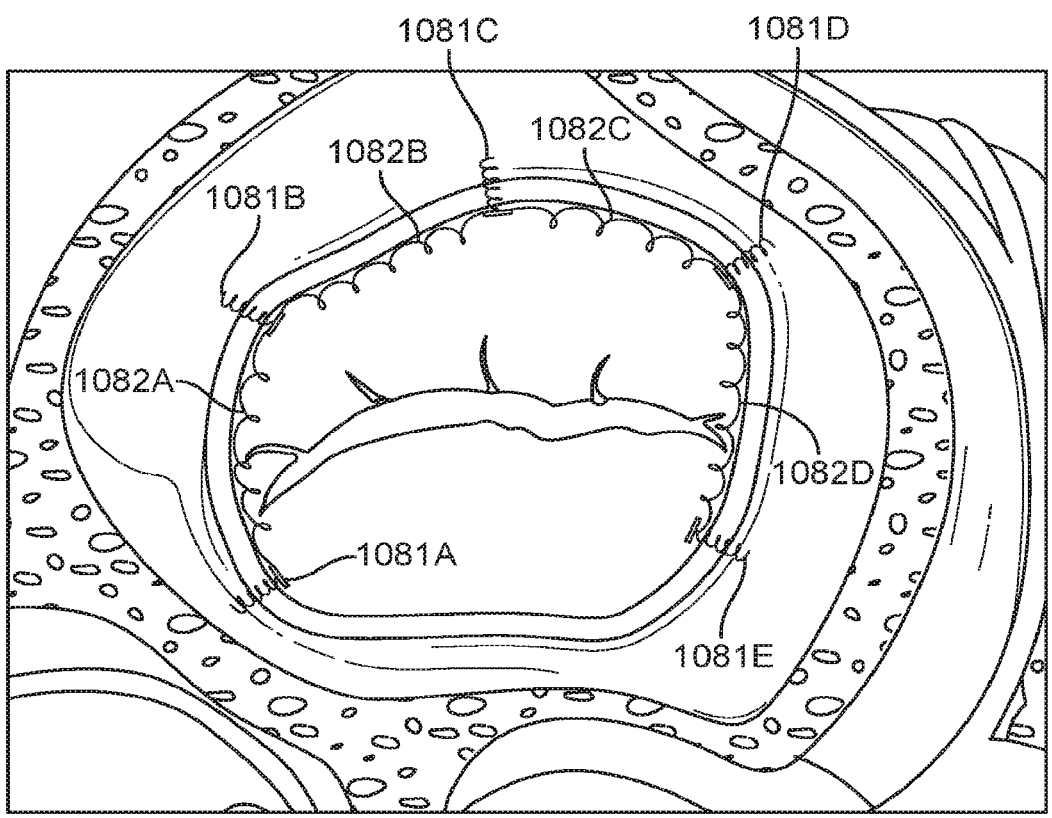
FIG. 80 shows an implant applied to an enlarged valve annulus consisting of multiple elastic segments, shown in the extended position.

FIG. 80 shows an implant consisting of an array of extensible members in the extended position 1082A-D, anchored to an annulus by a corresponding array of anchors 1081A-E. As shown, the extensible members in the extended position 1082A-D are attached to the enlarged annulus to be treated. Extensible members can be constructed of a resilient material or using a spring design known to the art to allow a sufficient range of elastic deformation. The materials of the extensible members can be superelastic nitinol, muscle fibers, flexinol), rubber, plastics, metals, or alloys with a high yield strength to provide appropriate elastic range for the desired function. Alternately, the extensible members may be constructed in a manner makes them transformable between an elongated configuration (as shown) and a shorter configuration (see FIG. 81.) Various transformable structures that would fit this purpose (including stents, balloons, linkages, or closed cellular structures) are known to the art. The numbers of extensible segments and anchors may be altered as needed to provide varying degrees of effect.

Figure 81:
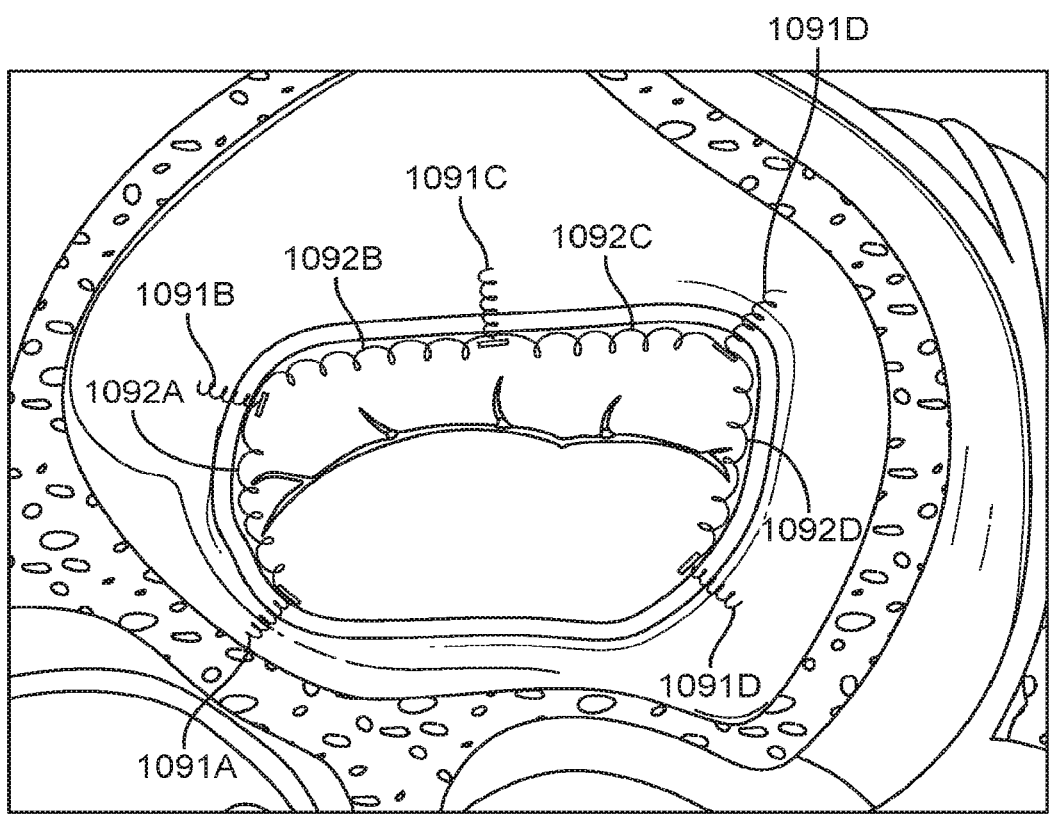
FIG. 81 shows an implant applied to an enlarged valve annulus consisting of multiple elastic segments, shown in the contracted position.
Figure 82:
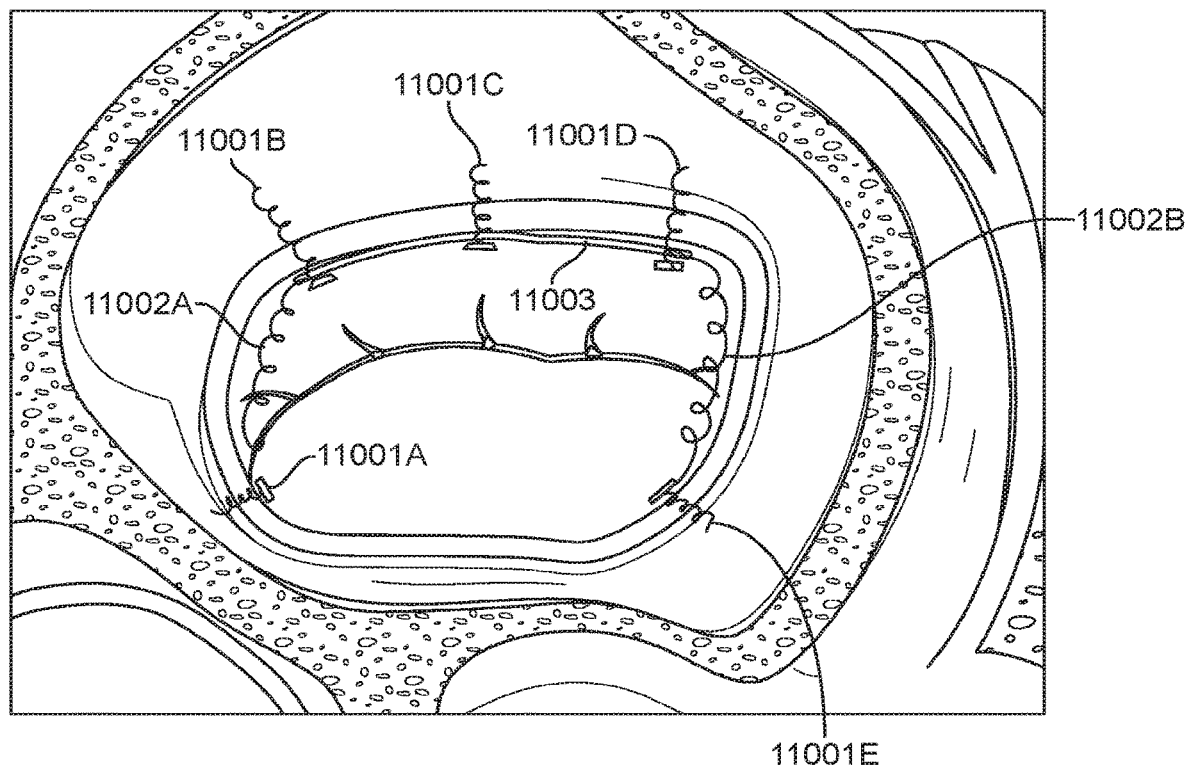
FIG. 82 shows an implant with a combination of substantially rigid segment and elastic segments, shown in the contracted position.

FIG. 81 shows an implant consisting of an array of extensible members in the compressed position 1092A-D, anchored to an annulus by a corresponding array of anchors 1091A-E. As shown, the extensible members in the compressed position 1092A-D have compressed the previously enlarged annulus to effect a reduction in the annular circumference, the annular area, the annular diameter, or some combination thereof. FIG. 82 shows a combination implant, including a semi-rigid shaping segment 11003, which is attached to the annulus by an array of anchors 11001B-11001D. The motion of this semi rigid shaping element 11003 is augmented by extensible elements 11002A and 11002B having both an extended and a contracted configuration, which are attached to the semi rigid shaping element 11003 and/or the anchors 11001B and 11001C and are further anchored to the annulus in the extended configuration at a distance from the anchors. The materials of the extensible members can be superelastic nitinol, muscle fibers (flexinol), rubbers, plastics, metal, or alloys with a high yield strength to provide appropriate elastic range for the desired function. Alternately, the extensible members may be constructed in a manner makes them transformable between an extended configuration and a contracted configuration. Various transformable structures that would fit this purpose (including stents, balloons, linkages, or closed cellular structures) are known to the art. When the extensible elements 11002A and 11002B are released/transformed to their contracted configuration, they act to additionally reduce the annular circumference, the annular area, the annular diameter, or some combination thereof.

Figure 83:
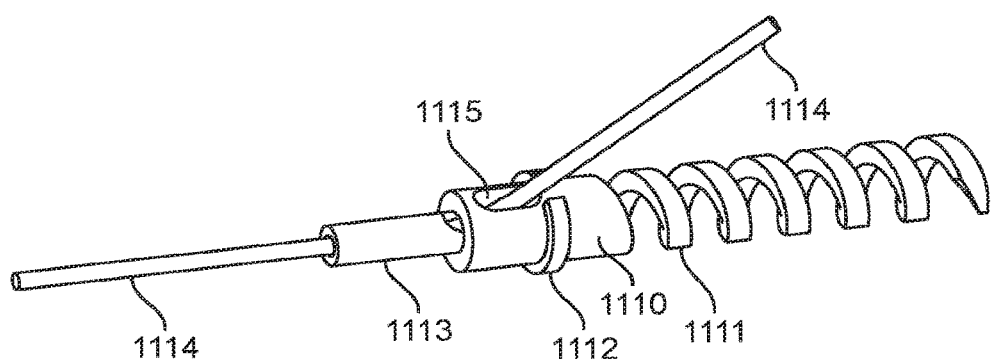
FIG. 83 shows an anchor for fastening implants to tissue which includes a helical coil, a torque member, and a key wire locking the two together against translational and rotational motion.

FIG. 83 shows an anchor for fastening an implant to tissue, including an anchor member 1110 having a helical coil section 1111, an implant stop feature 1112, and a locking feature 1115. The anchor system also includes a torque member 1113 and a locking wire 1114. The helical coil section 1111 of the anchor member 1110 can be fastened into the tissue by twisting the torque member 1114, which transfers the torque through the locking wire 1114 to the anchor member 1110 via the locking feature 1115. The locking wire also holds the anchor member 1110 to the torque member 1114 in the longitudinal Withdrawing the locking wire 1114 by pulling it proximally releases the anchor member 1110 from the torque member 1113 allowing removal of the torque member 1113 and locking wire 1114.

Figure 84:
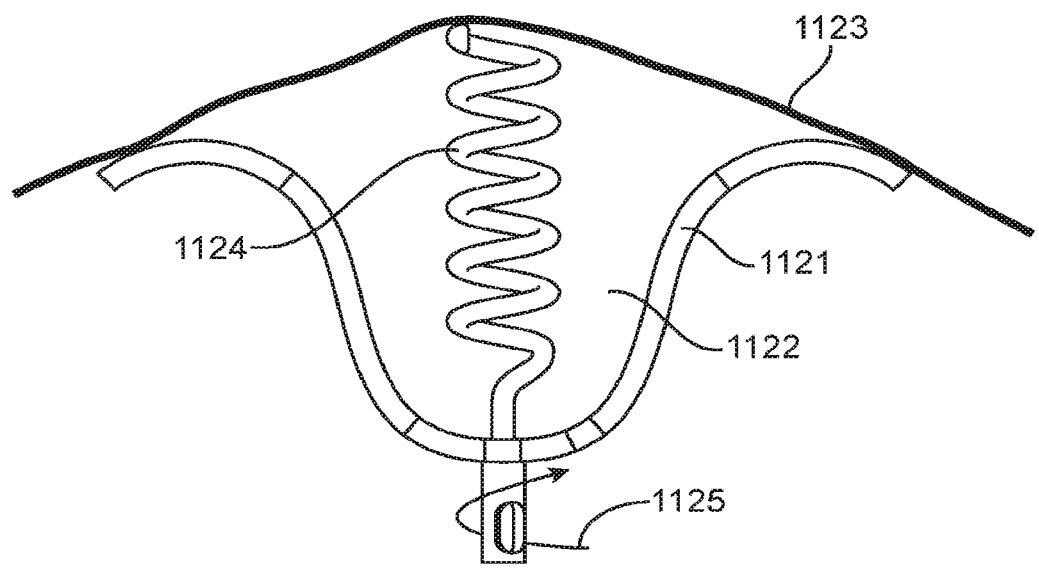
FIG. 84 shows an implant which includes a helical coil in position in tissue prior to activation of the helical coil

FIG. 84 shows an implant 1121 which defines a concave space 1122. The concave space is also referred to herein as a "concavity," as defined previously. The tissue 1123 is shown in place in contact with both the implant 1121 and a helical coil 1124 having a sharpened tip of the implant, but not entering the concave space 1122. Rotating the helical coil 1124 in the direction of the arrow 1125 will cause the helical coil 1124 to draw the tissue 1123 into the concave space 1122. A single implant could define multiple concave spaces, and include multiple helical coils, or multiple single-concave space implants could be used. Prior to rotating the helical coil, its sharpened tip extends beyond both sides of the implant to facilitate penetration of the tissue.

Figure 85:
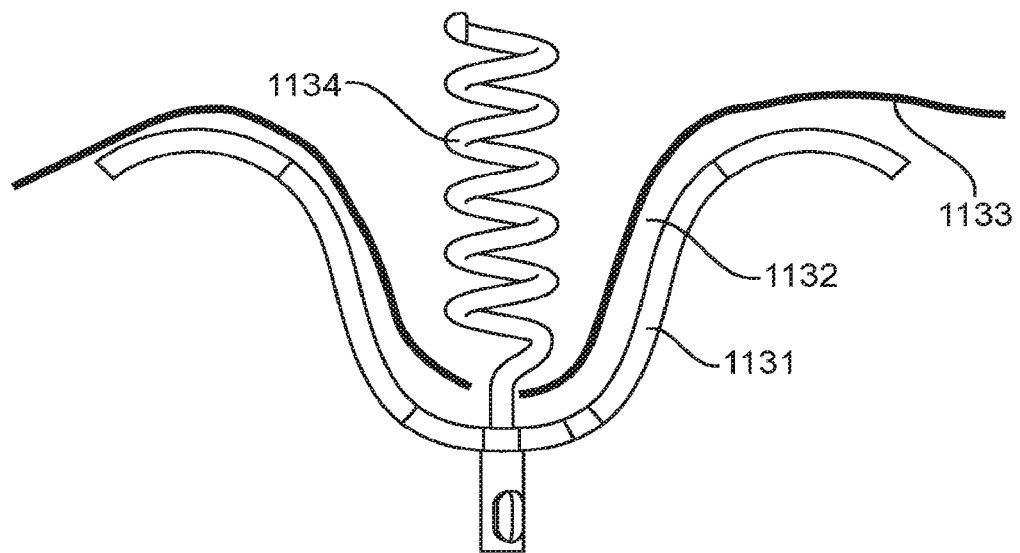
FIG. 85 shows an implant which includes a helical coil in position in tissue after activation of the helical coil

FIG. 85 shows an implant 1131 in place in tissue 1133. In this figure, the helical coil 1134 has been activated to draw the surrounding tissue 1133 into the concave space 1132, substantially filling the space 1132.

Figure 86:
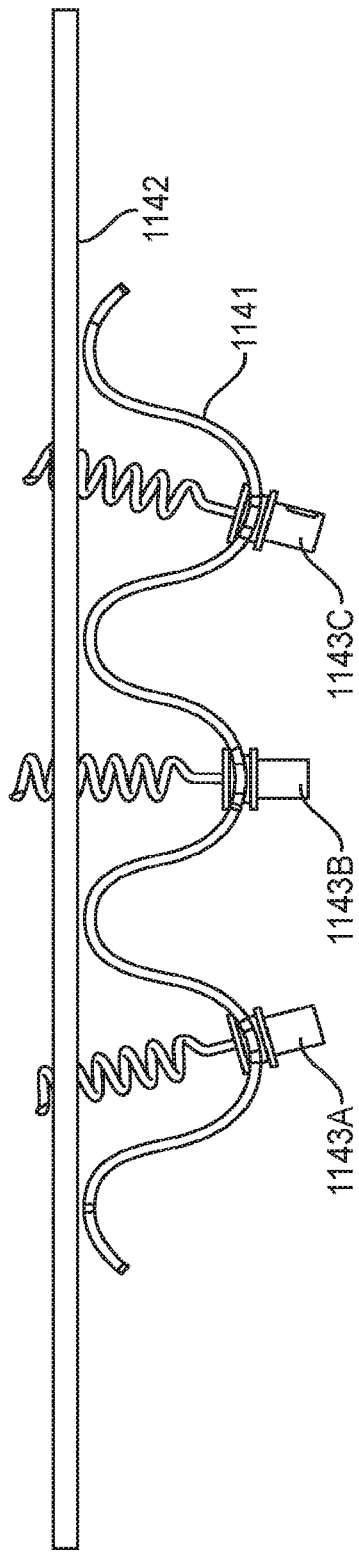
FIG. 86 shows an implant with helical coils in place against a substantially straight section of tissue which is significantly longer than the implant itself

FIG. 86 shows an undulating template 1141 in place against a substantially straight segment of tissue 1142, with three helical anchors 1143A-1143C connecting the undulating implant 1141 to the tissue segment 1142 without substantially deforming the tissue segment 1142. The ends of the tissue segment 1142 are substantially farther apart than the ends of the undulating template 1141, although their lengths are comparable.

Figure 87:
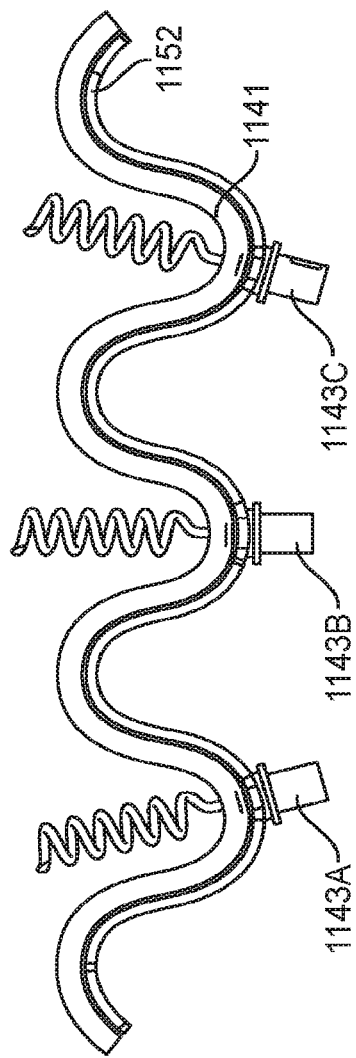
FIG. 87 shows the implant of FIG. 86 with the same tissue of FIG. 86 having been drawn into the concavities of the implant, bringing the ends of the tissue into approximation with the ends of the implant.

FIG. 87 shows the undulating template 1141 of FIG. 86 with the now undulating tissue segment 1152 having been pulled tightly against the undulating template 1141 by the helical anchors 1143A-1143C. The ends of the now undulating tissue segment 1152 are proximate to the ends of the undulating template 1141, although its length is comparable to the substantially straight segment of tissue 1142 from FIG. 86.

Figure 88:
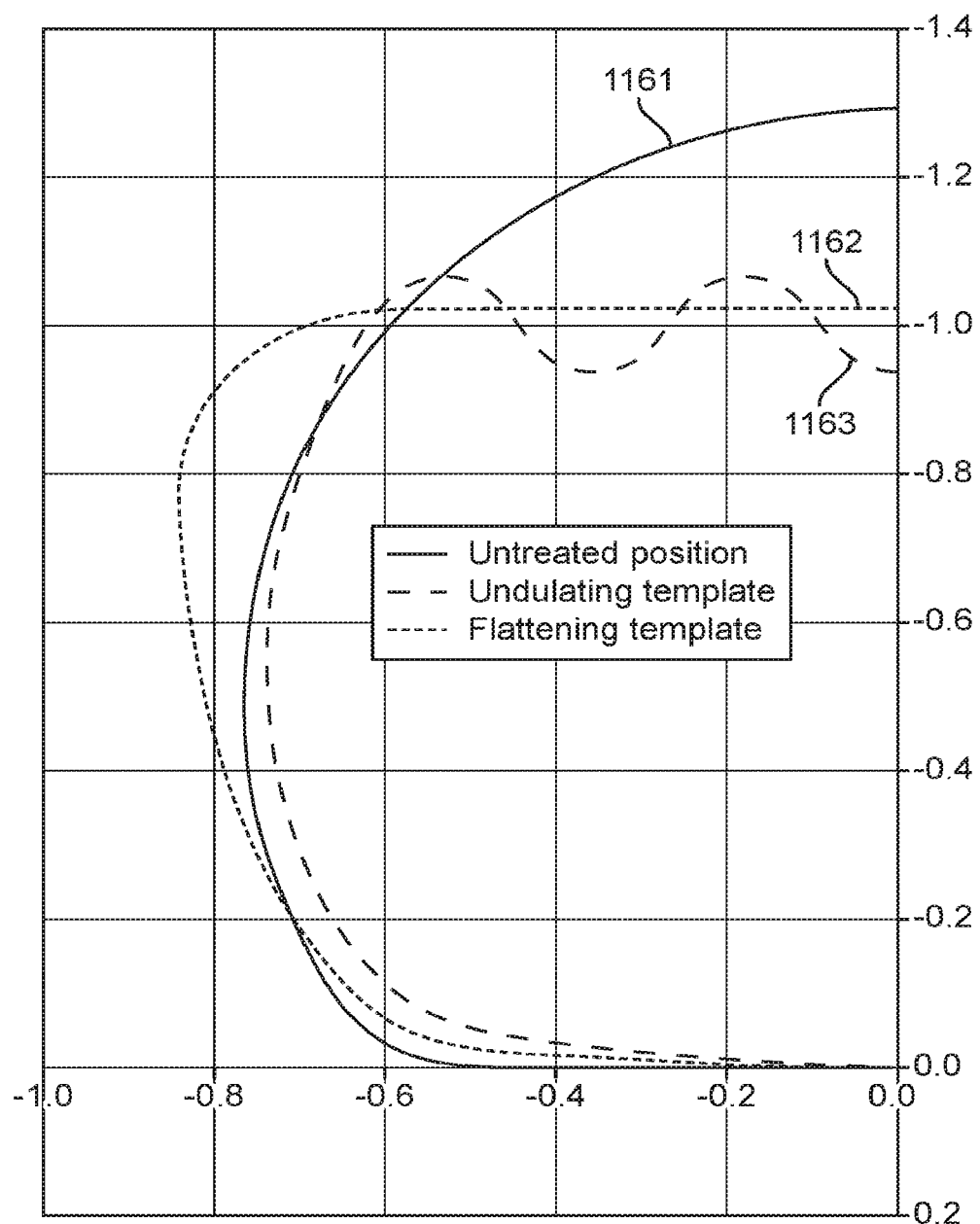
FIG. 88 shows projected shapes of a model mitral annulus, that annulus treated with a flattening implant, and that annulus treated with an undulating implant.

FIG. 88 shows the deformations projected on an untreated mitral valve annulus 1161 by a flattening template 1162 and an undulating template 1163. The undulating template creates similar reduction in vertical dimension as shown, without substantially increasing horizontal dimension as shown.

Figure 89:
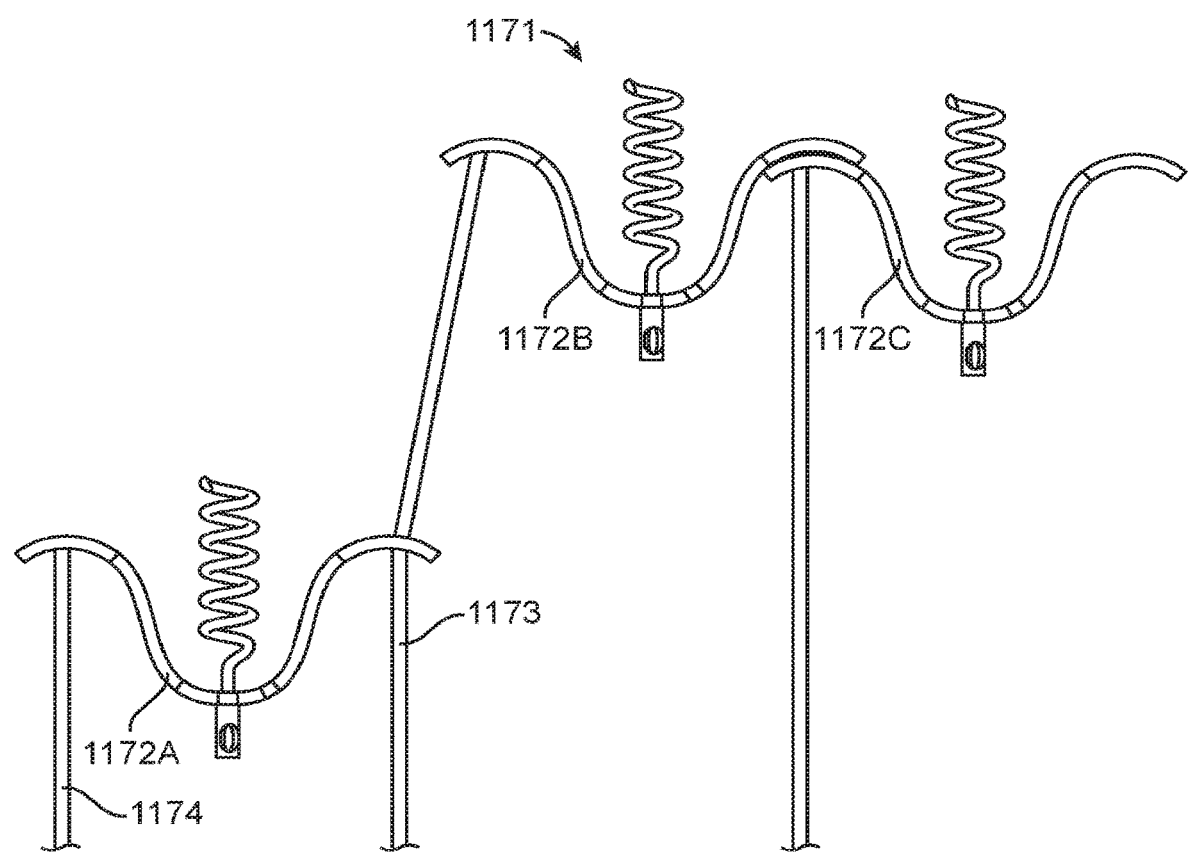
FIG. 89 illustrates an undulating implant that is assembled in place from sub-sections of the implant.

FIG. 89 shows a segmented undulating template 1171, consisting of segments 1172A-1172C. As shown, segments 1172B and 1172C have been delivered into the desired position, and segment 1172A is being delivered to the desired position by sliding it along an elongate locating member 1173 which is attached to the already placed segment 1172B. An elongate locating member 1174 is attached to the segment 1172A which is in the process of being placed, offering guidance for placement of an additional segment (not shown). In this way, it is possible to place an arbitrary number of segments by sliding the next segment up the outermost elongate locating member 1174.

Figure 90:
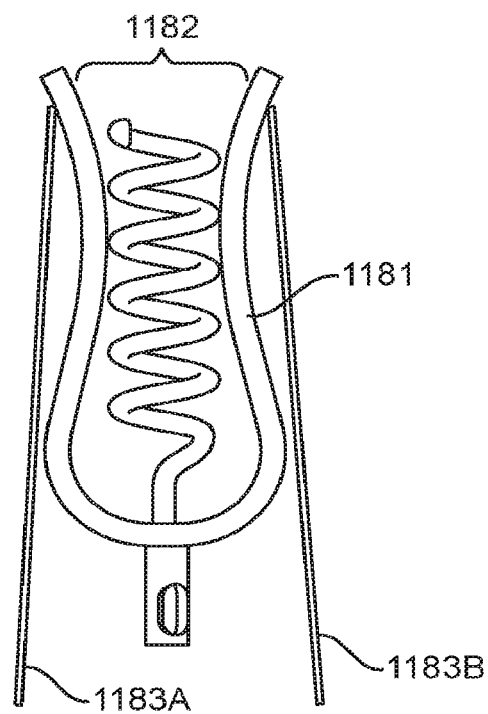
FIG. 90 shows a subsection of an undulating implant folded to a reduced diameter for ease of delivery through a tube or tubular structure

FIG. 90 shows a segment of an undulating template 1181 folded distally for delivery through a tube or tubular structure. The ends of the segment of the undulating template 1181 are held together by a removable shaper 1182 which holds the undulating template 1181 in its folded configuration during delivery. In addition, two elongated control elements such as control wires 1183A and 1183B are shown attached near the ends of the segment of the undulating template 1181.

Figure 91:
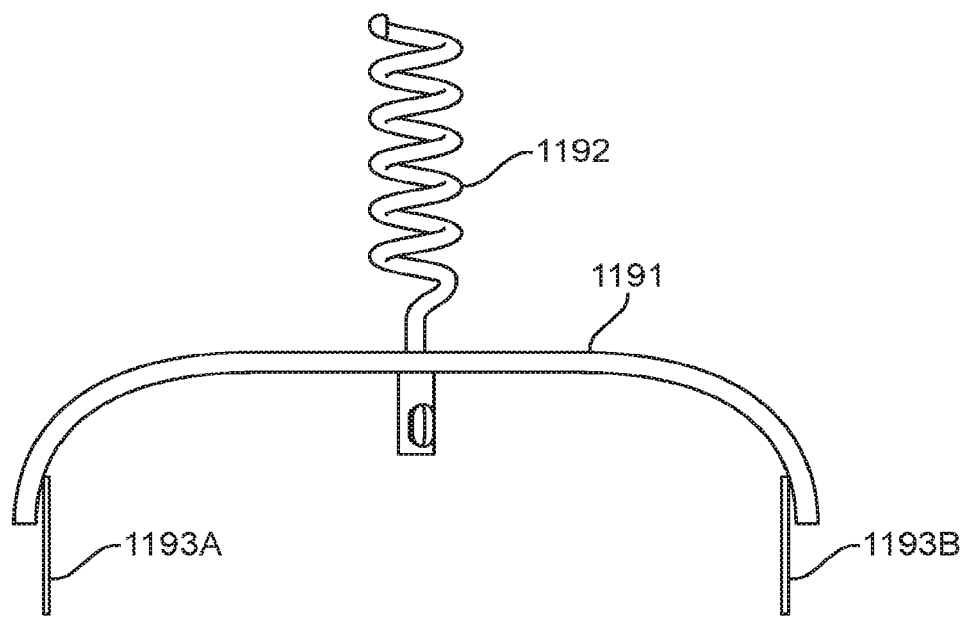
FIG. 91 shows a subsection of an undulating implant expanded to allow ease of anchor placement

FIG. 91 shows a segment of an undulating template 1191 which has been expanded by applying tension to the control wires 1193A and 1193B. The anchor 1192 extends away from the segment of the undulating template 1191 to allow easy anchoring in tissue (not shown)

Figure 92:
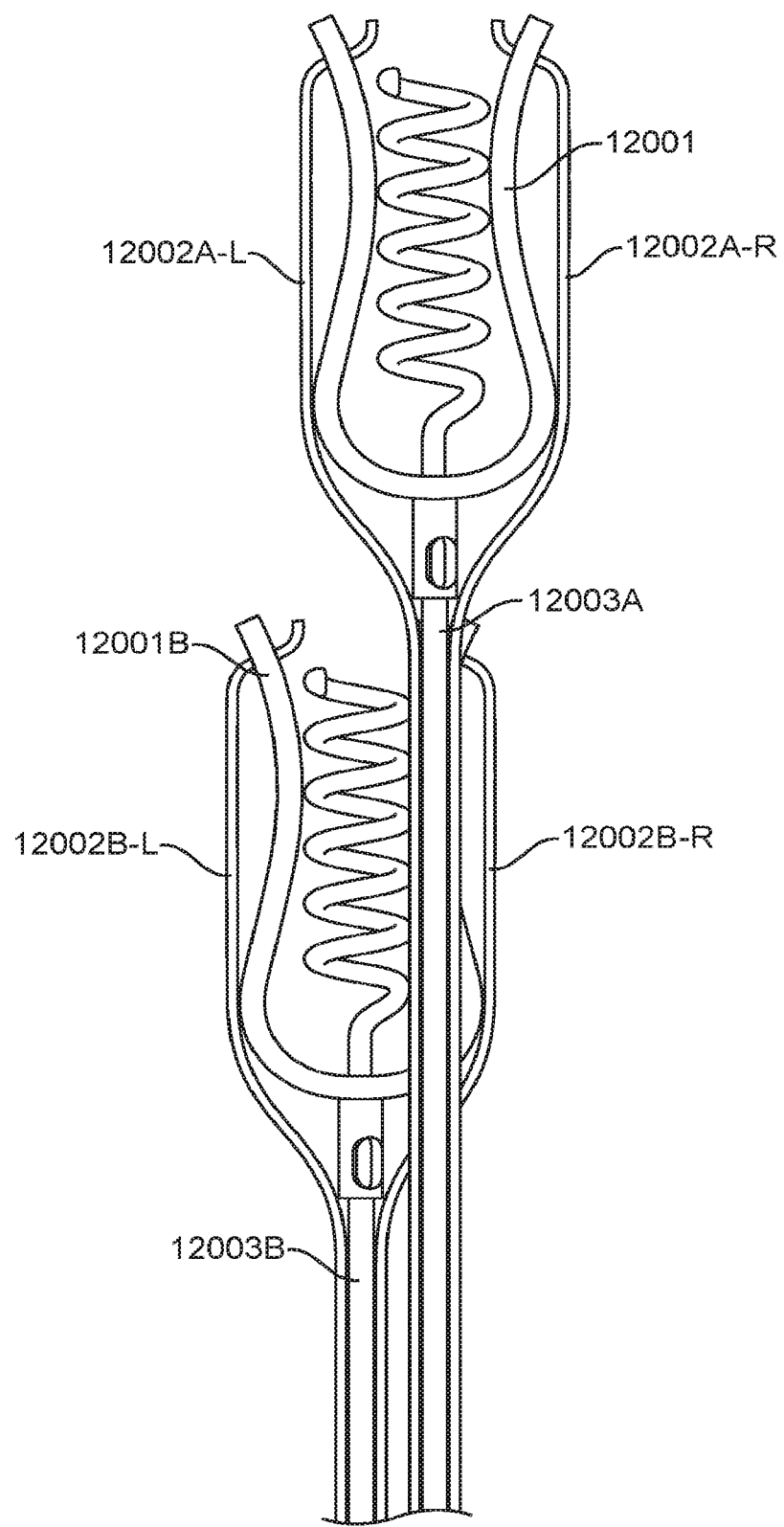
FIG. 92 shows a pair of subsections of an undulating implant arranged one in front of the other for simultaneous delivery through a tube or tubular structure.

FIG. 92 shows two segments of undulating templates 12001A and 12001B attached to control wires 12002A-R, 12002A-L, 12002B-R, and 12002B-L and torque members 12003A and 12003B, arranged one behind the other for delivery through a tubular structure (not shown). The alignment of the segments 12001A and 12001B is shown slightly offset, but should be adjusted to allow for minimum tube diameter that allows passage of the segments of undulating templates 12001A and 12001B, control wires 12002A-R, 12002A-L, 12002B-R, and 12002B-L and torque members 12003A and 12003B through as small a diameter tubular structure as practical. Additional segments of undulating template (not shown) can be arranged in similar fashion for placement through a tubular structure as needed.

Figure 93:
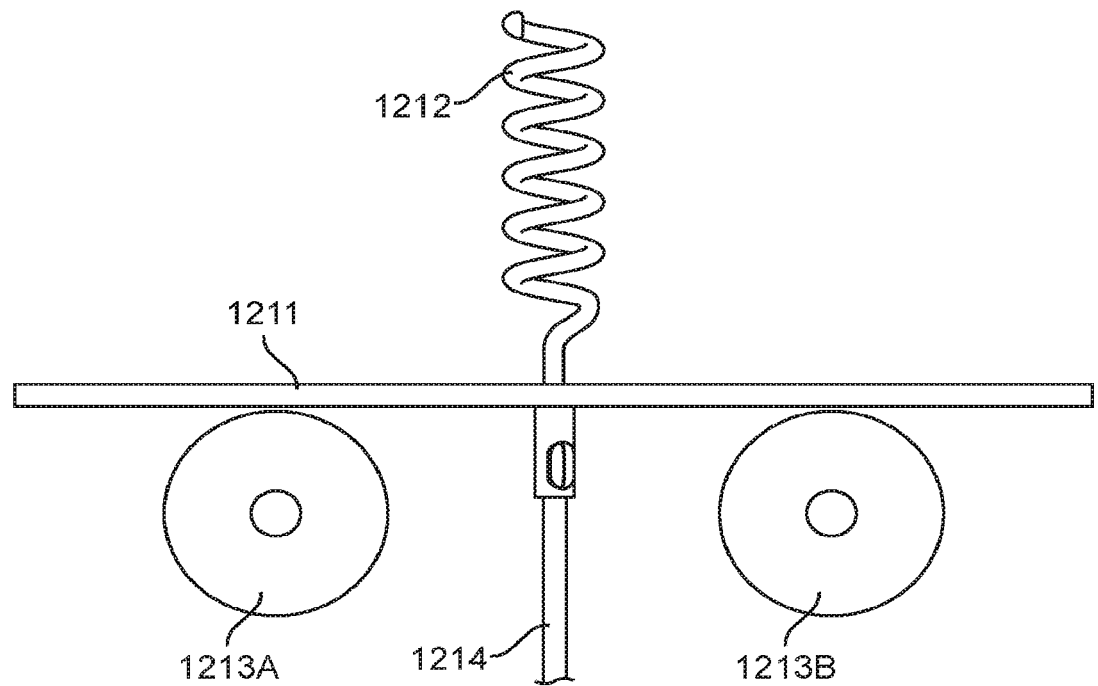
FIG. 93 shows an implant template that is placed in a substantially straight configuration, with deforming members in apposition to the implant template.

FIG. 93 shows a substantially flat, shapeable template 1211 with an anchor 1212 with torque member 1214 and forming dies 1213A and 1213B. The orientation of the forming dies 1213A and 1213B relative to the anchor 1212 and torque member 1214 is such that the forming dies 1213A and 1213B appose the shapeable template 1211 in its substantially flat configuration. In this substantially flat configuration, the shapeable template 1211 can be firmly attached to the target tissue (not shown) through activation of the anchor 1212.

Figure 94:
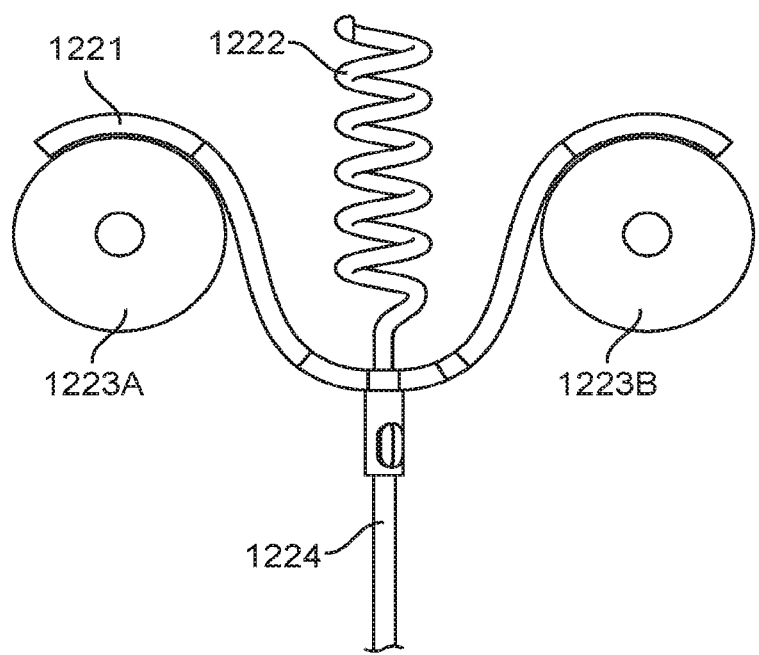
FIG. 94 shows the implant template of FIG. 93 having been deformed by the deforming members as they are moved distal relative to the anchor.

FIG. 94 shows a shapeable template 1221 in the shaped configuration, created by relative motion between the anchor 1222 and forming dies 1223A and 1223B. When the shapeable template 1221 is firmly attached to tissue via the anchor 1223, the tissue will move along with the template as it is shaped, creating a desired shaping and/or shortening effect.

Figure 95:
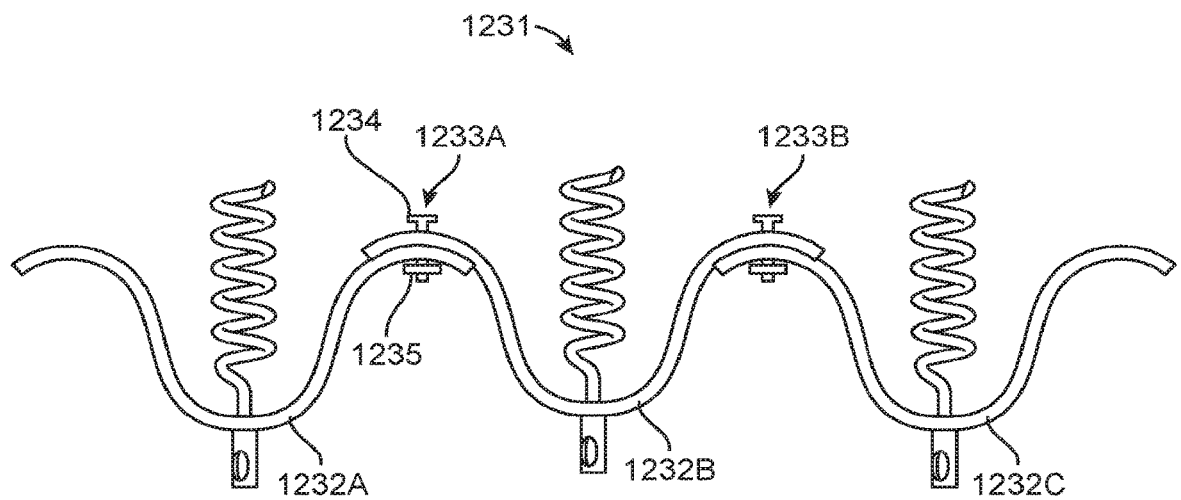
FIG. 95 shows an array of subsections of an undulating implant pinned together via a pin extending through the two subsections with a locking cap to hold the two subsections together.

FIG. 95 shows an assembled undulating template 1231 made up of three undulating template segments 1232A-1232C. The segments are connected with pin connectors 1233A and 1233B, each of which is made up of a pin element 1234 attached to an undulating template segment through an attachment device 1235. Typical attachment devices known to the art which may be applicable to this mechanism include threaded fasteners such as nuts, crimp connectors, and push-on retaining rings.

Figure 96:
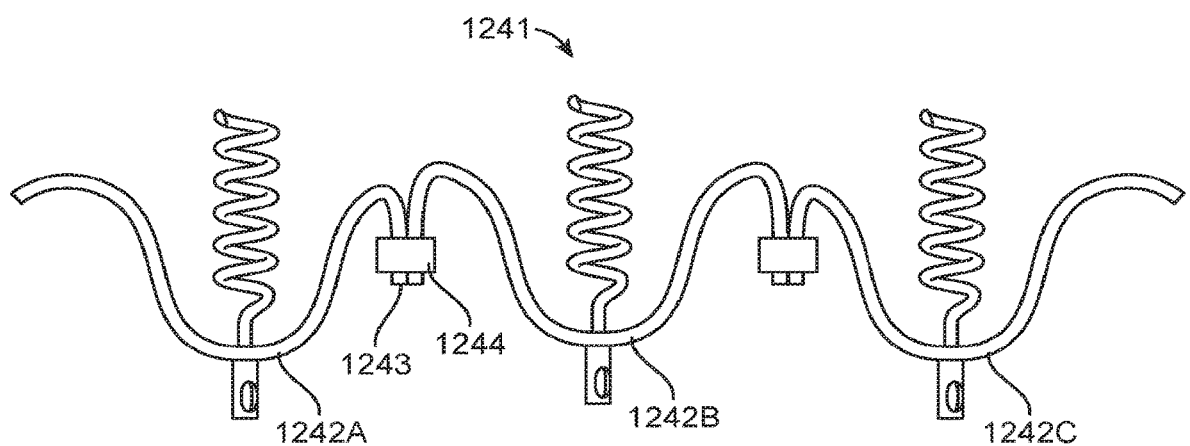
FIG. 96 shows an array of subsections of an undulating implant having extensions that are substantially parallel to the anchor member which are held together with locking devices.

FIG. 96 shows an assembled undulating template 1241 made up of three undulating template segments 1242A-1242C. The segments are connected by an integral post 1243 joined by an attachment device 1244. Typical attachment devices known to the art which may be applicable to this mechanism include threaded fasteners such as nuts, crimp connectors, and push-on retaining rings.

Figure 97:
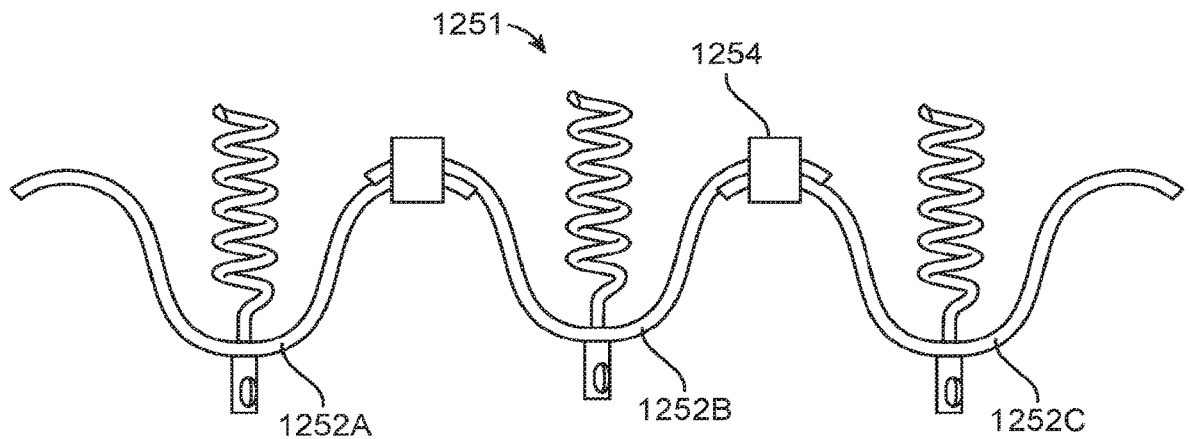
FIG. 97 shows an array of subsections of an undulating with ends that are held together with locking devices.

FIG. 97 shows an assembled undulating template 1251 made up of three undulating template segments 1252A-1252C. The segments are connected by mechanical connectors 1254. Typical mechanical connectors applicable to this mechanism include crimp connectors and clips.

Figure 98:
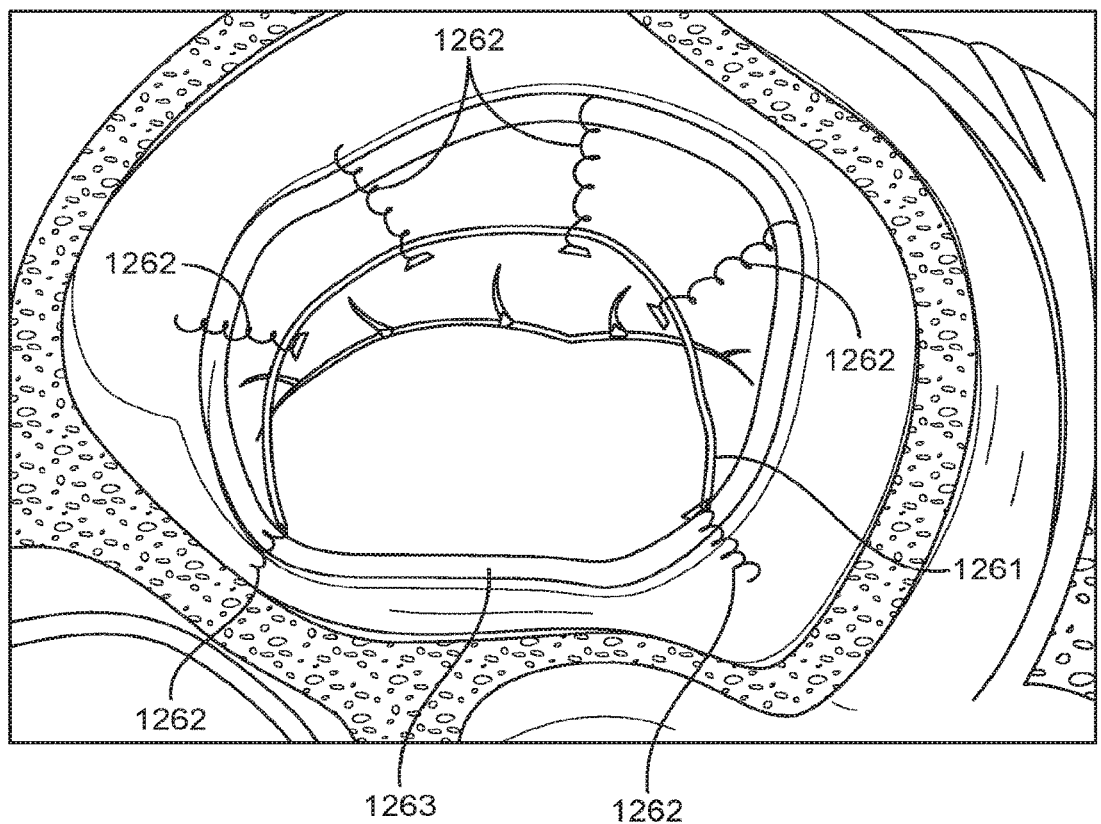
FIG. 98 shows a partial ring template with multiple anchors, the partial ring template being smaller than the mitral annulus, and the multiple anchors being used to draw the annulus towards the template.

FIG. 98 shows a partial annular ring 1261 with multiple anchors 1262 disposed within a valve annulus 1263. The anchors 1262 are of sufficient length to bridge the gap between the partial annular ring and the valve annulus 1263. Activating the anchors 1262 draws the annulus 1263 toward the partial ring 1261, reshaping the annulus 1263 to the desired configuration. It is possible to apply this approach to a closed ring of the desired shape as well as the partial annular ring 1261 as shown. Desired shapes for the partial or close ring may include circular, D-shaped, oval, elliptical, or with a concave section corresponding to one or more anchor 1262 positions.

Figure 99:
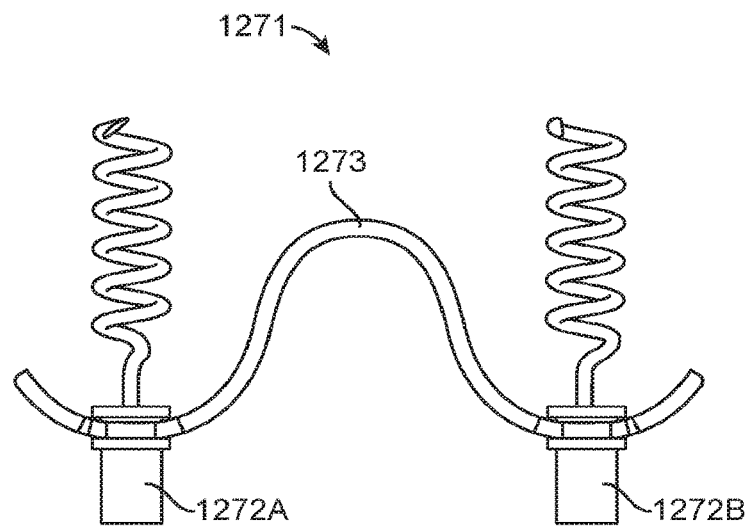
FIG. 99 shows a two-anchor segment with a convex profile for shaping the valve annulus

FIG. 99 shows an alternate segment of an undulating template 1271 having two anchors 1272A and 1272B separated by a convex segment 1273.

Figure 100:
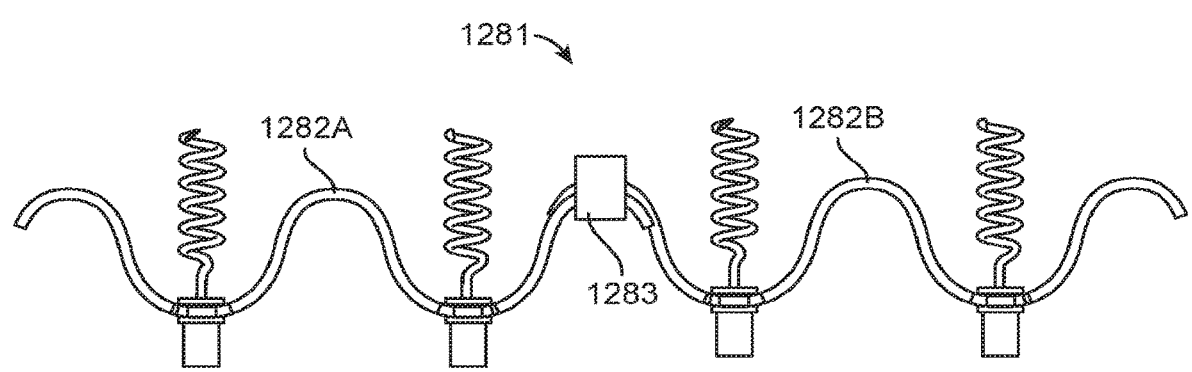
FIG. 100 shows a template constructed from two two-anchor segments with convex profiles

FIG. 100 shows an undulating template 1281 consisting of two alternate segments 1282A and 1282B each having two anchors separated by a convex segment, joined by an attachment mechanism 1283. Typical mechanical connectors applicable to this mechanism include crimp connectors, clips, sutures, or the like.

Figure 101:
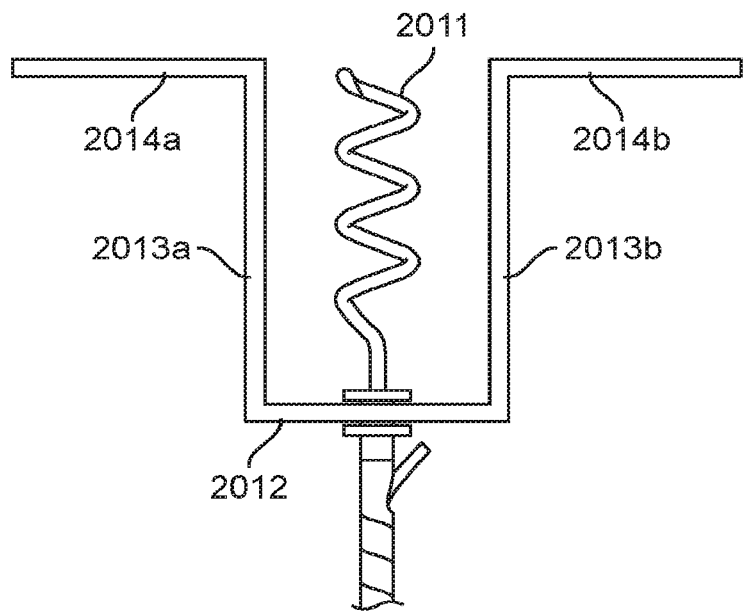
FIG. 101 shows an undulating template with a single undulation composed of straight segments aligned horizontally and vertically.

FIG. 101 shows an undulating template 2012 composed of approximately straight segments arranged in a rectilinear pattern with angled bends or corners, with a tissue coupling mechanism 2011 attached approximating the mid-point of the body of the template, two body segments 2013*a* and 2013*b* rising from the point of attachment of the tissue coupling mechanism 2011, and two compressive peaks 2014*a* and 2014*b*. The area of the undulating template 2012 where the tissue coupling mechanism is attached as well as the area of the compressive peaks 2014*a* and 2014*b* are substantially horizontal, while the rising body segments 2013*a* and 2013*b* are substantially vertical.

Figure 102:
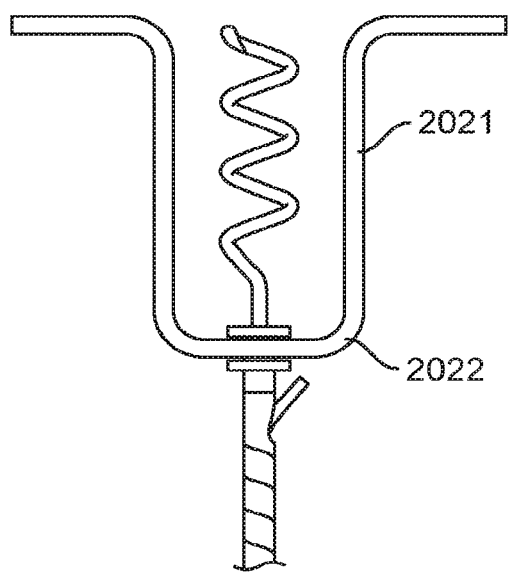
FIG. 102 shows an undulating template with a single undulation composed of a combination of straight and curved segments aligned perpendicularly to each other.

FIG. 102 shows an undulating template 2021 composed of approximately straight segments connected by arcuate segments including the lower right arcuate segment 2022.

Figure 103:
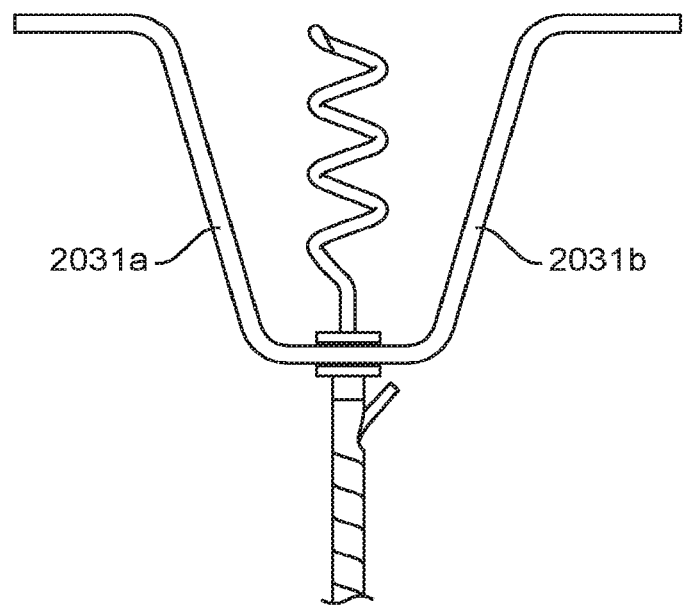
FIG. 103 shows an undulating template with a single undulation composed of a combination of straight and curved segments aligned at non-perpendicular angles to each other.

FIG. 103 shows an undulating template where the rising body segments 2031*a* and 2031*b* form a diverging angle relative to each other and the point of attachment of the tissue coupling mechanism. As tissue is drawn towards the base of the tissue coupling mechanism, the gap between the rising body segments 2031*a* and 2031*b* narrows, causing increasing compressive forces on the tissue.

Figure 104:
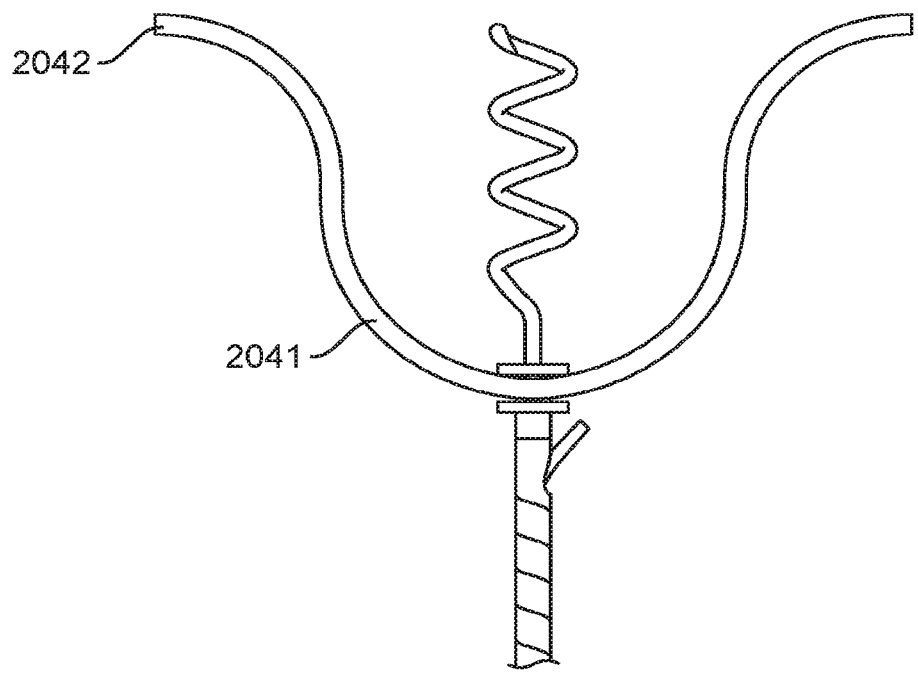
FIG. 104 shows an undulating template with a single undulation composed of curved segments with the ends configured so that the tangent to the curved segment at the end is parallel to the tangent at the location where the tissue coupling mechanism is attached.

FIG. 104 shows an undulating template 2041 composed of arcuate segments ending so that the segment ends near the compressive peak 2042.

Figure 105:
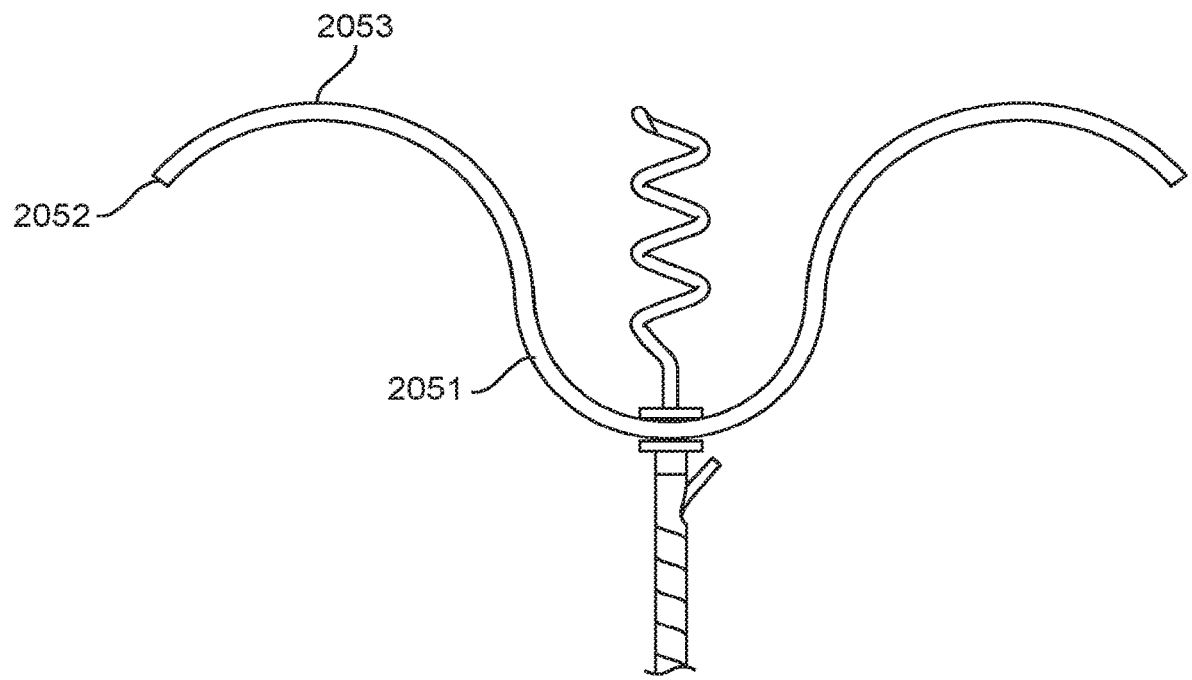
FIG. 105 shows an undulating template with a single undulation composed of curved segments with the ends extending past the point at which the tangent to the curved segment is parallel to the tangent at the location where the tissue coupling mechanism is attached

FIG. 105 shows an undulating template 2051 composed of arcuate segments ending so that the segment end 2052) extends past the compressive peak 2053.

Figure 106:
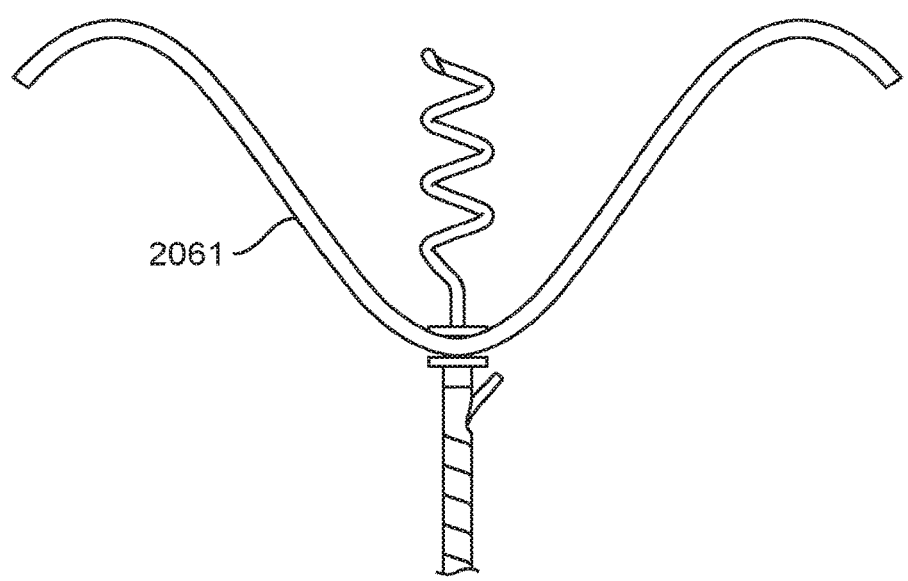
FIG. 106 shows an undulating template with a single undulation with a continuous non-circular shape.

FIG. 106 shows an undulating template 2061 composed of a continuous, non-circular shape. As shown, the shape is a sinusoidal curve.

Figure 107:
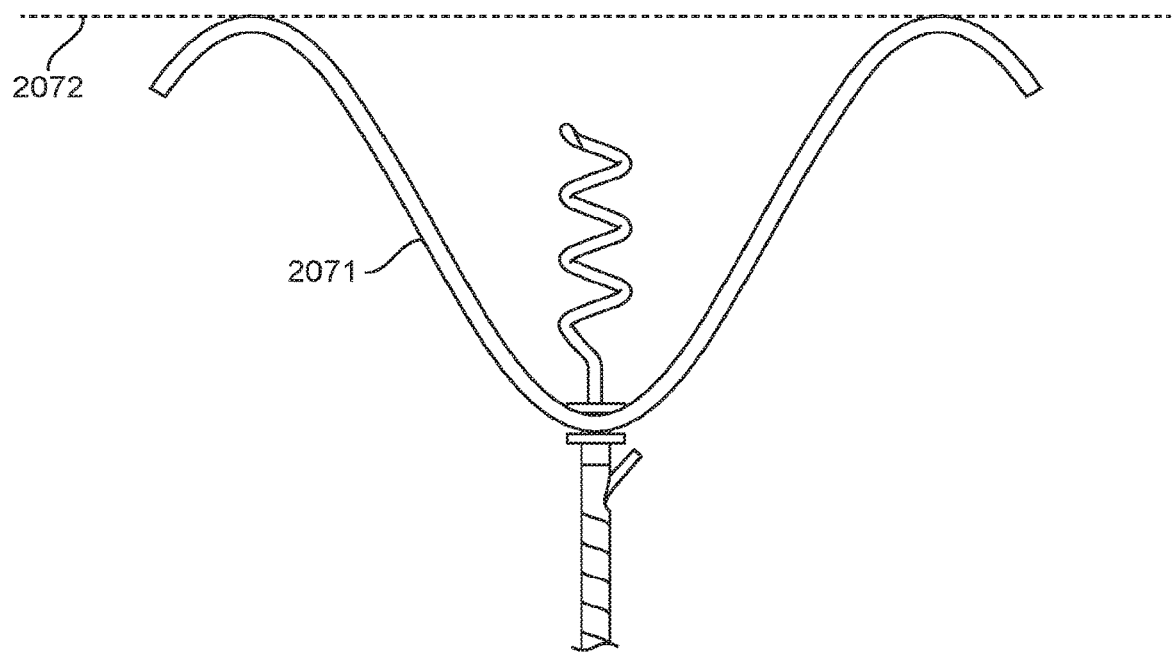
FIG. 107 shows an undulating template where the distance from the point where the tissue coupling mechanism is attached to the highest peaks of the body of the template is greater than the length of the tissue coupling mechanism

FIG. 107 shows an undulating template 2071 where the distance from the point where the tissue coupling mechanism is attached to the compression peaks of the body of the template is greater than the length of the tissue coupling mechanism. A line 2072 tangent to the compression peaks is not crossed by the distal tip of the tissue coupling mechanism. Placement of such a template can be accomplished, for example, by deflecting the template proximally so that the tissue coupling mechanism can penetrate the target tissue.

Figure 108:
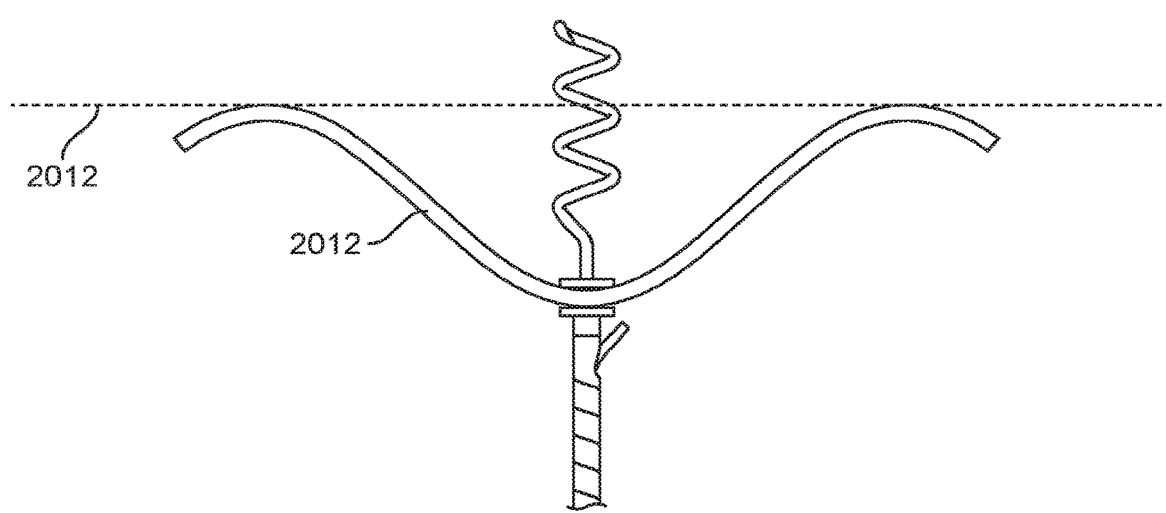
FIG. 108 shows an undulating template where the distance from the point where the tissue coupling mechanism is attached to the highest peaks of the body of the template is less than the length of the tissue coupling mechanism

FIG. 108 shows an undulating template 2081 where the distance from the point where the tissue coupling mechanism is attached to the compression peaks of the body of the template is less than the length of the tissue coupling mechanism. The distal tip of the coupling mechanism crosses a line 2082 tangent to the compression peak. Placement of such a template can be accomplished, for example, with the ends of the template in the relaxed and non-deflected position.

Figure 109:
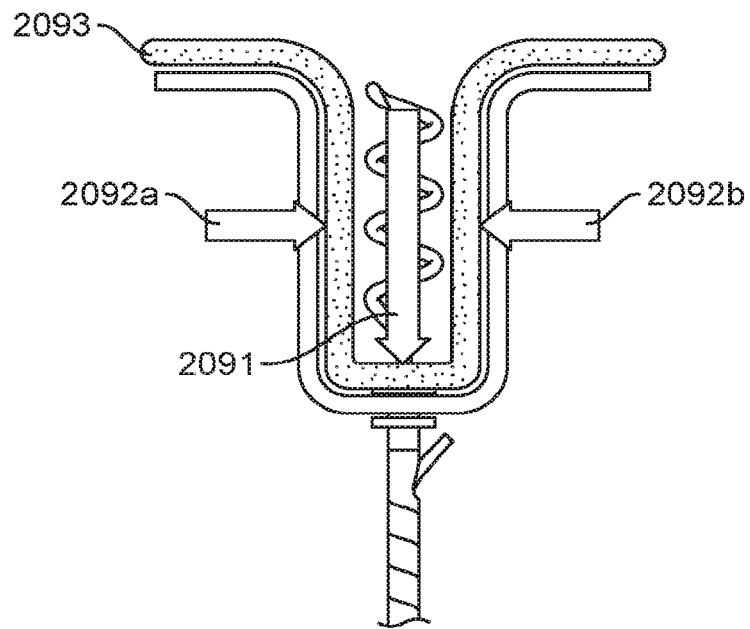
FIG. 109 shows an undulating template with tissue held in place by a tissue coupling mechanism, causing the template to exert forces in a tensile manner normal to the original position of the tissue (via the tissue coupling mechanism) and in an inward manner, tangential to the original position of the tissue.

FIG. 109 shows an undulating template with tissue 2093 held in place by a tissue coupling mechanism, causing the template to exert tensile force 2091 normal to the original position of the tissue (via the tissue coupling mechanism) and inward forces 2092*a* and 2092*b*, tangential to the original position of the tissue.

Figure 110:
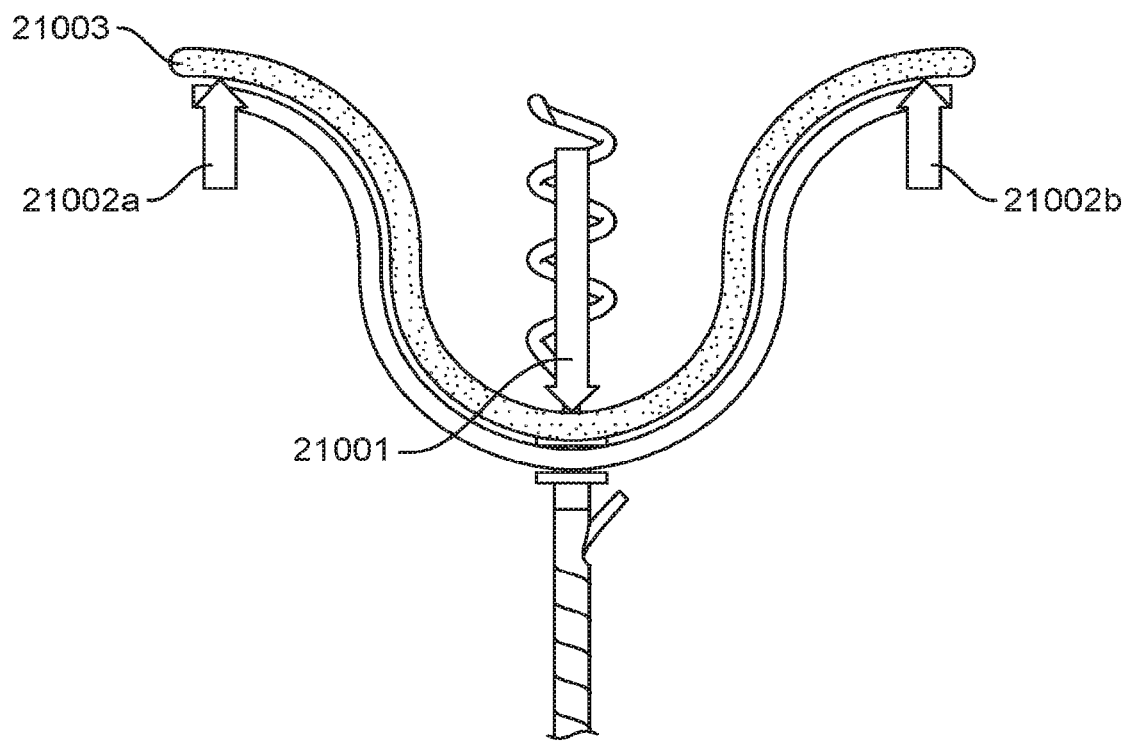
FIG. 110 shows an undulating template with tissue held in place by a tissue coupling mechanism, causing the template to exert forces in a tensile manner normal to the original position of the tissue (via the tissue coupling mechanism) and in a compressive manner normal to the original position of the tissue at the peaks of the undulations.

FIG. 110 shows an undulating template with tissue 21003 held in place by a tissue coupling mechanism, causing the template to exert tensile force 21001 normal to the original position of the tissue (via the tissue coupling mechanism) and compressive forces 21002*a* and 21002*b*, normal to the original position of the tissue in substantially the opposite direction as the tensile force 21001.

Figure 111:
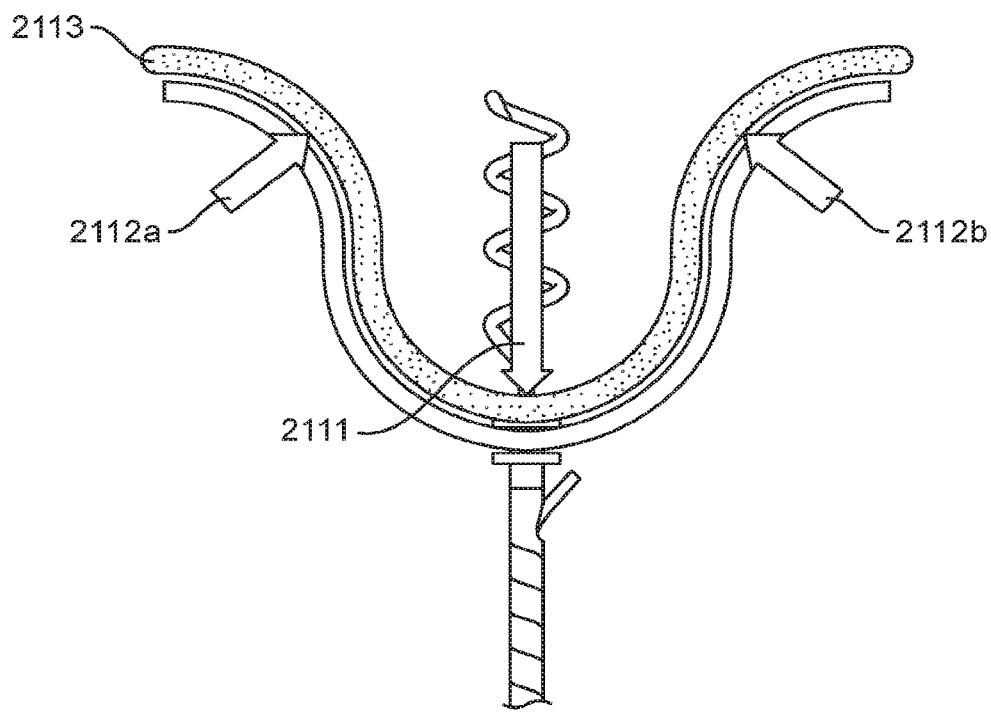

FIG. 111 shows an undulating template with tissue 2113 held in place by a tissue coupling mechanism, causing the template to exert tensile force 2111 normal to the original position of the tissue (via the tissue coupling mechanism) and compressive-inward forces 2112*a* and 2112*b*, between normal and tangential to the original position of the tissue.

Figure 112:
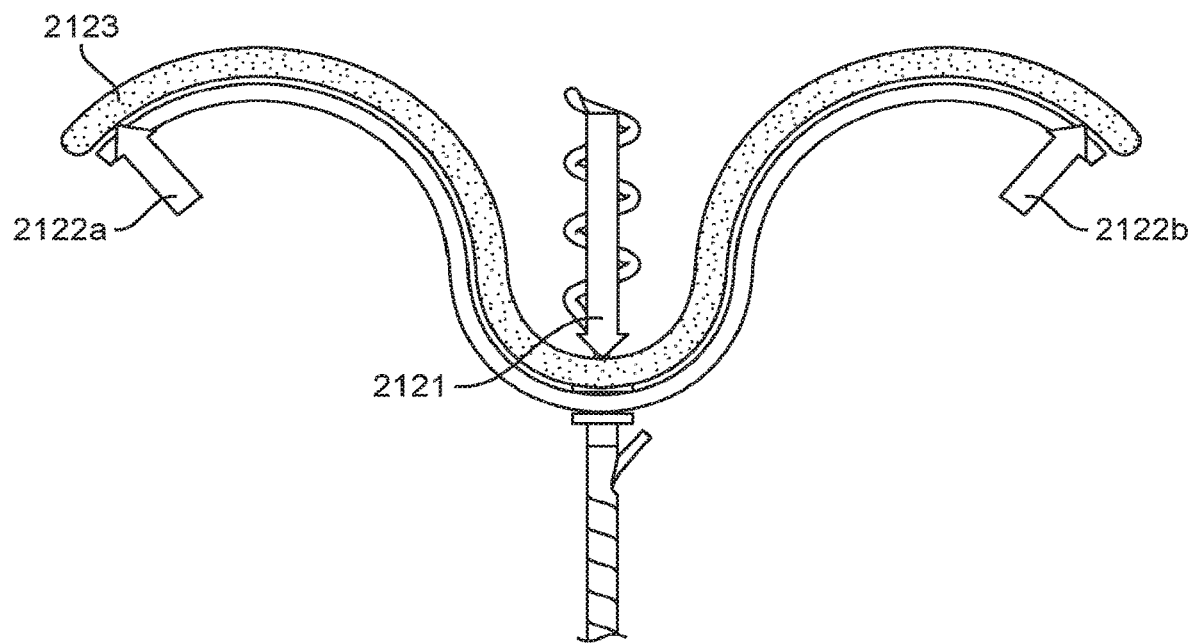

FIG. 112 shows an undulating template with tissue 2123 held in place by a tissue coupling mechanism, causing the template to exert tensile force 2121 normal to the original position of the tissue (via the tissue coupling mechanism) and compressive-outward forces 2122*a* and 2122*b*, between normal and tangential to the original position of the tissue.

Figure 113:
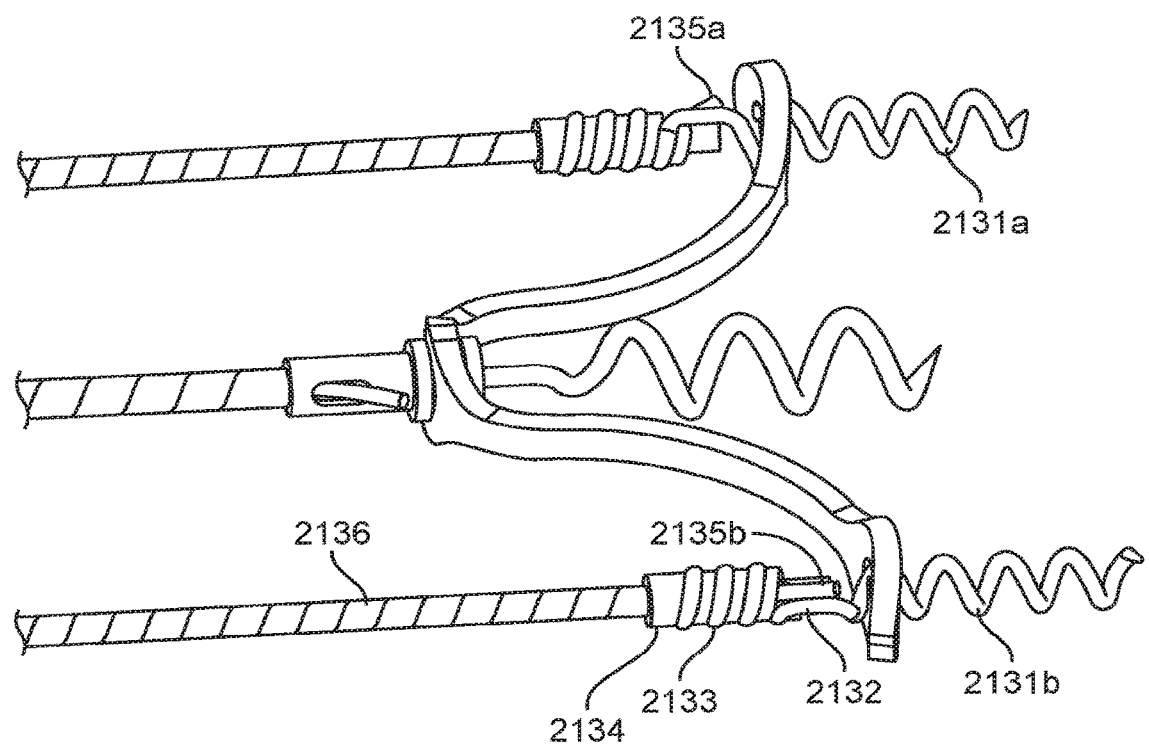

FIG. 113 shows an undulating template with stabilizing tissue coupling mechanisms 2131*a* and 2131*b* at each end of the body, in addition to the primary tissue coupling mechanism in the middle. The stabilizing tissue coupling mechanisms 2131*a* and 2131*b* each have a penetrating coil at their distal ends, and a coupling coil 2133 at the proximal end with the opposite handedness of the penetrating coil. The stabilizing tissue coupling mechanisms 2131*a* and 2131*b* are releasably coupled via coupling bushings 2134 attached to small torque members 2136. The coupling bushings 2134 guide and capture the coupling coil 2133 of the stabilizing tissue coupling mechanisms 2131*a* and 2131*b* against turning in one direction. They are prevented from turning relative to each other by a key wire 2135*a* and 2135*b*. Removing the key wire 2135*a* or 2135*b* allows the small torque members 2136 and attached coupling bushings 2134 to turn relative to the coupling coil 2133, releasing the stabilizing tissue coupling mechanisms 2131*a* and 2131*b* from the coupling bushing 2134. A slot in the undulating template is arranged so that the stabilizing tissue coupling mechanisms 2131*a* and 2131*b* will not slide freely through the undulating template when coupled to adjacent tissues by twisting.

Figure 114:
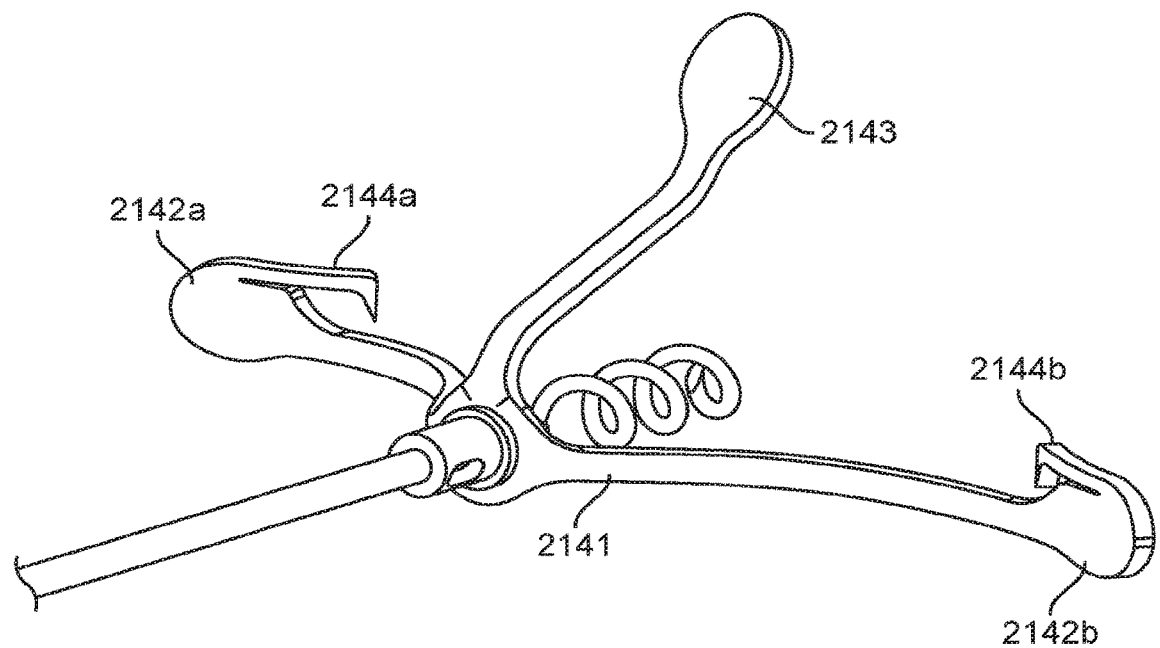

FIG. 114 shows and undulating template 2141 with two principal ends 2142*a* and 2142*b*, and an additional stabilizing arm 2143 extending from the body, as well as stabilizing penetrating points 2144*a* and 2144*b*, in this example disposed near the principal ends 2142*a* and 2142*b*. The body of the template 2141 may include a single stabilizing penetrating point, two stabilizing penetrating points 2144*a* and 2144*b* as shown, or more as required. The stabilizing penetrating points 2144*a* and 2144*b* may include curves, barbs, bends, or other such features to allow them to passively penetrate the tissue adjacent to the undulating template 2141, or may benefit from action on behalf of the user to actuate the stabilizing penetrating point 2144*a* and 2144*b*.

Figure 115:
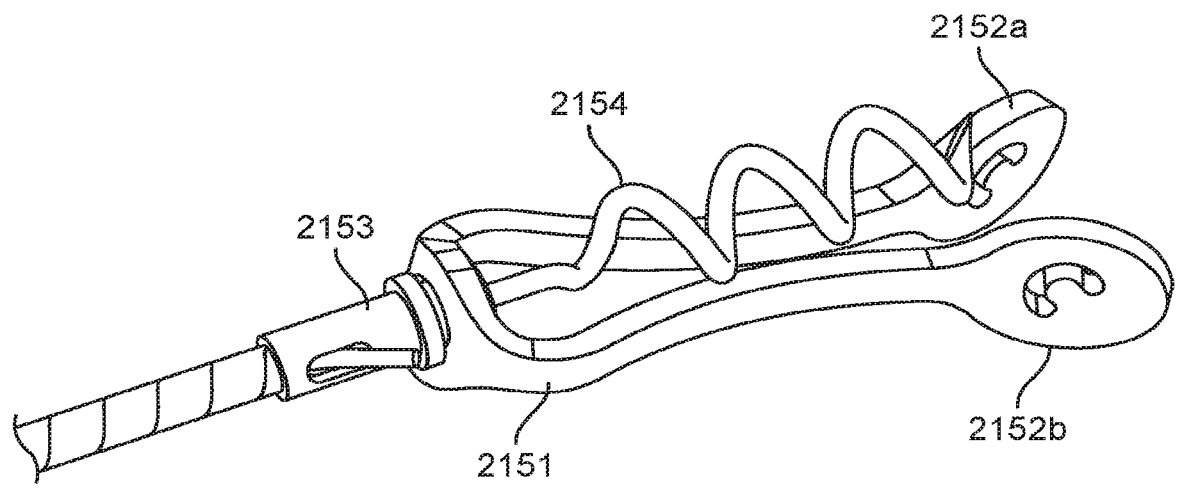

FIG. 115 shows an undulating template 2151 with the ends 2152*a* and 2152*b* folded away from the tissue coupling mechanism attachment 2153 to a delivery position as shown, where the tissue coupling mechanism attachment 2153 and or flexibility in the tissue coupling mechanism 2154 allow the template arms to fold together alongside the tissue coupling mechanism 2154. This configuration may allow for more compact delivery size of the implant compared to configurations where the delivery position has the tissue coupling mechanism 2154 disposed between the arms 2152*a* and 2152*b* of the undulating template 2151

Figure 116:
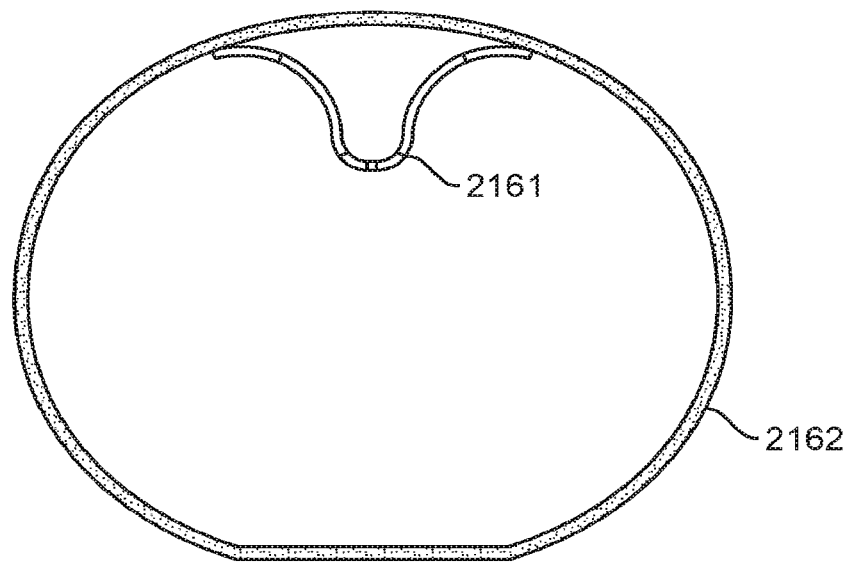

FIG. 116 shows an undulating template 2161 in position adjacent to a mitral annulus 2162 in the untreated state. As shown, the undulating template 2161 is not interacting with the tissue but is positioned approximately as it would be prior to coupling it to the tissue via a tissue coupling mechanism (not shown).

Figure 117:
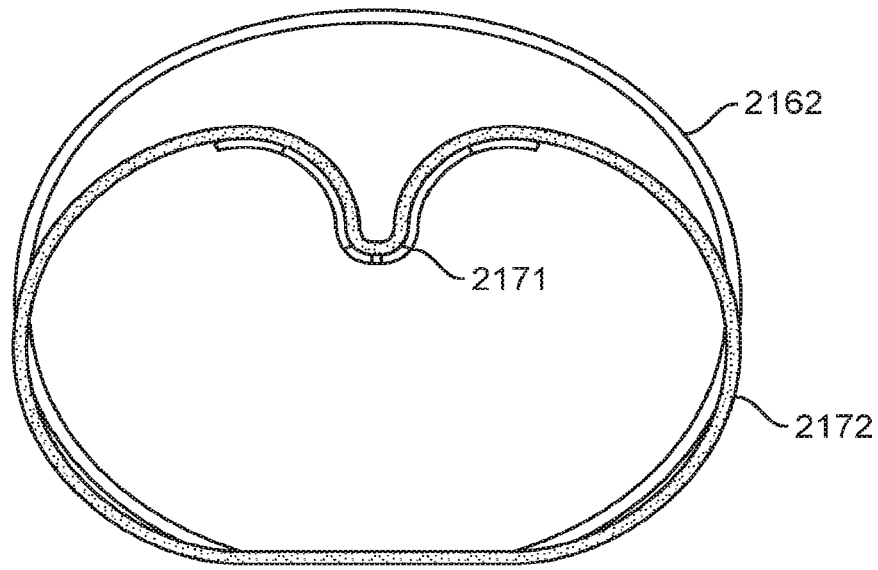

FIG. 117 shows an undulating template 2171 with a mitral annulus 2172, where the tissue coupling mechanism has drawn the annulus tightly against the template. As shown, the circumference of the annulus following the template is essentially unchanged, but the effective circumference of the annulus (bypassing the segment captured by the template) has decreased. The effect of decreasing the effective circumference of the annulus, in combination with deforming the central portion of the annulus toward the middle of the valve, reduces both the minor axis diameter of the valve and the area of the valve. The original position of the annulus 2162 from FIG. 116 is also shown for reference.

Figure 118:
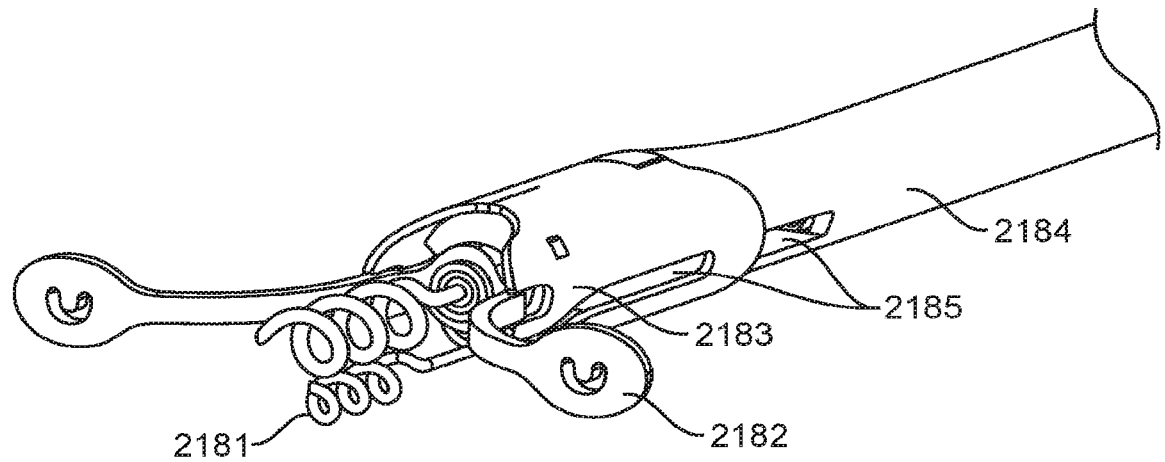

FIG. 118 illustrates a delivery device 2184 for placing an undulating template 2182 over a pre-anchor guide 2181. The pre-anchor guide 2181 runs through a receiving slot in the delivery device 2184. The pre-anchor guide 2181 consists of a tissue coupling feature (a penetrating coil as shown) and a long guide wire. It may be advantageous to place the pre-anchor guide 2181 with a separate delivery device prior to introducing the undulating template 2182. In that case, the delivery device 2184 for the undulating template 2182 may have reduced flexibility, steer-ability, diameter, torquability, or other requirements since the target position has been pre-selected and verified during pre-anchor guide 2181 placement. The pre-anchor delivery device may include an outer steerable sheath, and an inner steerable sheath, the outer steerable sheath being steerable along a radius of from 1cm to 3 cm, and capable of bending to and angle between 90 and 200 degrees. The inner steerable sheath is able to be rotated within the outer sheath, and extended or retracted relative to the outer sheath, allowing between 1cm and 10 cm of the inner sheath to extend past the tip of the outer sheath. The inner steerable sheath may be steerable along a radius of from 0.5 cm to 3 cm, through an angle between 30 and 90 degrees. There may be features on the template 2182 that interact with the delivery device 2184 to stabilize the template 2182 for improved maneuverability during placement. Such features could also be used with a remotely actuated powered system for increased precision control.

The delivery device 2184 provides channels for the releasable torque member attached to the primary tissue coupling mechanism, for the small torque members attached to the stabilizing tissue coupling mechanisms (not shown), and for the pre-anchor guide 2181. These channels may be formed as an extrusion with four distinct inner lumens. The channels for the pre-anchor guide 2181 and the primary tissue coupling mechanism exit the distal end of the delivery device 2184, while the channels for the small torque members attached to the stabilizing tissue coupling mechanisms (not shown) have a side exit 2185 that communicates with the distal end of the delivery device 2184, allowing the small torque members (not shown) to be delivered within the outer diameter of the delivery device 2184 when the undulating template 2182 is folded forward in the delivery configuration (as shown in FIG. 115), and then to extend outside the diameter of the delivery device 2184 when the arms are in the placement position.

The delivery device 2184 also incorporates a rotational guide member 2183 which couples the undulating template 2182 to the delivery device 2184. Depending on the exact use configuration of the delivery device 2184, the body of the delivery device 2184 may be long and flexible to function as a catheter, or short and rigid for open surgical procedures. The delivery device 2184 may include an outer steerable sheath, and an inner steerable sheath, the outer steerable sheath being steerable along a radius of from 1cm to 3 cm, and capable of bending to and angle between 90 and 200 degrees. The inner steerable sheath can be rotated within the outer sheath, and extended or retracted relative to the outer sheath, allowing between 1cm and 10 cm of the inner sheath to extend past the tip of the outer sheath. The inner steerable sheath may be steerable along a radius of from 0.5 cm to 3 cm, through an angle between 30 and 90 degrees.

Figure 119:
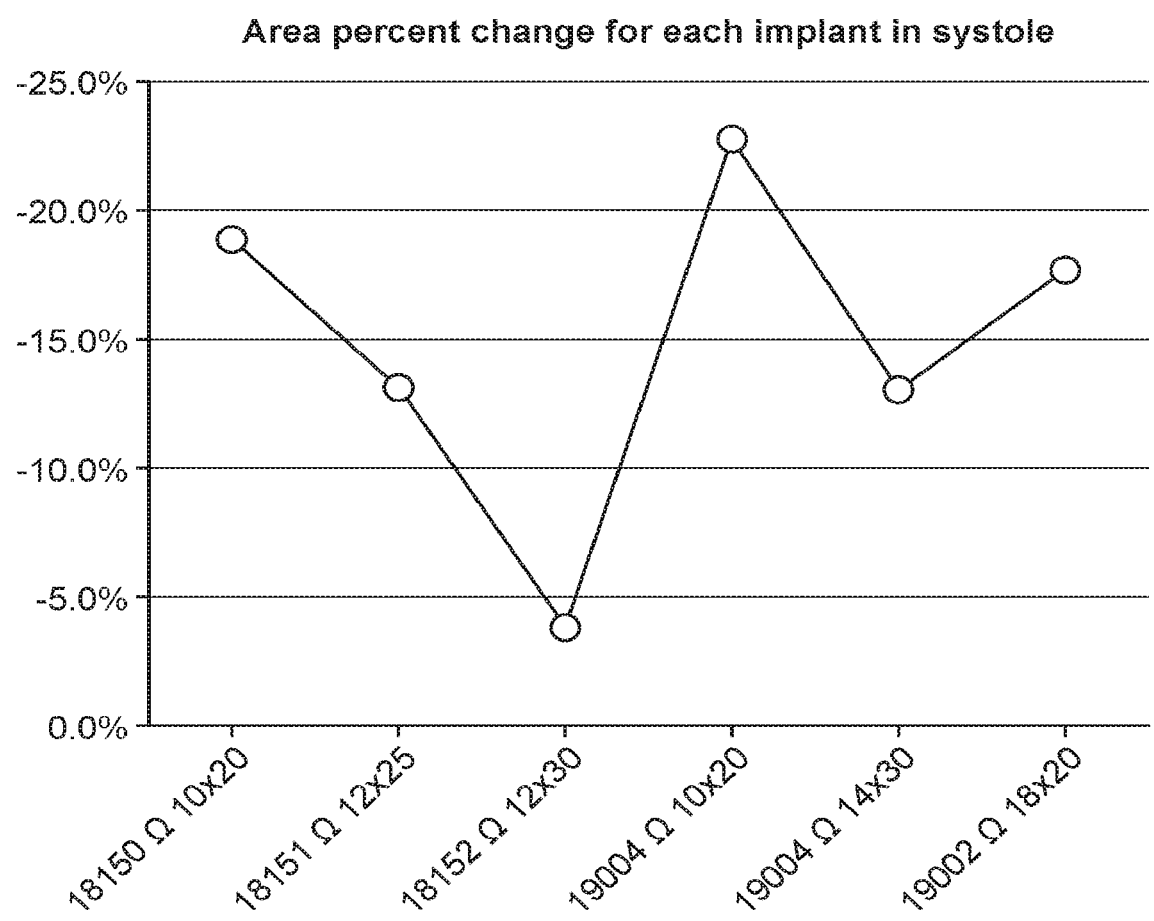
Figure 120:
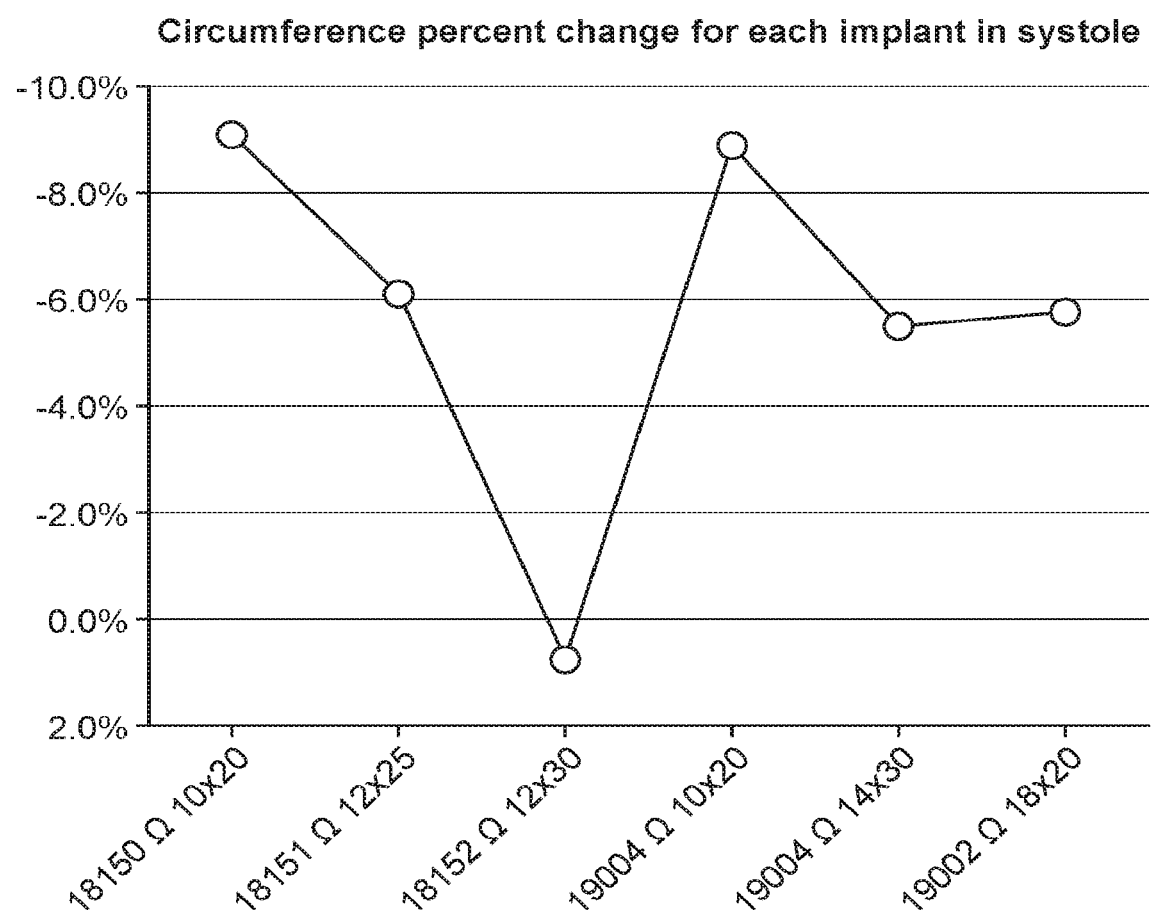
Figure 121:
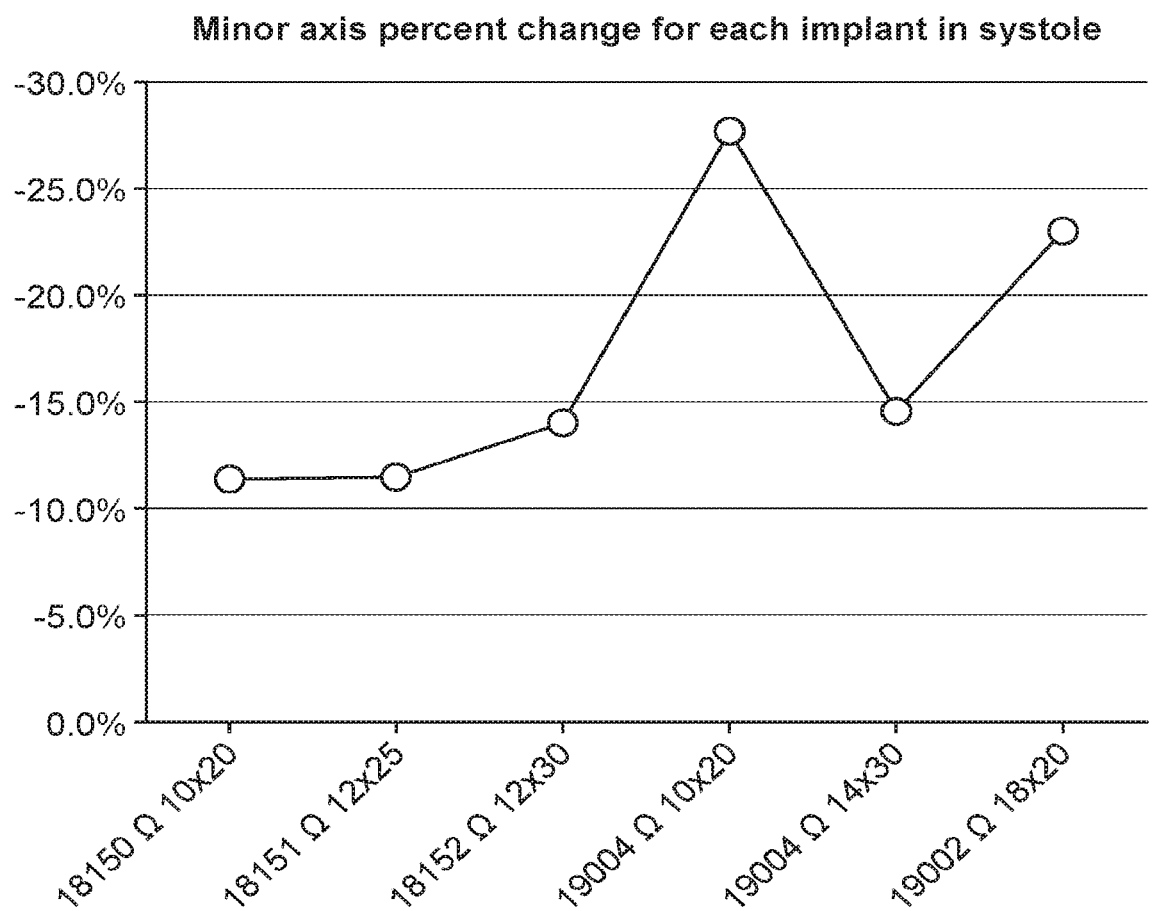

FIGS. 119-121 show percent change for annular dimensions in various templates implanted in-vivo. These data were collected during open heart implantations in the porcine model; the chest was opened, bypass readied, and pre-op measurements made. The animal was then put on bypass, the device implanted, the heart closed and taken off bypass. When the heart was pumping successfully on its own, post-operative measurements were taken and compared to the pre-op measurements. All measurements were taken in systole.

FIG. 119 shows percent area change for various templates implanted in-vivo.

FIG. 120 shows percent circumference change for various templates implanted in-vivo.

FIG. 121 shows percent minor axis change for various templates implanted in-vivo.

Figure 122:
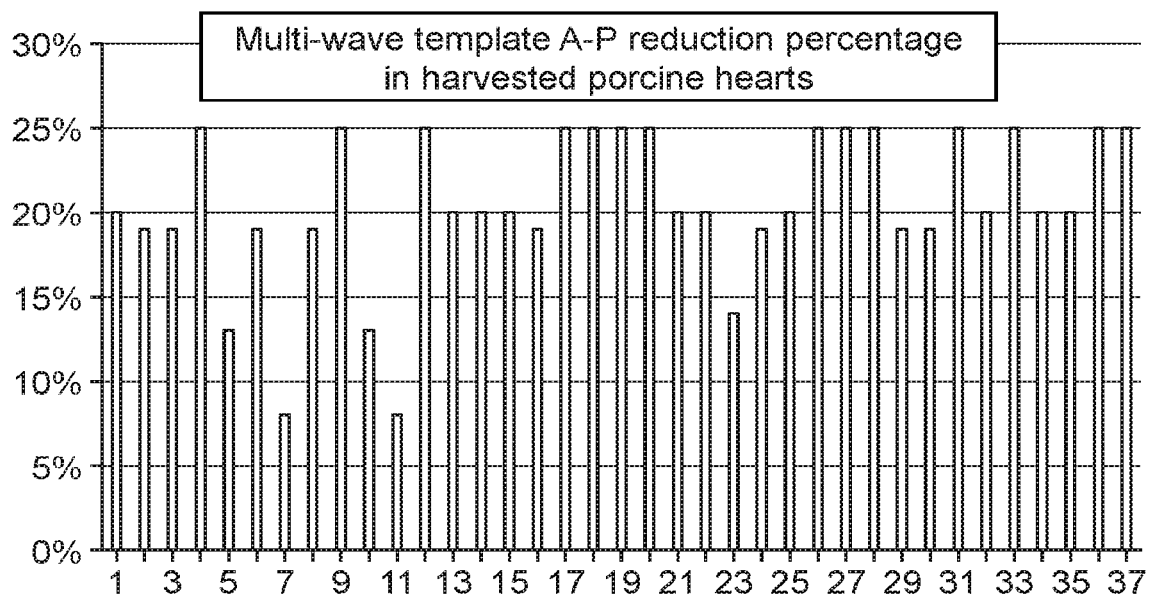

FIGS. 122-123 show percent change in the minor axis diameter for various templates in excised porcine hearts. Hearts were obtained fresh, mounted in a stand so that the mitral annulus was approximately horizontal, and held so that the pre-procedure ratio of major to minor axis was between 1.2:1 and 1.3:1 as verified by D-shaped valve sizers. The implants were placed, and the altered dimension of the mitral valve again measured by D-shaped valve sizers.

FIG. 122 shows percent A-P (minor axis) reduction for various multi-wave templates implanted in excised porcine mitral annuli.

FIG. 123 shows percent A-P (minor axis) reduction for various single-wave templates implanted in excised porcine mitral annuli.

FIG. 124 shows a continuous ring template 2241, having a single undulating region with one or more tissue anchors 2242 separated by one or more wave peaks 2243. This ring template 2241 may include a latching discontinuity 2244, allowing it to be inserted and deployed in a substantially straight configuration, and connected to form a semi-rigid structure. Such a structure may be used as a stabilizer for placement of a replacement valve as required.

FIG. 125 shows a continuous ring template 2251, having multiple undulating region with one or more tissue anchors 2252 separated by one or more wave peaks 2253. This ring template 2251 may include a latching discontinuity 2254, allowing it to be inserted and deployed in a substantially straight configuration, and connected to form a semi-rigid structure. Such a structure may be used as a stabilizer for placement of a replacement valve as required.

FIG. 126 shows a continuous ring template 2261, having one undulating region which covers essentially the entire circumference of the ring template 2261, with one or more tissue anchors 2262 separated by one or more wave peaks 2263. This ring template 2261 may include a latching discontinuity 2264, allowing it to be inserted and deployed in a substantially straight configuration, and connected to form a semi-rigid structure. Such a structure may be used as a stabilizer for placement of a replacement valve as required.

FIG. 127 shows an undulating template with an angle 2271 between the anchor 2274 and the compression pad feature 2273. This angle 2271 causes the line of tensile force 2272 and the line of compressive force 2273 to intersect, encouraging the anchor 2274 to form a desired angle with the target tissue. This angle 2271 can be built into the template, formed after the template is in position, or can be one stable state of a bi-stable system, which goes in straight and snaps to the angled configuration.

FIG. 128 shows an undulating template with a parallel offset between the tensile forces 2281 on the anchor 2283 and the compressive force 2282 on the compression pads 2284. The offset between these forces creates a moment that biases the anchor attachment point 2285 to move in a desired angular direction relative to the target tissue.

FIG. 129 shows an end-on view of the implant from FIG. 128, illustrating the separation between the plane of the center anchor 2291 and the plane of the side anchors 2292.

As shown in FIG. 130A, a tissue shaping template 13001 has a preformed shape it takes in the unconstrained configuration. The unconstrained configuration is optimized for tissue interaction, but not for delivery to the desired site on the tissue. FIG. 130B shows the tissue shaping template 13001 in a first crimped position, having been constrained in a way that brings the two ends (13002 and 13003) closer together by forcing them toward the middle of the implant. In certain implant configurations, it may be advantageous to push the ends very closely together, arriving at a crimped configuration that is small enough for insertion through a delivery catheter or other device to the desired location in the tissue. FIG. 130C shows the tissue shaping implant 13001 having been curved, bending one end in a clockwise direction 13004 and the opposite end in a counterclockwise direction 13005 to form a substantially circular crimped configuration. This crimped configuration may be easier to deliver through a small diameter tube than the unconstrained configuration.

FIG. 131A shows an unconstrained preformed or pre-shaped template 13101. The unconstrained preformed or pre-shaped template 13101 is coupled to control wires 13104A and 13104B, as well as an anchor 13102 which is in turn coupled to an anchor control device 13103. FIG. 131B shows the template of FIG. 131A in a crimped configuration 13105, which is constrained with the ends or wings of the template retracted proximally relative to the anchor 13102 by control wires 13104A and 13104B which apply a proximal tension to deform the wings proximally away from the anchor. This crimped configuration allows the anchor to be coupled to the desired tissue by initially or fully penetrating the anchor 13102 while the wings are in the constrained configuration 13105, which may simplify the placement of the template. After the anchor 13102 has been fully or partially penetrated into the target site, the retracted ends or wings of the template may be released from the control wires to return to the configuration of FIG. 131A. Depending upon how far the anchor 13102 has been penetrated, the tissue of the annulus will be fully or partially drawn into the convexity between the wings. The anchor 13102 may be further rotated to fully draw in the tissue as needed.

FIG. 132 shows various dimensions on a typical preformed or pre-shaped template 13200 having a concavity segment 13205 and two apex or convex segments 13206A and 13206B. The end-to-end length 13201, the peak-to-peak length 13202, the concavity width 13203 and concavity depth 13204 are illustrated on the diagram. The relationship between the concavity width 13203 and concavity depth 13204 may affect the magnitude of the tissue reshaping effect, as well as the suitability of the preformed or pre-shaped template 13200 for reshaping various different target tissues. Similarly, the relationship between the end-to-end length 13201 of the template 13200, and the overall length of the flattened template shape (not shown) may be indicative of the magnitude of the reshaping effect.

FIG. 133A shows a pre-delivery position of a preformed or pre-shaped template 13301 slidably engaged with a shaft of an anchor control device 13303. As shown, the template 13301 is spaced proximally from the anchor 13302, where the anchor 13302 may be releasably coupled to the shaft of the anchor control device 13303. FIG. 133B shows the preformed or pre-shaped template 13301 in a final delivery position 13305, having slid distally to engage the anchor 13302. Of particular significance, by allowing the preformed or pre-shaped template 13301 to slide over the shaft anchor control device 13303, the anchor control device 13303 can act as a guide to properly position the template 13301 at a target tissue site in the annulus or other tissue.

The template 13301 in final delivery position 13305 may be coupled to the anchor control device 13303 by an anchor coupling device 13304. The anchor coupling device can take several forms, including elastic tabs (similar to those in FIG. 65) that capture the template in final delivery position 13305, a nut that is screwed on to the anchor 13302, or other such mechanisms known to the art. When the anchor control device 13303 is released from the anchor 13302, for example by removing a key wire 13306, the anchor control device 13303 can be removed, while the template in final delivery position 13305 remains coupled to the anchor 13302 in the tissue.

While preferred examples of the present invention have been shown and described herein, it will be obvious to those skilled in the art that such examples are provided by way of example only. Numerous variations, changes, and substitutions will now occur to those skilled in the art without departing from the invention. It should be understood that various alternatives to the examples of the invention described herein may be employed in practicing the invention. It is intended that the following claims define the scope of the invention and that methods and structures within the scope of these claims and their equivalents be covered thereby.

Examples

In a preferred example, the template outline was laser cut from a 0.020" thick sheet of superelastic Nitinol® to the desired flat shape, which was cleaned and polished by ultrasonic cleaning and manual polishing, then the flat was clamped into a shaping fixture made of heat resistant aluminum that held the flat shape in a configuration with a single concavity and two convexity or apex or convex segment regions, and the heat set assembly was heated to 485° C. for 4 minutes by submerging in a fluidized bed of aluminum oxide, then was rapidly quenched in a room temperature water bath to set the shape. The now preformed shape was removed from the shaping fixture, inspected, cleaned, and finished (by rounding sharp edges with a hand tool), then covered with an ePTFE sleeve, and attached to an anchor in the concavity region.

In this example, the initial implants were performed via open heart bypass procedure in the ovine model. Templates and anchors were attached to an open surgical delivery device in a substantially unconstrained state. The heart was accessed through a thoracotomy, the animal was put on bypass, the heart stopped, and the mitral valve was accessed through the left atrial wall. The template was maneuvered into position with the delivery device. The apex anchor control devices were retracted, the central anchor positioned on the annulus, and the central anchor control device was twisted to engage the central anchor with the annular tissue. The apex anchor control devices were advanced, and the apex anchors twisted to engage them with the tissue. All three key wires were removed, and the delivery device and anchor control devices were removed, leaving the template, center anchor, and apex anchors in place. The opening in the left atrial wall was closed, the heart was restarted, and measurements of the annulus were taken via ultrasound. In sterile procedures, the implant, anchors, and delivery device were attached to a protective card, sealed into a Tyvek pouch, and sterilized by exposure to EtO gas. At the conclusion of survival implant procedures, the thoracotomy was closed, and the animal moved to an intensive care suite to recover.

In this example, the template was implanted through a trans-septal catheterization. First, the formed single concavity template with anchor was loaded into a delivery catheter by attaching the anchor to an anchor control device with a key wire and placing two convexity or apex or convex segment anchors (having been previously attached to the convexity or apex anchor control devices via key wires) to the convexity or apex regions of the formed template. Trans-septal access was gained through the femoral vein, and a needle and steerable outer catheter advanced across the septum. The apex regions of the template were forced distally (relative to the concavity anchor) to reduce the assembly diameter and inserted through the steerable delivery catheter for delivery to the target annulus. The formed template with anchors was pushed distally through the steerable outer catheter, where it substantially regained its formed shape, and the apexes or wings were retracted distally by pulling on the apex anchor control devices. Pulling the apex anchor control devices independently allowed an added means of control of the curvature and position of the distal end of the tubular catheter, anchors and template. The anchor control device was rotated to couple the convexity anchor to the annulus, the apex control devices were released to bring the apexes into apposition with the annulus tissue, the apex control devices were rotated to couple the apex anchors to the annular tissue. The 3 key wires were then removed, and the control devices and delivery catheter withdrawn, leaving the formed template with attached anchor, as well as the two apex anchors, in place on the annulus.

In another preferred example, the template outline was laser cut from a 0.020" thick sheet of superelastic Nitinol® to the desired flat shape, which was cleaned and polished by ultrasonic cleaning and manual polishing, then the flat was clamped into a shaping fixture made of heat resistant aluminum that held the flat template in a configuration with three concavities and four apex or convex regions, and the heat set assembly was heated to 485° C. for 4 minutes by submerging in a fluidized bed of aluminum oxide, then was rapidly quenched in a room temperature water bath to set the shape. The now preformed shape was removed from the shaping fixture, inspected, cleaned, and finished (by rounding sharp edges with a hand tool), then covered with an ePTFE sleeve, and one anchor was attached to each of the three concavity regions.

In this example, the formed triple concavity template with anchors was then loaded into a delivery catheter by attaching the anchors to anchor control devices with key wires. The apex or convex regions were forced medially (toward the middle of the implant) and then wrapped into a substantially circular shape to reduce the assembly diameter and inserted through an elongated tubular catheter for delivery to the target annulus. The formed template with anchors was pushed distally out of the tubular catheter, where it substantially regained its formed shape, and the outer concavities were retracted distally by pulling on the outer anchor control devices. Pulling the outer anchor control devices independently allowed an added means of control of the curvature and position of the distal end of the tubular catheter, anchors and template. The central anchor control device was rotated to couple the central convexity anchor to the annulus, the outer control devices were released to bring the outer anchors into apposition with the annulus tissue, and the outer control devices were rotated to couple the outer concavity anchors to the annular tissue. The 3 key wires were then removed, and the control devices and delivery catheter withdrawn, leaving the formed template with attached anchors in place on the annulus.

What is claimed is:

1. An implant for reshaping a valve annulus, said implant comprising:
    a pre-shaped template having a tissue-engaging surface having first and second convex regions joined by at least one concave region, wherein the pre-shaped template extends between a first terminal end comprising the first convex region and a second terminal end comprising the second convex region; and
    at least one rotatable anchor configured to penetrate tissue when rotated;
    wherein the pre-shaped template is configured to be coupled to the at least one rotatable anchor and wherein the pre-shaped template is configured to draw at least one segment of a valve annulus into the concave region.

2. The implant of claim 1, wherein at least one of the first and second terminal ends extends beyond the first and second convex regions, respectively.

3. The implant of claim 1, wherein the pre-shaped template is configured to be coupled to the at least one rotatable anchor after said at least one rotatable anchor has penetrated the tissue.

4. The implant of claim 1, wherein the pre-shaped template is rotatably coupled to the at least one rotatable anchor before said at least one rotatable anchor has penetrated the tissue.

5. The implant of claim 1, wherein the at least one rotatable anchor extends into the concave region between the convex regions when coupled to the pre-shaped template.

6. The implant of claim 1, further comprising at least one rotatable tissue-penetrating side anchor configured to be coupled to each of said first and second convex regions.

7. The implant of claim 1, wherein said convex regions extend in opposite directions from said concave region.

8. The implant of claim 1, wherein the rotatable anchor is configured to be coupled to an anchor segment of said concave region of said template.

9. The implant of claim 8, wherein the rotatable anchor is configured to be coupled to an anchor segment at the base of said concave region of said template.

10. The implant of claim 9, wherein a coupling end of the at least one rotatable anchor extends outwardly from the anchor segment in a direction opposite to that of the tissue-penetrating end.

11. The implant of claim 10, further comprising a rotatable driver detachably secured to the coupling end of the at least one rotatable anchor.

12. The implant of claim 1, further comprising at least one rotatable side anchor on each of the convex regions disposed near the terminal end of each convex region, wherein each rotatable side anchor further comprises a coupling end and a rotatable driver detachably secured to the coupling end of the at least one rotatable side anchor.

13. The implant of claim 8, wherein template comprises an inwardly curving region on each side of said anchor segment to form the concave region and an outwardly curving regions extending from each of said inwardly curving regions to form the convex regions.

14. The implant of claim 1, wherein the pre-shaped template comprises a super-elastic metal.

15. The implant of claim 1, wherein the pre-shaped template is configured to draw at least one segment of a posterior mitral valve annulus into the concave region.

16. The implant of claim 1, wherein the pre-shaped template comprises an elongate structure having a length in a range from 10 mm to 75 mm.

17. The implant of claim 1, wherein the pre-shaped template has only a single concave region.

18. The implant of claim 16, wherein the pre-shaped template has only two convex regions.

19. The implant of claim 1, wherein the pre-shaped template has a plurality of concave regions.

20. The implant of claim 1, wherein the at least one rotatable anchor is configured to penetrate and draw in at least a segment of an inner surface of the valve annulus into the concave region of the pre-shaped template.

21. The implant of claim 20, wherein the at least one rotatable anchor comprises at least one of a helix, a coil, a screw, and a spiral.

22. The implant of claim 1, wherein the at least one rotatable anchor comprises a helical anchor rotatably secured in the concave region of the template and having a distal end and a proximal end, said distal end having a sharpened tip configured to penetrate tissue as the at least one anchor is rotated and said proximal end having a coupling configured to be detachably secured to a driver to rotate the helical anchor to drive the sharpened tip into the annulus and enabling the anchor to draw at least a segment of an inner surface of the annulus into the concave region.

23. The implant of claim 21, wherein the helical anchor comprises a helical coil, a helical screw, or a helical spiral.

24. The implant of claim 21, wherein the pre-shaped template has an axis between the terminal ends and the concave region has a depth in a direction lateral to the axis.

25. The implant of claim 24, wherein the helical anchor has a length which is less than or greater than the depth of the concave region.

26. The implant of claim 21, wherein said template comprises an opening in said concave region through which said at least one rotatable anchor can slide and couple to said template.

27. The implant of claim 26, wherein said convex regions further comprises an opening through which at least one side anchor can slide and couple to said template.

28. The implant of claim 1, wherein said pre-shaped template and said at least one rotatable anchor are configured to be assembled in-situ.

29. The implant of claim 28, wherein said template is further configured for attachment to side anchors placed into a valve annulus prior to coupling of said pre-shaped template to the at least one rotatable anchor.

30. The implant of claim 1, wherein said implant is configured for placement of said at least one rotatable anchor into said valve annulus with a driver, sliding the pre-shaped template over said driver and then coupling said pre-shaped template to said anchor followed by releasing said driver from said anchor.

* * * * *